United States Patent
Hatakeyama et al.

(10) Patent No.: US 11,409,194 B2
(45) Date of Patent: Aug. 9, 2022

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP); Takayuki Fujiwara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 397 days.

(21) Appl. No.: 16/530,438

(22) Filed: Aug. 2, 2019

(65) Prior Publication Data

US 2020/0050105 A1   Feb. 13, 2020

(30) Foreign Application Priority Data

Aug. 9, 2018  (JP) .............................. JP2018-150050

(51) Int. Cl.
| | |
|---|---|
| *G03F 7/004* | (2006.01) |
| *G03F 7/038* | (2006.01) |
| *C07D 295/088* | (2006.01) |
| *C07C 217/06* | (2006.01) |
| *C07D 235/12* | (2006.01) |
| *C07D 211/22* | (2006.01) |
| *C07D 207/08* | (2006.01) |
| *C07D 211/46* | (2006.01) |
| *C07D 453/02* | (2006.01) |
| *C07D 209/52* | (2006.01) |
| *C07D 451/02* | (2006.01) |
| *G03F 7/039* | (2006.01) |
| *G03F 7/32* | (2006.01) |
| *G03F 7/16* | (2006.01) |
| *G03F 7/20* | (2006.01) |
| *G03F 7/38* | (2006.01) |

(52) U.S. Cl.
CPC .......... *G03F 7/0045* (2013.01); *C07C 217/06* (2013.01); *C07D 207/08* (2013.01); *C07D 209/52* (2013.01); *C07D 211/22* (2013.01); *C07D 211/46* (2013.01); *C07D 235/12* (2013.01); *C07D 295/088* (2013.01); *C07D 451/02* (2013.01); *C07D 453/02* (2013.01); *G03F 7/0382* (2013.01); *G03F 7/0392* (2013.01); *G03F 7/162* (2013.01); *G03F 7/168* (2013.01); *G03F 7/2006* (2013.01); *G03F 7/322* (2013.01); *G03F 7/38* (2013.01)

(58) Field of Classification Search
CPC .. C07C 217/06; C07D 207/08; C07D 209/52; C07D 211/22; C07D 211/46; C07D 235/12; C07D 295/088; C07D 451/02; C07D 453/02
See application file for complete search history.

(56) References Cited

U.S. PATENT DOCUMENTS

| | | | |
|---|---|---|---|
| 2,714,594 A | 8/1955 | Cusic et al. | |
| 4,064,139 A * | 12/1977 | Anderson | ............ C07D 471/18 548/425 |
| 9,017,922 B2 * | 4/2015 | Hatakeyama | ......... G03F 7/0382 430/270.1 |
| 2012/0202158 A1 | 8/2012 | Hatakeyama et al. | |
| 2014/0205947 A1 * | 7/2014 | Iwato | ........................ G03F 7/38 430/270.1 |
| 2018/0143532 A1 | 5/2018 | Hatakeyama | |
| 2020/0073237 A1 * | 3/2020 | Hatakeyama | ......... G03F 7/0397 |
| 2020/0192222 A1 * | 6/2020 | Hatakeyama | ......... G03F 7/0397 |

FOREIGN PATENT DOCUMENTS

| | | |
|---|---|---|
| EP | 0972764 A1 | 1/2000 |
| JP | 2001-194776 A | 7/2001 |
| JP | 2002-226470 A | 8/2002 |
| JP | 2002-363148 A | 12/2002 |
| JP | 2018-087971 A | 6/2018 |
| JP | 2018-097356 A | 6/2018 |
| KR | 10-2012-0092064 A | 8/2012 |
| WO | 2008/066011 A1 | 6/2008 |

OTHER PUBLICATIONS

Office Action dated May 8, 2020, issued in counterpart TW Application No. 108127976 (5 pages).
Office Action dated Jun. 11, 2021, issued in counterpart KR Application No. 10-2019-0097610, with English Translation. (11 pages).

* cited by examiner

*Primary Examiner* — Amanda C. Walke
(74) *Attorney, Agent, or Firm* — WHDA, LLP

(57) ABSTRACT

A resist composition comprising a base polymer and a quencher in the form of an amine compound having an iodized aromatic ring bonded to the nitrogen atom via a divalent hydrocarbon group offers a high sensitivity and minimal LWR or improved CDU, independent of whether it is of positive or negative tone.

14 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2018-150050 filed in Japan on Aug. 9, 2018, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

As the pattern feature size is reduced, approaching to the diffraction limit of light, light contrast lowers. In the case of positive resist film, a lowering of light contrast leads to reductions of resolution and focus margin of hole and trench patterns. For mitigating the influence of reduced resolution of resist pattern due to a lowering of light contrast, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 to 3.

With respect to the acid labile group used in methacrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 4 discloses a resist composition comprising a sulfonium or iodonium salt capable of generating carboxylic acid as a quencher.

Patent Document 5 discloses a resist composition comprising an iodized aniline as a quencher. The aniline has a low basicity which is insufficient to suppress acid diffusion.

Sulfonium and iodonium salt type quenchers are photo-decomposable like photoacid generators. That is, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

CITATION LIST

Patent Document 1: JP-A 2001-194776
Patent Document 2: JP-A 2002-226470
Patent Document 3: JP-A 2002-363148
Patent Document 4: WO 2008/066011
Patent Document 5: JP-A 2018-097356

DISCLOSURE OF INVENTION

For the acid-catalyzed chemically amplified resist, it is desired to develop a quencher capable of reducing the LWR of line patterns or the CDU of hole patterns and improving sensitivity.

An object of the invention is to provide a resist composition which exhibits a high sensitivity and a reduced LWR or improved CDU, independent of whether it is of positive tone or negative tone; and a pattern forming process using the same.

The inventors have found that using an amine compound having an iodine-substituted aromatic ring (also referred to as iodized aromatic ring-containing amine compound, hereinafter) as the quencher, a resist material having a reduced LWR, improved CDU, high contrast, improved resolution, and wide process margin is obtainable.

In one aspect, the invention provides a resist composition comprising a base polymer and a quencher, the quencher being an amine compound having an iodine-substituted aromatic ring bonded to the nitrogen atom via a $C_1$-$C_{20}$ divalent hydrocarbon group which may contain at least one moiety selected from ester bond and ether bond.

Specifically, the amine compound has the formula (A).

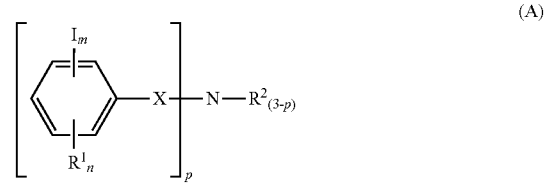

(A)

Herein $R^1$ is hydroxyl, $C_1$-$C_6$ alkyl group, $C_1$-$C_6$ alkoxy group, $C_2$-$C_6$ acyloxy group, fluorine, chlorine, bromine, amino group, —$NR^{1A}$—C(=O)—$R^{1B}$, or —$NR^{1A}$—C(=O)—O—$R^{1B}$, $R^{1A}$ is hydrogen or a $C_1$-$C_6$ alkyl group, $R^{1B}$ is a $C_1$-$C_6$ alkyl, $C_2$-$C_8$ alkenyl, $C_6$-$C_{12}$ aryl or $C_7$-$C_{13}$ aralkyl group; $R^2$ is hydrogen, nitro, or a $C_1$-$C_{20}$ monovalent hydrocarbon group which may contain at least one moiety selected from hydroxyl, carboxyl, thiol, ether bond, ester bond, nitro, cyano, halogen and amino moiety, in case of p=1, $R^2$ may bond together to form a ring with the nitrogen atom to which they are attached, the ring optionally containing a double bond, oxygen, sulfur or nitrogen, or $R^2$ and X may bond together to form a ring with the nitrogen atom to which they are attached, the ring optionally containing a double bond, oxygen, sulfur or nitrogen; X is a $C_1$-$C_{20}$ divalent hydrocarbon group which may contain at least moiety selected from ester bond and ether bond; m and n are independently an integer meeting $1 \leq m \leq 5$, $0 \leq n \leq 4$ and $1 \leq m+n \leq 5$, and p is 1, 2 or 3.

The resist composition may further comprise an acid generator capable of generating a sulfonic acid, imide acid or methide acid.

The resist composition may further comprise an organic solvent.

In a preferred embodiment, the base polymer comprises recurring units having the formula (a1) or recurring units having the formula (a2).

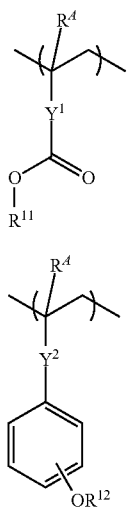

(a1)

(a2)

Herein $R^A$ is each independently hydrogen or methyl, $R^{11}$ and $R^{12}$ each are an acid labile group, $Y^1$ is a single bond, phenylene group, naphthylene group, or $C_1$-$C_{12}$ linking group containing at least one moiety selected from ester bond and lactone ring, and $Y^2$ is a single bond or ester bond.

Typically, the resist composition is a chemically amplified positive resist composition.

In another embodiment, the base polymer is free of an acid labile group.

Also typically, the resist composition is a chemically amplified negative resist composition.

In a preferred embodiment, the base polymer further comprises recurring units of at least one type selected from recurring units having the formulae (f1) to (f3).

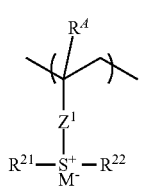

(f1)

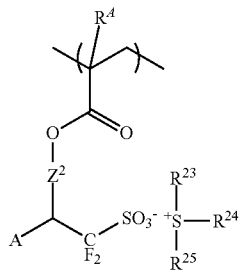

(f2)

(f3)

Herein $R^A$ is each independently hydrogen or methyl. $Z^1$ is a single bond, phenylene group, —O—$Z^{11}$—, —C(=O)—O—$Z^{11}$—or —C(=O)—NH—$Z^{11}$—, $Z^{11}$ is a $C_1$-$C_6$ alkanediyl group, $C_2$-$C_6$ alkenediyl group, or phenylene group, which may contain a carbonyl, ester bond, ether bond or hydroxyl moiety. $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain a carbonyl moiety, ester bond or ether bond. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain a carbonyl moiety, ester bond, ether bond or hydroxy moiety. $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl, and $M^-$ is a non-nucleophilic counter ion.

The resist composition may further comprise a surfactant.

The resist composition may further comprise a quencher other than the amine compound.

In another aspect, the invention provides a process for forming a pattern comprising the steps of applying the resist composition defined herein onto a substrate, baking to form a resist film, exposing the resist film to high-energy radiation, and developing the exposed resist film in a developer.

Typically, the high-energy radiation is ArF excimer laser radiation of wavelength 193 nm, KrF excimer laser radiation of wavelength 248 nm, EB, or EUV of wavelength 3 to 15 nm.

In a further aspect, the invention provides an amine compound having the formula (A').

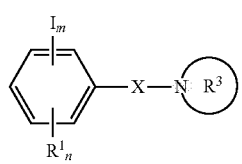

(A')

Herein $R^1$, X, m and n are as defined above. The ring $R^3$ is a $C_4$-$C_6$ heterocycle formed with the nitrogen atom, which may contain an ether bond, thioether bond, —N($R^4$)—, carbonyl group or sulfonyl group, $R^4$ is hydrogen, $C_1$-$C_6$ alkyl, $C_2$-$C_6$ alkenyl, $C_2$-$C_8$ acyl, $C_7$-$C_{20}$ aralkyl or $C_1$-$C_{16}$ alkoxycarbonyl group.

Advantageous Effects of Invention

The iodized aromatic ring-containing amine compound is fully absorptive to EUV due to the inclusion of iodine, has a sensitizing effect, and is quite effective for suppressing acid diffusion by virtue of the large atomic weight of iodine. Since the compound is not photosensitive and is not decomposed in the exposed region, it has a high ability to control acid diffusion in the exposed region and is also effective for preventing a pattern from any film thickness loss by alkaline developer. Thus a resist composition having a high sensitivity, low LWR and improved CDU is designed.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. As used herein, the term "iodized" compound means an iodine-substituted compound. In chemical formulae, Me stands for methyl, and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a quencher in the form of an iodized aromatic ring-containing amine compound.

Iodized Aromatic Ring-Containing Amine Compound

The iodized aromatic ring-containing amine compound is an amine compound having an iodine-substituted aromatic ring bonded to the nitrogen atom via a $C_1$-$C_{20}$ divalent hydrocarbon group which may contain at least one moiety selected from ester bond and ether bond. Preferably the amine compound has the formula (A).

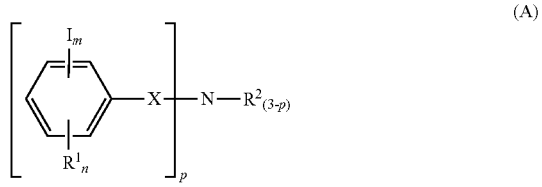

(A)

In formula (A), $R^1$ is hydroxyl, a $C_1$-$C_6$ alkyl group, $C_1$-$C_6$ alkoxy group, $C_2$-$C_6$ acyloxy group, fluorine, chlorine, bromine, amino group, —$NR^{1A}$—C(=O)—$R^{1B}$, or —$NR^{1A}$—C(=O)—O—$R^{1B}$. $R^{1A}$ is hydrogen or a $C_1$-$C_6$ alkyl group. $R^{1B}$ is a $C_1$-$C_6$ alkyl, $C_2$-$C_8$ alkenyl, $C_6$-$C_{12}$ aryl or $C_7$-$C_{13}$ aralkyl group.

The $C_1$-$C_6$ alkyl group may be straight, branched or cyclic, and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, and cyclohexyl. Examples of the alkyl moiety in the $C_1$-$C_6$ alkoxy and $C_2$-$C_6$ acyloxy groups are as exemplified above for the alkyl group.

The $C_2$-$C_8$ alkenyl group may be straight, branched or cyclic, and examples thereof include vinyl, 1-propenyl, 2-propenyl, butenyl, hexenyl and cyclohexenyl.

Suitable $C_6$-$C_{12}$ aryl groups include phenyl, tolyl, xylyl, 1-naphthyl and 2-naphthyl. Suitable $C_7$-$C_{13}$ aralkyl groups include benzyl and phenethyl.

Among others, $R^1$ is preferably fluorine, chlorine, bromine, hydroxyl, amino, $C_1$-$C_3$ alkyl, $C_1$-$C_3$ alkoxy, $C_2$-$C_4$ acyloxy, —$NR^{1A}$—C(=O)—$R^{1B}$ or —$NR^{1A}$—C(=O)—O—$R^{1B}$. When n is 2 or more, a plurality of groups $R^1$ may be the same or different.

$R^2$ is hydrogen, nitro, or a $C_1$-$C_{20}$ monovalent hydrocarbon group. The $C_1$-$C_{20}$ monovalent hydrocarbon group may be straight, branched or cyclic. Examples thereof include $C_1$-$C_{20}$ straight or branched alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl, and icosyl; $C_3$-$C_{20}$ monovalent saturated cycloaliphatic hydrocarbon groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ straight or branched alkenyl groups such as vinyl, propenyl, butenyl and hexenyl; $C_2$-$C_{20}$ monovalent unsaturated cycloaliphatic hydrocarbon groups such as cyclohexenyl and norbornenyl; $C_2$-$C_{20}$ alkynyl groups such as ethynyl, propynyl, butynyl, 2-cyclohexylethynyl, and 2-phenylethynyl; $C_6$-$C_{20}$ aryl groups such as phenyl, methylphenyl, ethylphenyl, n-propylphenyl, isopropylphenyl, n-butylphenyl isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl; and $C_7$-$C_{20}$ aralkyl groups such as benzyl and phenethyl. The foregoing monovalent hydrocarbon groups may contain at least one moiety selected from hydroxyl, carboxyl, thiol, ether bond, ester bond, nitro, cyano, halogen and amino moiety.

In case of p=1, two groups $R^2$ may be the same or different. In case of p=1, $R^2$ may bond together to form a ring with the nitrogen atom to which they are attached, the ring optionally containing a double bond, oxygen, sulfur or nitrogen. Alternatively, $R^2$ and X may bond together to form a ring with the nitrogen atom to which they are attached, the ring optionally containing a double bond, oxygen, sulfur or nitrogen.

X is a $C_1$-$C_{20}$ divalent hydrocarbon group. The divalent hydrocarbon group may be straight, branched or cyclic. Examples thereof include straight or branched alkanediyl groups such as methylene, ethylene, propane-1,2-diyl, propane-1,3-diyl, butane-1,2-diyl, butane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, and dodecane-1,12-diyl; $C_3$-$C_{20}$ divalent saturated cyclic hydrocarbon groups such as cyclopentanediyl, cyclohexanediyl, norbornanediyl, and adamantanediyl; $C_2$-$C_{20}$ divalent unsaturated aliphatic hydrocarbon groups such as vinylene and propene-1,3-diyl; $C_6$-$C_{20}$ divalent aromatic hydrocarbon groups such as phenylene and naphthylene; and combinations thereof. The divalent hydrocarbon group may contain at least moiety selected from ester bond and ether bond.

The subscripts m and n are independently an integer meeting 1≤m≤5, 0≤n≤4 and 1≤m+n≤5, preferably m is an integer of 2 to 4 and n is 0 or 1, and p is 1, 2 or 3.

Of the amine compounds having formula (A), amine compounds having the following formula (A') are preferred.

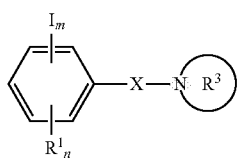

(A')

In formula (A'), $R^1$, X, m and n are as defined above. The ring $R^3$ is a $C_4$-$C_6$ heterocycle formed with the nitrogen atom, which may contain an ether bond, thioether bond, —N($R^4$)—, carbonyl group or sulfonyl group.

$R^4$ is hydrogen, $C_1$-$C_6$ alkyl, $C_2$-$C_6$ alkenyl, $C_2$-$C_8$ acyl, $C_7$-$C_{20}$ aralkyl or $C_1$-$C_{16}$ alkoxycarbonyl group. Examples of the alkyl group and the alkyl moiety in the acyl group are as exemplified above for the alkyl group. Examples of the alkenyl group are as exemplified above for the alkenyl group. Examples of the aralkyl group include benzyl, phenethyl, and 9-fluorenylmethyl. The alkoxy moiety in the alkoxycarbonyl group may be either aliphatic or aromatic, and the aliphatic alkoxy moiety may be straight, branched or cyclic. Suitable alkoxycarbonyl groups include alkyloxycarbonyl, alkenyloxycarbonyl, and aralkyloxycarbonyl groups, and the alkyl, alkenyl and aralkyl moieties therein are as exemplified above for the alkyl, alkenyl and aralkyl groups represented by $R^4$.

Examples of the iodized aromatic ring-containing amine compound are shown below, but not limited thereto.

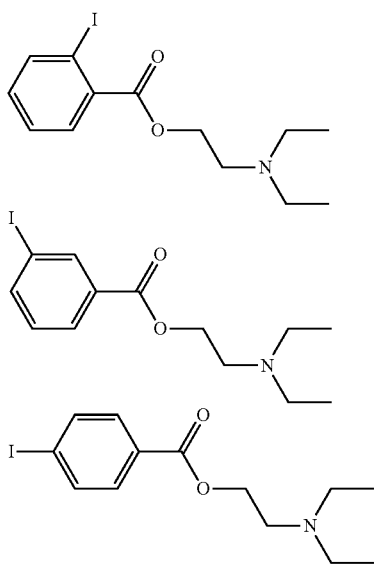

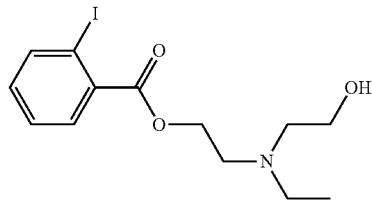

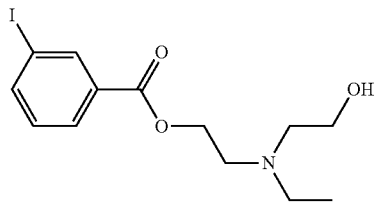

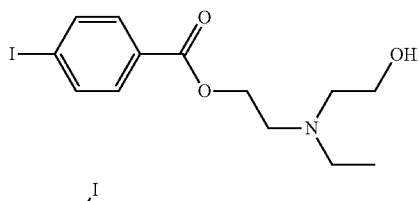

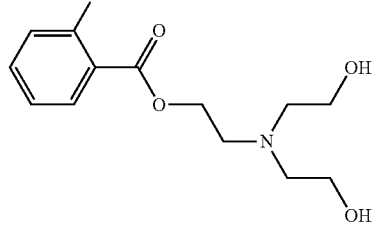

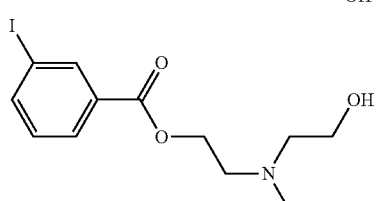

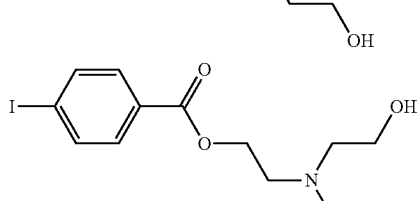

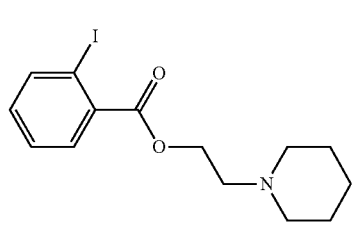

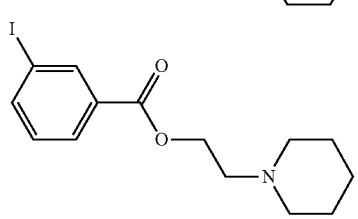

-continued
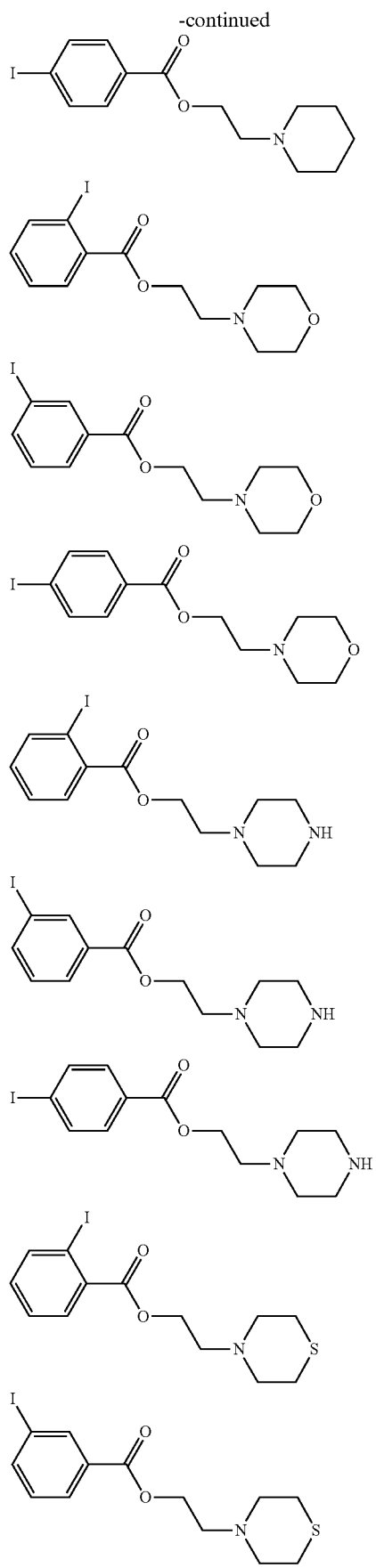
-continued
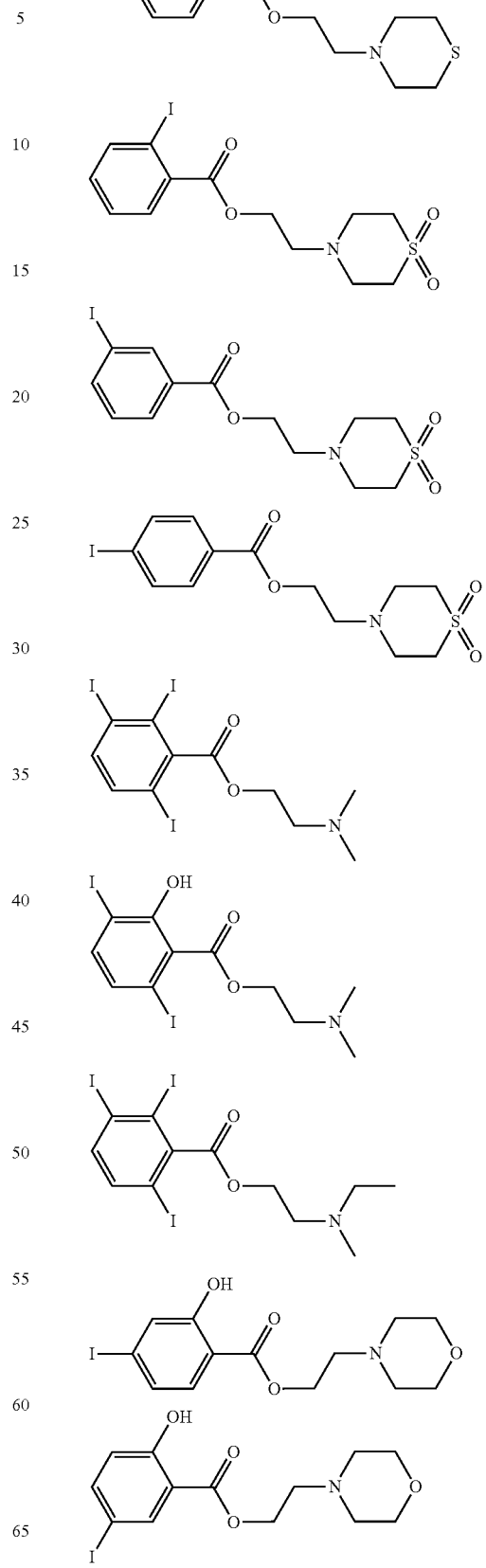

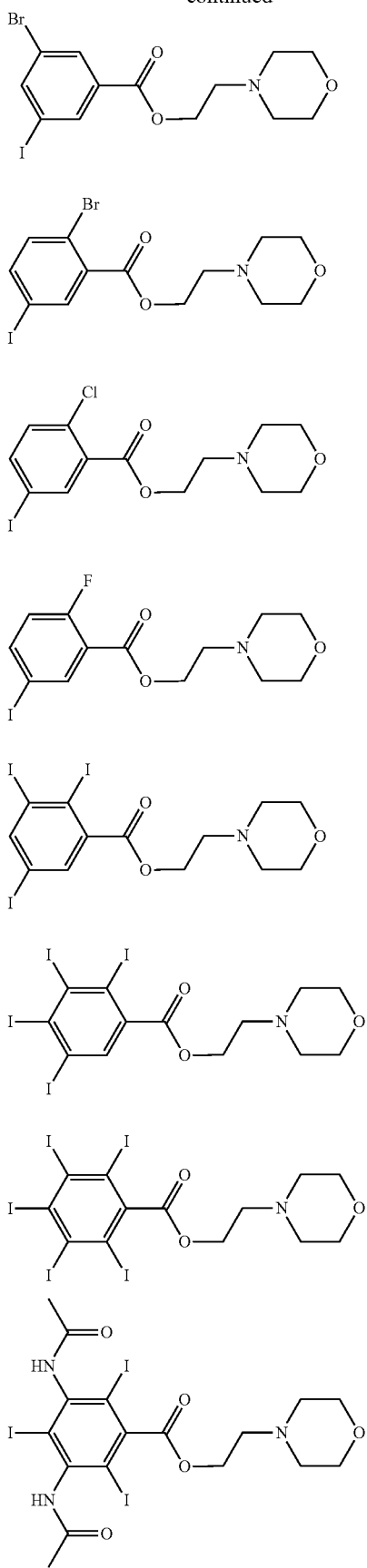
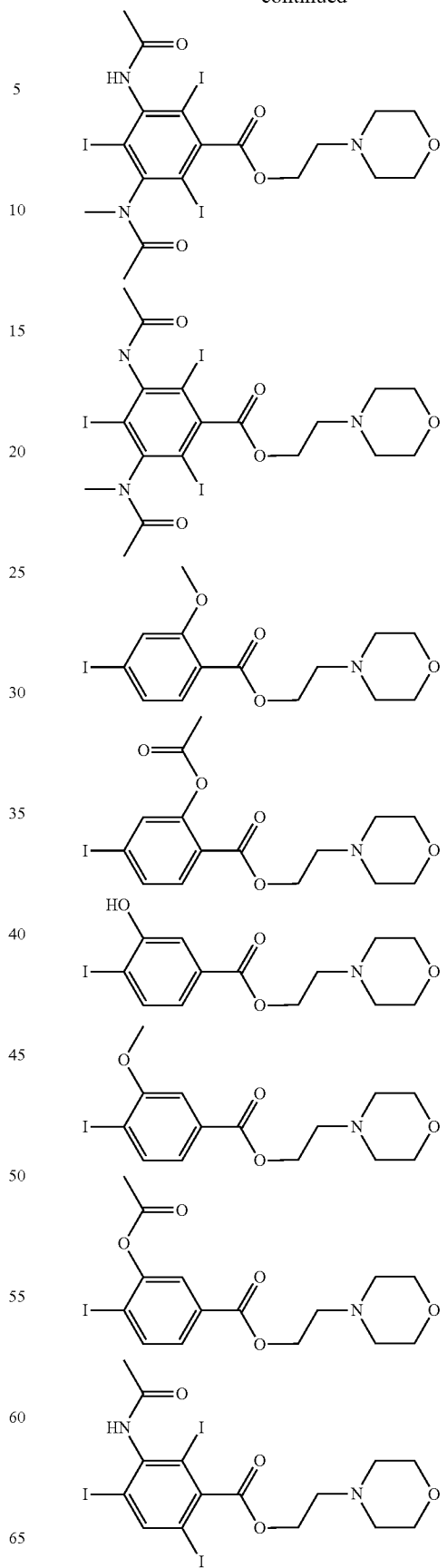

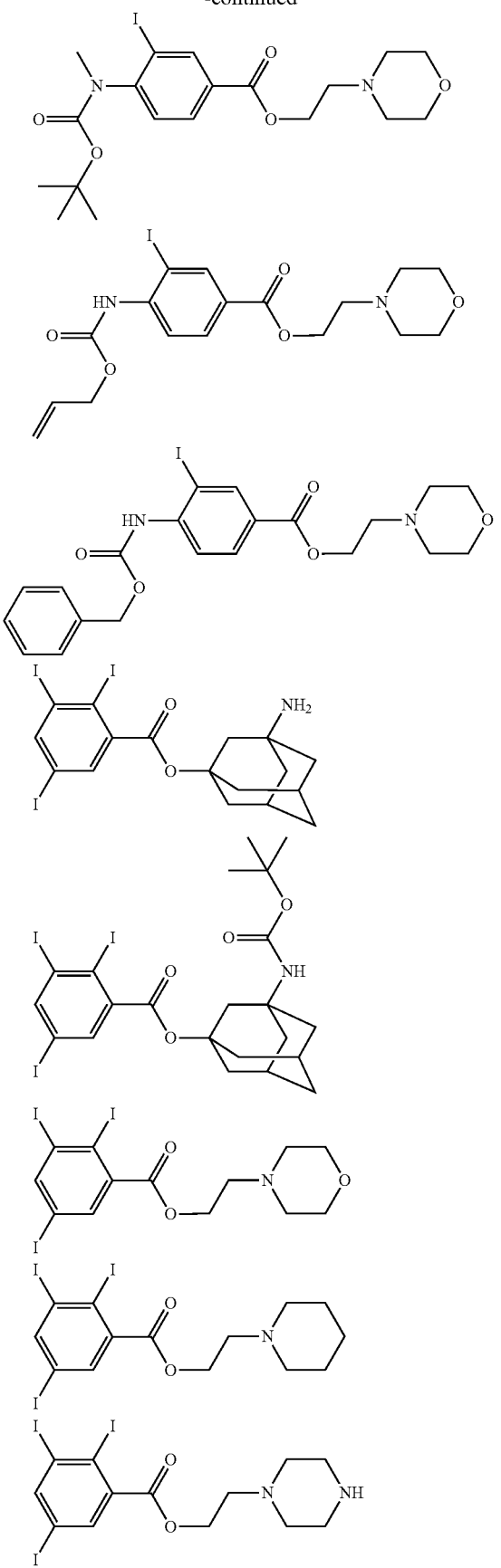
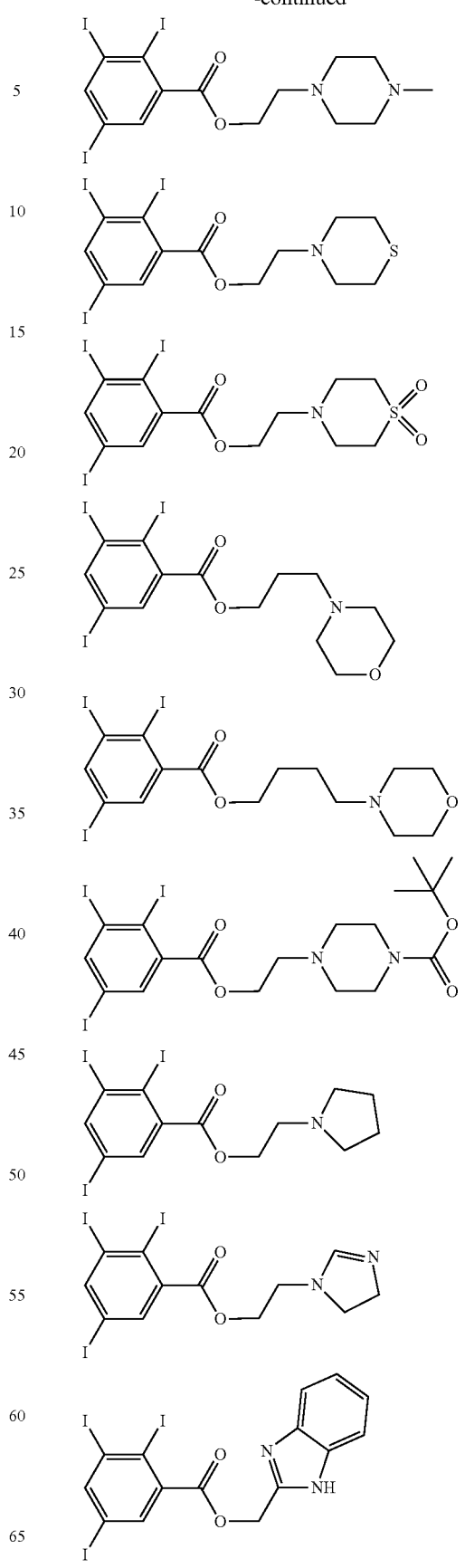

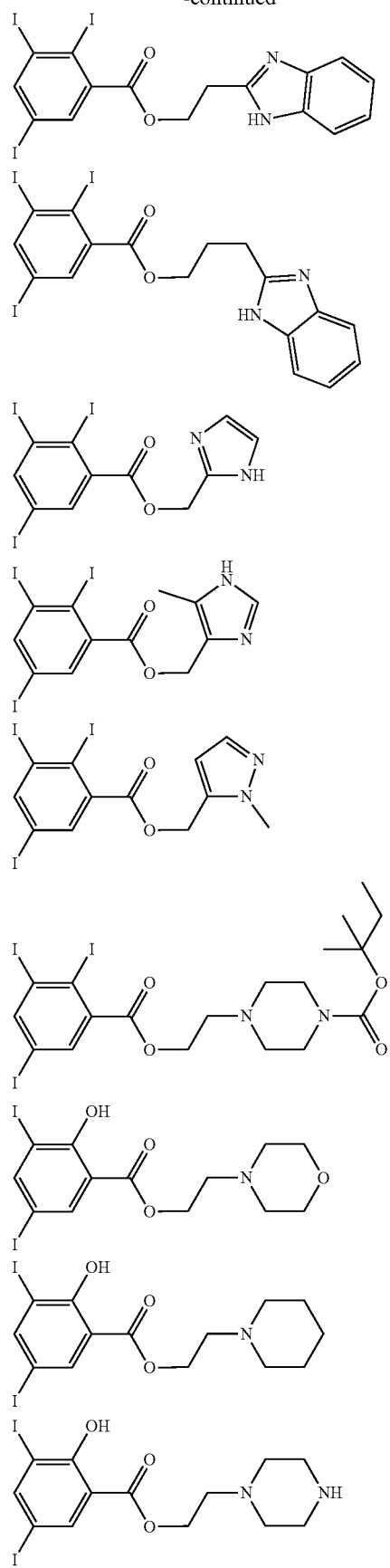
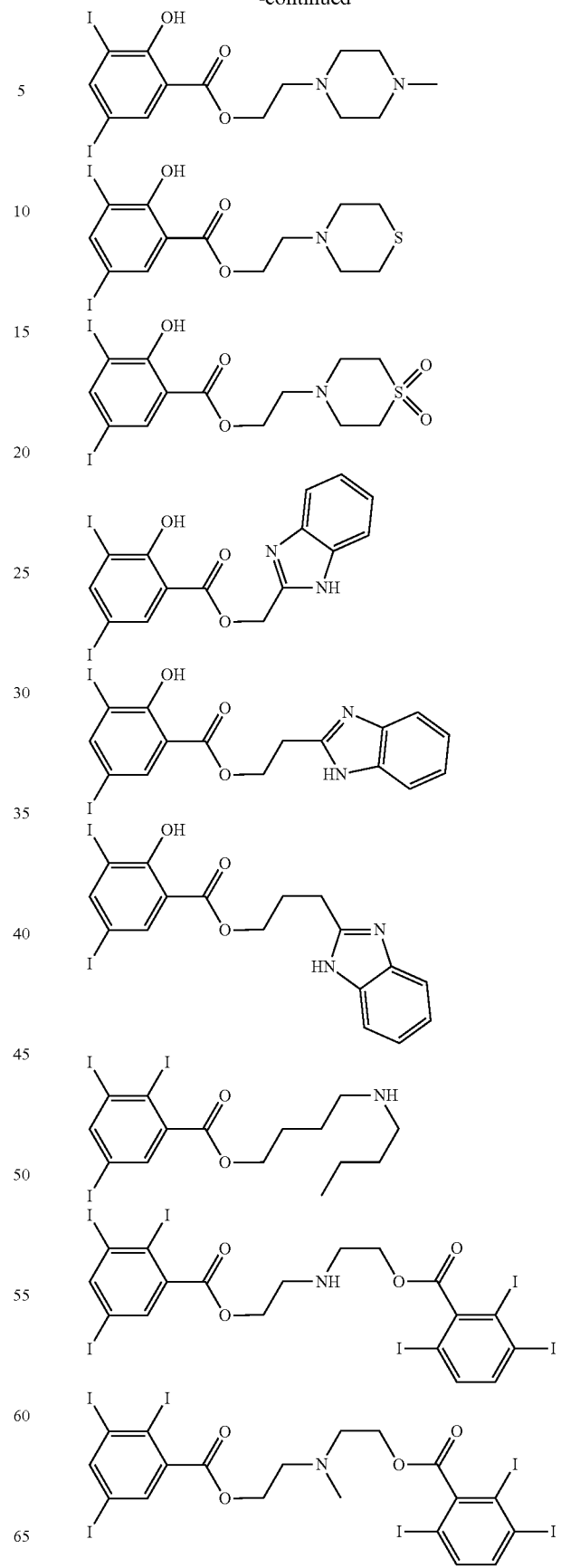

17
-continued
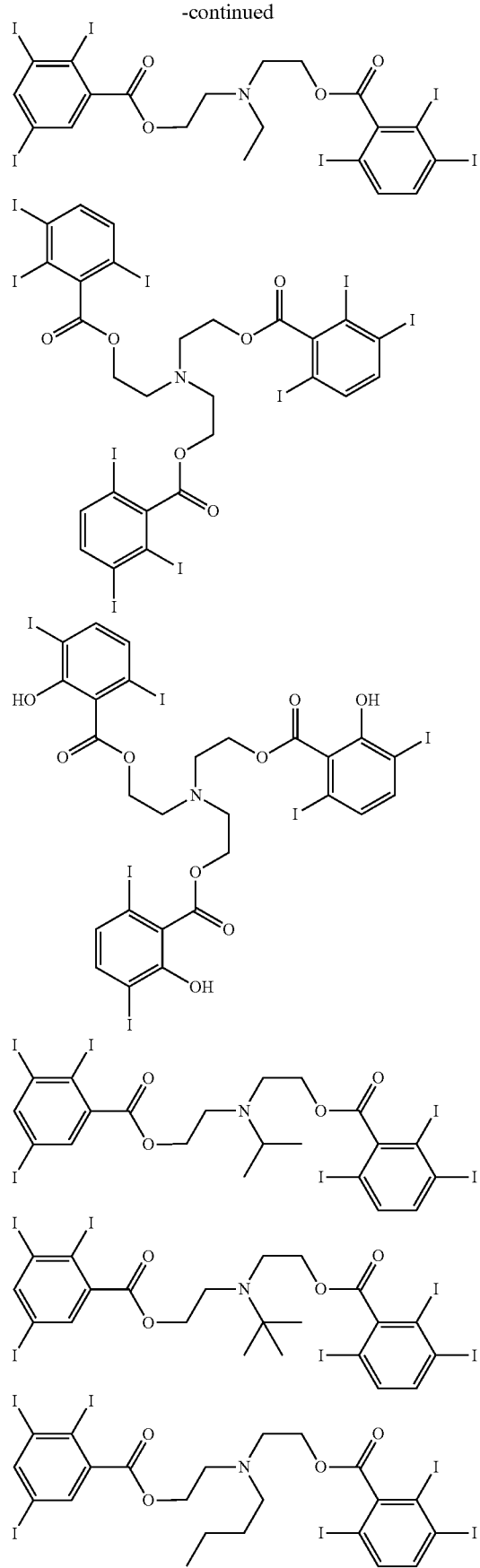
18
-continued
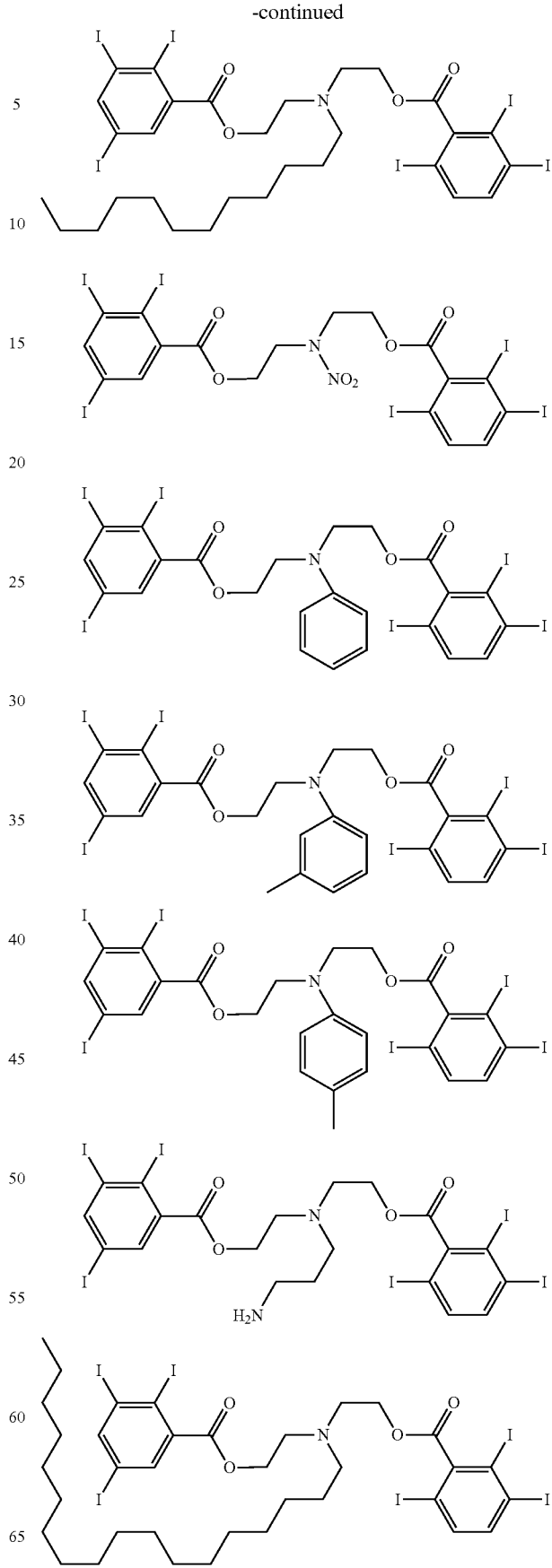

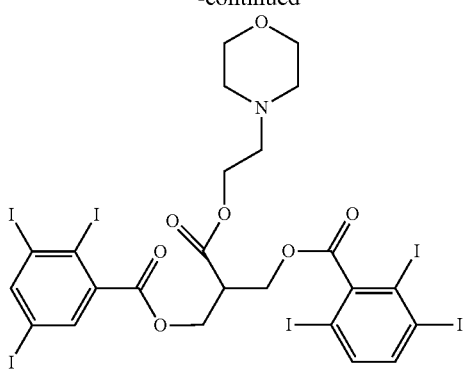
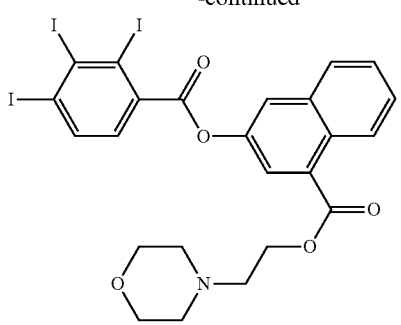

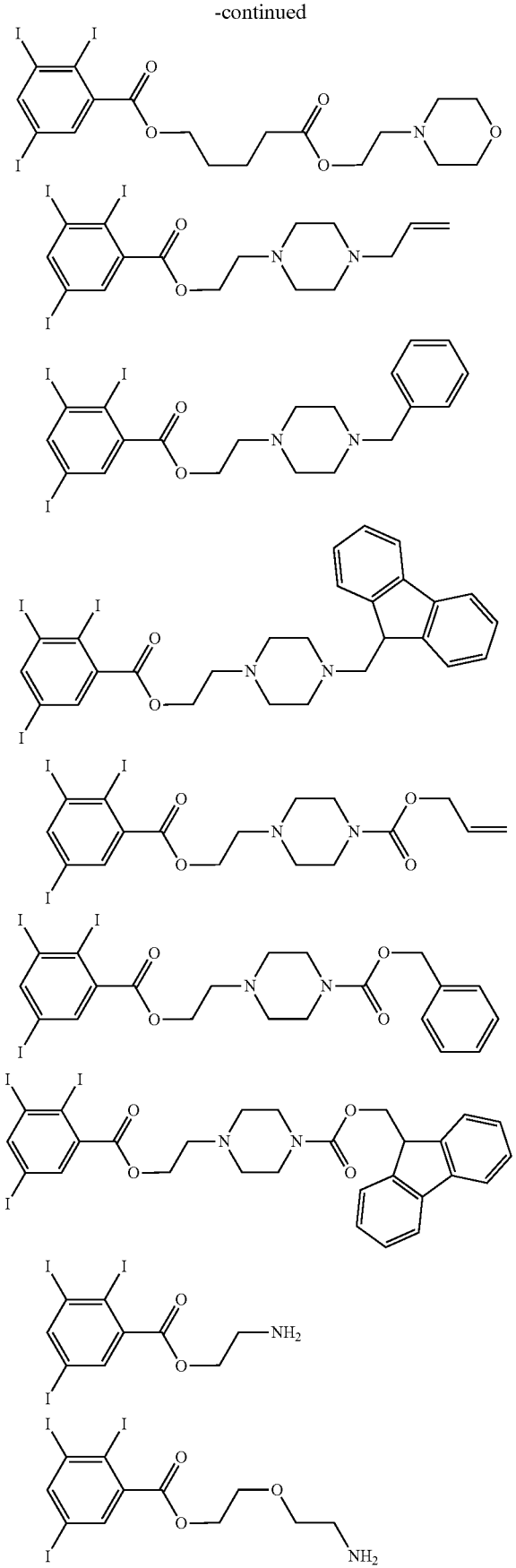
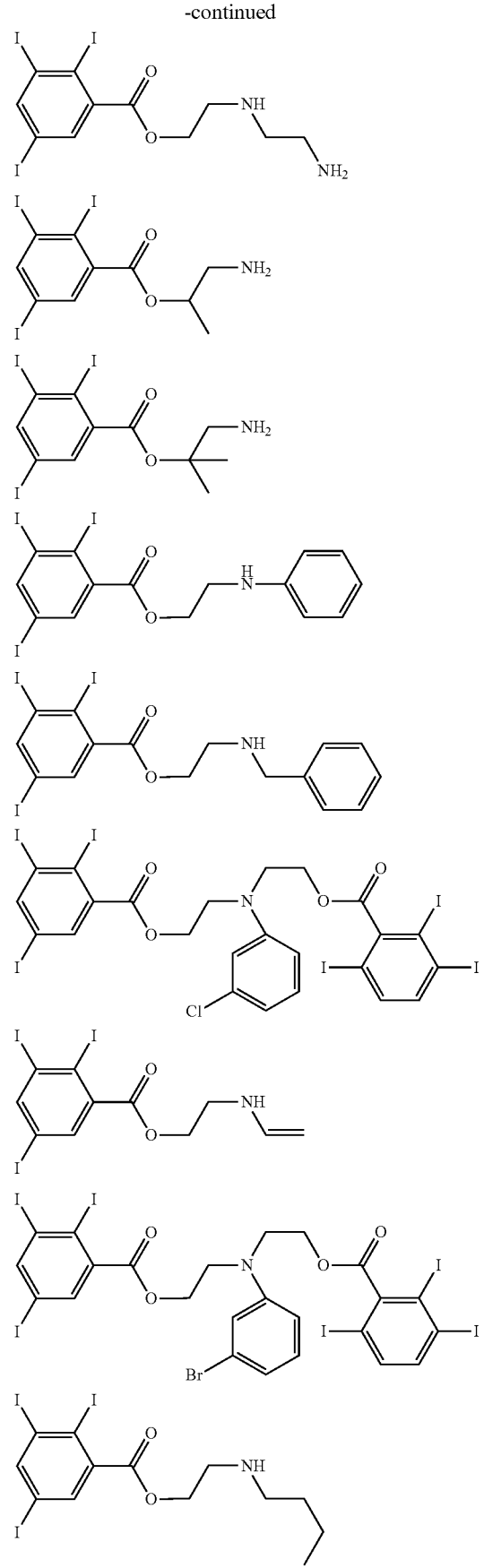

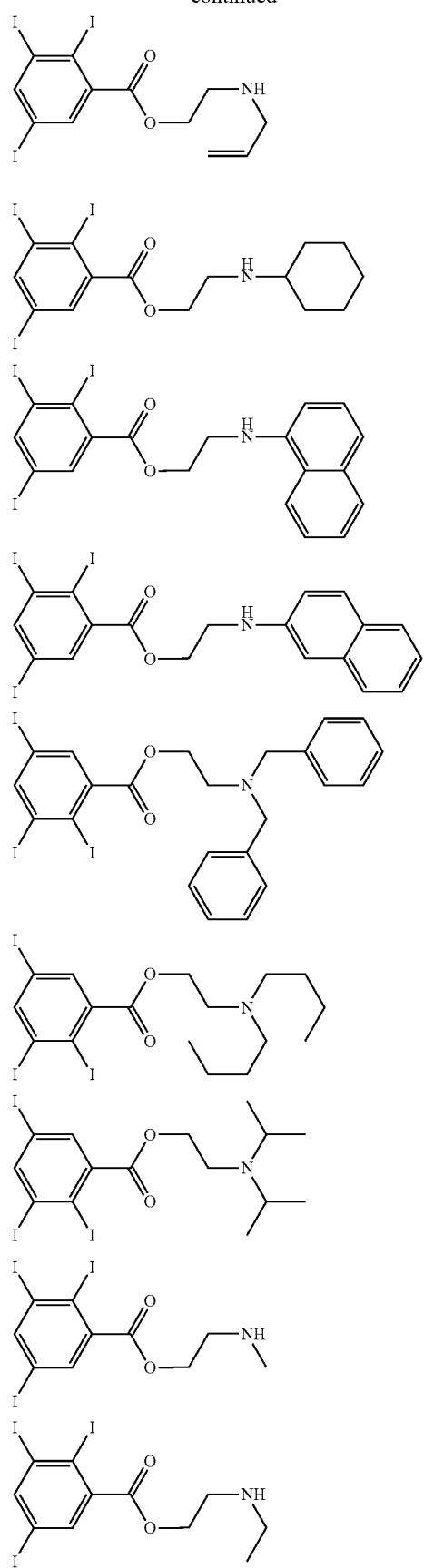
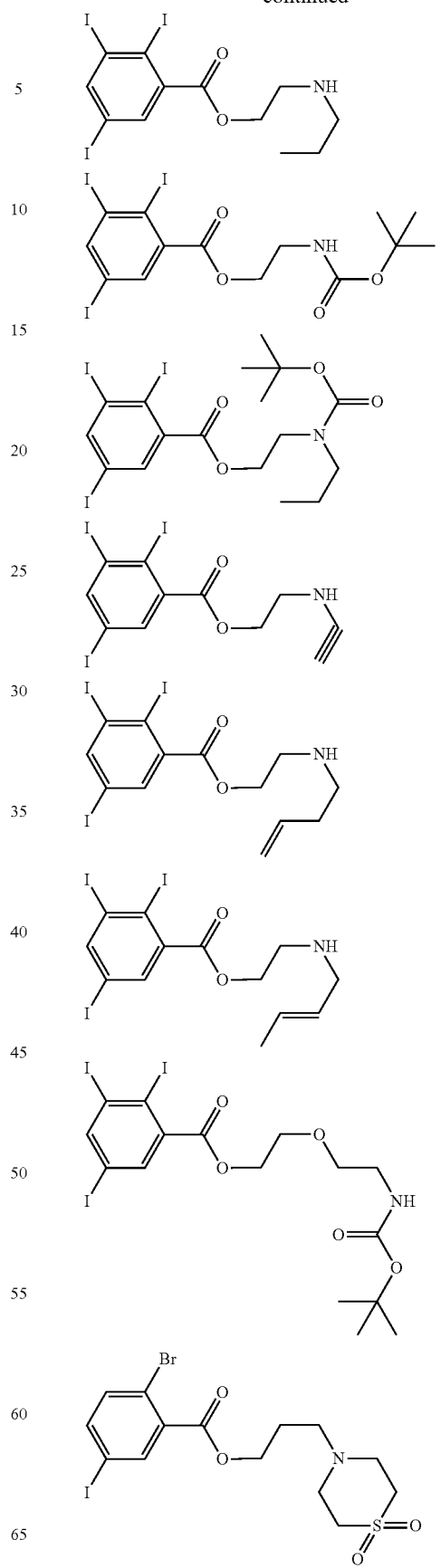

25
-continued
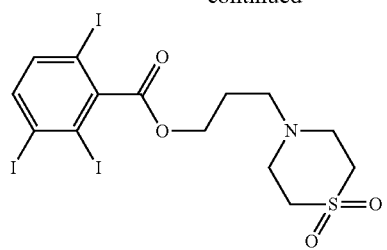
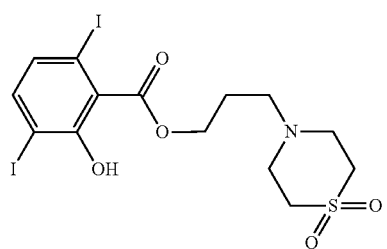
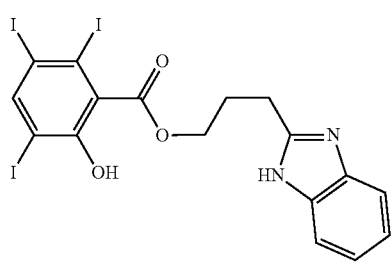
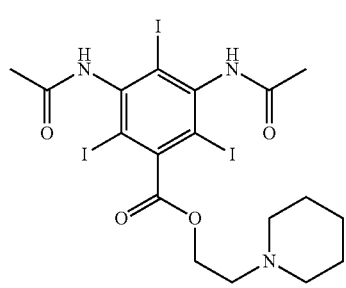
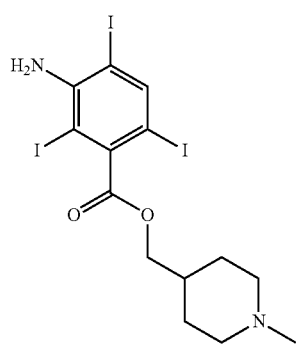
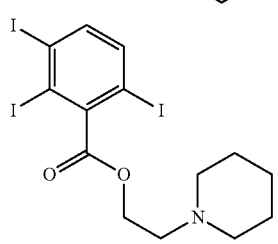
26
-continued
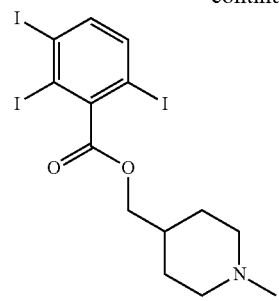
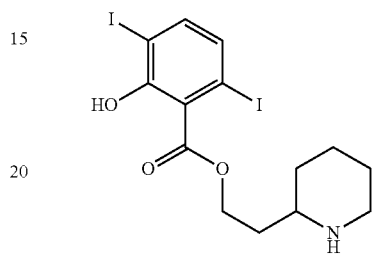
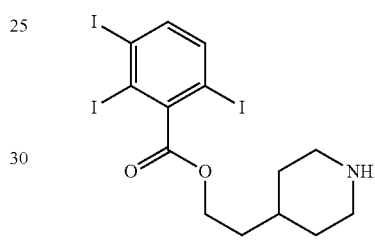
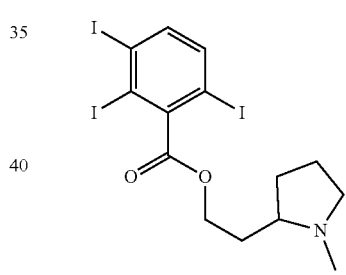
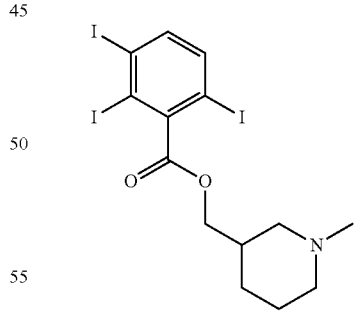
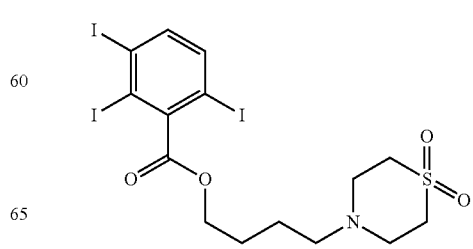

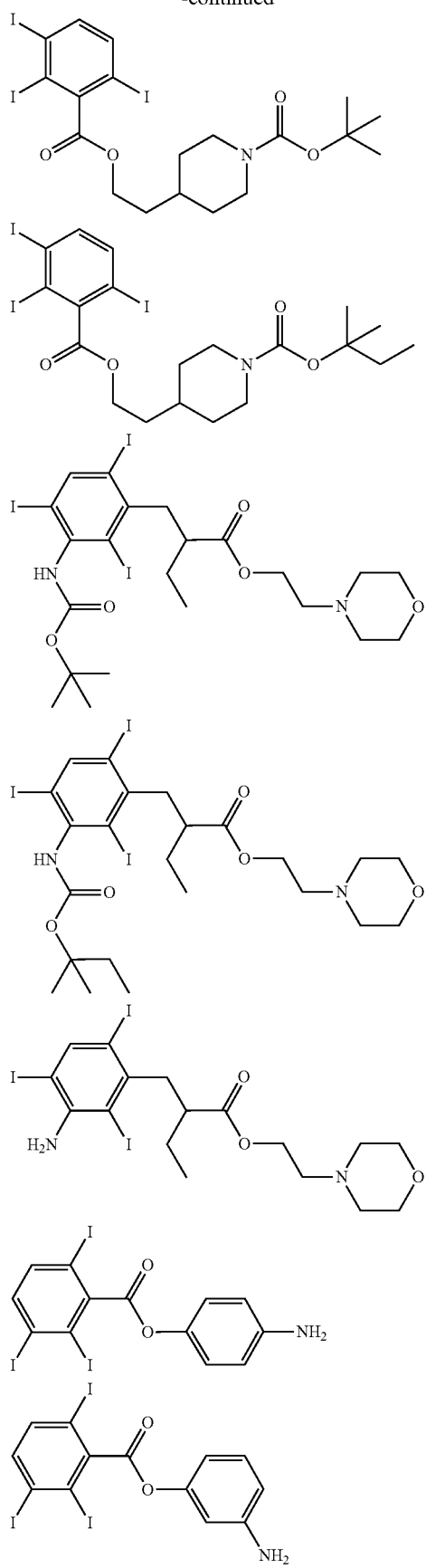
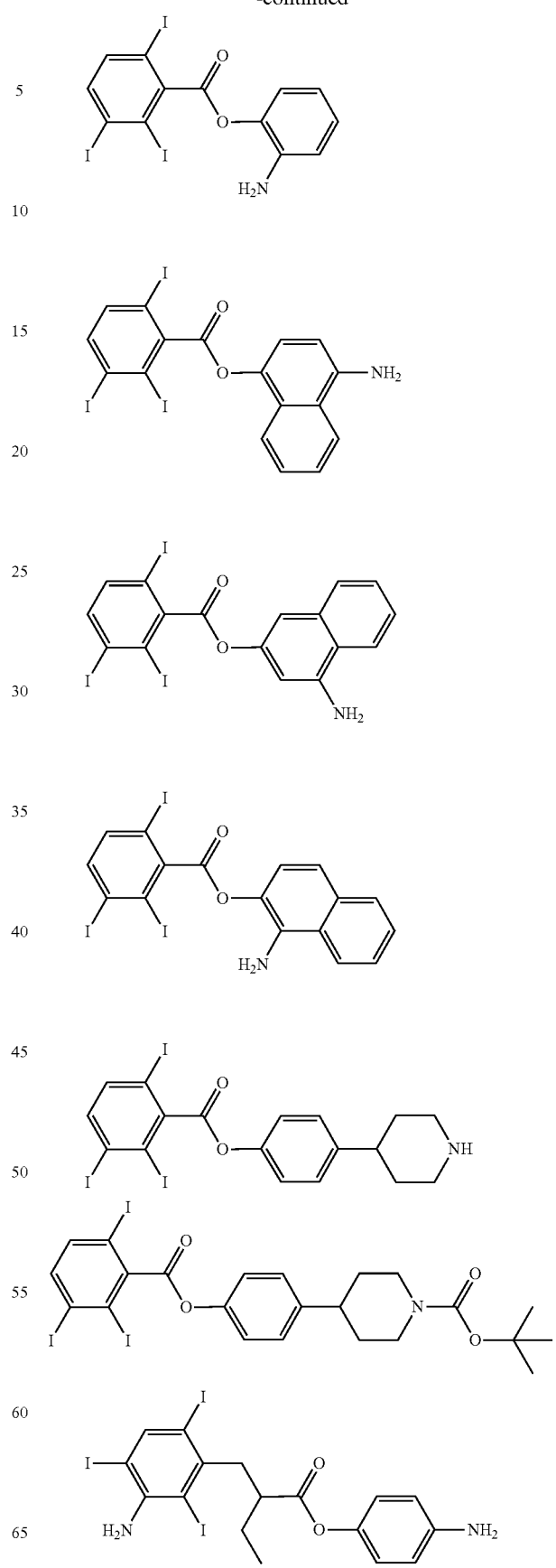

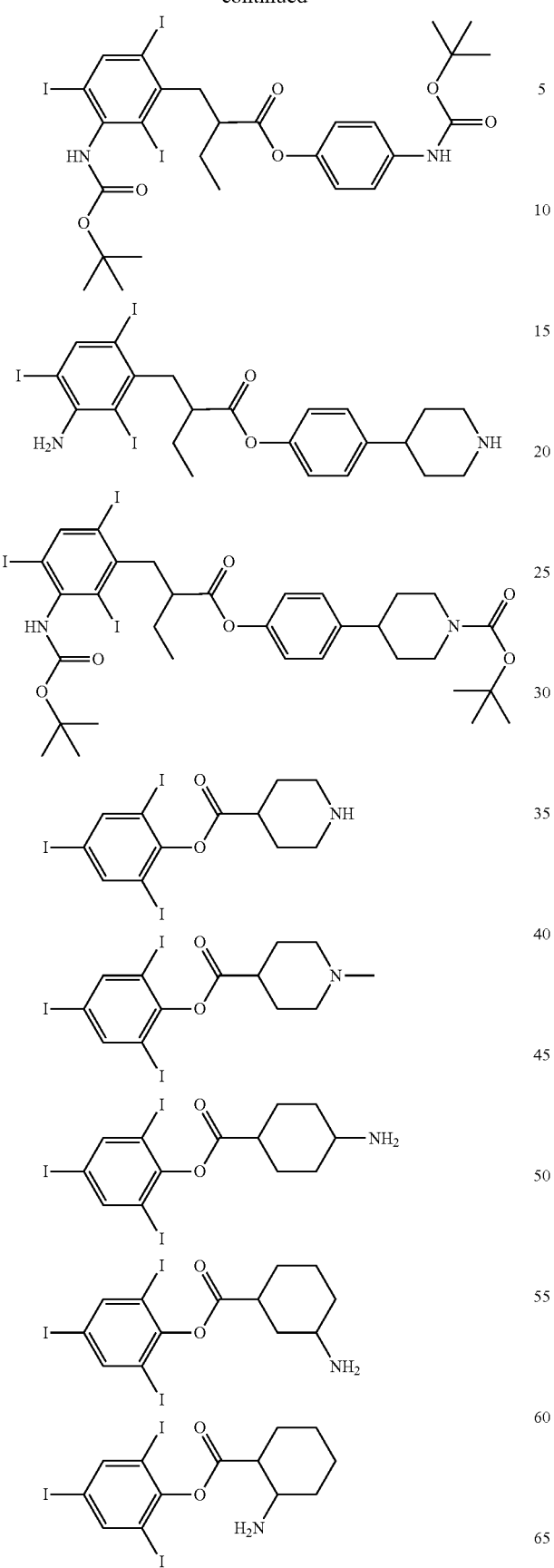
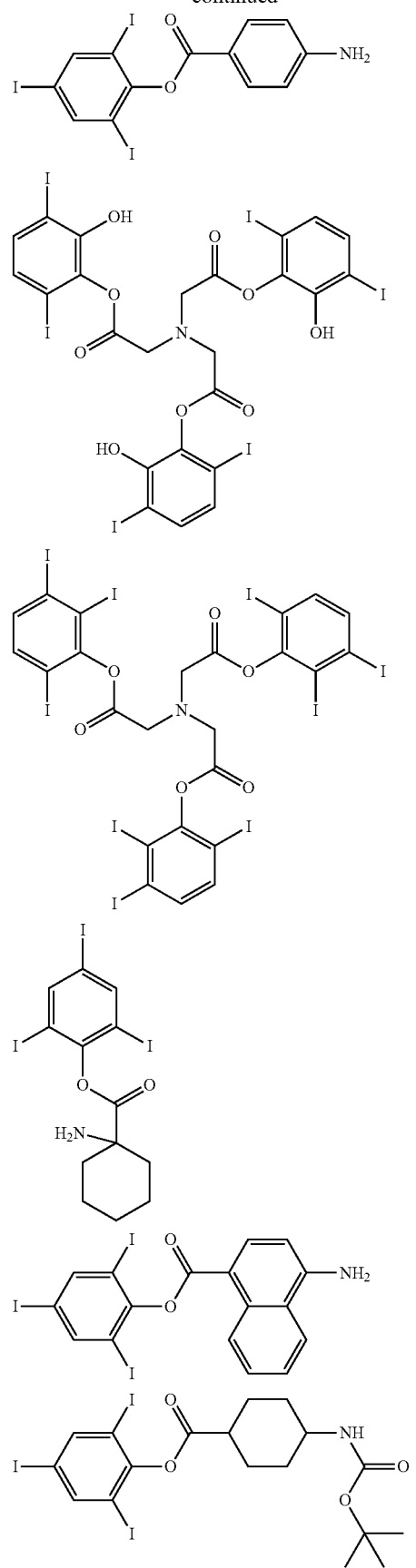

-continued

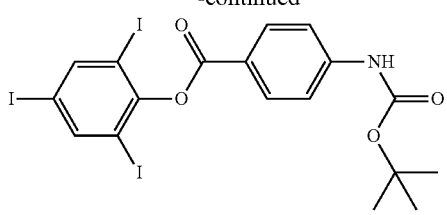
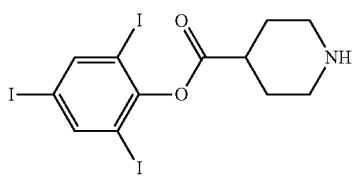
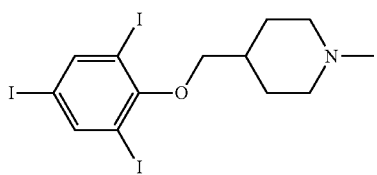
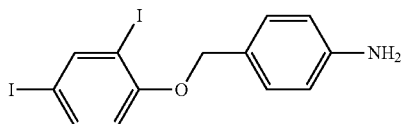
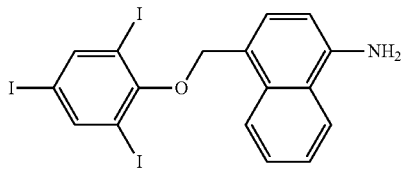
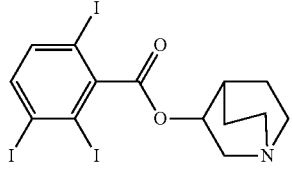
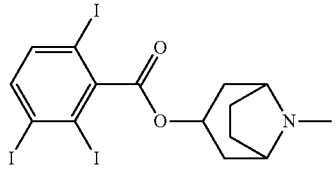
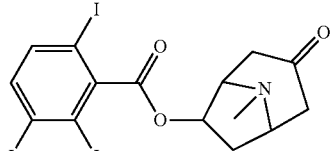
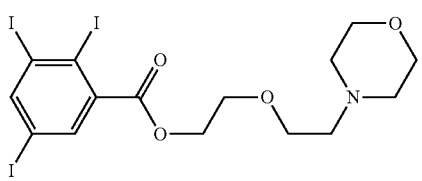

-continued

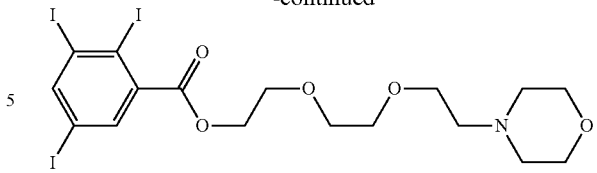

The iodized aromatic ring-containing amine compound may be synthesized, for example, by esterification reaction of a carboxylic acid having an iodized aromatic ring with an amine compound.

The iodized aromatic ring-containing amine compound functions as a quencher having a sensitizing effect in a resist composition. While a conventional quencher functions to control acid diffusion to endow a resist material with a lower sensitivity for thereby reducing LWR or CDU, the iodized aromatic ring-containing amine compound has an acid diffusion controlling effect owing to the amino group and iodine having a large atomic weight, and a sensitizing effect due to the inclusion of a plurality of iodine atoms with substantial EUV absorption, contributing to a high sensitivity.

In the resist composition, the iodized aromatic ring-containing amine compound is preferably present in an amount of 0.001 to 50 parts by weight, more preferably 0.01 to 40 parts by weight per 100 parts by weight of the base polymer.

The iodized aromatic ring-containing amine compound can suppress acid diffusion in the exposed region because it is not photosensitive and is thus not decomposed upon light exposure. Also the iodized aromatic ring-containing amine compound has an effect of suppressing any film thickness loss of resist pattern because it is not a salt and is thus not effective for promoting dissolution in alkaline developer.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

 (a1)

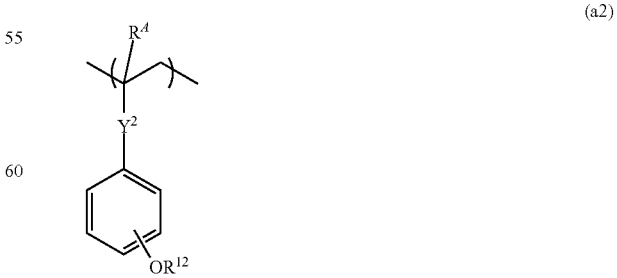 (a2)

Herein $R^A$ is each independently hydrogen or methyl. $R^{11}$ and $R^{12}$ each are an acid labile group. $Y^1$ is a single bond, phenylene or naphthylene group, or $C_1$-$C_{12}$ linking group containing at least one moiety selected from ester bond and lactone ring. $Y^2$ is a single bond or ester bond. When the base polymer contains both recurring units (a1) and (a2), $R^{11}$ and $R^{12}$ may be the same or different.

Examples of the monomer from which the recurring units (a1) are derived are shown below, but not limited thereto. $R^A$ and $R^{11}$ are as defined above.

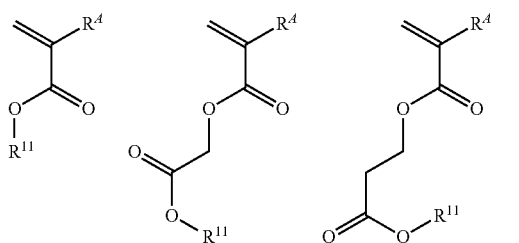

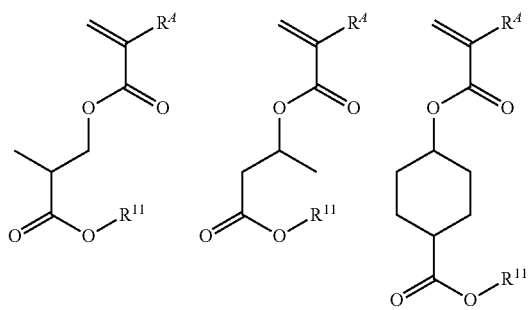

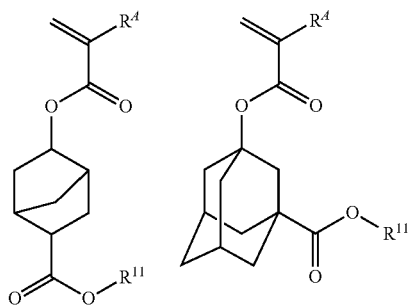

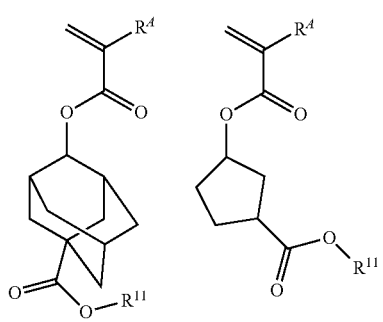

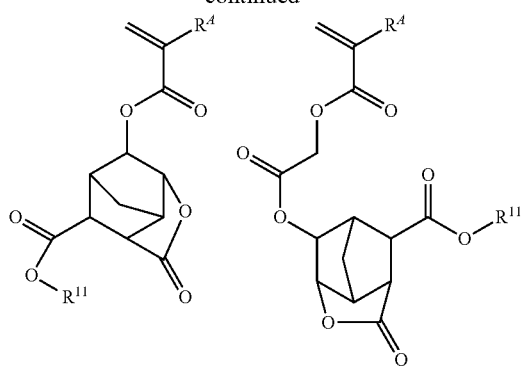

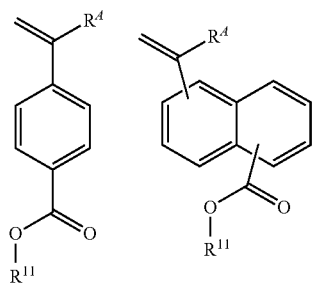

Examples of the monomer from which the recurring units (a2) are derived are shown below, but not limited thereto. $R^A$ and $R^{12}$ are as defined above.

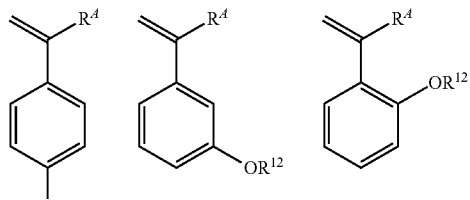

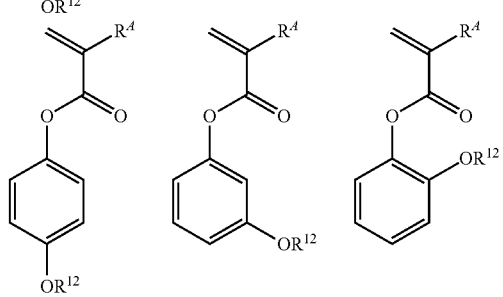

The acid labile groups represented by $R^{11}$ and $R^{12}$ in the recurring units (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

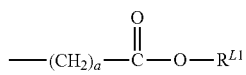

(AL-1)

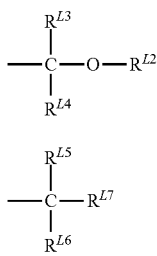
(AL-2)

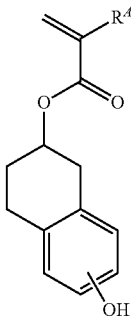
(AL-3)

In formulae (AL-1) and (AL-2), $R^{L1}$ and $R^{L2}$ are each independently a $C_1$-$C_{40}$ monovalent hydrocarbon group which may contain a heteroatom such as oxygen, sulfur, nitrogen or fluorine. The monovalent hydrocarbon groups may be straight, branched or cyclic while $C_1$-$C_{40}$ alkyl groups are preferred, and $C_1$-$C_{20}$ alkyl groups are more preferred. In formula (AL-1), "a" is an integer of 0 to 10, preferably 1 to 5.

In formula (AL-2), $R^{L3}$ and $R^{L4}$ are each independently hydrogen or a $C_1$-$C_{20}$ monovalent hydrocarbon group which may contain a heteroatom such as oxygen, sulfur, nitrogen or fluorine. The monovalent hydrocarbon groups may be straight, branched or cyclic while $C_1$-$C_{20}$ alkyl groups are preferred. Any two of $R^{L2}$, $R^{L3}$ and $R^{L4}$ may bond together to form a ring, typically alicyclic, with the carbon atom or carbon and oxygen atoms to which they are attached, the ring containing 3 to 20 carbon atoms, preferably 4 to 16 carbon atoms.

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon groups may be straight, branched or cyclic while $C_1$-$C_{20}$ alkyl groups are preferred. Any two of $R^{L5}$, $R^{L6}$ and $R^{L7}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

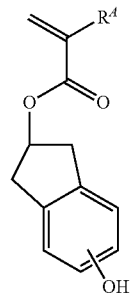

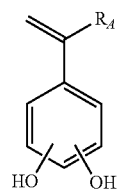

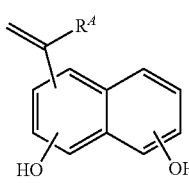

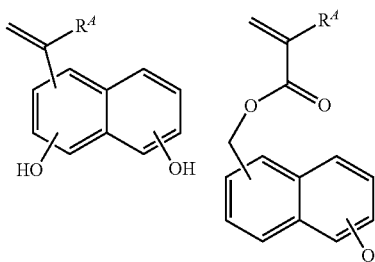

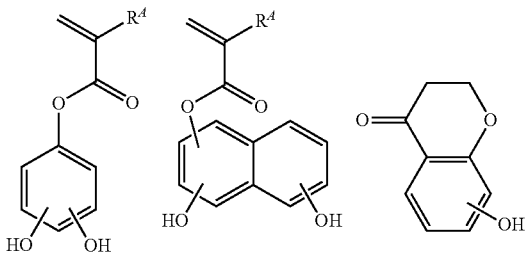

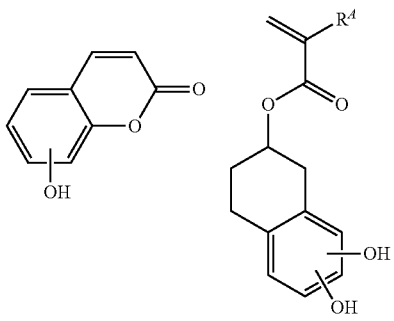

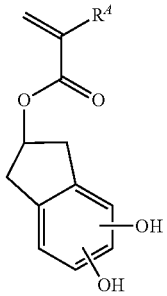

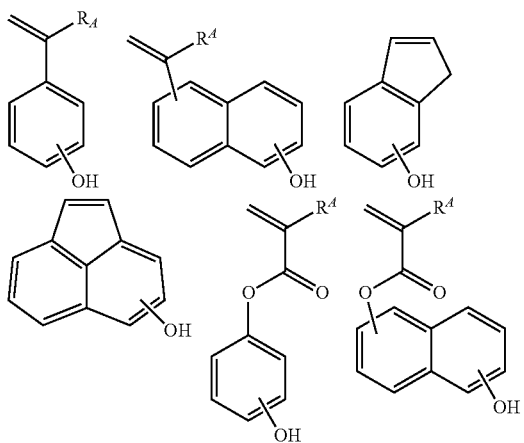

Further, recurring units (c) having another adhesive group selected from hydroxyl (other than the foregoing phenolic hydroxyl), lactone ring, ether bond, ester bond, carbonyl, cyano, and carboxyl groups may also be incorporated in the base polymer. Examples of suitable monomers from which recurring units (c) are derived are given below, but not to limited thereto. Herein $R^A$ is as defined above.

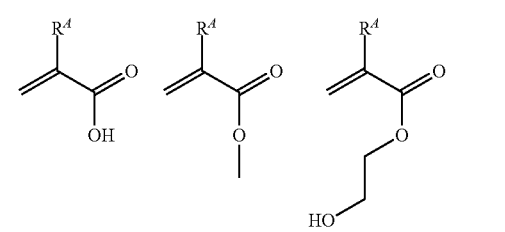
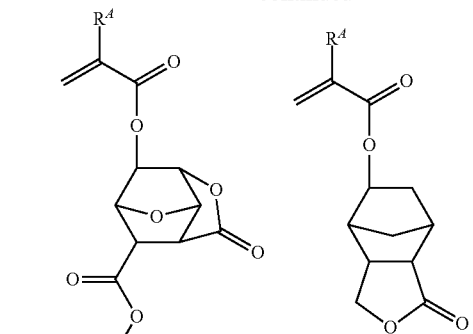
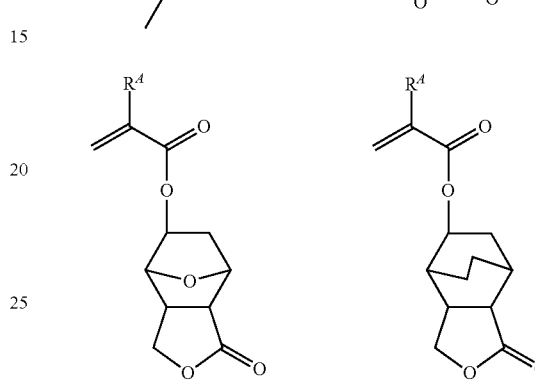
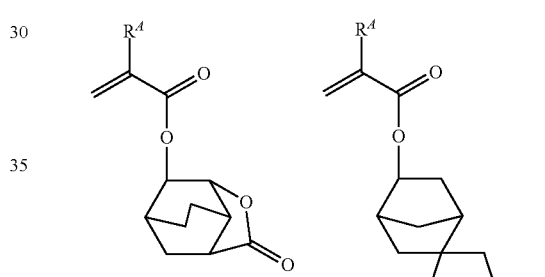
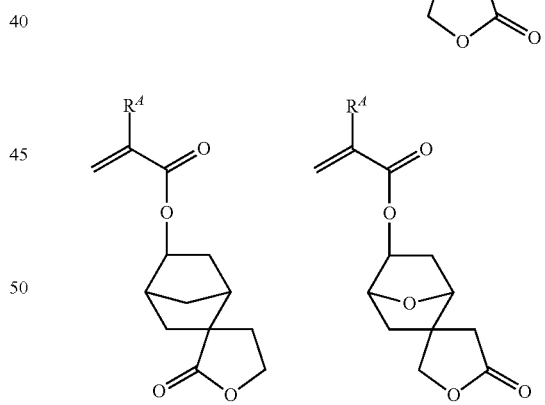
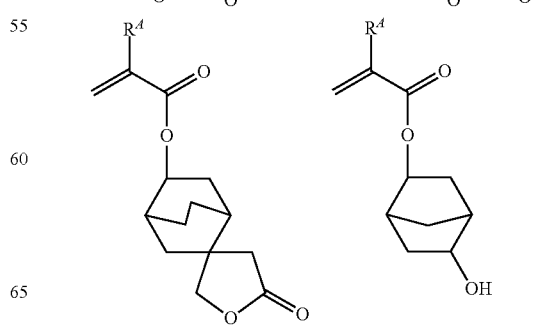

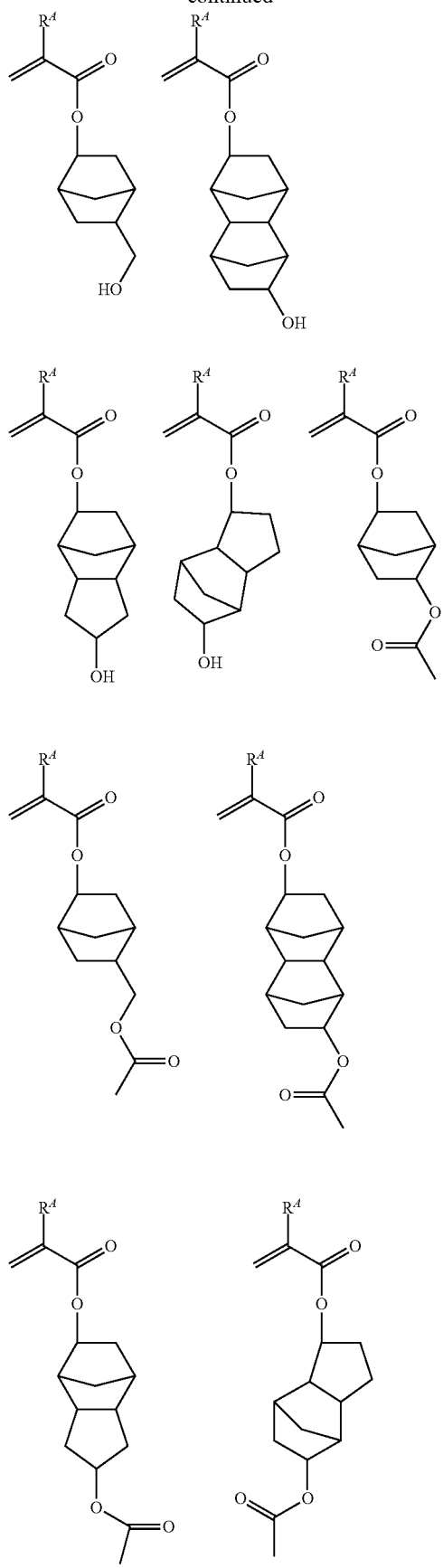
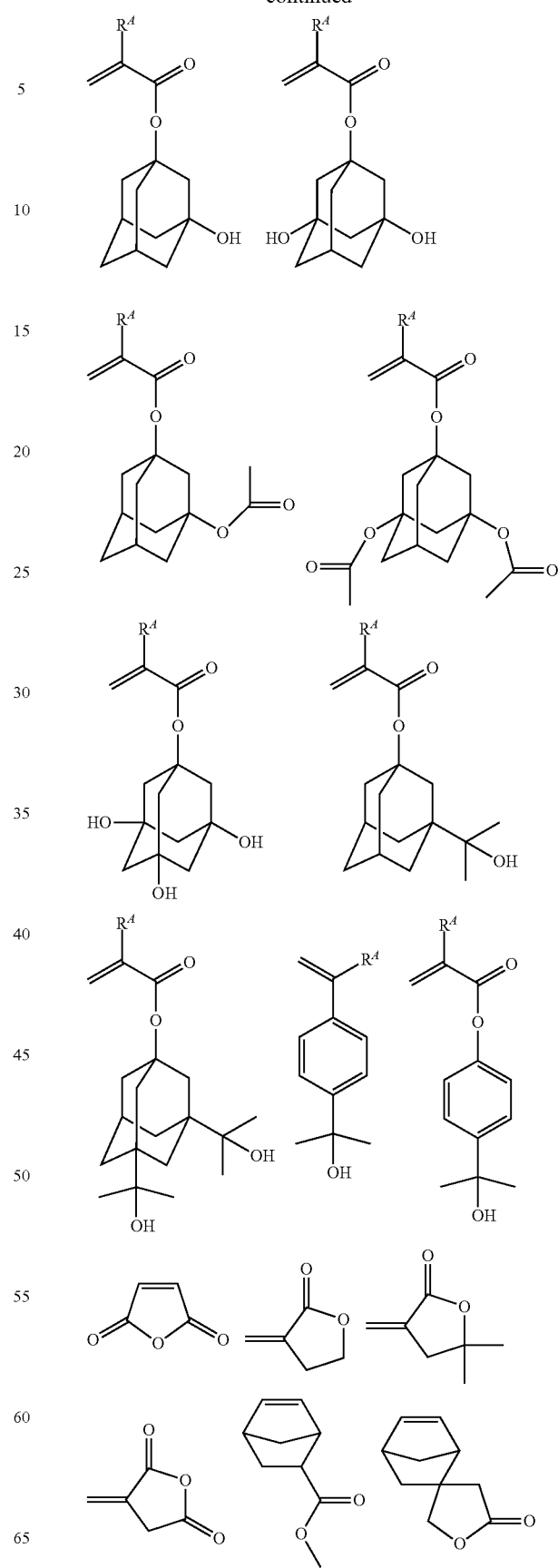

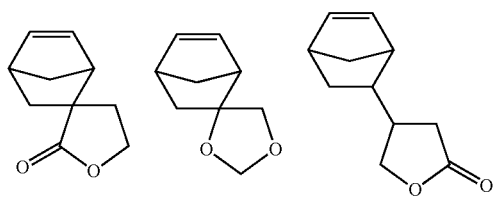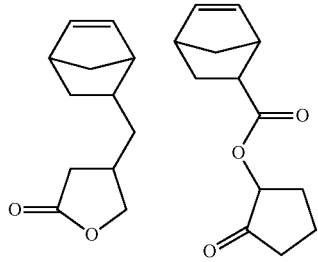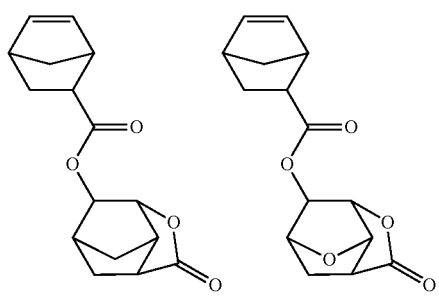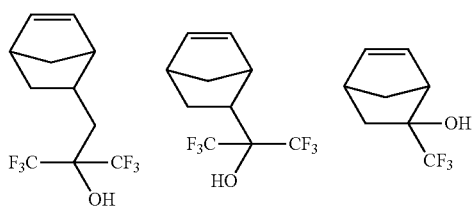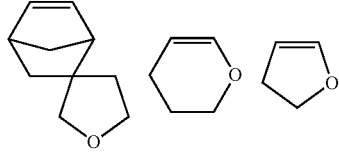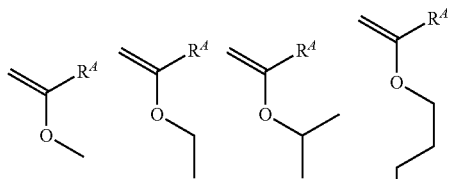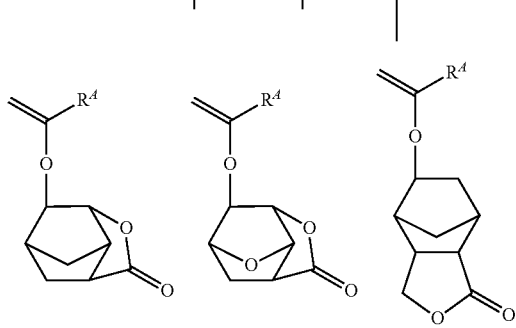
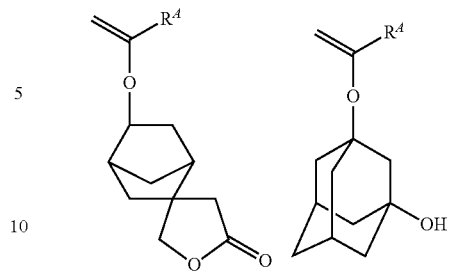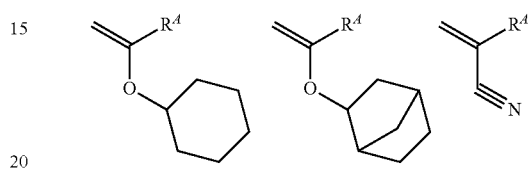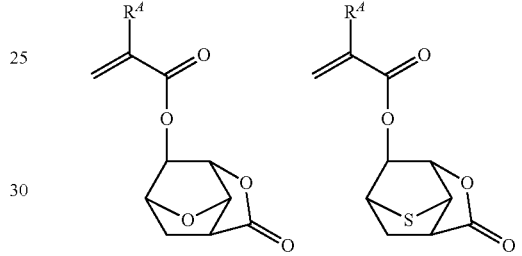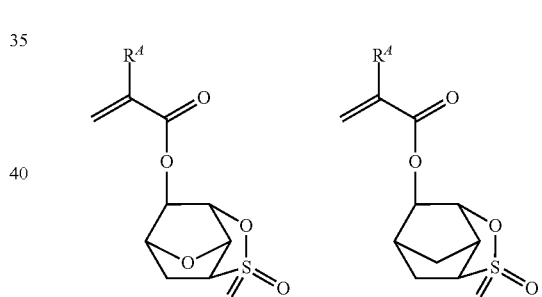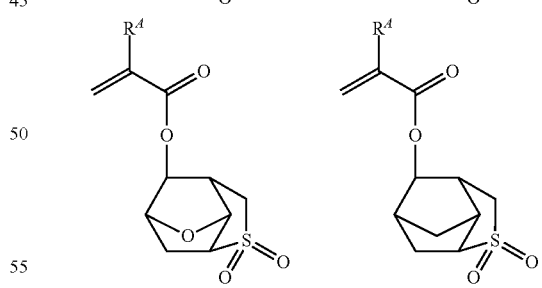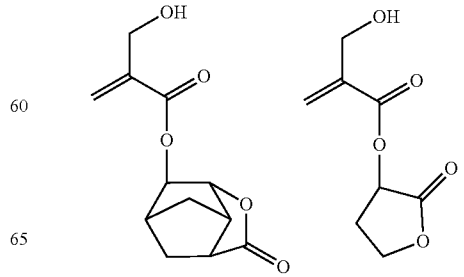

-continued
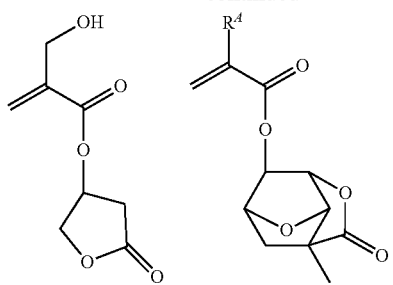
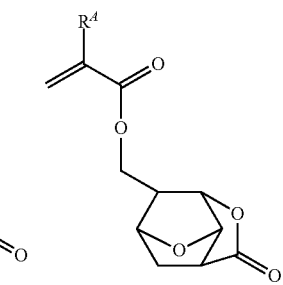
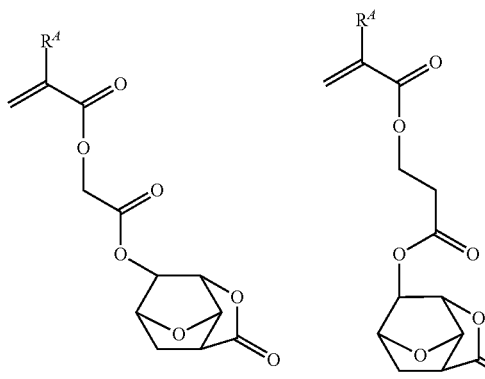
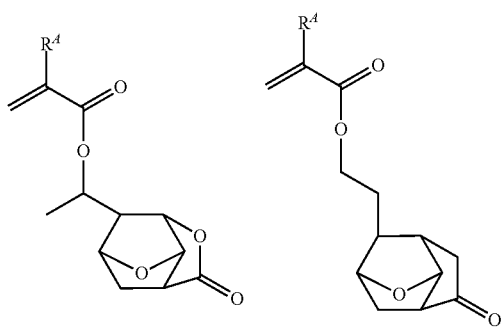
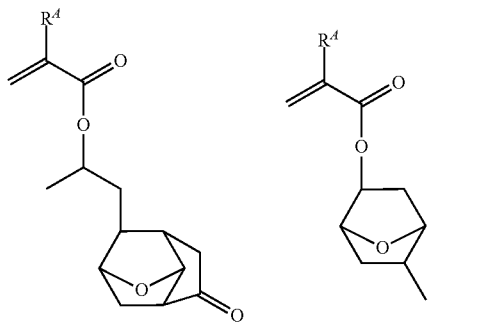
-continued
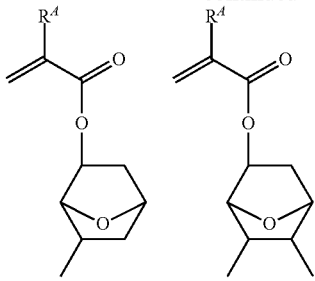
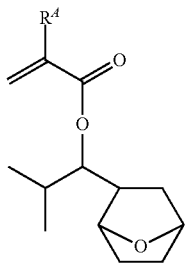
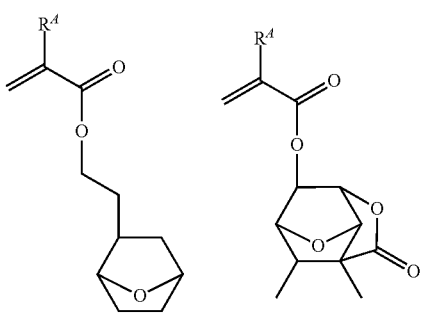
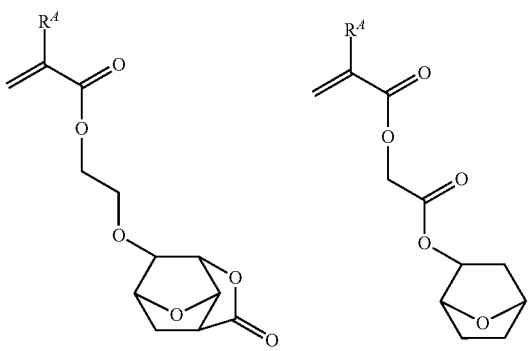
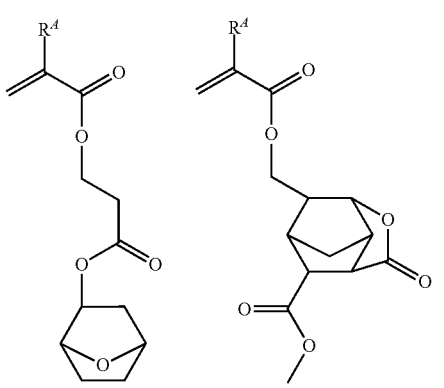

-continued
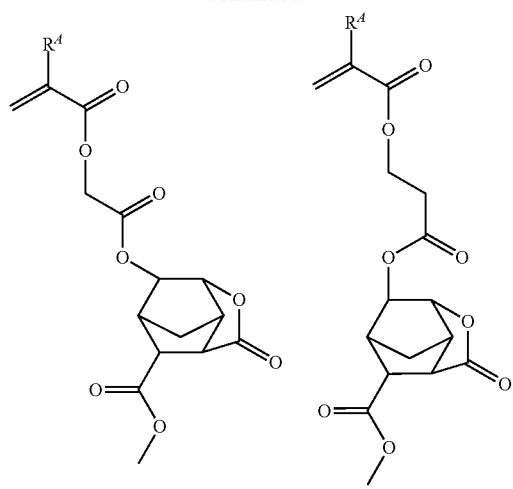
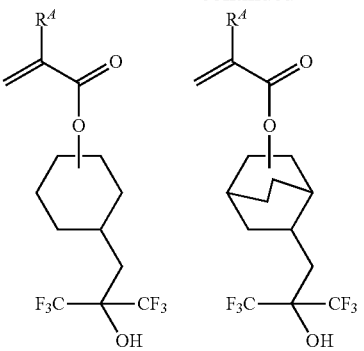
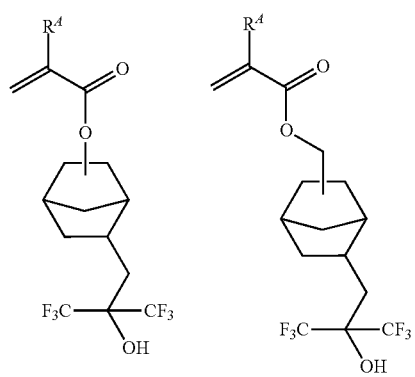
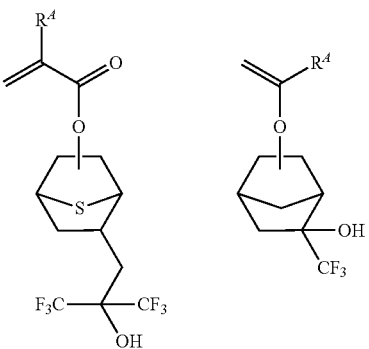
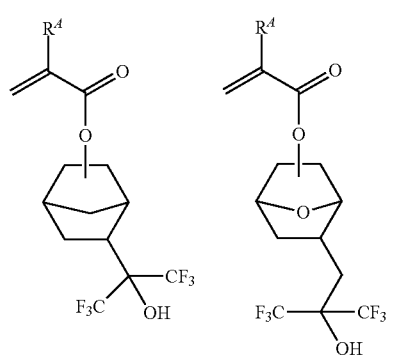
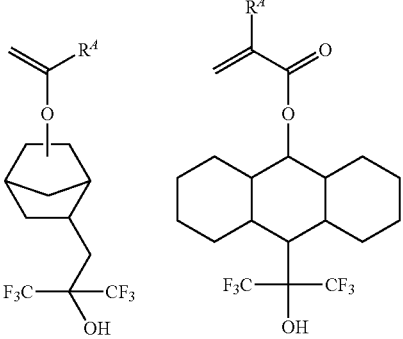
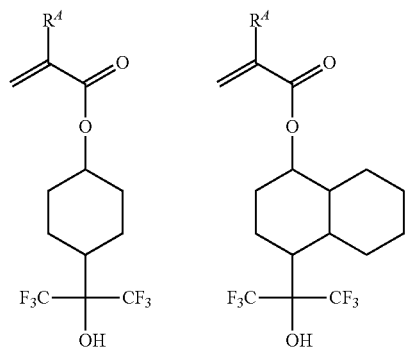
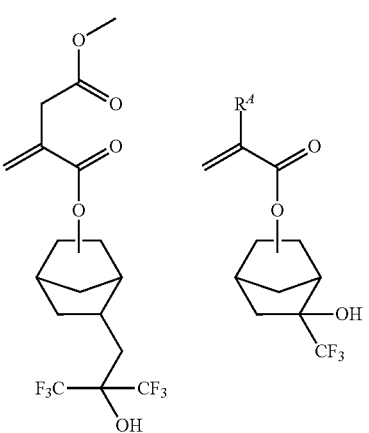

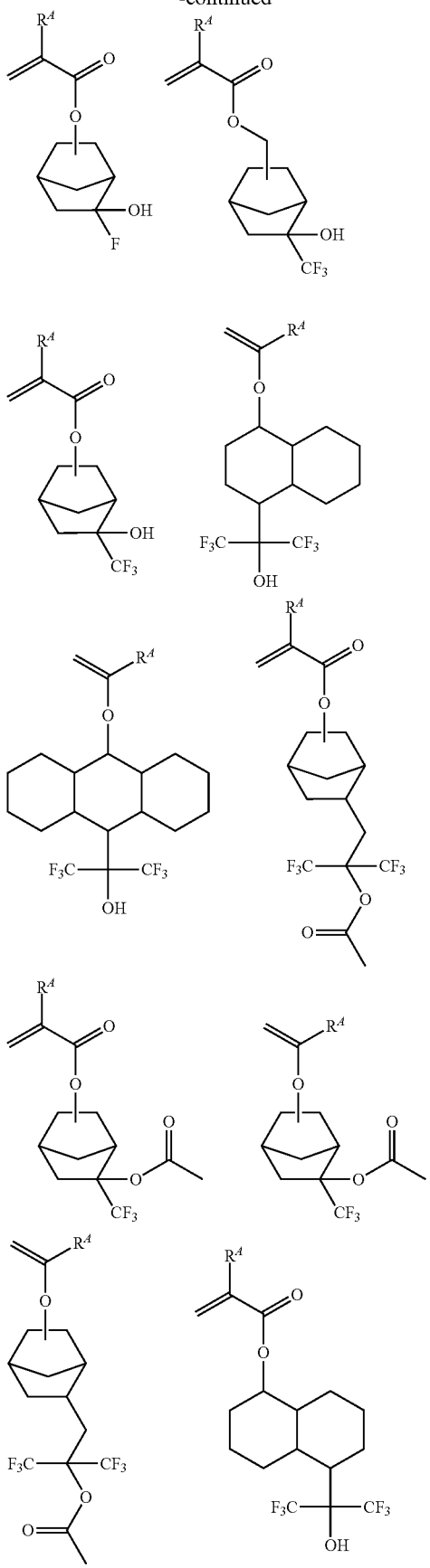
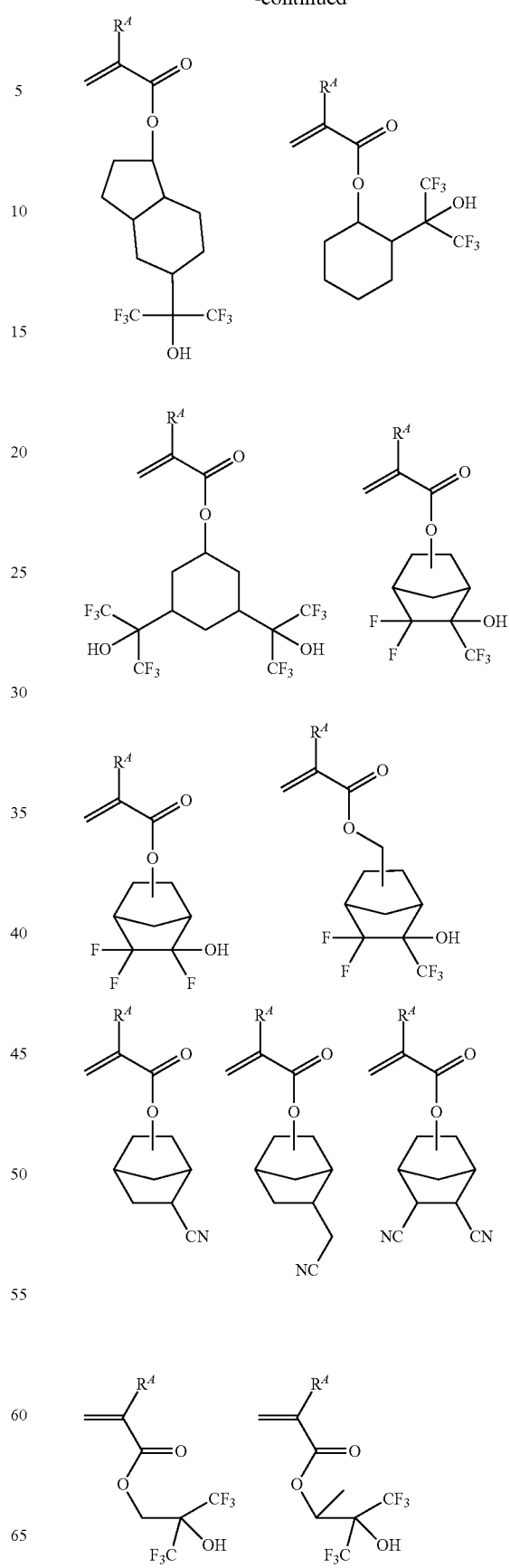

-continued
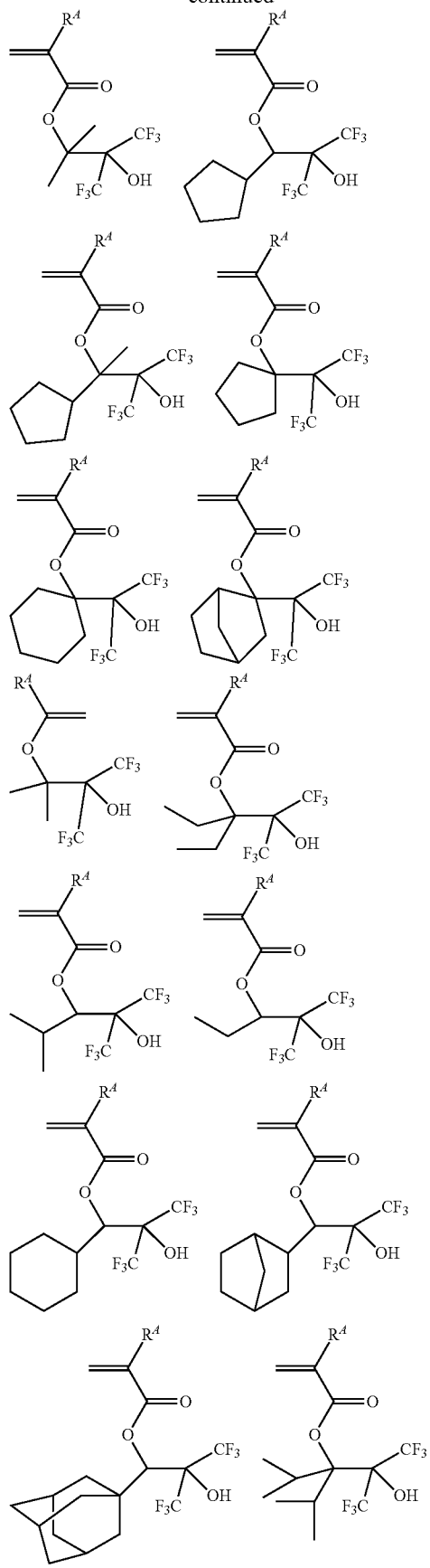
-continued
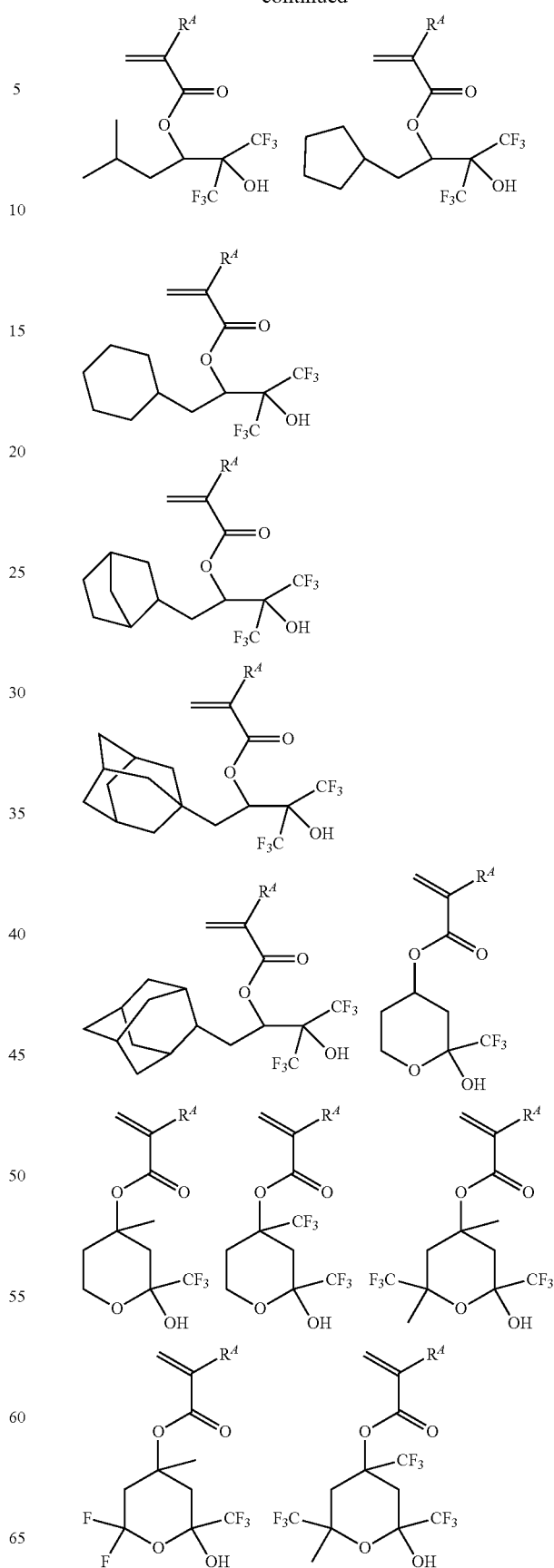

-continued
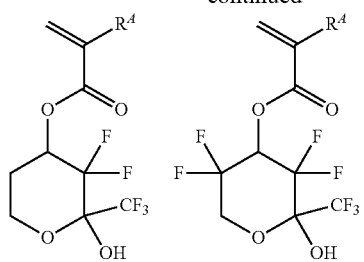
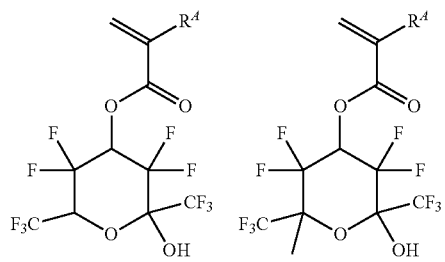
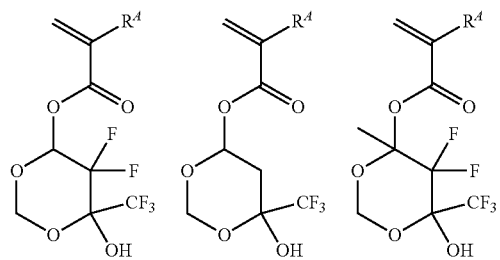
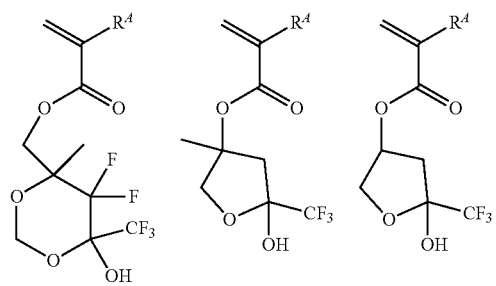
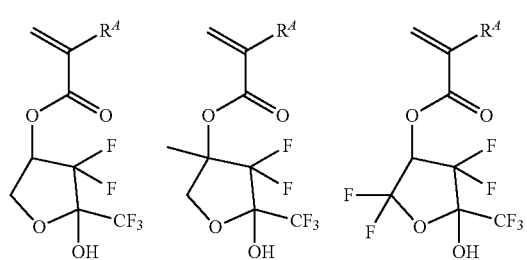
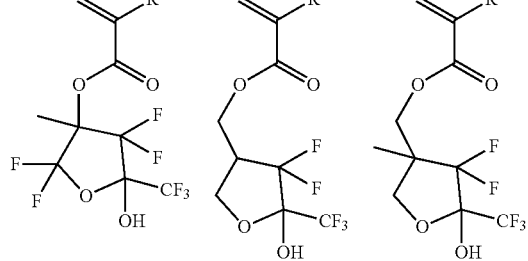
-continued
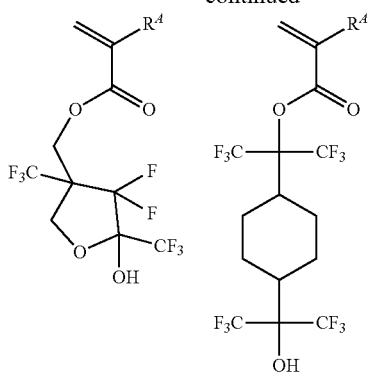
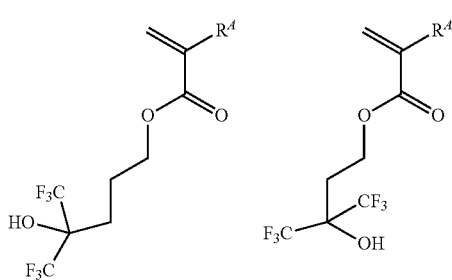
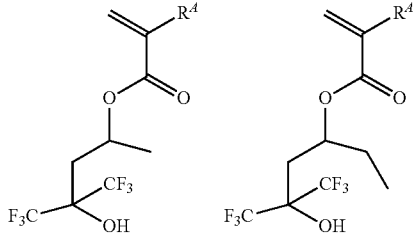
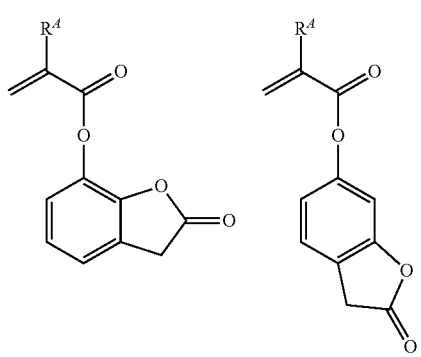

53
-continued
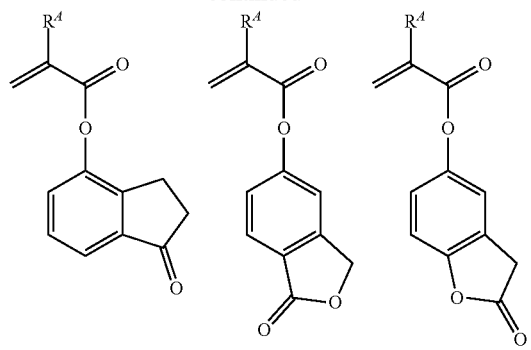
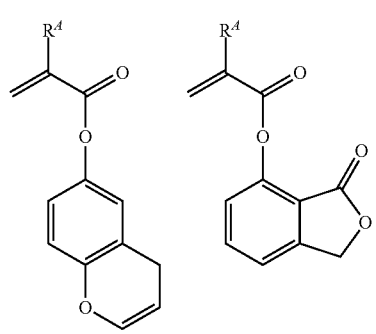
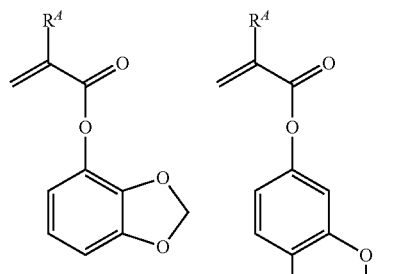
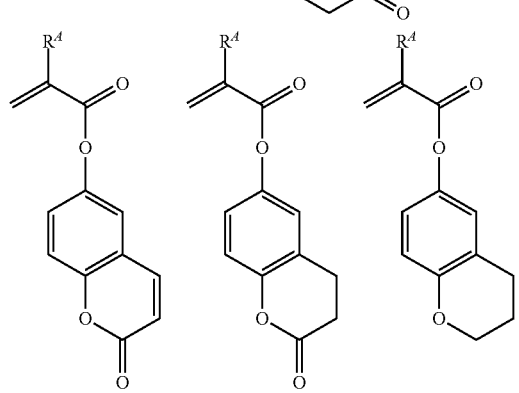
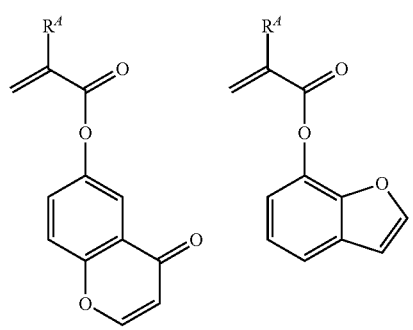
54
-continued
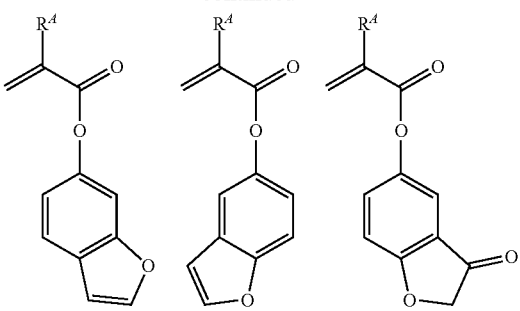
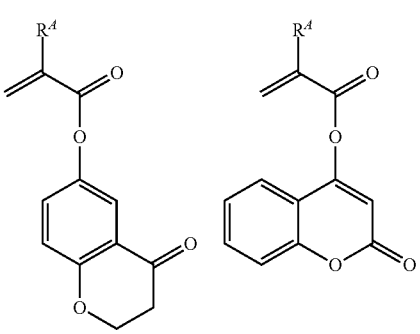
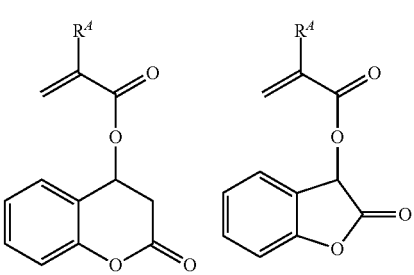
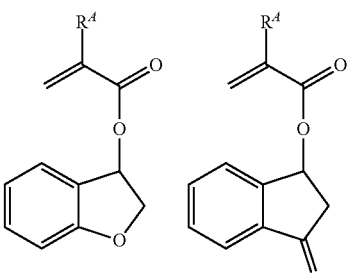
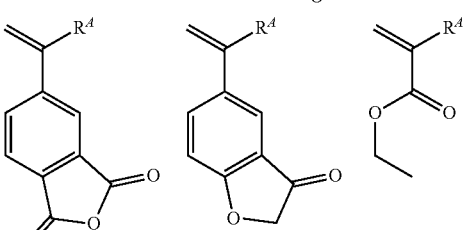
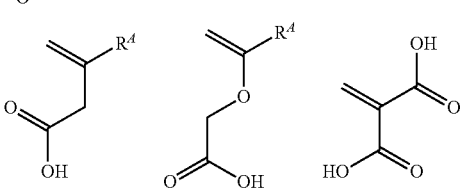

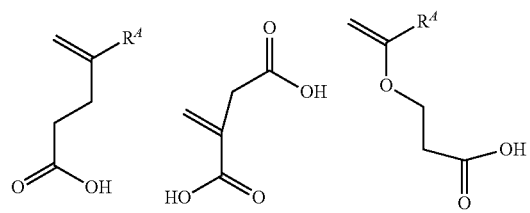
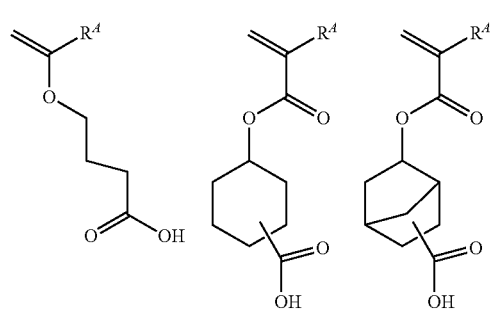
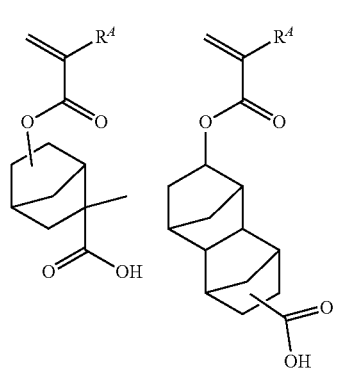
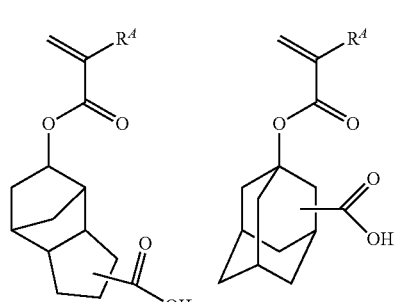
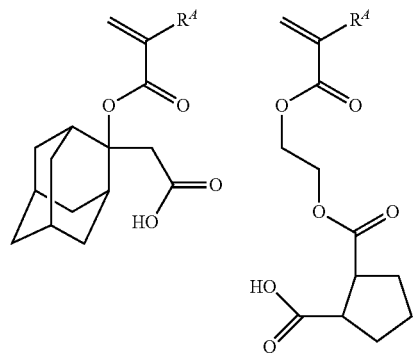
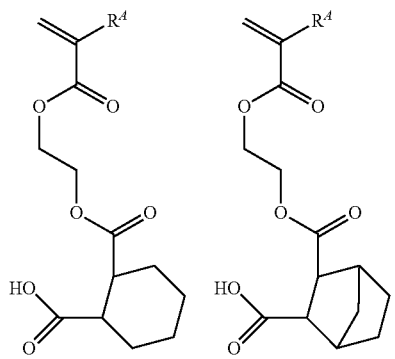
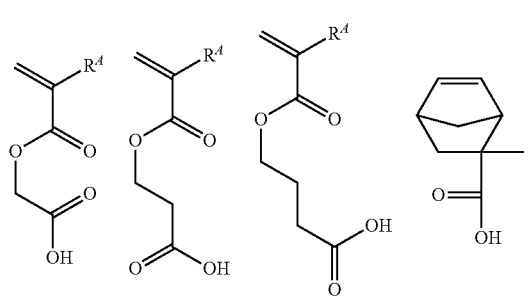
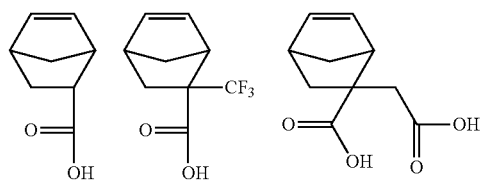
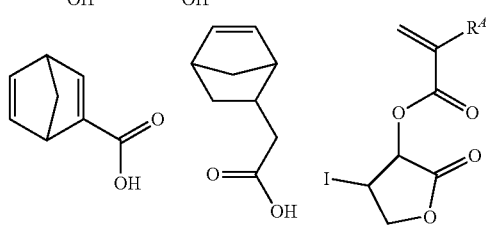
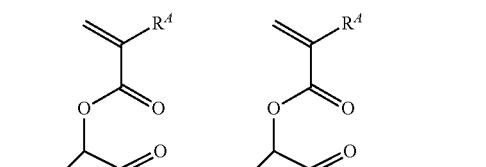
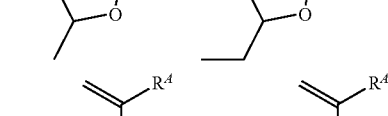
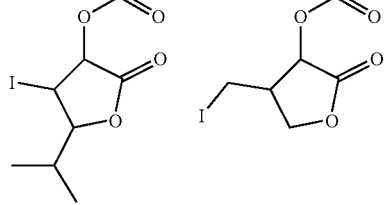

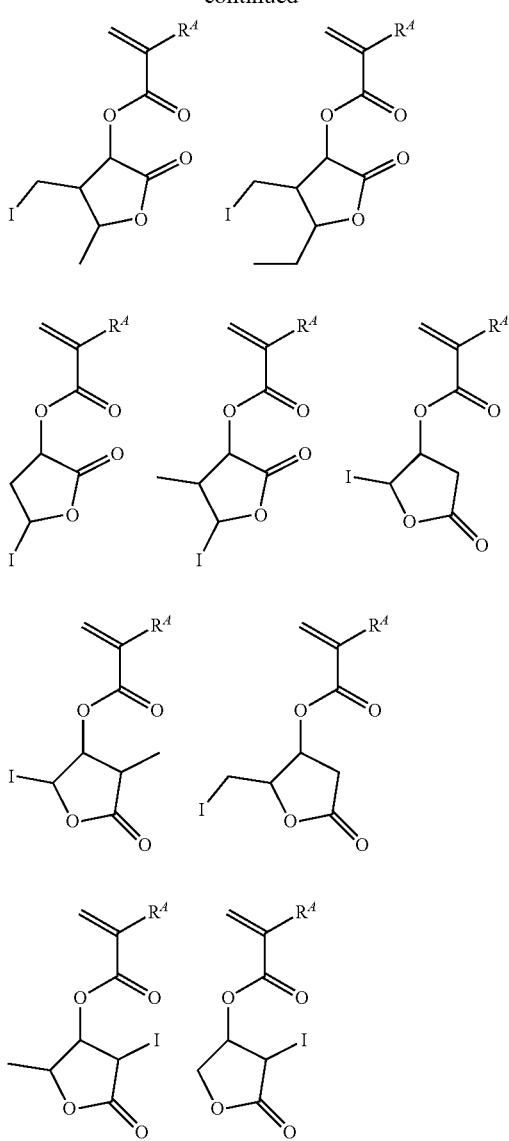

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

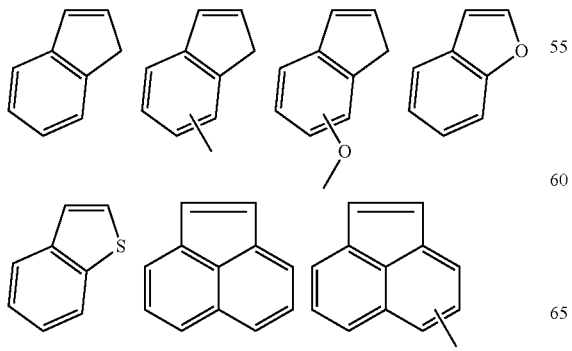

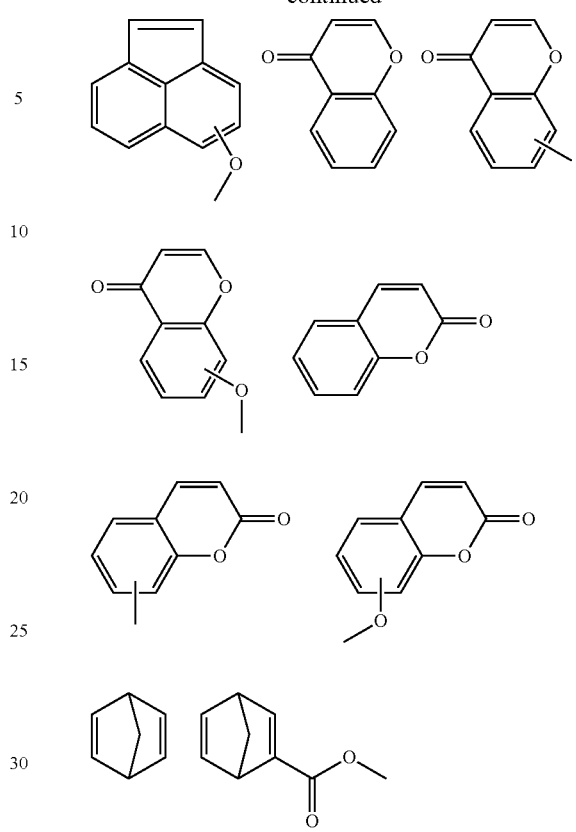

Furthermore, recurring units (e) may be incorporated in the base polymer, which are derived from styrene, vinylnaphthalene, vinylanthracene, vinylpyrene, methyleneindene, vinylpyridine, and vinylcarbazole.

In a further embodiment, recurring units (f) derived from an onium salt having a polymerizable unsaturated bond may be incorporated in the base polymer. Specifically, the base polymer may comprise recurring units of at least one type selected from formulae (f1), (f2) and (f3). These units are simply referred to as recurring units (f1), (f2) and (f3), which may be used alone or in combination of two or more types.

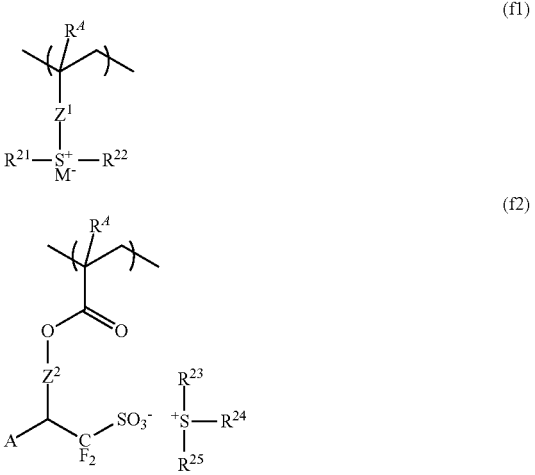

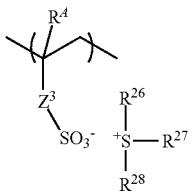

(f3)

In formulae (f1) to (f3), $R^A$ is independently hydrogen or methyl. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl group, $C_2$-$C_6$ alkenediyl group, or phenylene group, which may contain a carbonyl, ester bond, ether bond or hydroxyl moiety. $Z^2$ is a single bond, —$Z^{21}$—C(=O)—O—, or —$Z^{21}$—O—C(=O)—, wherein $Z^{21}$ is a $C_1$-$C_{12}$ alkanediyl group which may contain a carbonyl moiety, ester bond or ether bond. "A" is hydrogen or trifluoromethyl. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, wherein $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain a carbonyl moiety, ester bond, ether bond or hydroxyl moiety. The alkanediyl and alkenediyl groups may be straight, branched or cyclic.

In formulae (f1) to (f3), $R^{21}$ to $R^{28}$ are each independently a $C_1$-$C_{20}$ monovalent hydrocarbon group which may contain a heteroatom. The monovalent hydrocarbon groups may be straight, branched or cyclic, and examples thereof include $C_1$-$C_{12}$ alkyl groups, $C_6$-$C_{12}$ aryl groups, and $C_7$-$C_{20}$ aralkyl groups. In these groups, some or all of the hydrogen atoms may be substituted by $C_1$-$C_{10}$ alkyl groups, halogen, trifluoromethyl, cyano, nitro, hydroxyl, mercapto, $C_1$-$C_{10}$ alkoxy groups, $C_2$-$C_{10}$ alkoxycarbonyl groups, or $C_2$-$C_{10}$ acyloxy groups, and some carbon atom may be replaced by a carbonyl moiety, ether bond or ester bond. Any two of $R^{23}$, $R^{24}$ and $R^{25}$ or any two of $R^{26}$, $R^{27}$ and $R^{28}$ may bond together to form a ring with the sulfur atom to which they are attached.

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α- and β-positions as represented by the formula (K-2).

 (K-1)

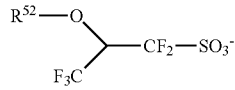 (K-2)

In formula (K-1), $R^{51}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2), $R^{52}$ is hydrogen, or a $C_1$-$C_{30}$ alkyl group, $C_2$-$C_{20}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl, acyl and alkenyl groups may be straight, branched or cyclic.

Examples of the monomer from which recurring unit (f1) is derived are shown below, but not limited thereto. $R^A$ and $M^-$ are as defined above.

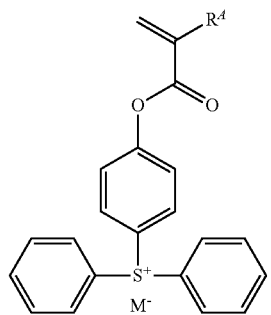

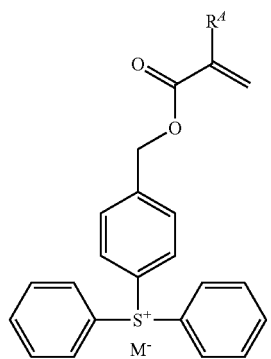

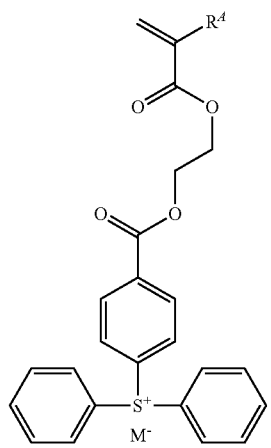

61
-continued
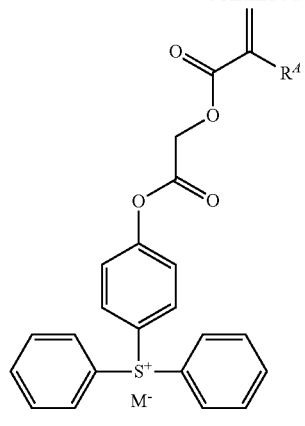
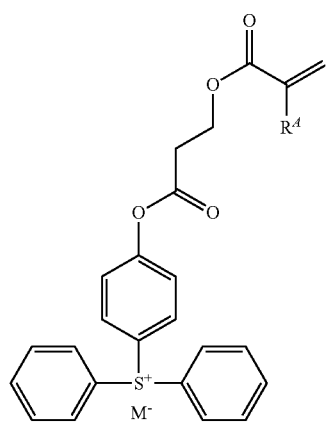
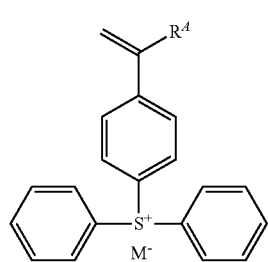
62
-continued
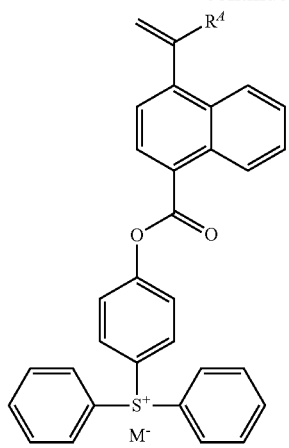
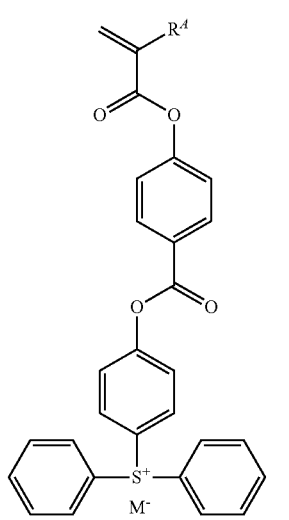
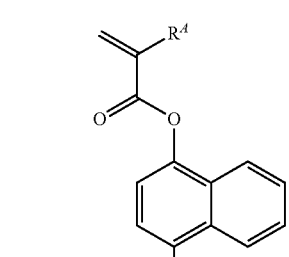
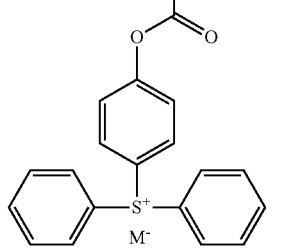

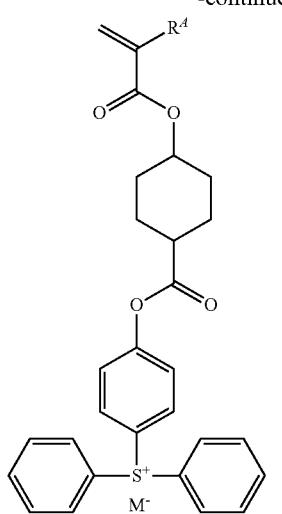
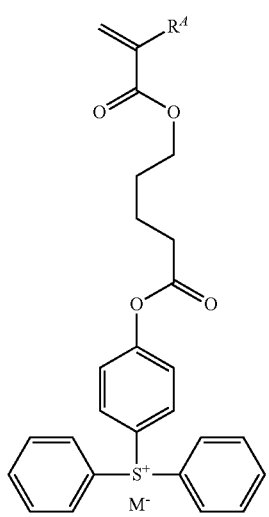
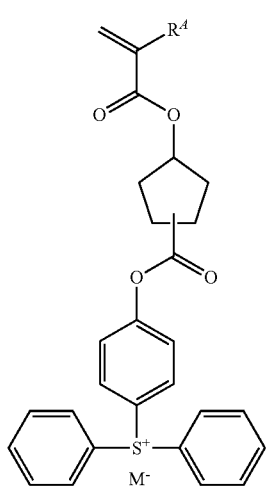
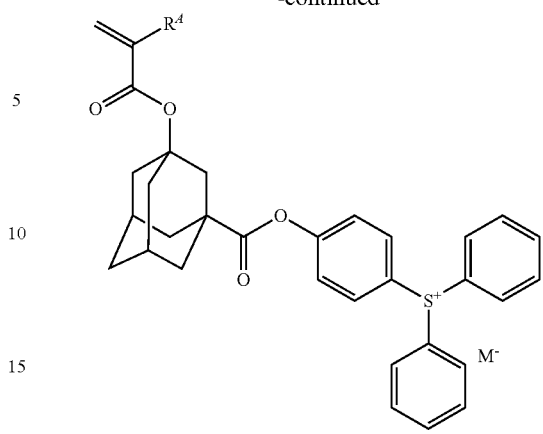
Examples of the monomer from which recurring unit (f2) is derived are shown below, but not limited thereto. $R^A$ is as defined above.
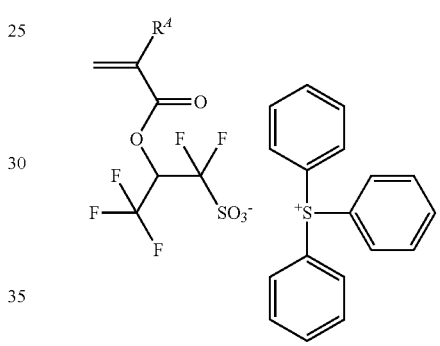
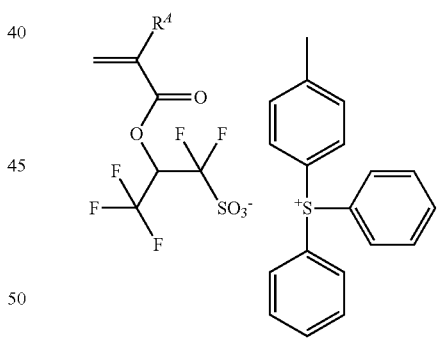
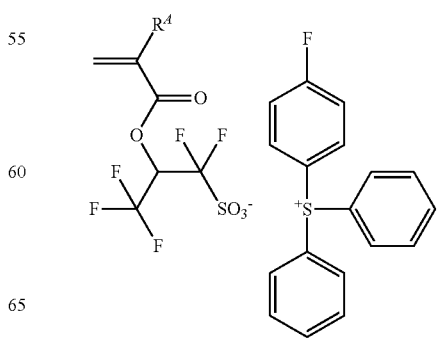

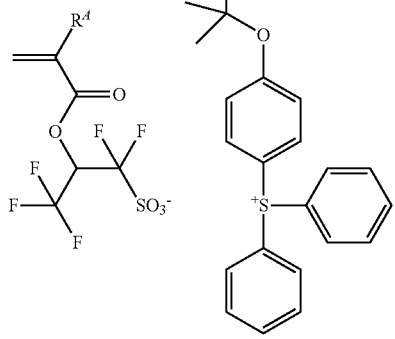
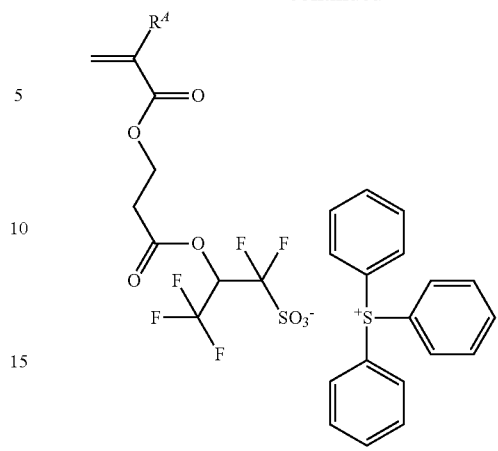
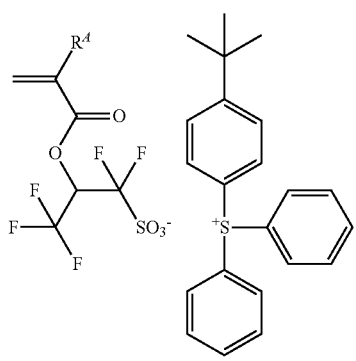
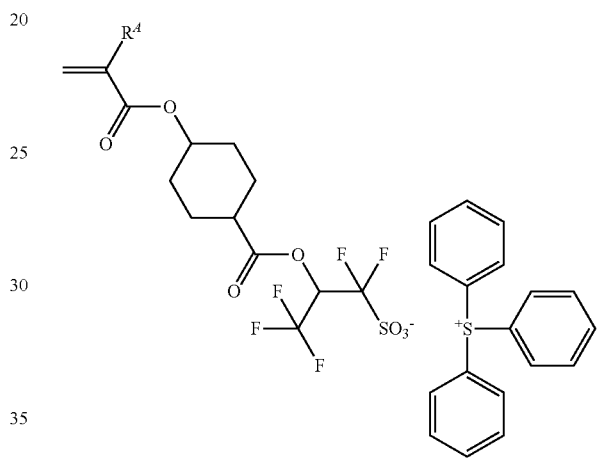
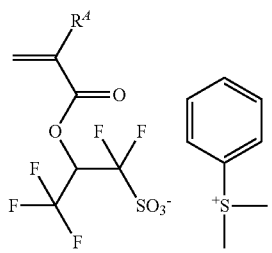
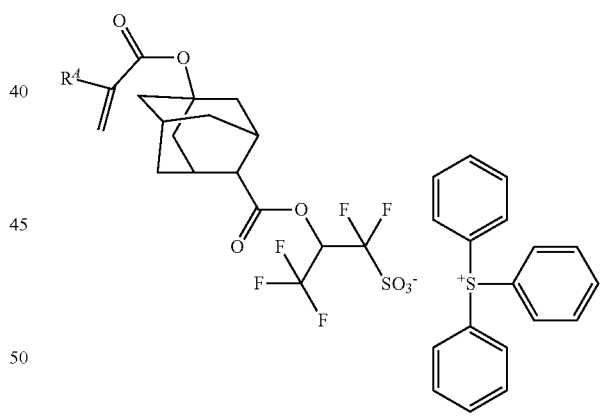
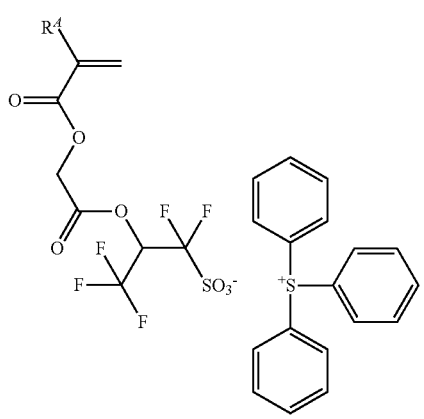
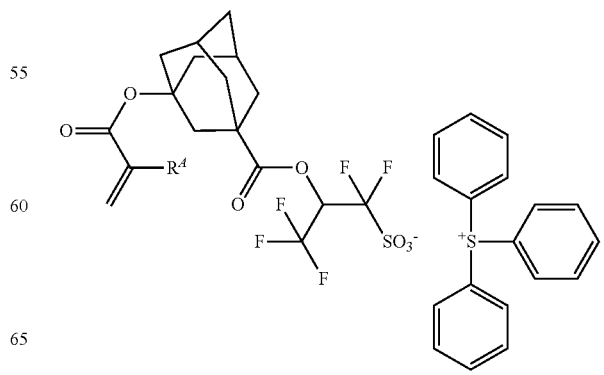

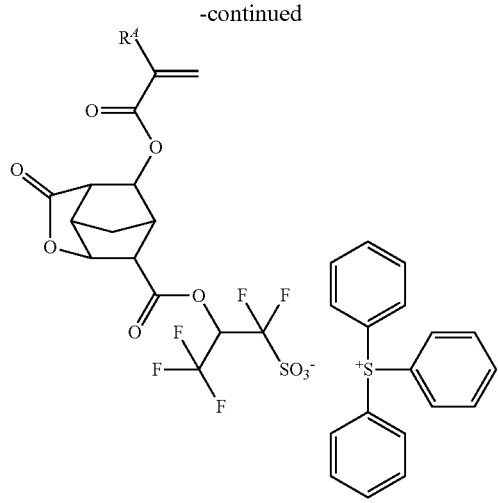
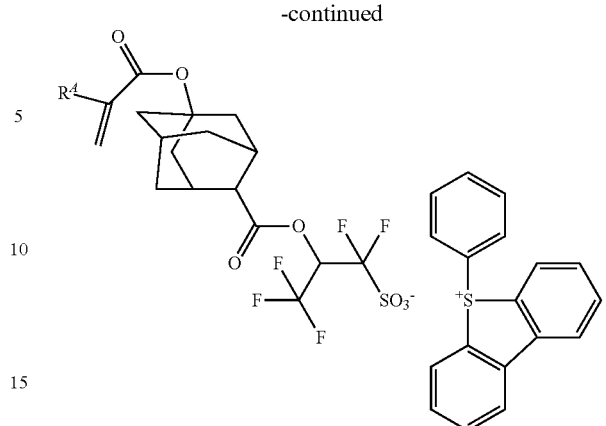
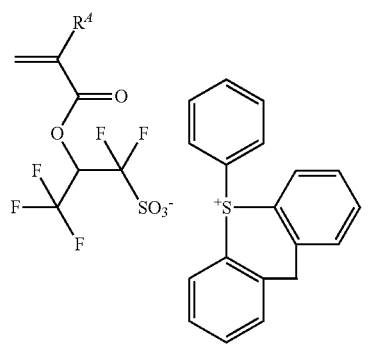
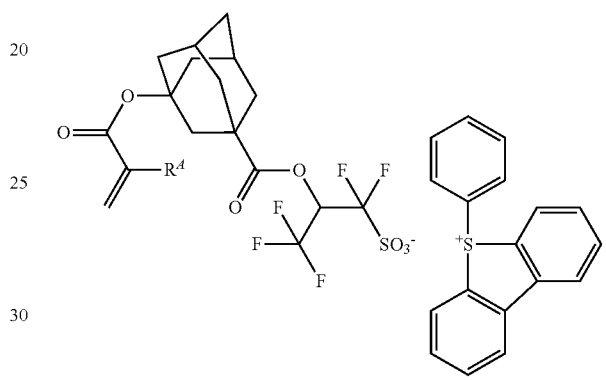
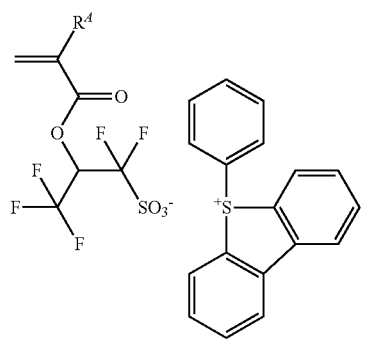
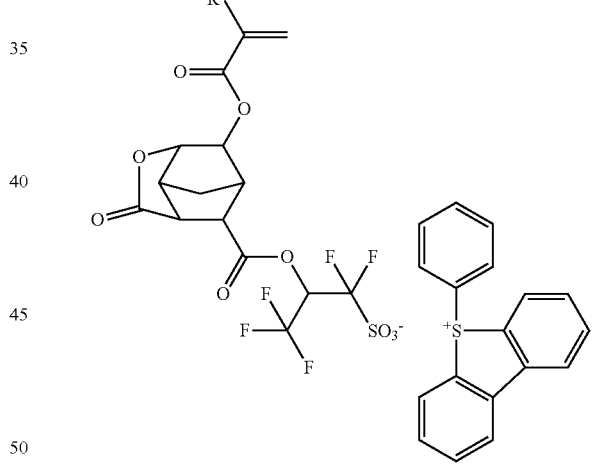
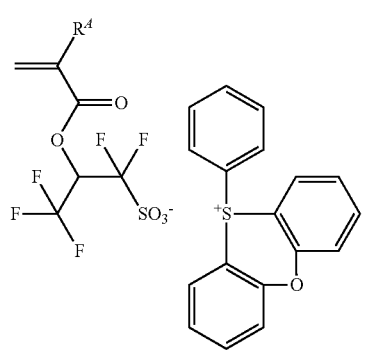
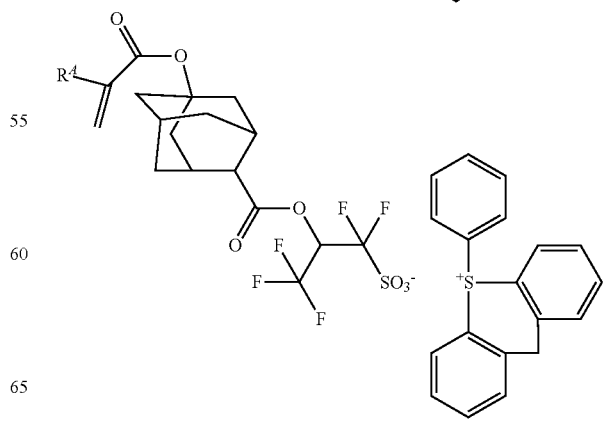

-continued
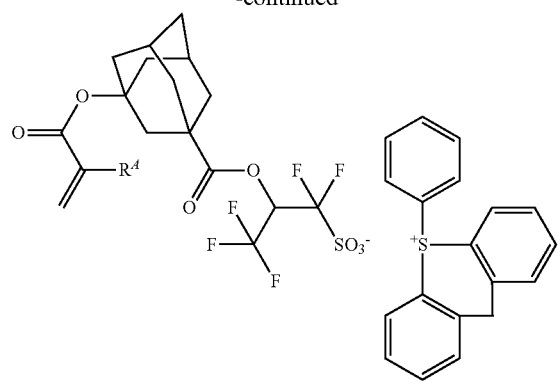
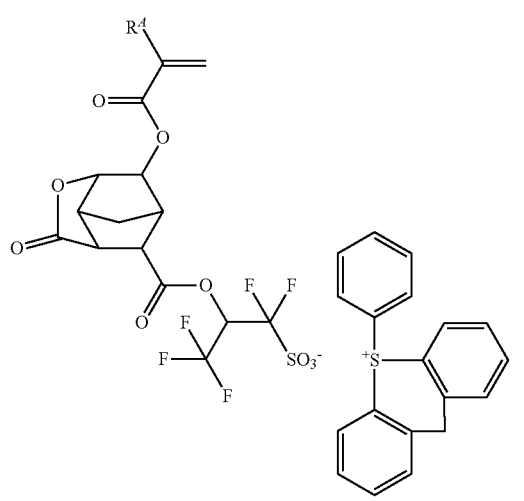
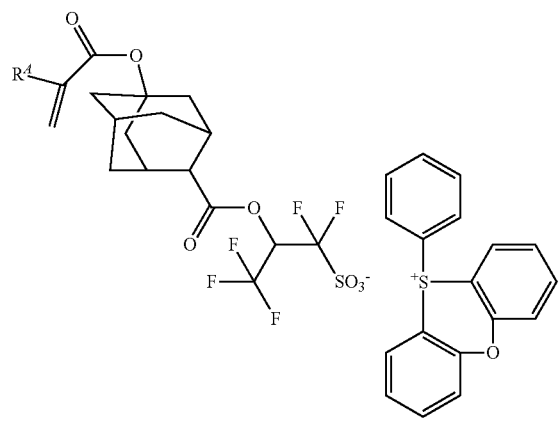
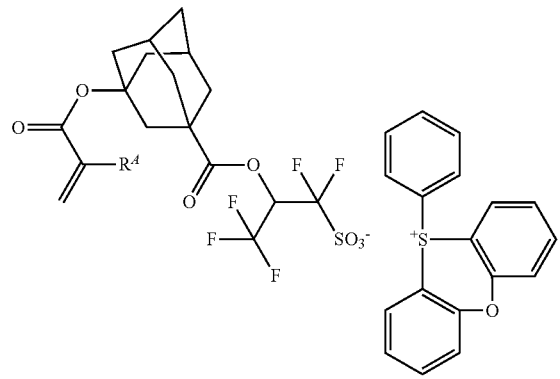
-continued
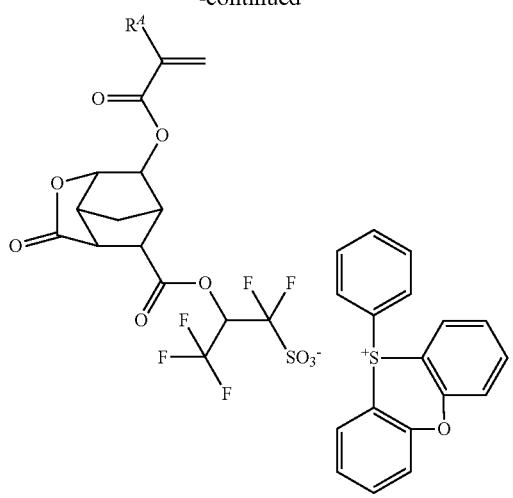
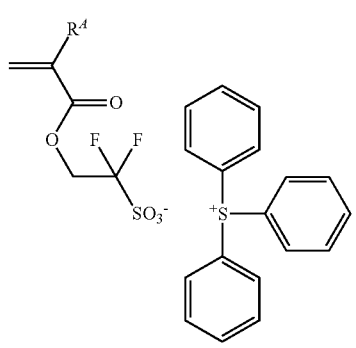
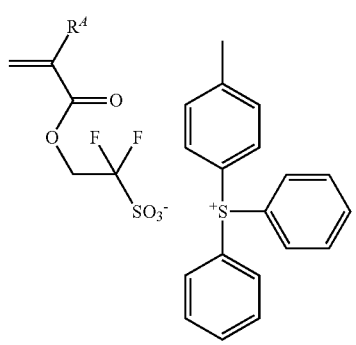
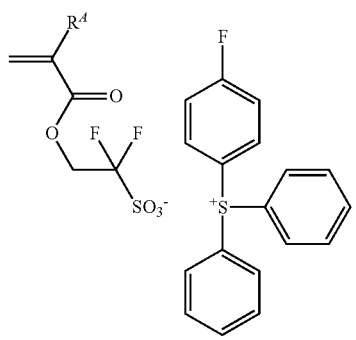

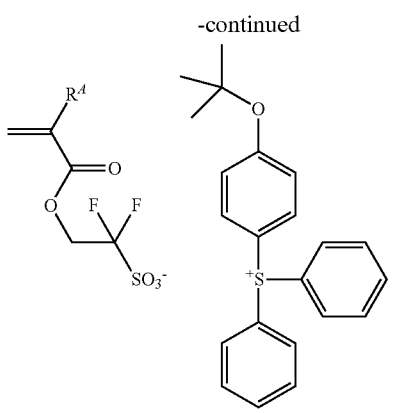
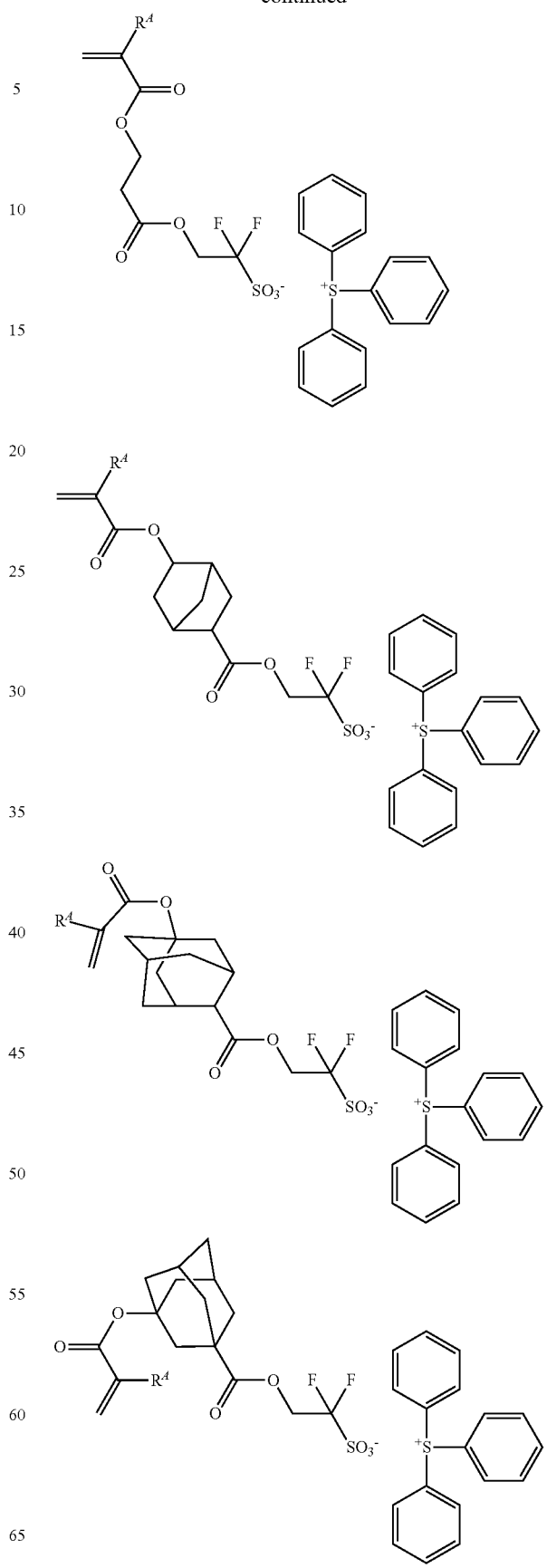

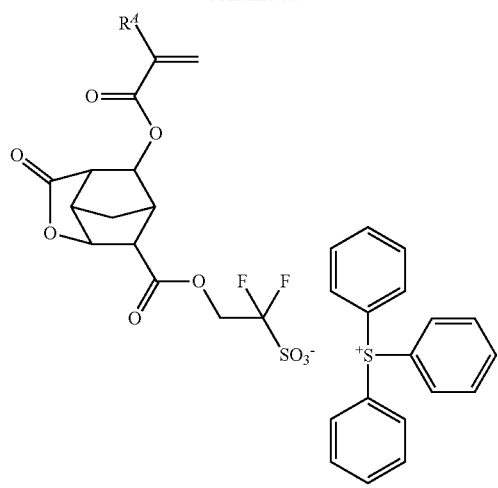
Examples of the monomer from which recurring unit (f3) is derived are shown below, but not limited thereto. $R^4$ is as defined above.
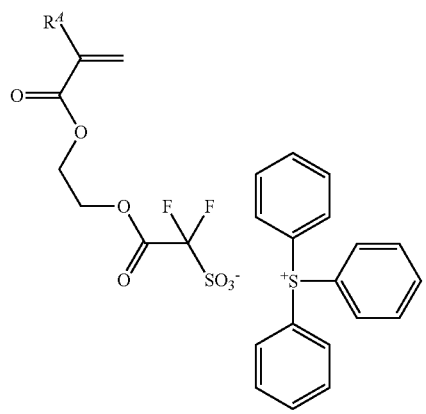
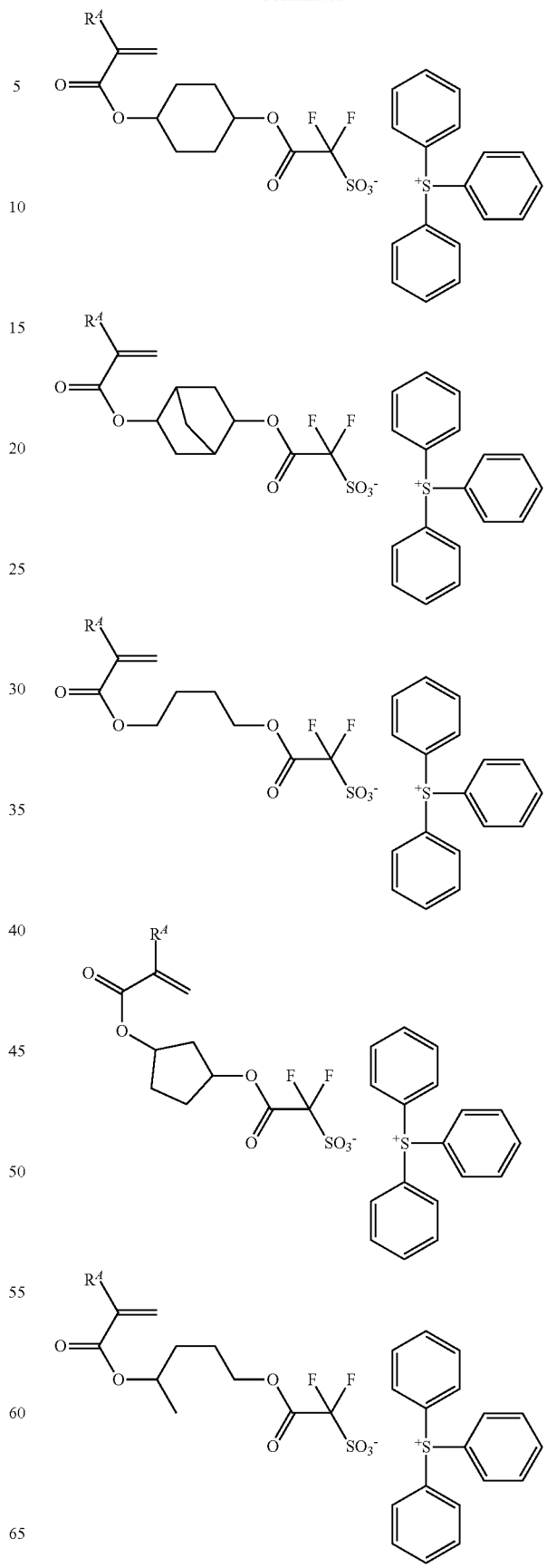

-continued
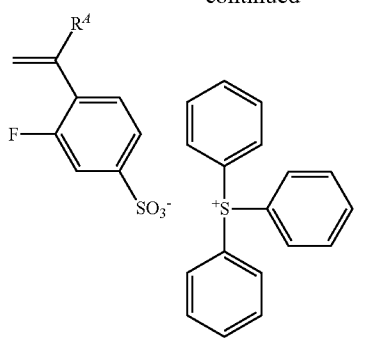
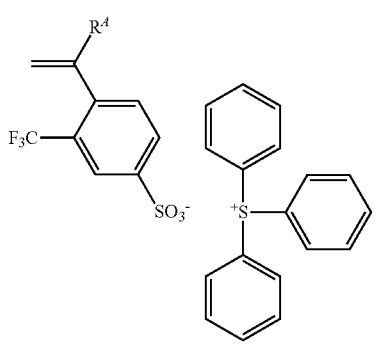
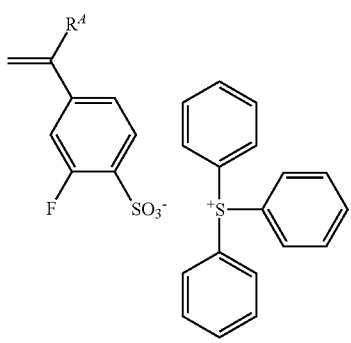
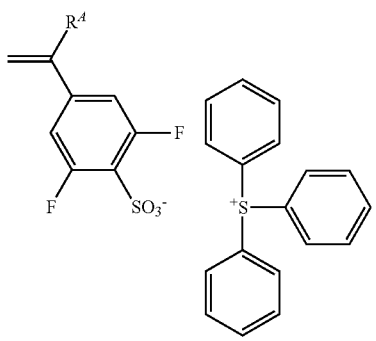
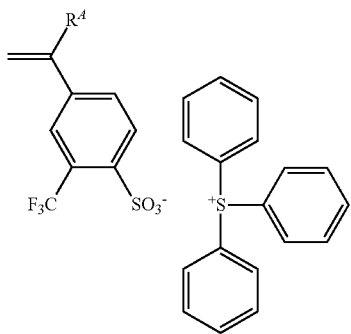
-continued
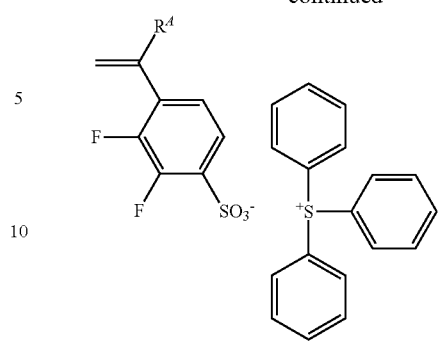
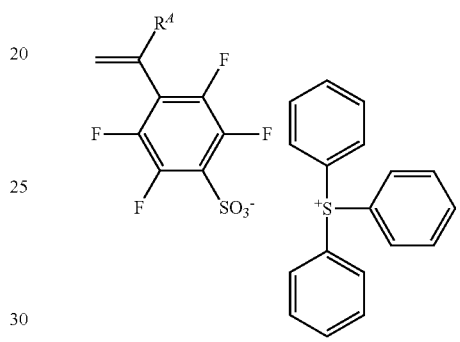
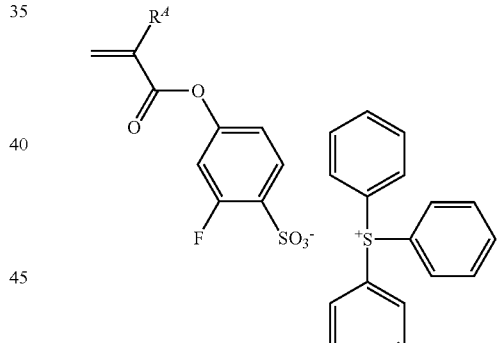
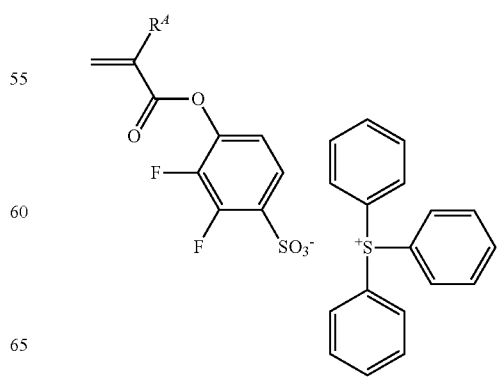

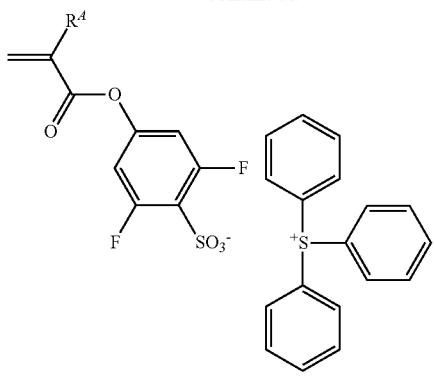
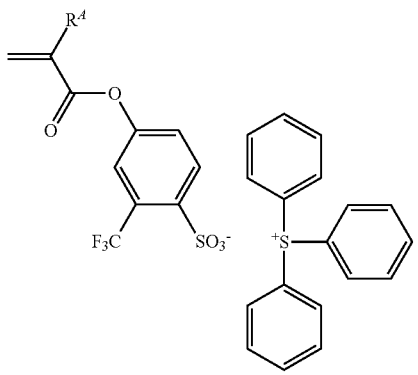
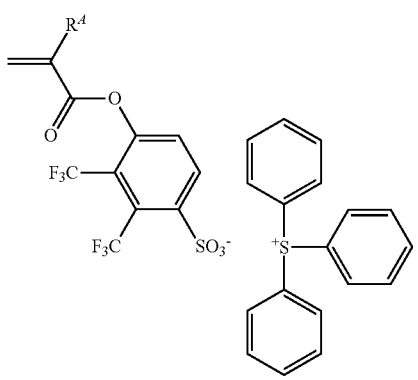
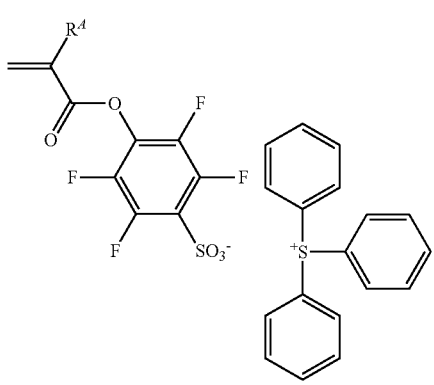
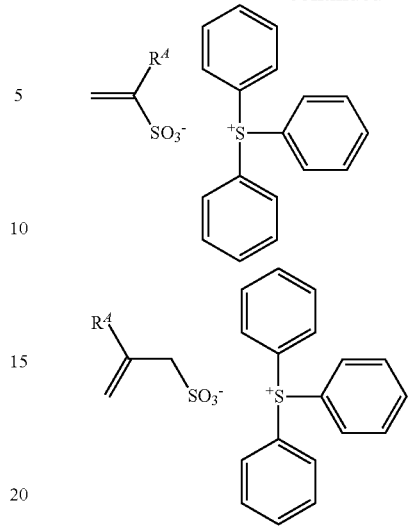

The attachment of an acid generator to the polymer main chain is effective in restraining acid diffusion, thereby preventing a reduction of resolution due to blur by acid diffusion. Also LWR is improved since the acid generator is uniformly distributed. Where a base polymer containing recurring units (f) is used, the blending of an acid generator of addition type may be omitted.

The base polymer for formulating the positive resist composition comprises recurring units (a1) or (a2) having an acid labile group as essential component and additional recurring units (b), (c), (d), (e), and (0 as optional components. A fraction of units (a1), (a2), (b), (c), (d), (e), and (f) is: preferably $0 \le a1 < 1.0$, $0 \le a2 < 1.0$, $0 < a1+a2 < 1.0$, $0 \le b \le 0.9$, $0 \le c \le 0.9$, $0 \le d \le 0.8$, $0 \le e \le 0.8$, and $0 \le f \le 0.5$; more preferably $0 \le a1 \le 0.9$, $0 \le a2 \le 0.9$, $0.1 \le a1+a2 \le 0.9$, $0 \le b \le 0.8$, $0 \le c \le 0.8$, $0 \le d \le 0.7$, $0 \le e\, 0.7$, and $0 \le f \le 0.4$; and even more preferably $0 \le a1 \le 0.8$, $0 \le a2 \le 0.8$, $0.1 \le a1+a2 \le 0.8$, $0 \le b \le 0.75$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \le 1.0$, $0 \le c \le 0.9$, $0 \le d \le 0.8$, $0 \le e \le 0.8$, and $0 \le f \le 0.5$; more preferably $0.2 \le b \le 1.0$, $0 \le c \le 0.8$, $0 \le d \le 0.7$, $0 \le e \le 0.7$, and $0 \le f \le 0.4$; and even more preferably $0.3 \le b \le 1.0$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is preferably 2 to 100 hours, more preferably 5 to 20 hours.

Where a monomer having a hydroxyl group is copolymerized, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the iodized aromatic ring-containing amine compound functions as a quencher and the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, sulfonium salts having the formula (1-1) and iodonium salts having the formula (1-2) are also preferred.

In formulae (1-1) and (1-2), $R^{101}$, $R^{102}$, $R^{103}$, $R^{104}$ and $R^{105}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group may be straight, branched or cyclic, and examples thereof include those exemplified above for $R^{21}$ to $R^{28}$ in formulae (f1) to (f3).

Examples of the cation in the sulfonium salt having formula (1-1) are shown below, but not limited thereto.

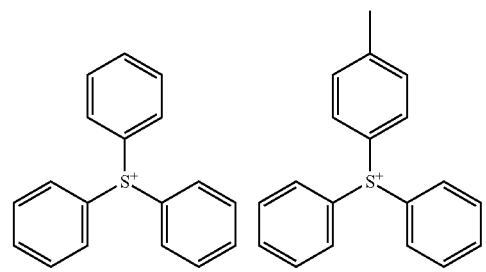

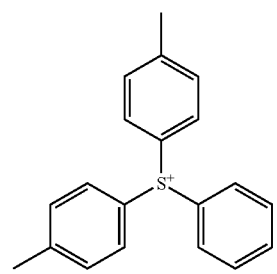

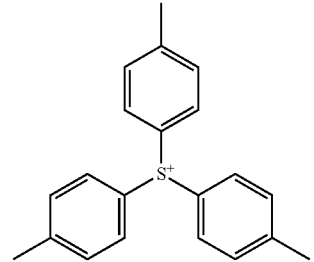

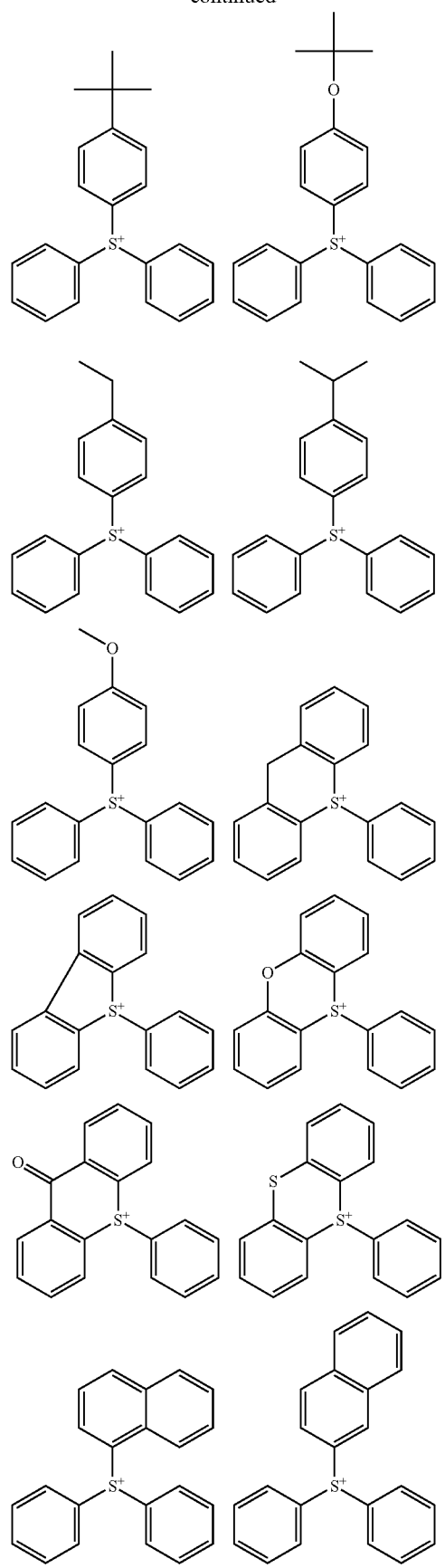
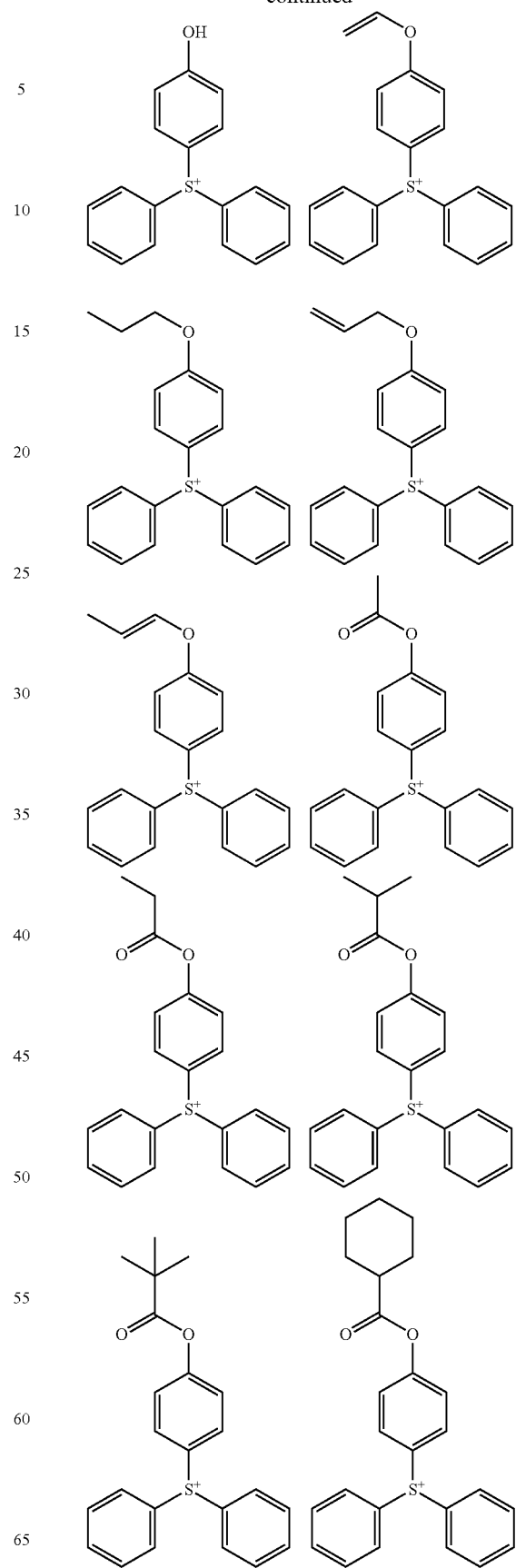

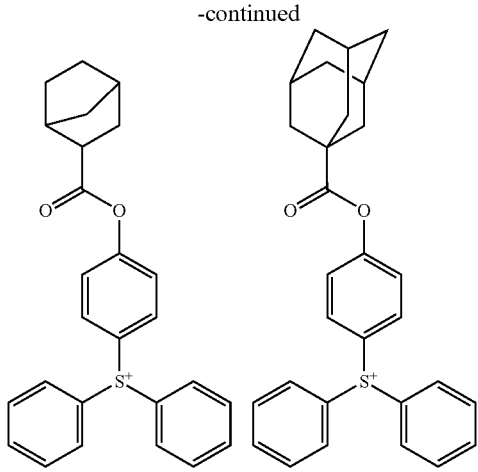
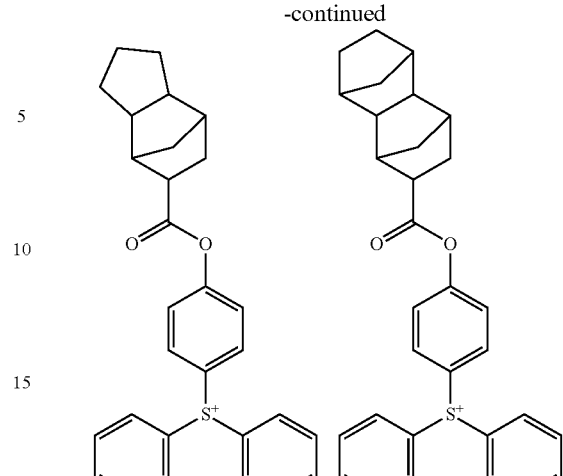
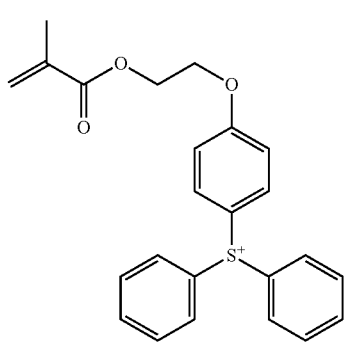
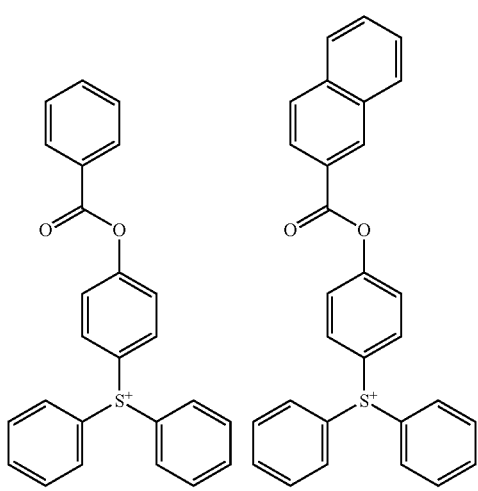
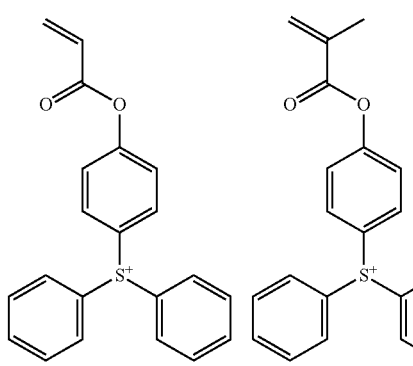
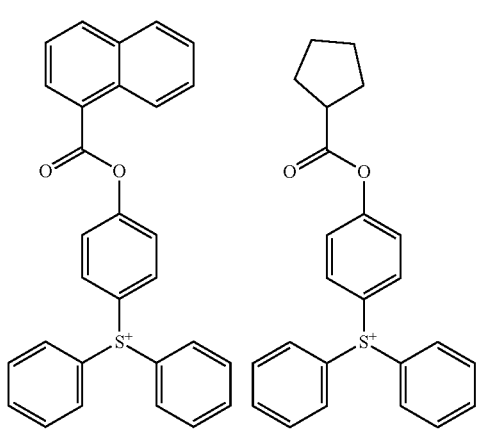
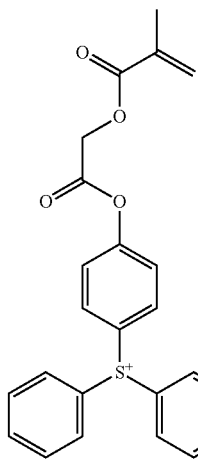

85
-continued
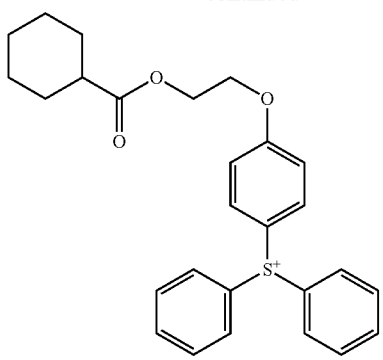
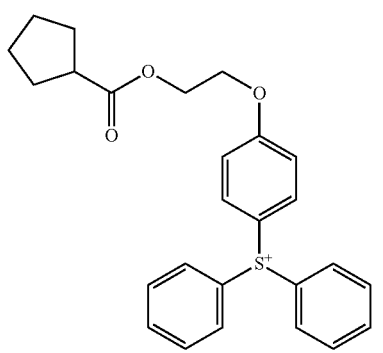
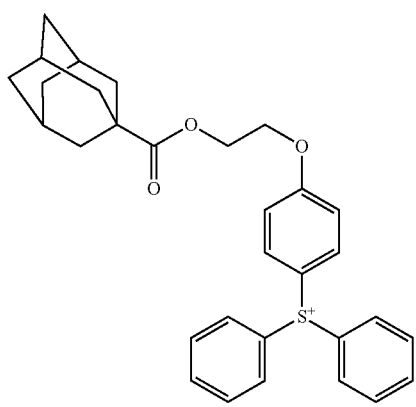
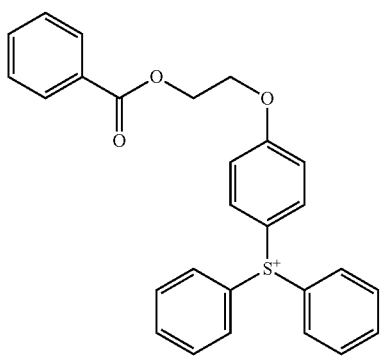
86
-continued
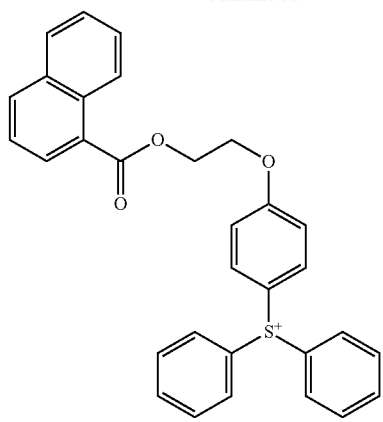
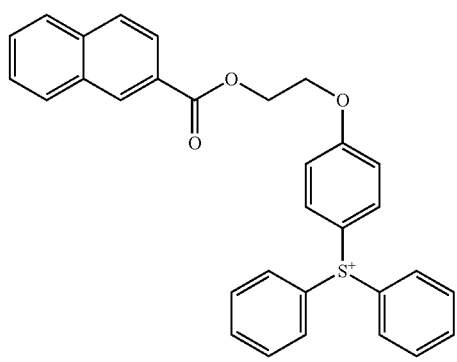
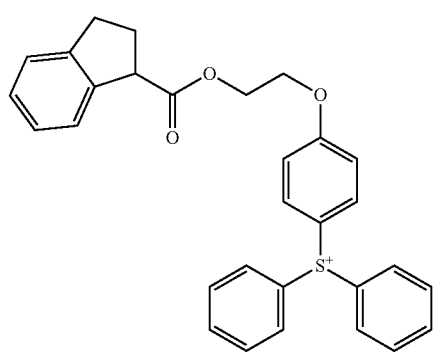
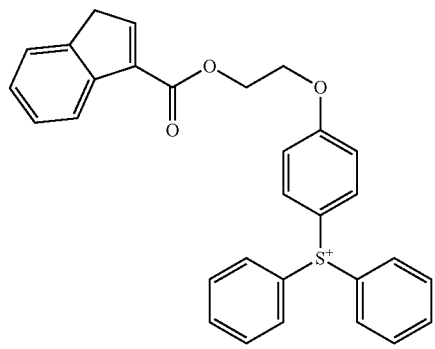

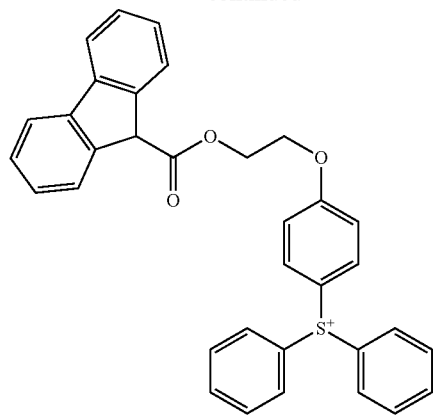
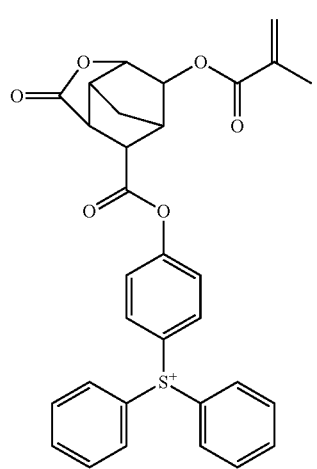
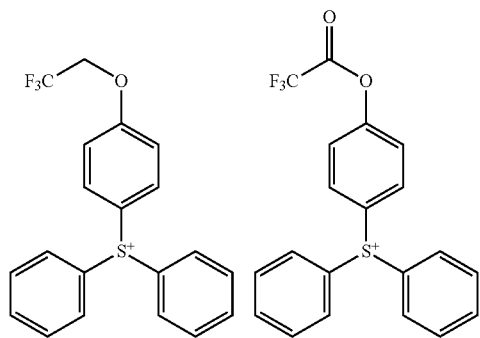
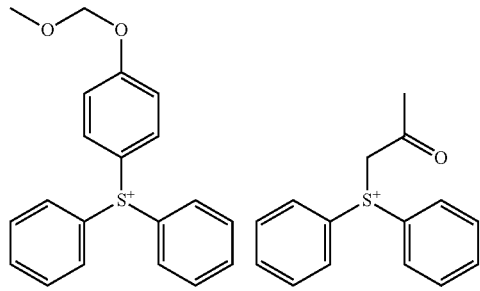
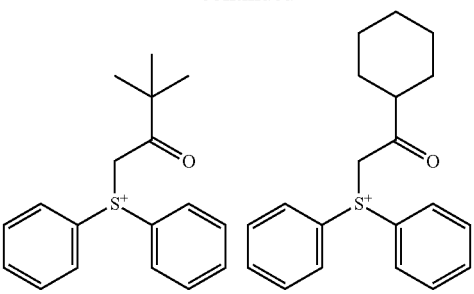
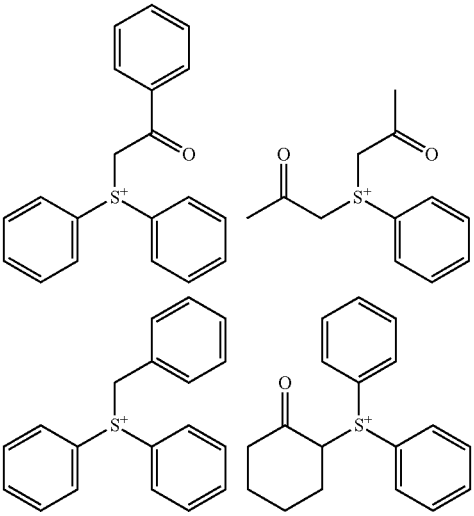
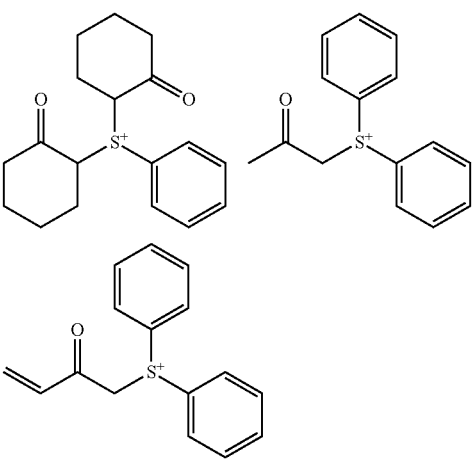
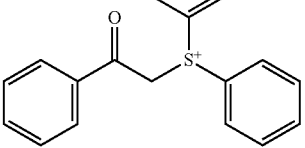
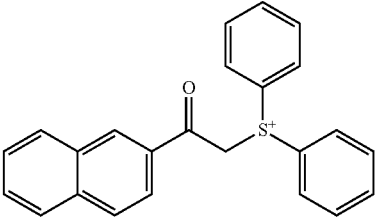

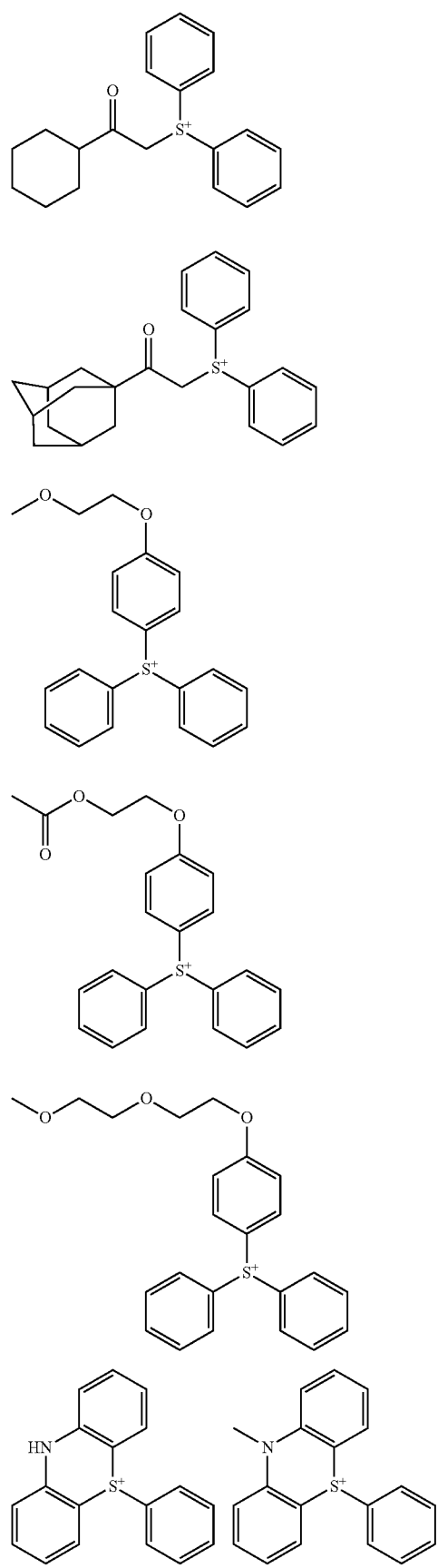
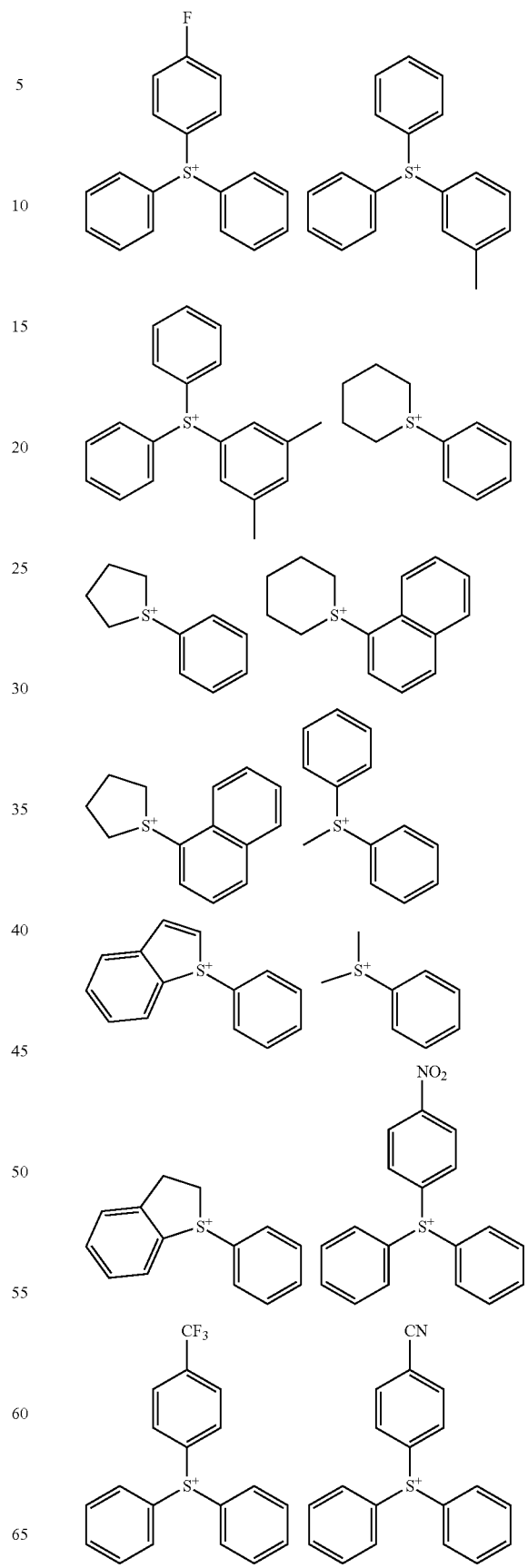

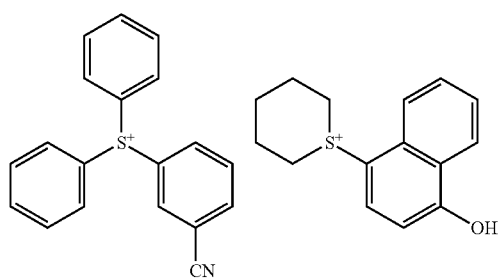
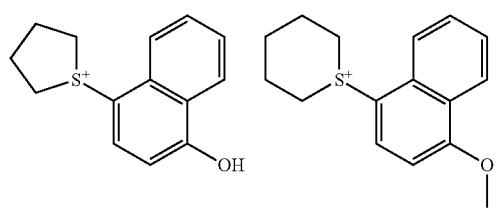
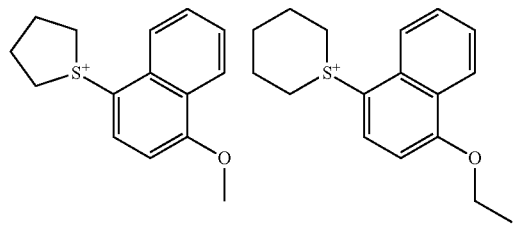
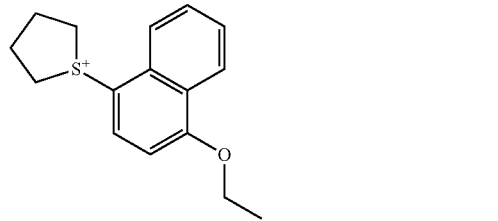
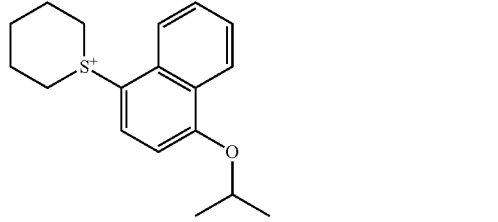
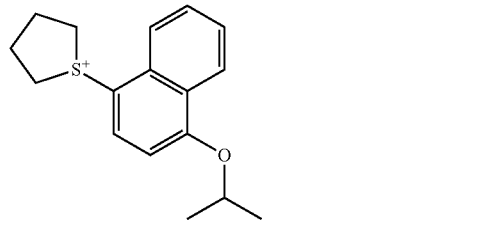
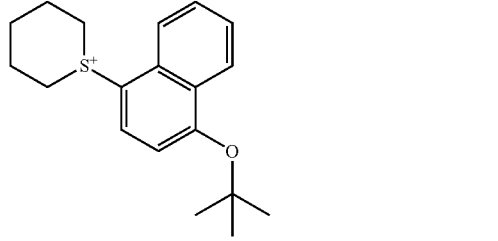
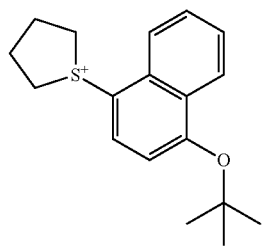
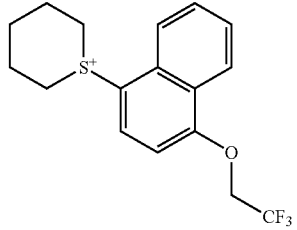
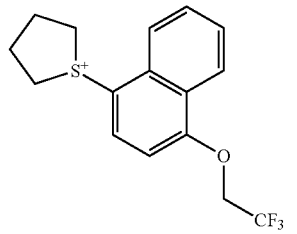
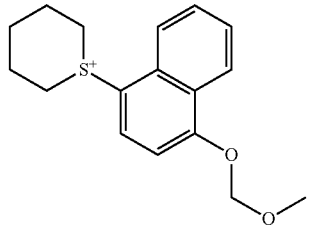
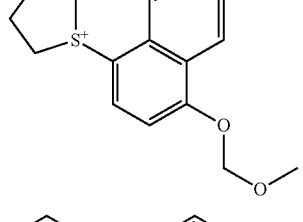
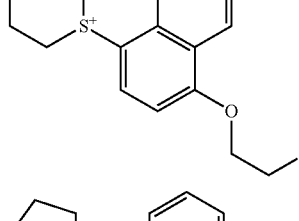

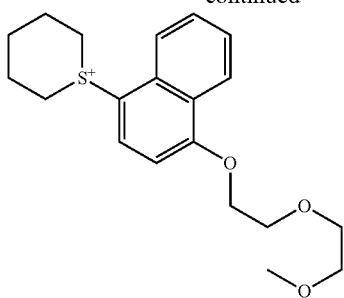
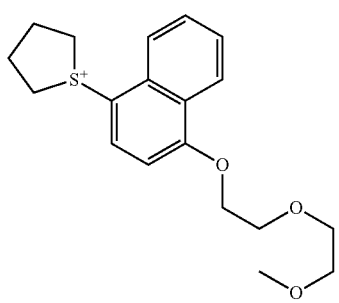
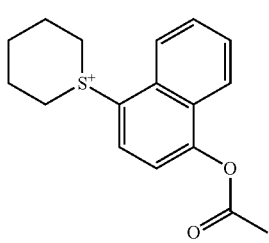
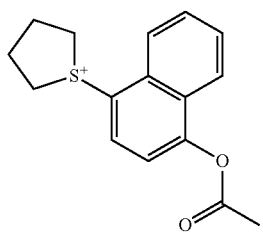
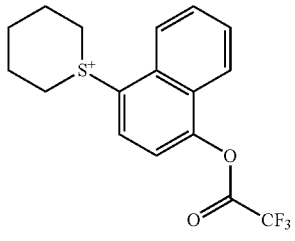
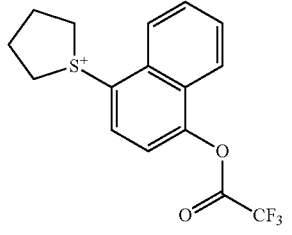
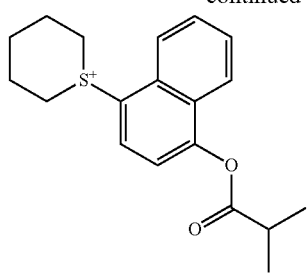
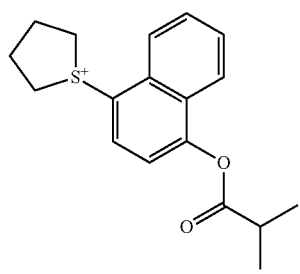
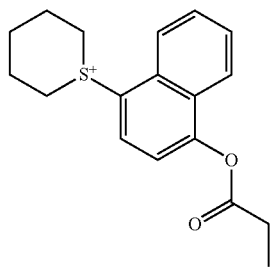
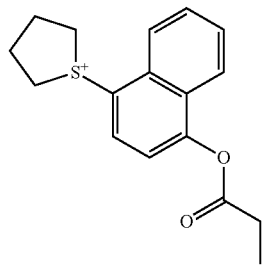
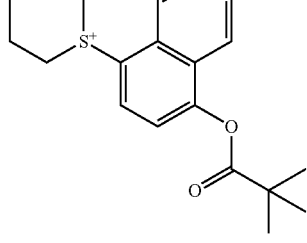
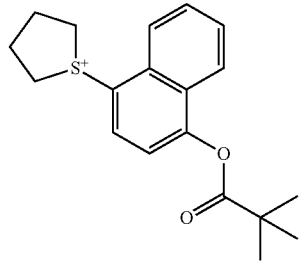
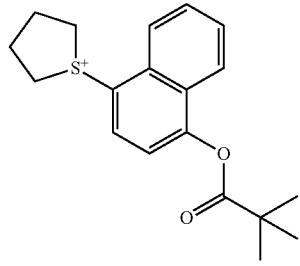

-continued

97
-continued
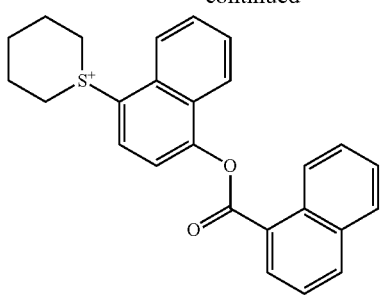
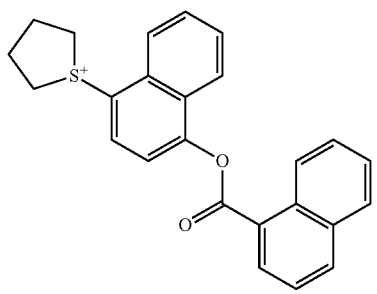
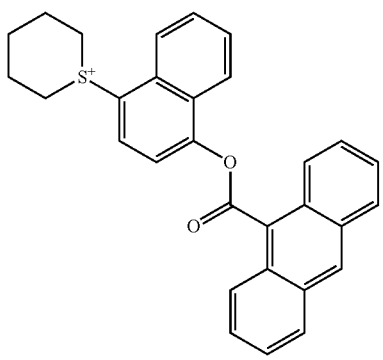
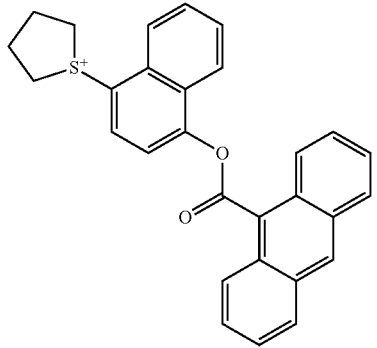
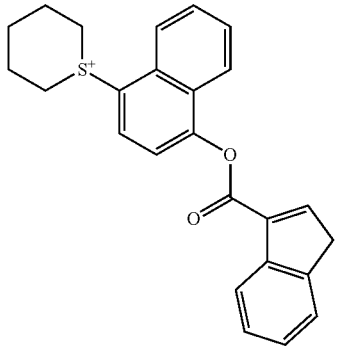
98
-continued
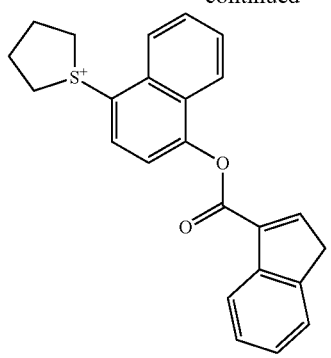
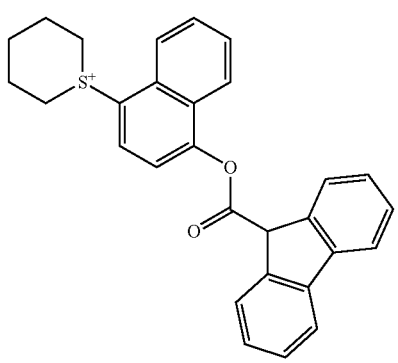
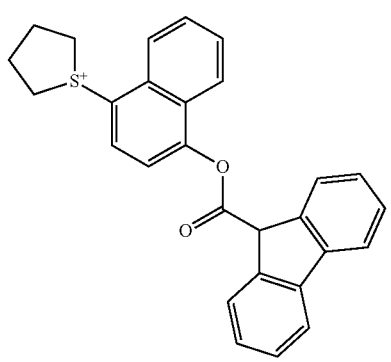
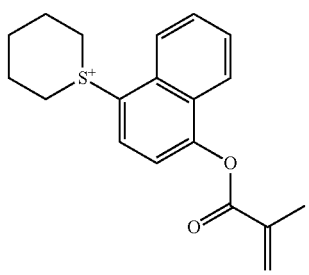
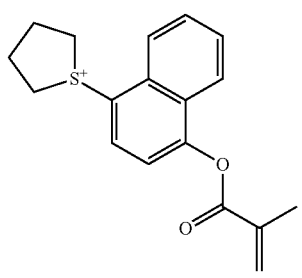

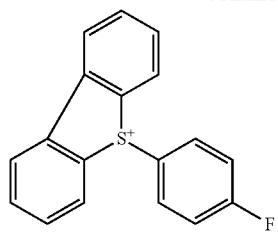
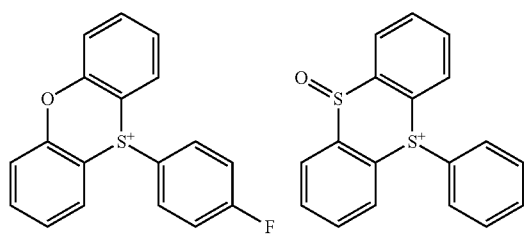
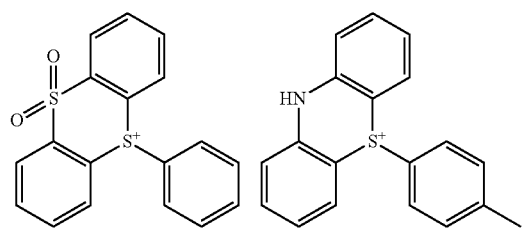
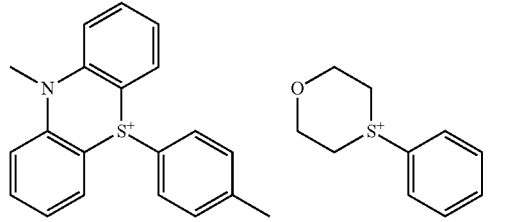
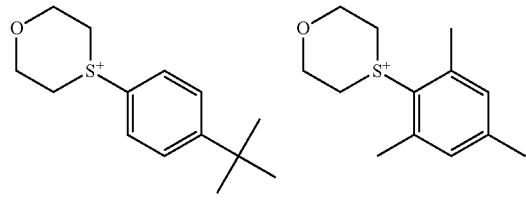
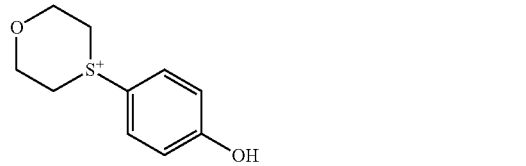
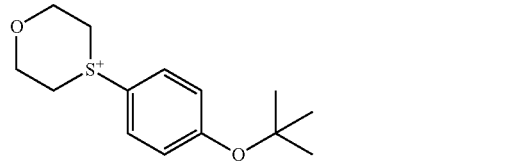
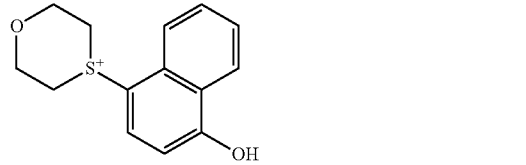
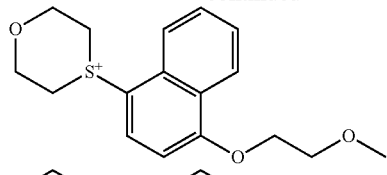
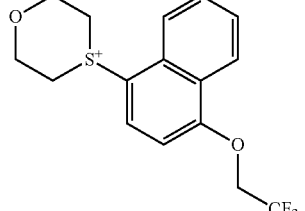
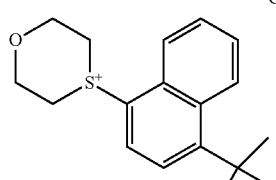
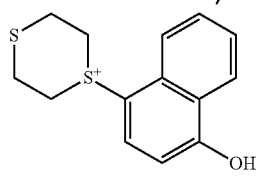
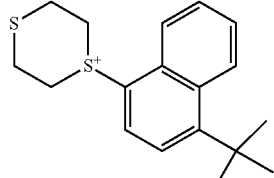
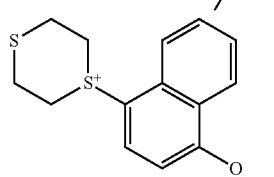
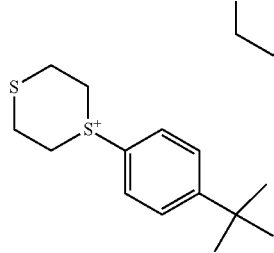
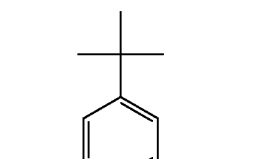
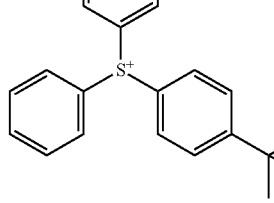

101
-continued
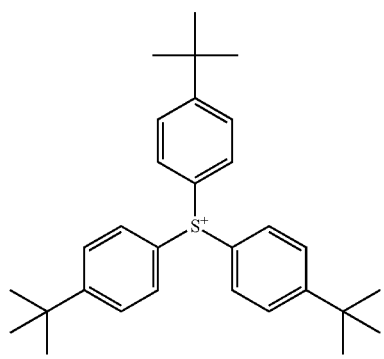
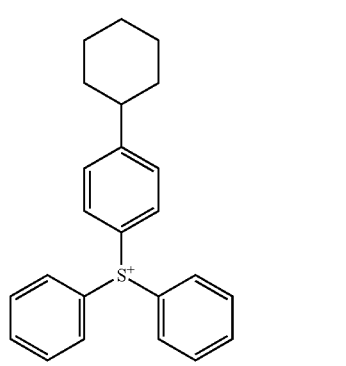
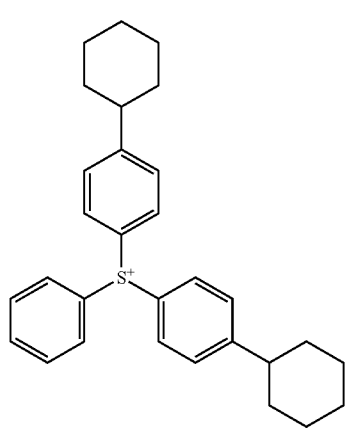
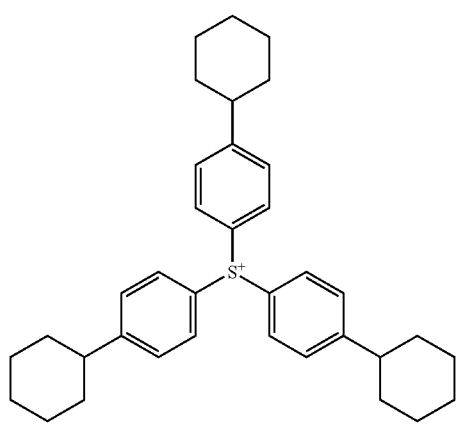
102
-continued
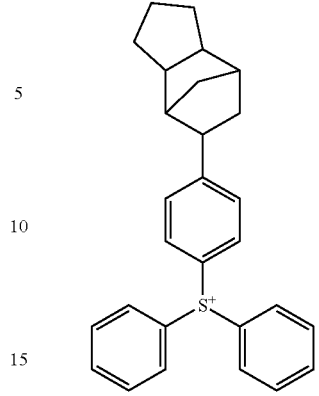
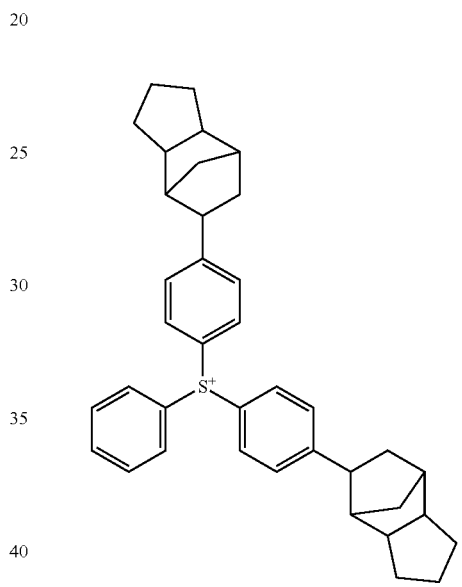
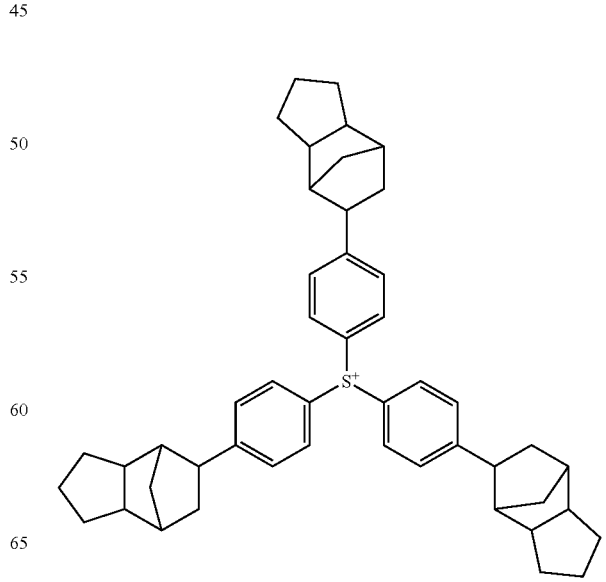

103
-continued
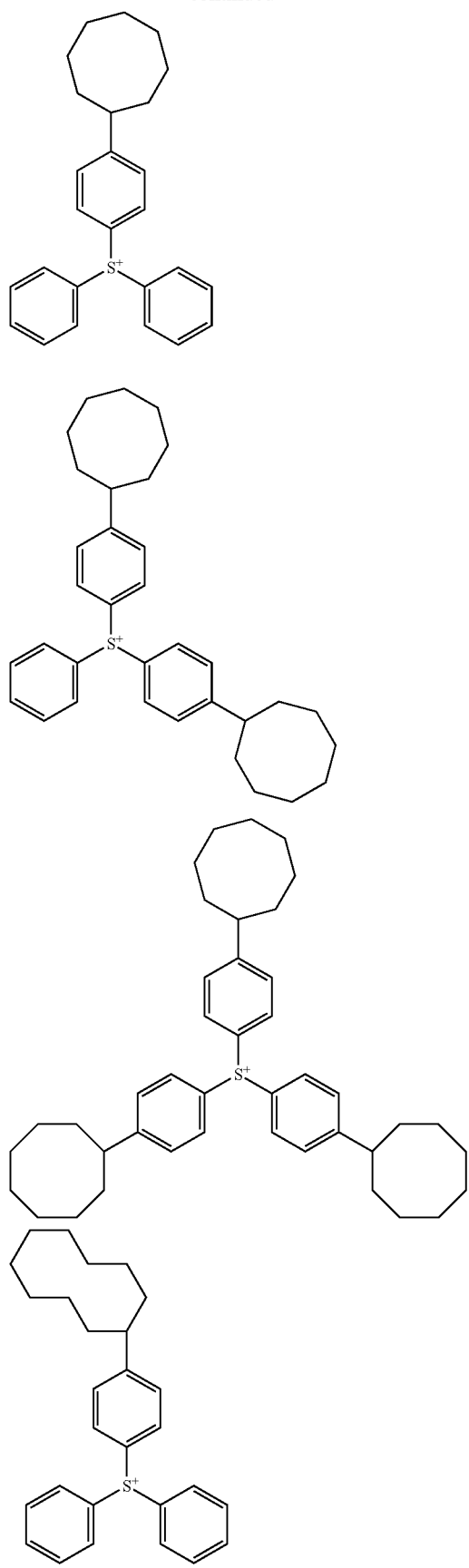
104
-continued
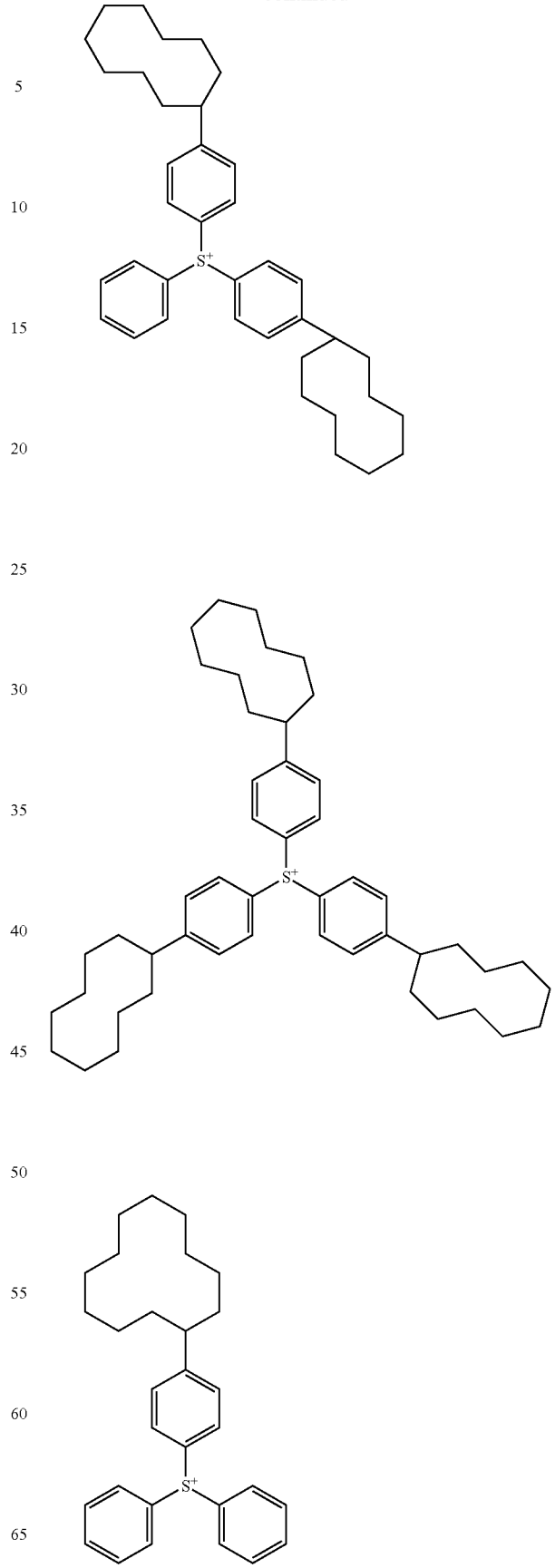

105
-continued
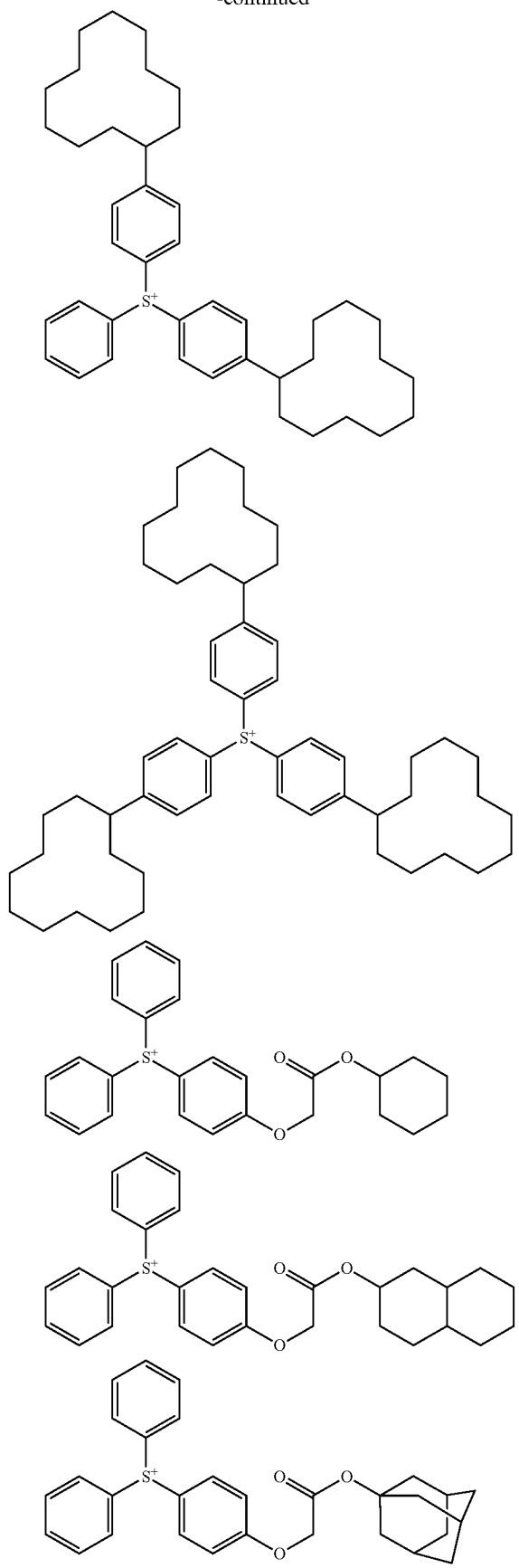
106
-continued
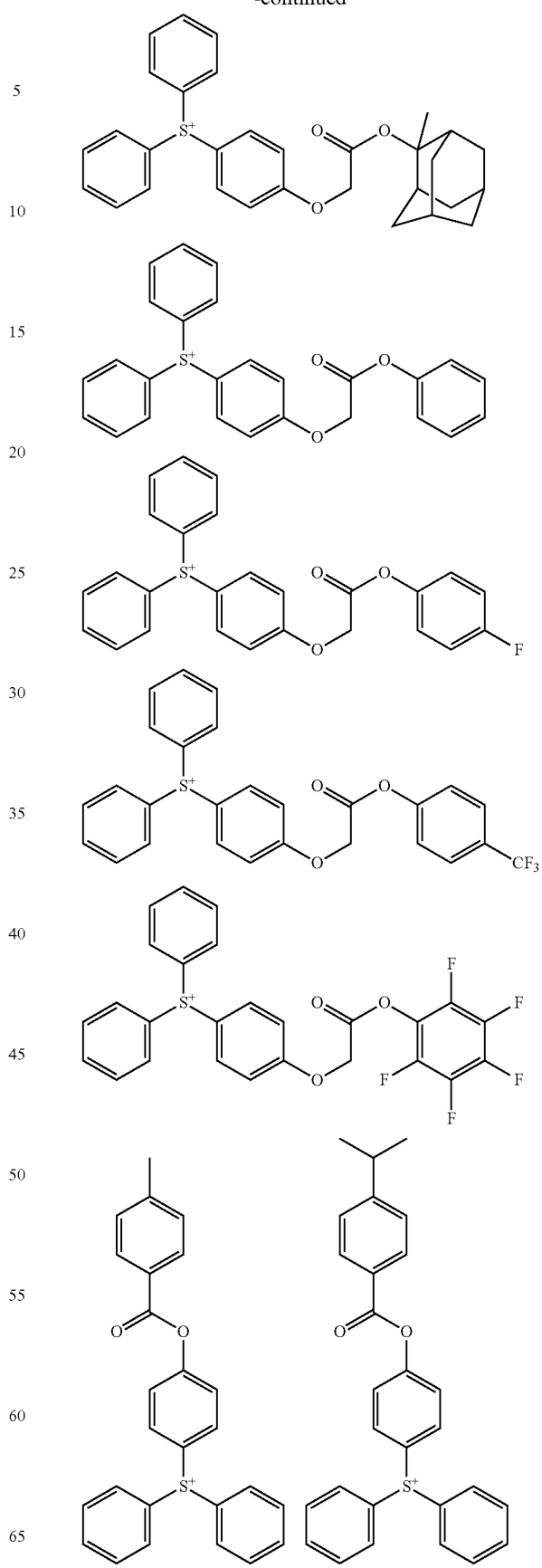

107
-continued
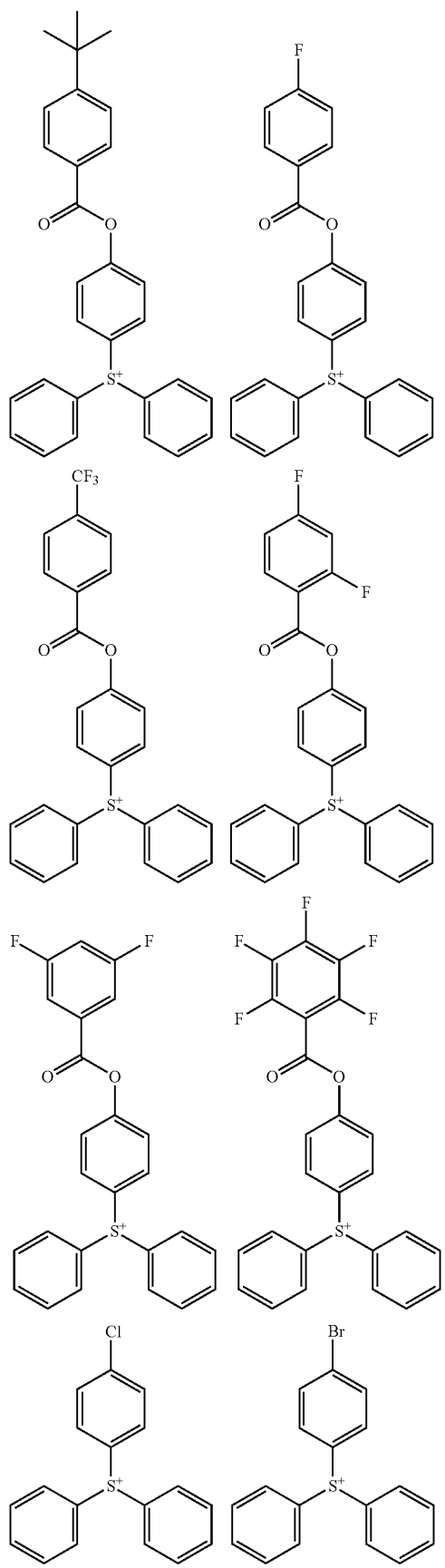
108
-continued
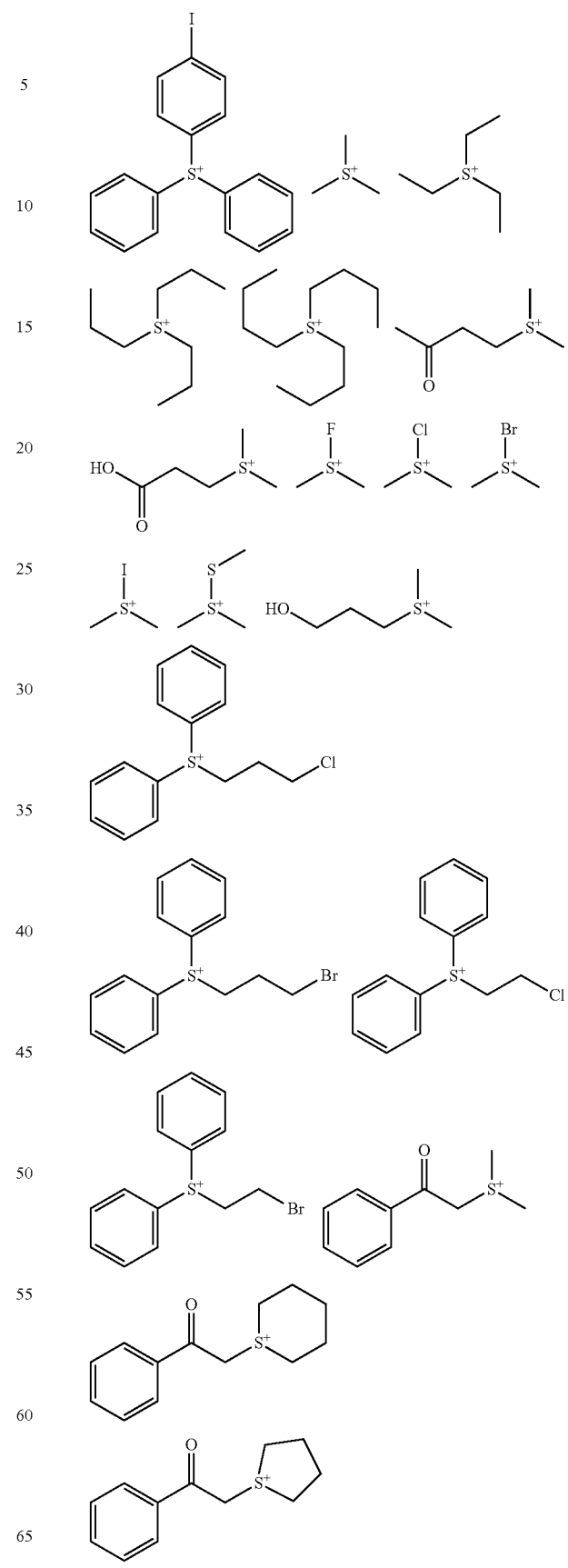

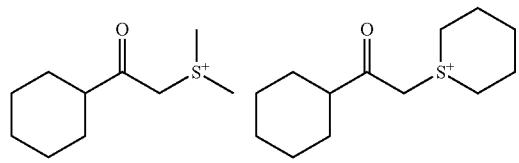
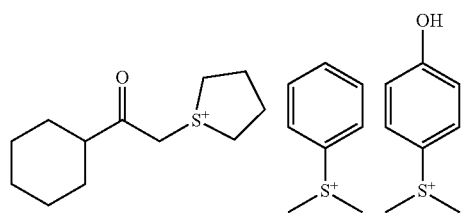
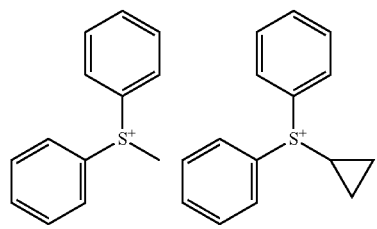
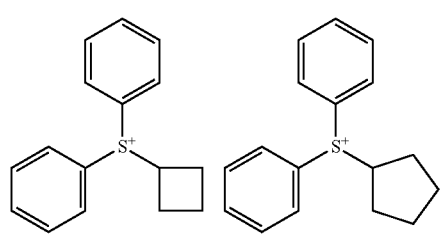
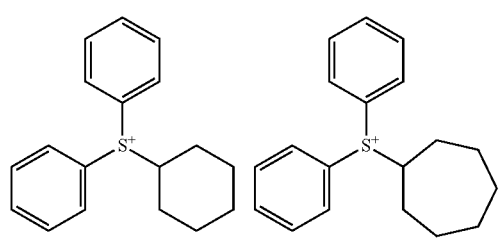
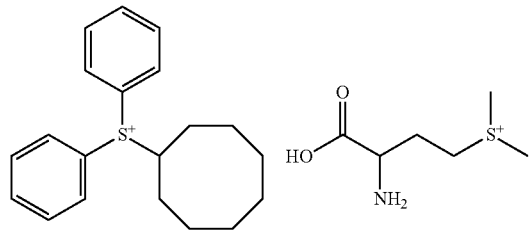
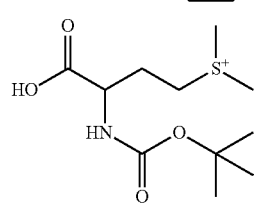
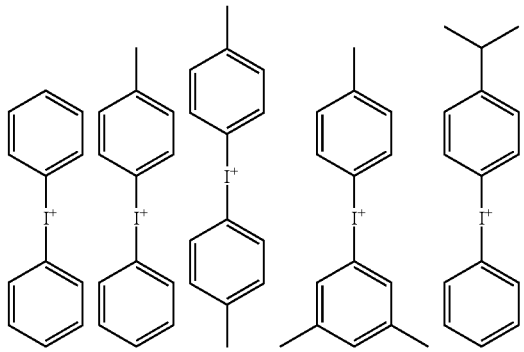
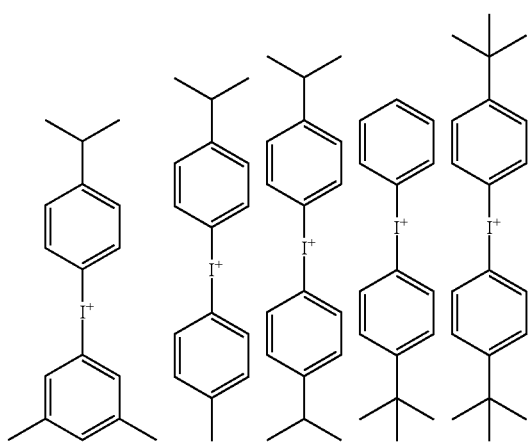
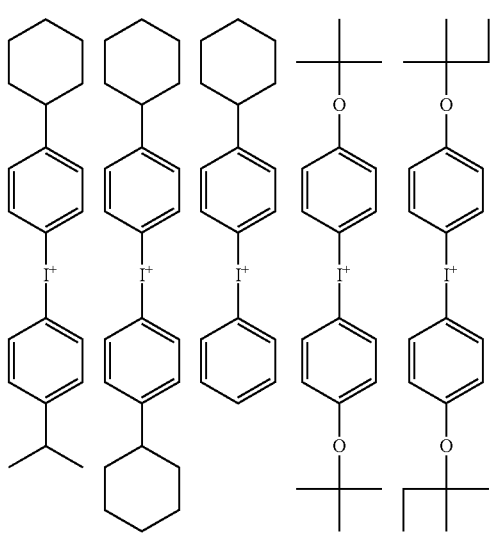
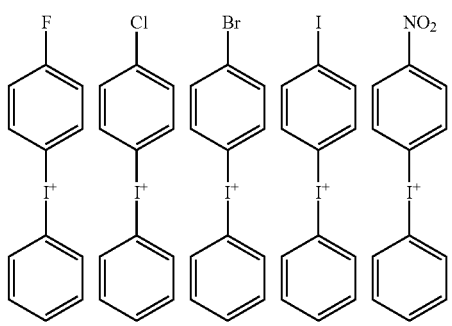
Examples of the cation in the iodonium salt having formula (1-2) are shown below, but not limited thereto.

-continued

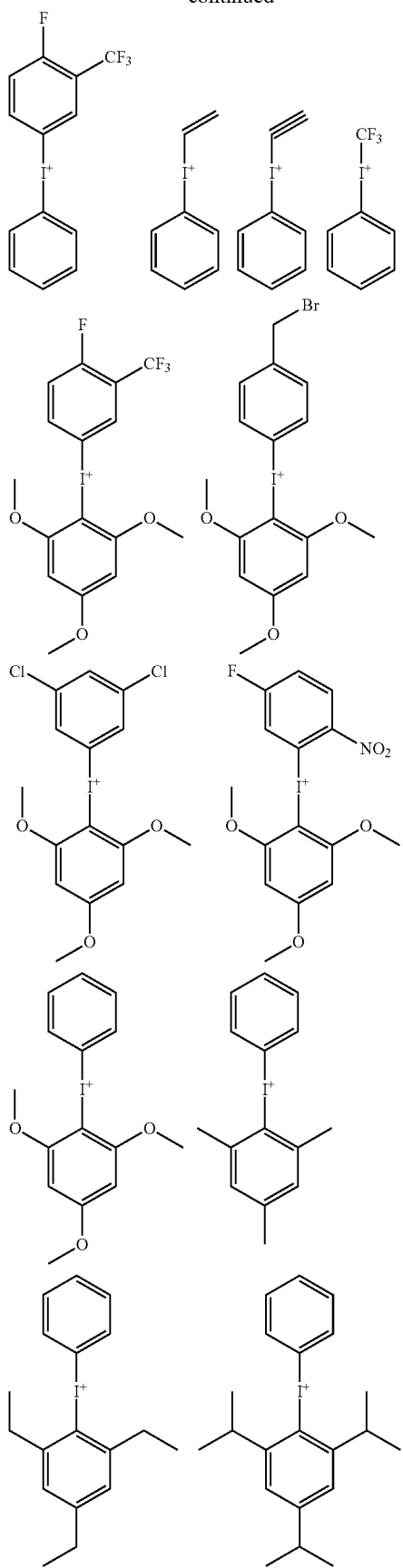

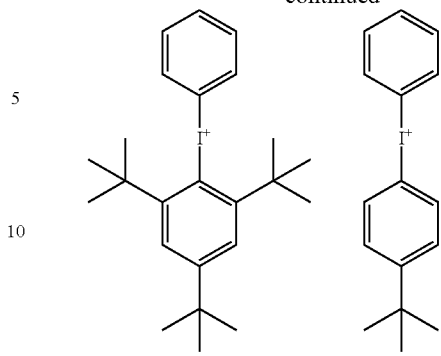

In formulae (1-1) and (1-2), X⁻ is an anion of the following formula (1A), (1B), (1C) or (1D).

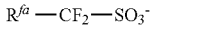  (1A)

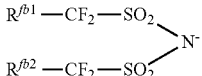  (1B)

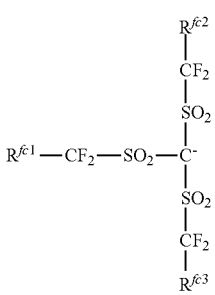  (1C)

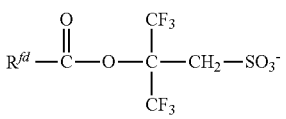  (1D)

In formula (1A), $R^{fa}$ is fluorine or a $C_1$-$C_{40}$ monovalent hydrocarbon group which may contain a heteroatom. The monovalent hydrocarbon group may be straight, branched or cyclic, and examples thereof include those exemplified later for $R^{107}$.

Of the anions of formula (1A), an anion having the formula (1A') is preferred.

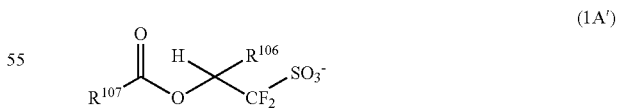  (1A')

In formula (1A'), $R^{106}$ is hydrogen or trifluoromethyl, preferably trifluoromethyl. $R^{107}$ is a $C_1$-$C_{38}$ monovalent hydrocarbon group which may contain a heteroatom. As the heteroatom, oxygen, nitrogen, sulfur and halogen atoms are preferred, with oxygen being most preferred. Of the monovalent hydrocarbon groups represented by $R^{107}$, those groups of 6 to 30 carbon atoms are preferred from the aspect of achieving a high resolution in forming patterns of fine feature size. The monovalent hydrocarbon groups may be straight, branched or cyclic. Examples thereof include, but are not limited to, straight or branched alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, eicosanyl, monovalent saturated alicyclic hydrocarbon groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; monovalent unsaturated aliphatic hydrocarbon groups such as allyl and 3-cyclohexenyl; aryl groups such as phenyl, 1-naphthyl and 2-naphthyl; and aralkyl groups such as benzyl and diphenylmethyl. Examples of the monovalent hydrocarbon group having a heteroatom include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

With respect to the synthesis of the sulfonium salt having an anion of formula (1A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

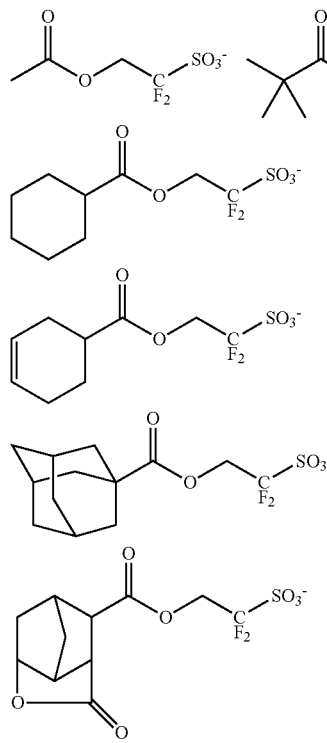

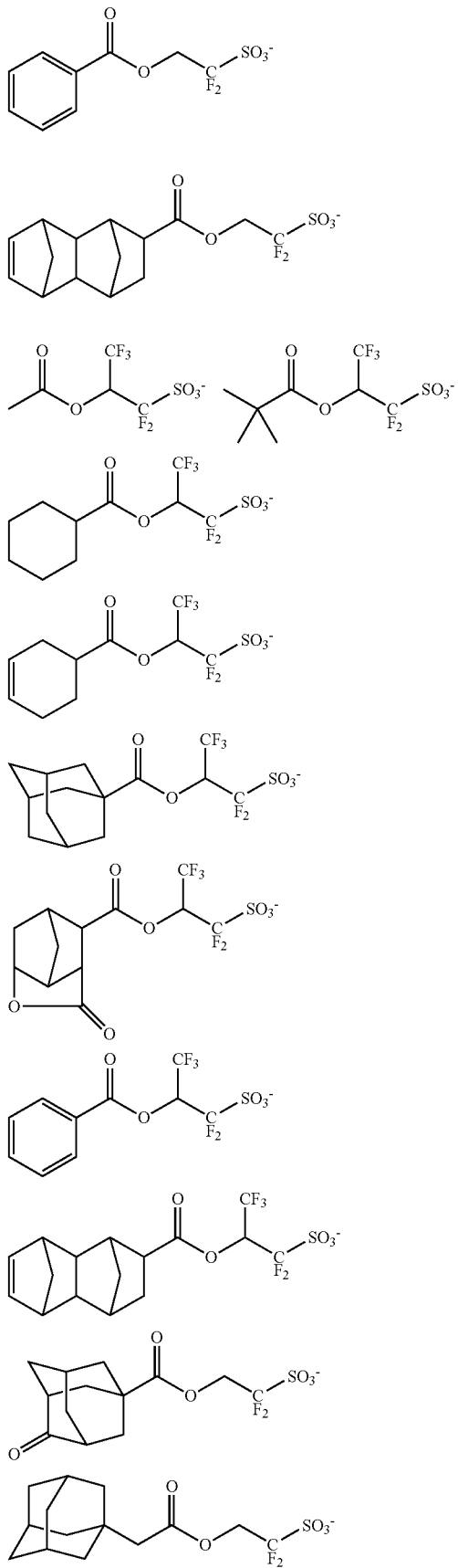

115
-continued

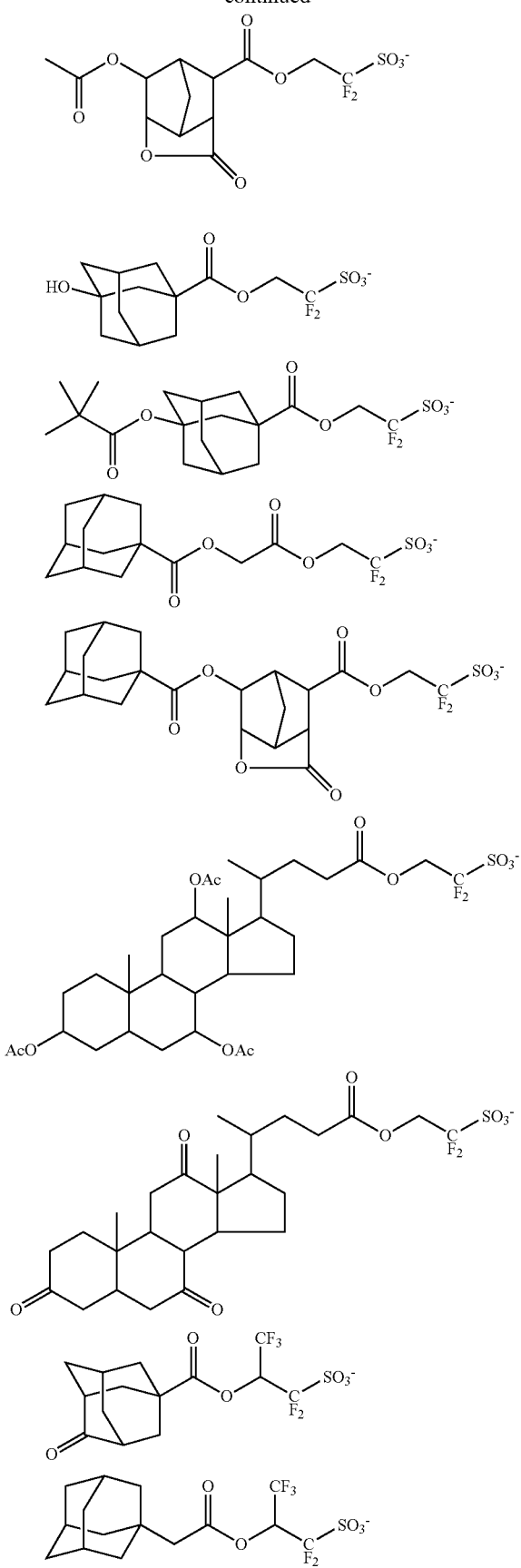

116
-continued

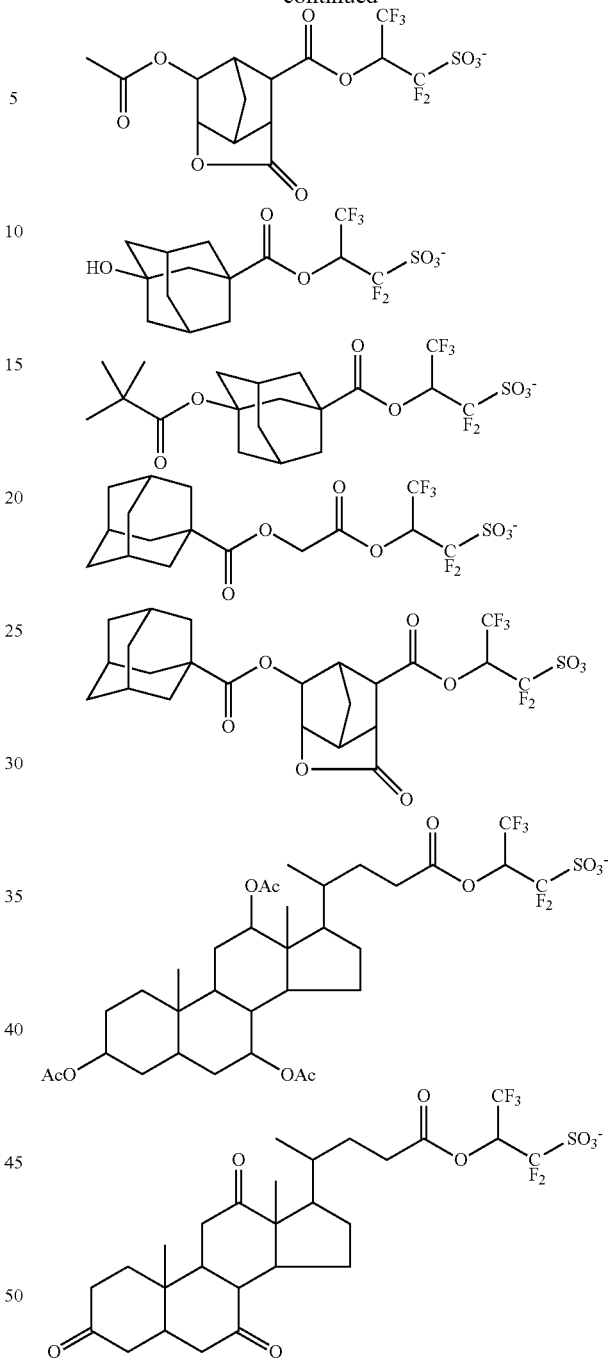

In formula (1B), $R^{fb1}$ and $R^{fb2}$ are each independently fluorine or a $C_1$-$C_{40}$ monovalent hydrocarbon group which may contain a heteroatom. The monovalent hydrocarbon group may be straight, branched or cyclic, and examples thereof are as exemplified for $R^{107}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred that a combination of $R^{fb1}$ and $R^{fb2}$ be a fluorinated ethylene or fluorinated propylene group.

In formula (1C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic, and examples thereof are as exemplified for $R^{107}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred that a combination of $R^{fc1}$ and $R^{fc2}$ be a fluorinated ethylene or fluorinated propylene group.

In formula (1D), $R^{fd}$ is a $C_1$-$C_{40}$ monovalent hydrocarbon group which may contain a heteroatom. The monovalent hydrocarbon group may be straight, branched or cyclic, and examples thereof are as exemplified above for $R^{107}$.

With respect to the synthesis of the sulfonium salt having an anion of formula (1D), reference may be made to JP-A 2010-215608 and JP-A 2014-133723.

Examples of the anion having formula (1D) are shown below, but not limited thereto.

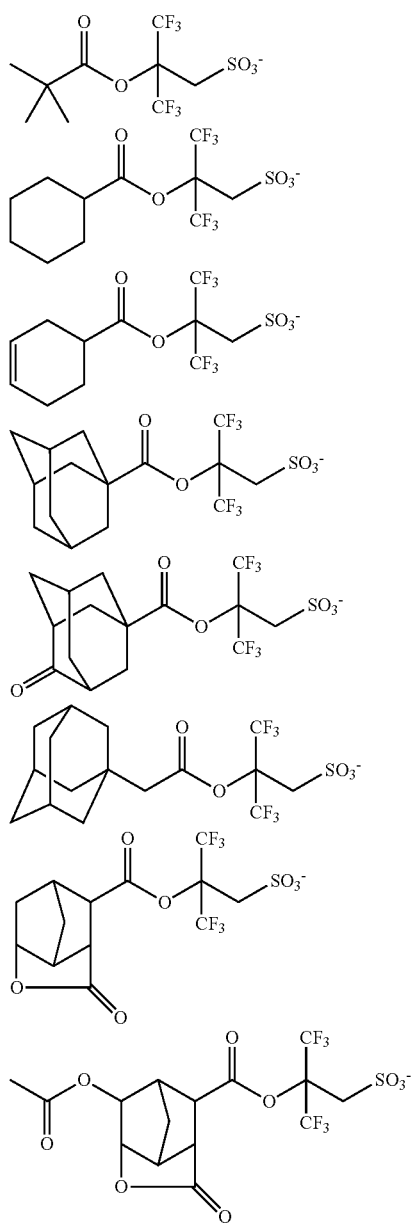

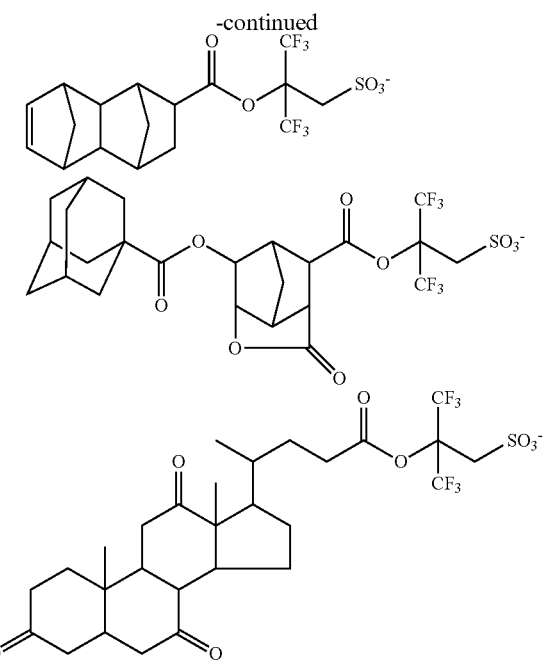

Notably, the compound having the anion of formula (1D) does not have fluorine at the α-position relative to the sulfo group, but two trifluoromethyl groups at the β-position. For this reason, it has a sufficient acidity to sever the acid labile groups in the resist polymer. Thus the compound is an effective PAG.

Another preferred PAG is a compound having the formula (2).

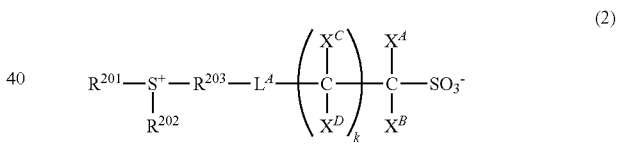

(2)

In formula (2), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R_{201}$, $R_{202}$ and $R_{203}$ may bond together to form a ring with the sulfur atom to which they are attached. $L^A$ is a single bond, ether bond or a $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

The monovalent hydrocarbon groups may be straight, branched or cyclic. Examples thereof include, but are not limited to, straight or branched alkyl groups such as methyl, ethyl, propyl, isopropyl, n-butyl, sec-butyl, tert-butyl, n-pentyl, tert-pentyl, n-hexyl, n-octyl, n-nonyl, n-decyl, and 2-ethylhexyl; monovalent saturated cyclic hydrocarbon groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; and aryl groups such as phenyl, naphthyl and anthracenyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

The divalent hydrocarbon groups may be straight, branched or cyclic. Examples thereof include straight or branched alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15 -diyl, hexadecane-1,16-diyl, and heptadecane-1,17-diyl; divalent saturated cyclic hydrocarbon groups such as cyclopentanediyl, cyclohexanediyl, norbornanediyl and adamantanediyl; and divalent unsaturated cyclic hydrocarbon groups such as phenylene and naphthylene. Some hydrogen on these groups may be substituted by an alkyl moiety such as methyl, ethyl, propyl, n-butyl or t-butyl; some hydrogen may be substituted by a moiety containing a heteroatom such as oxygen, sulfur, nitrogen or halogen; or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Of the heteroatoms, oxygen is preferred.

Of the PAGs having formula (2), those having formula (2') are preferred.

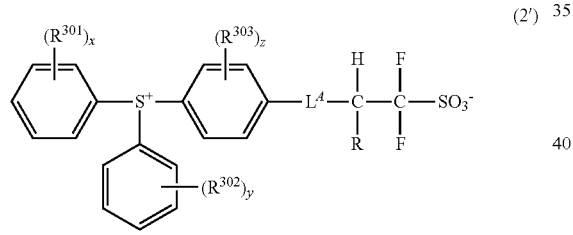

(2')

In formula (2'), $L^A$ is as defined above. R is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon groups may be straight, branched or cyclic, and examples thereof are as exemplified above for $R^{107}$. The subscripts x and y are each independently an integer of 0 to 5, and z is an integer of 0 to 4.

Examples of the PAG having formula (2) are shown below, but not limited thereto. Notably, R is as defined above.

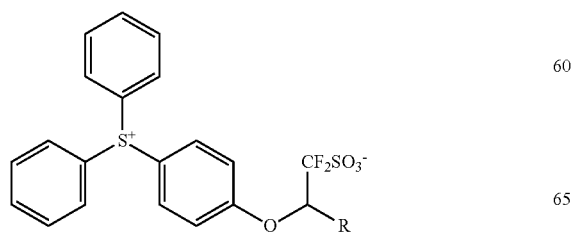

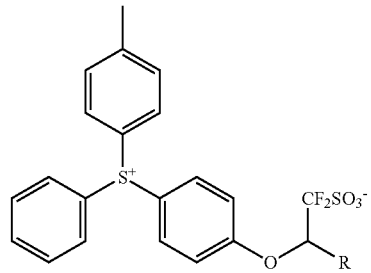

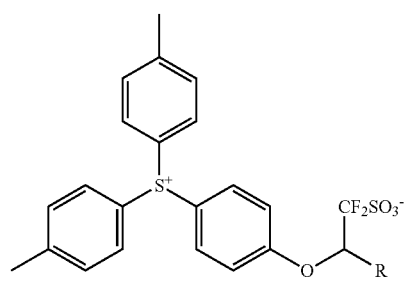

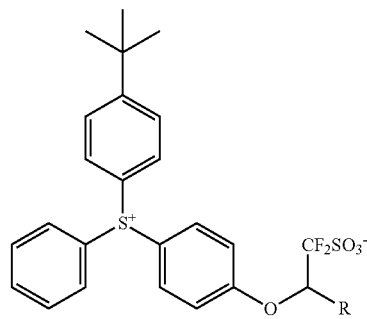

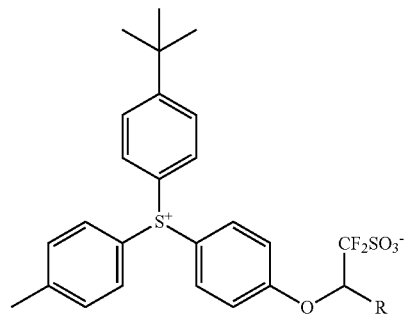

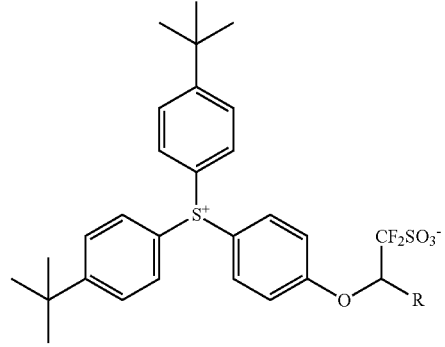

121
-continued
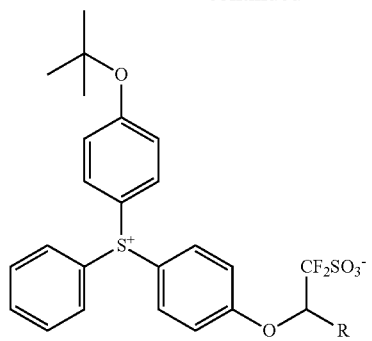
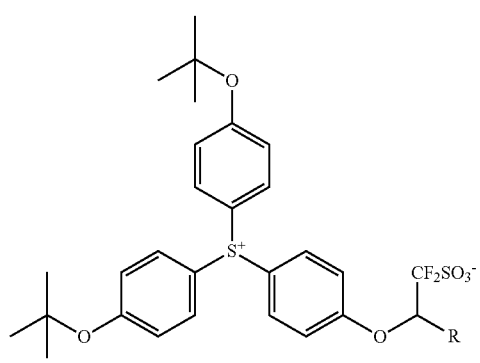
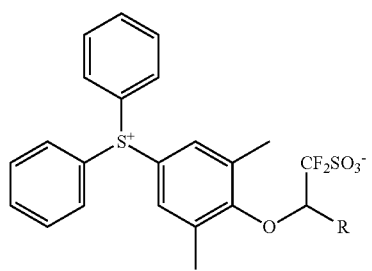
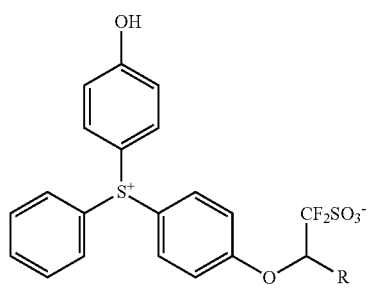
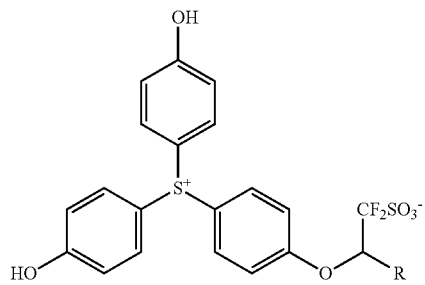
122
-continued
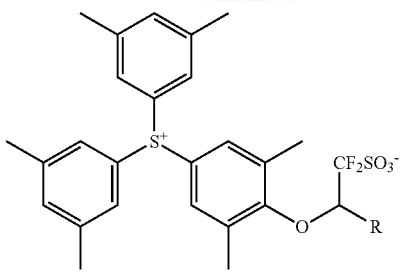
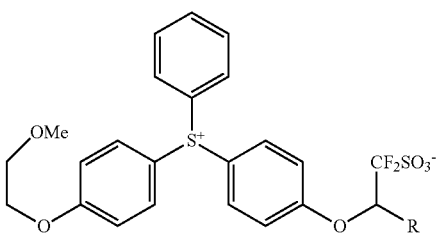
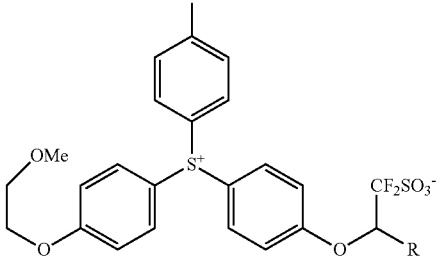
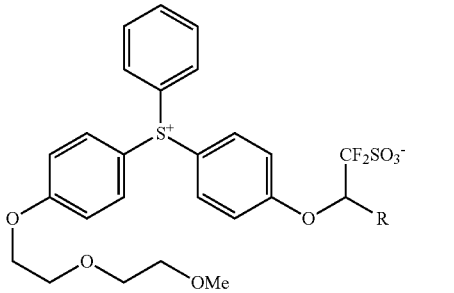
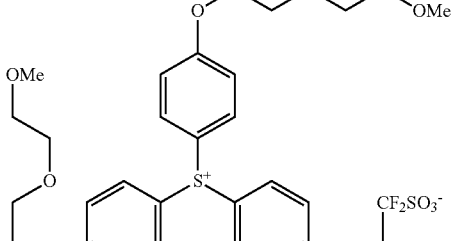
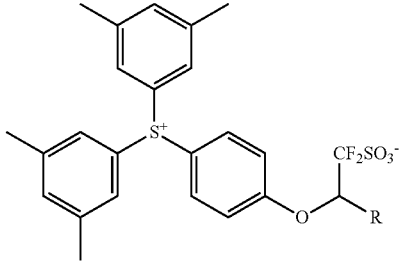

123
-continued
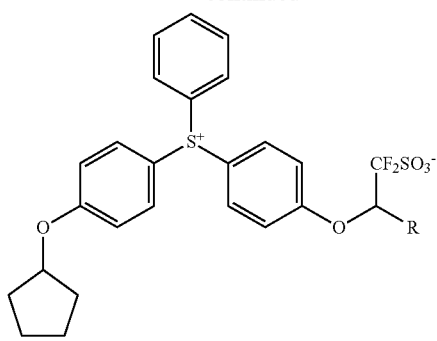
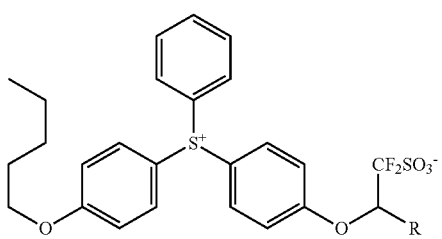
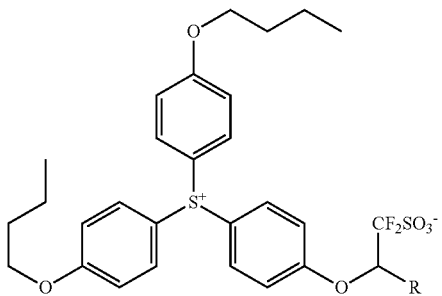
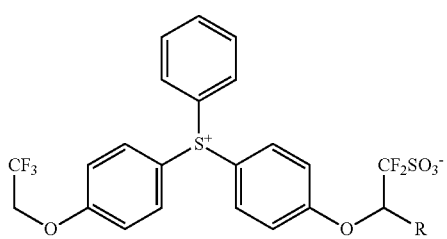
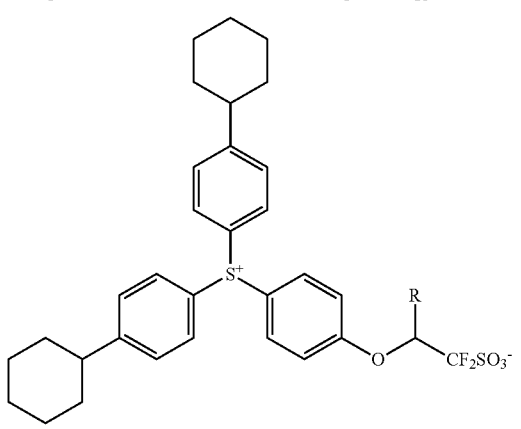
124
-continued
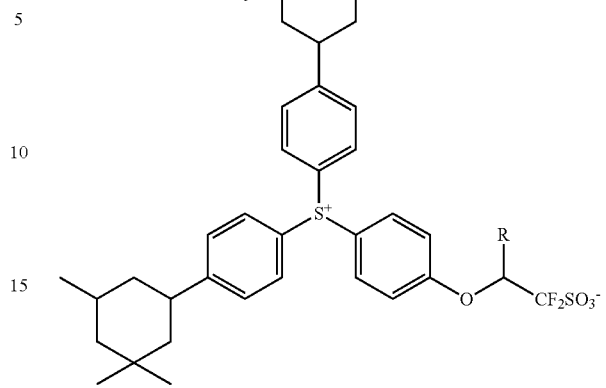
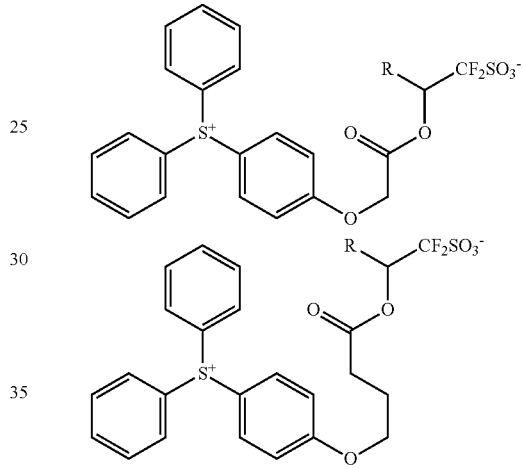
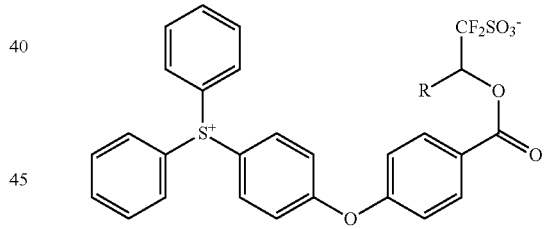
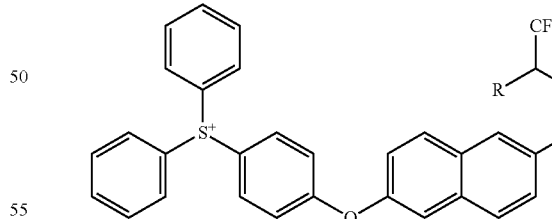
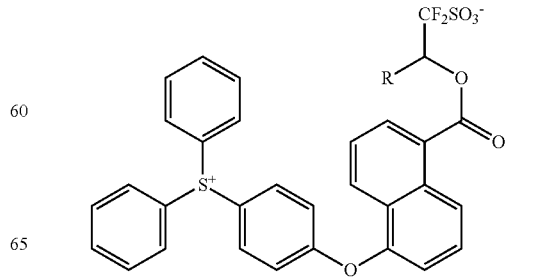

-continued

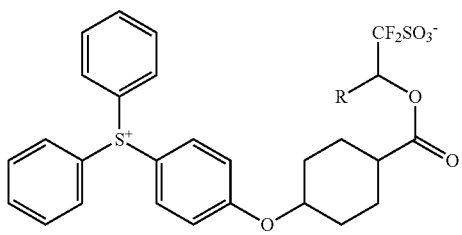

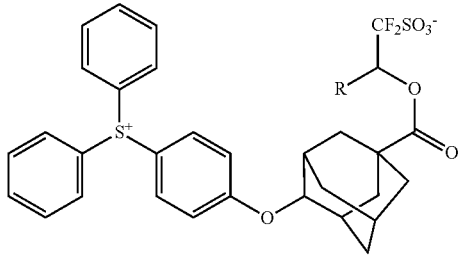

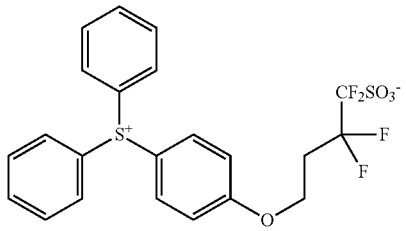

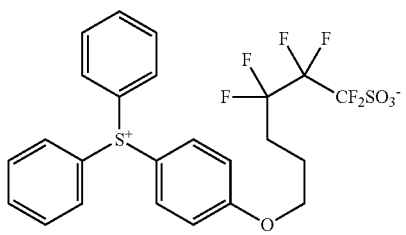

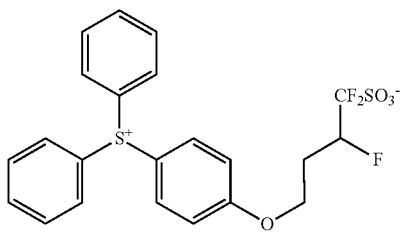

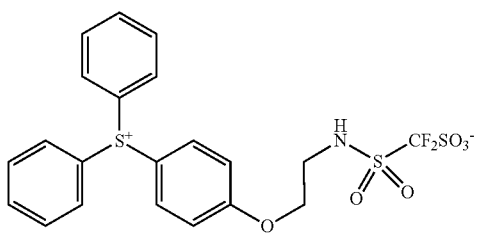

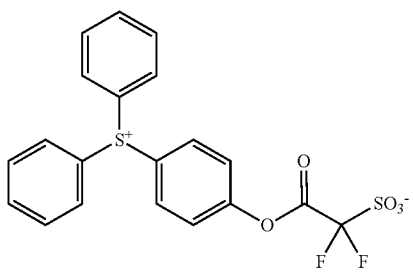

-continued

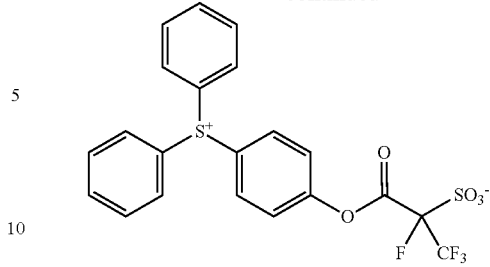

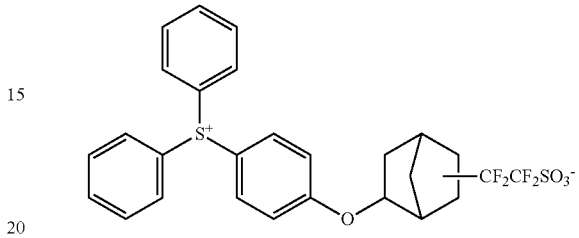

Of the foregoing PAGs, those having an anion of formula (1A') or (1D) are especially preferred because of reduced acid diffusion and high solubility in the resist solvent. Also those having an anion of formula (2') are especially preferred because of extremely reduced acid diffusion.

Also a sulfonium or iodonium salt having an iodized or brominated aromatic ring-containing anion may be used as the PAG. Suitable are sulfonium and iodonium salts having the formulae (3-1) and (3-2).

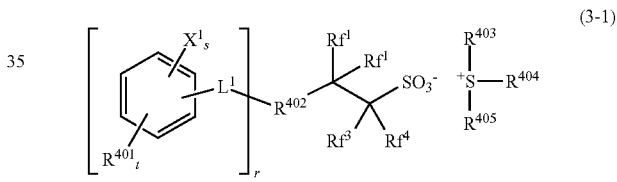
(3-1)

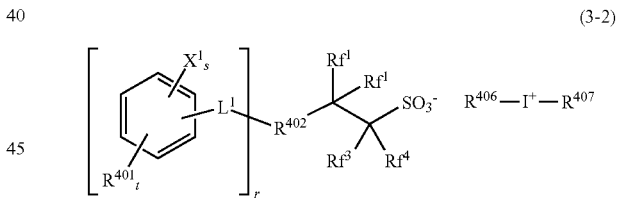
(3-2)

In formulae (3-1) and (3-2), $X^1$ is iodine or bromine, and may be the same or different when s is 2 or more.

$L^1$ is a single bond, ether bond, ester bond, or a $C_1$-$C_6$ alkanediyl group which may contain an ether bond or ester bond. The alkanediyl group may be straight, branched or cyclic.

$R^{401}$ is a hydroxyl group, carboxyl group, fluorine, chlorine, bromine, amino group, or a $C_1$-$C_{20}$ alkyl, $C_1$-$C_{20}$ alkoxy, $C_2$-$C_{20}$ alkoxycarbonyl, $C_2$-$C_{20}$ acyloxy or $C_1$-$C_{20}$ alkylsulfonyloxy group, which may contain fluorine, chlorine, bromine, hydroxyl, amino or $C_1$-$C_{10}$ alkoxy moiety, or —NR$^{401A}$—C(=O)—R—NR$^{401A}$—C(O)—O—R$^{401B}$, wherein $R^{401A}$ is hydrogen, or a $C_1$-$C_6$ alkyl group which may contain halogen, hydroxy, $C_1$-$C_6$ alkoxy, $C_2$-$C_6$ acyl or $C_2$-$C_6$ acyloxy moiety, $R^{401B}$ is a $C_1$-$C_{16}$ alkyl, $C_2$-$C_{16}$ alkenyl or $C_6$-$C_{12}$ aryl group, which may contain halogen, hydroxy, $C_1$-$C_6$ alkoxy, $C_2$-$C_6$ acyl or $C_2$-$C_6$ acyloxy moiety. The foregoing alkyl, alkoxy, alkoxycarbonyl, acyloxy, acyl and alkenyl groups may be straight, branched or cyclic.

When t is 2 or more, groups $R^{401}$ may be the same or different. Of these, $R^{401}$ is preferably hydroxyl, —$NR^{401A}$—C(=O)—$R^{401B}$, —$NR^{401A}$—C(=O)—O—$R^{401B}$, fluorine, chlorine, bromine, methyl or methoxy.

$R^{402}$ is a single bond or a $C_1$-$C_{20}$ divalent linking group when r=1, or a $C_1$-$C_{20}$ tri- or tetravalent linking group when r=2 or 3, the linking group optionally containing an oxygen, sulfur or nitrogen atom.

$Rf^1$ to $Rf^4$ are each independently hydrogen, fluorine or trifluoromethyl, at least one of $Rf^1$ to $Rf^4$ is fluorine or trifluoromethyl, or $Rf^1$ and $Rf^2$, taken together, may form a carbonyl group. Preferably, both $Rf^3$ and $Rf^4$ are fluorine.

$R^{403}$, $R^{404}$, $R^{405}$, $R^{406}$ and $R^{407}$ are each independently a $C_1$-$C_{20}$ monovalent hydrocarbon group which may contain a heteroatom. Any two of $R^{403}$, $R^{404}$ and $R^{405}$ may bond together to form a ring with the sulfur atom to which they are attached. The monovalent hydrocarbon group may be straight, branched or cyclic, and examples thereof include $C_1$-$C_{12}$ alkyl, $C_2$-$C_{12}$ alkenyl, $C_2$-$C_{12}$ alkynyl, $C_6$-$C_{20}$ aryl, and $C_7$-$C_{12}$ aralkyl groups. In these groups, some or all of the hydrogen atoms may be substituted by hydroxyl, carboxyl, halogen, cyano, amide, nitro, mercapto, sultone, sulfone, or sulfonium salt-containing moieties, and some carbon may be replaced by an ether bond, ester bond, carbonyl moiety, carbonate moiety or sulfonic acid ester bond.

In formulae (3-1) and (3-2), r is an integer of 1 to 3, s is an integer of 1 to 5, and t is an integer of 0 to 3, and 1≤s+t≤5. Preferably, s is an integer of 1 to 3, more preferably 2 or 3, and t is an integer of 0 to 2.

Examples of the cation in the sulfonium salt having formula (3-1) include those exemplified above as the cation in the sulfonium salt having formula (1-1). Examples of the cation in the iodonium salt having formula (3-2) include those exemplified above as the cation in the iodonium salt having formula (1-2).

Examples of the anion in the onium salts having formulae (3-1) and (3-2) are shown below, but not limited thereto. Herein $X^1$ is as defined above.

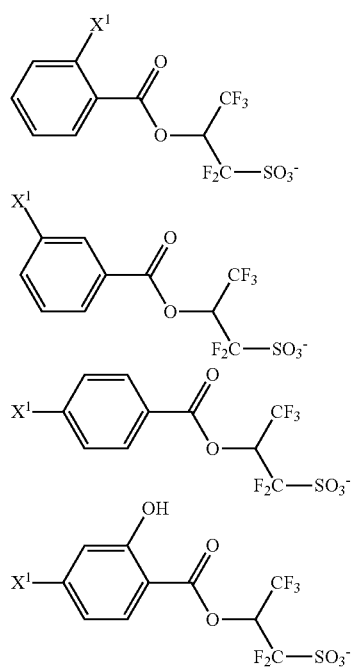

-continued

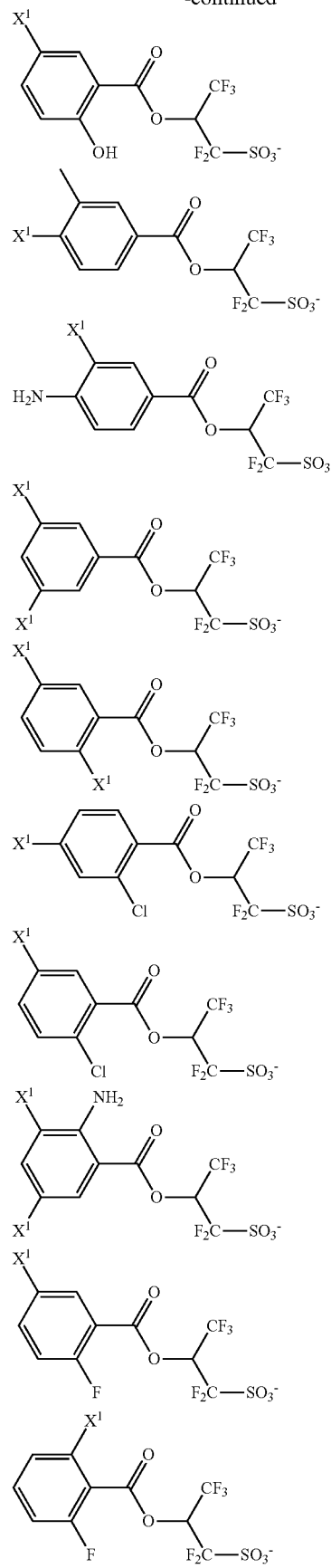

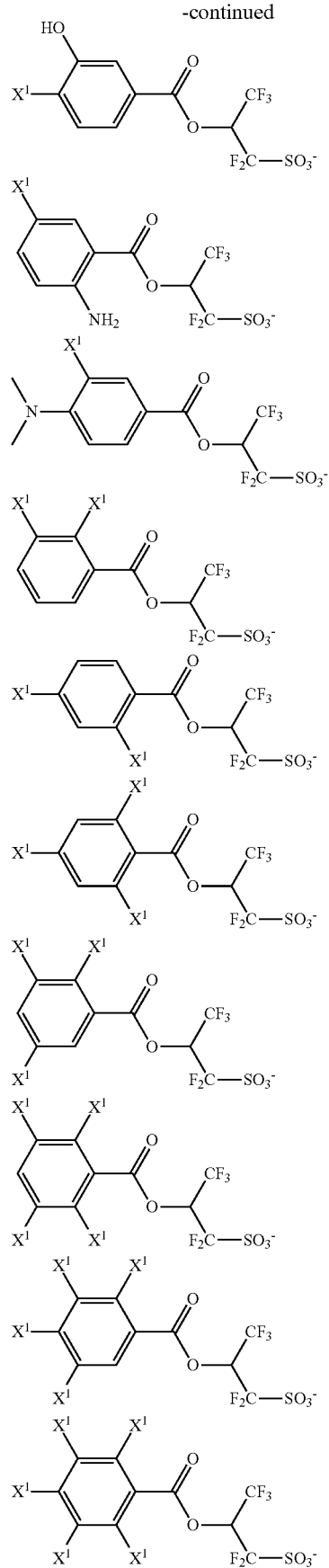
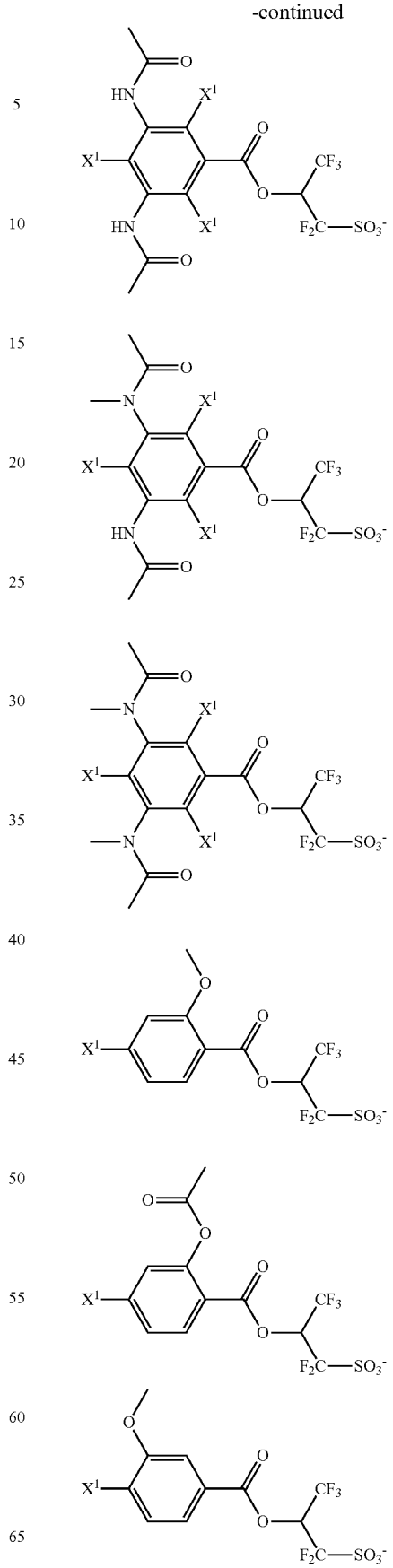

131
-continued
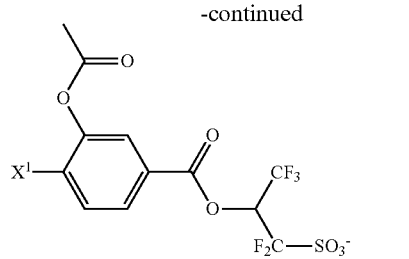
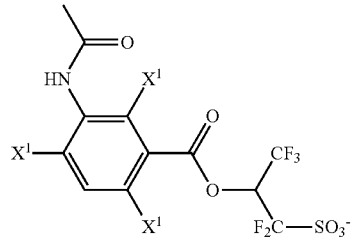
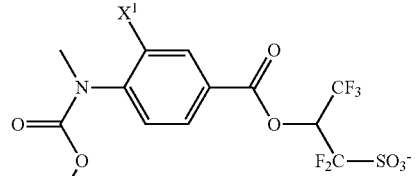
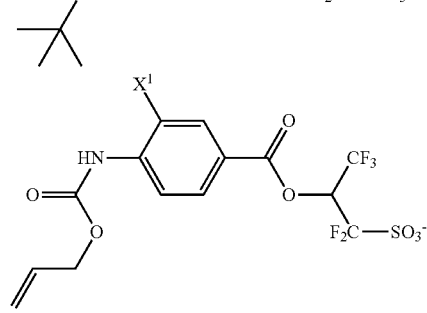
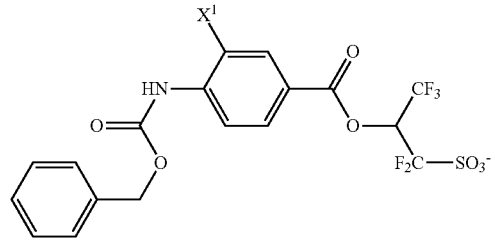
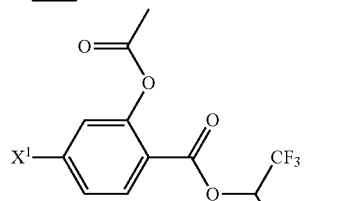
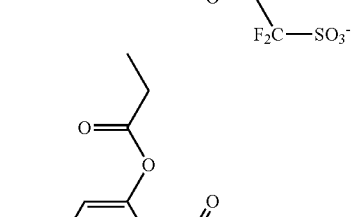
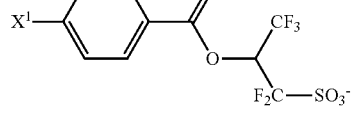
132
-continued
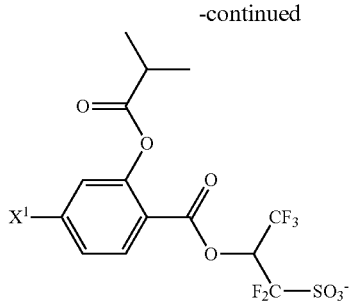
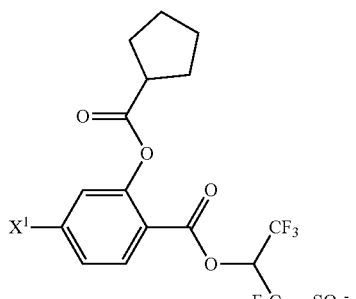
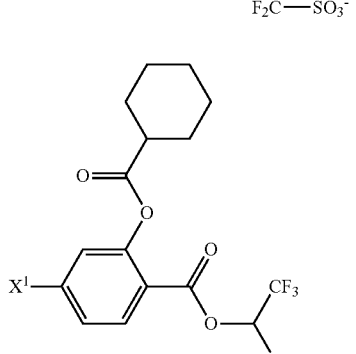
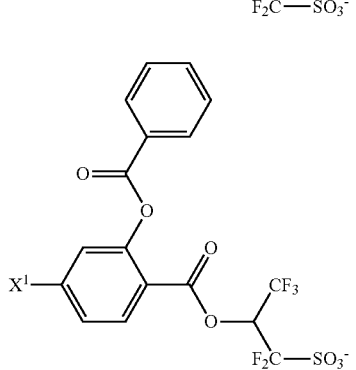
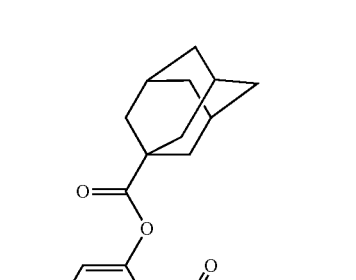
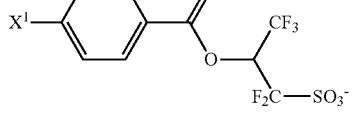

133
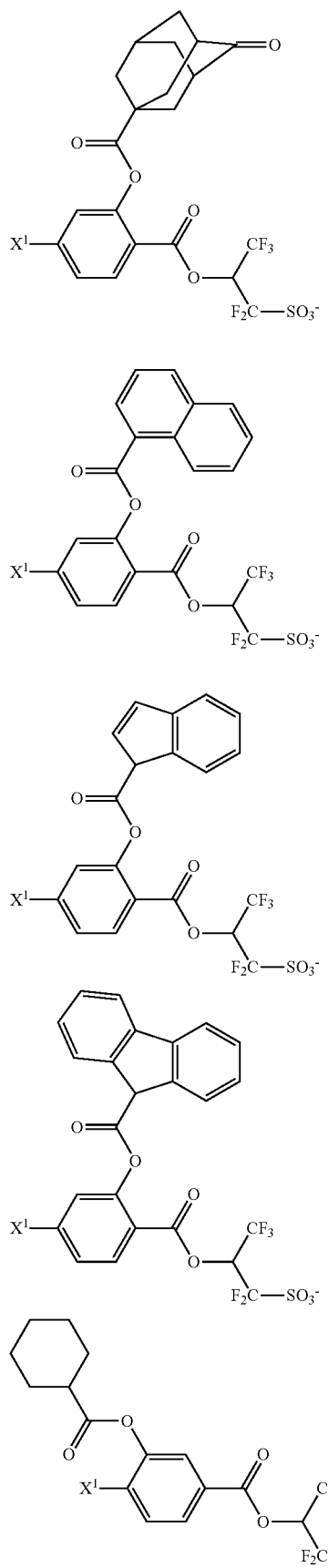
134
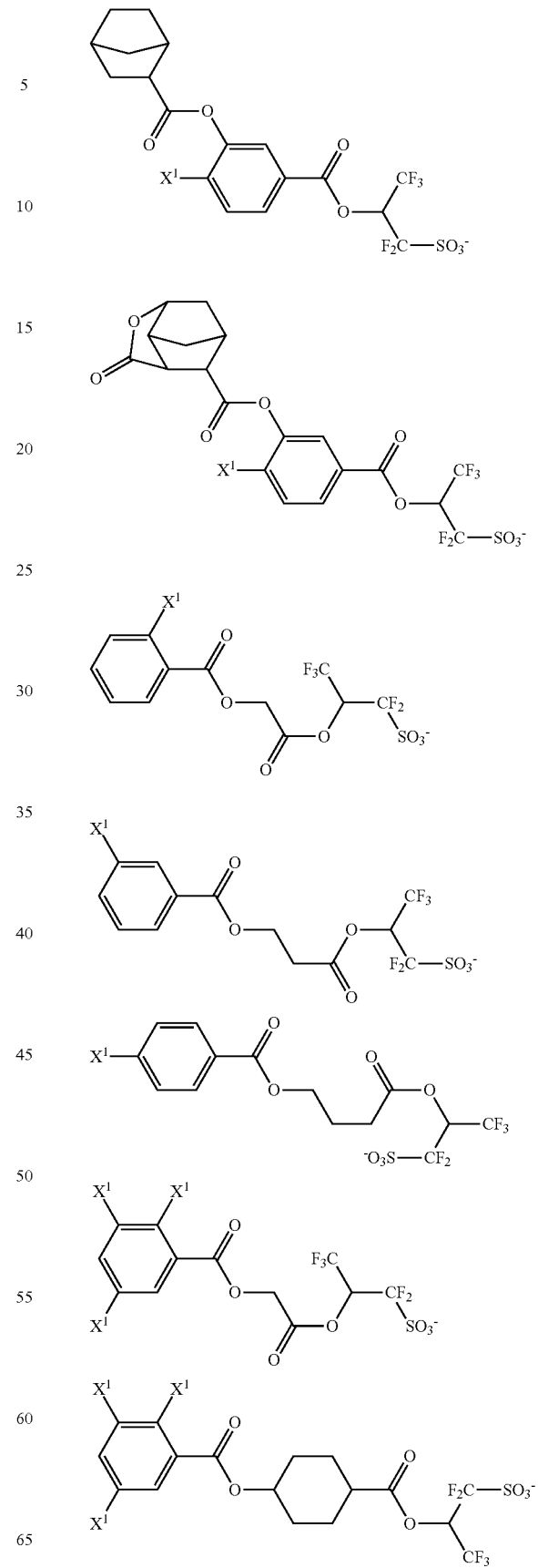

135
-continued
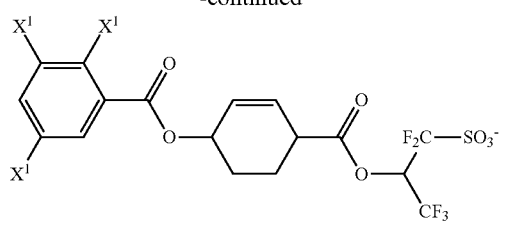
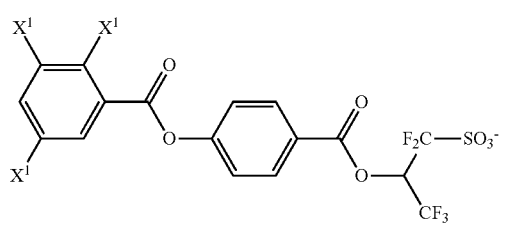
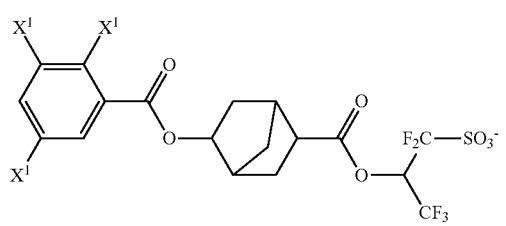
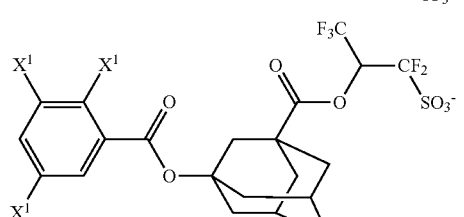
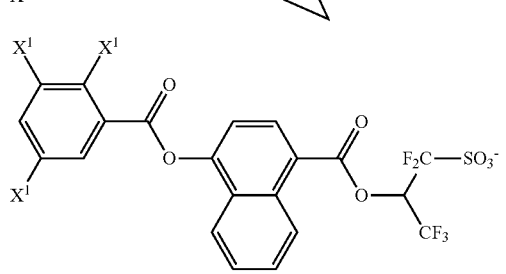
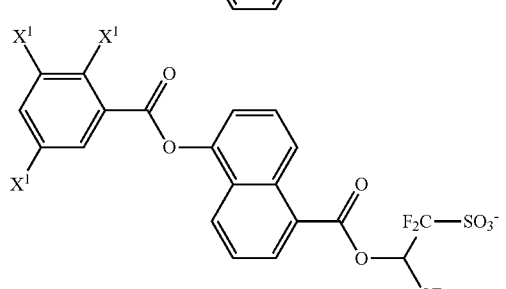
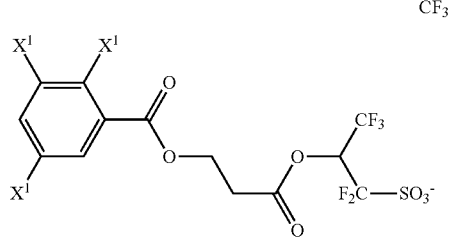
136
-continued
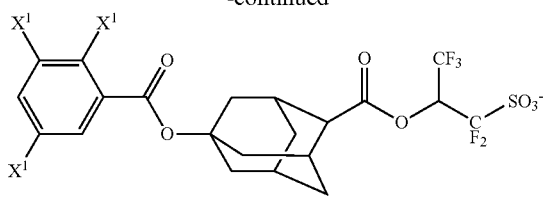
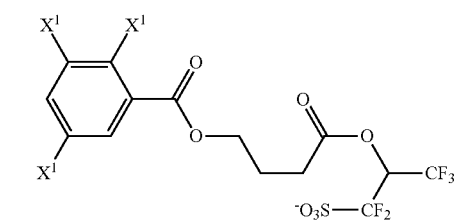
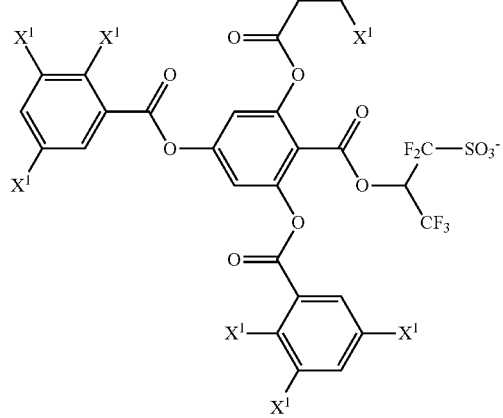
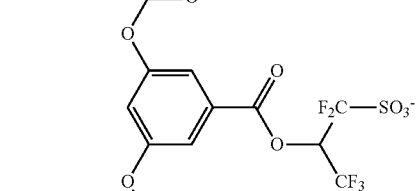
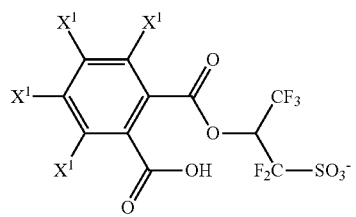

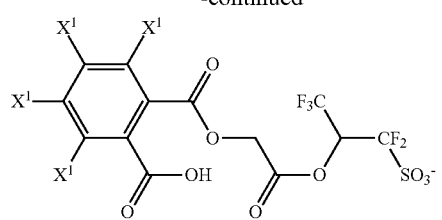
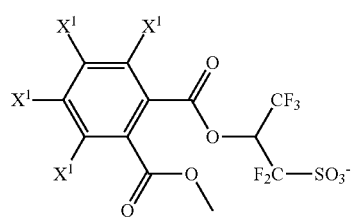
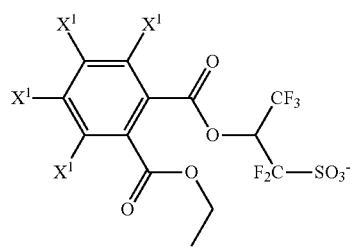
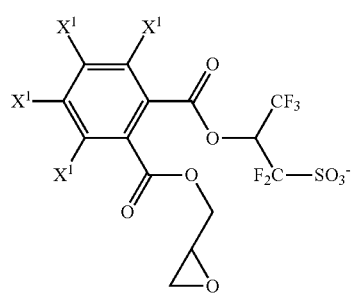
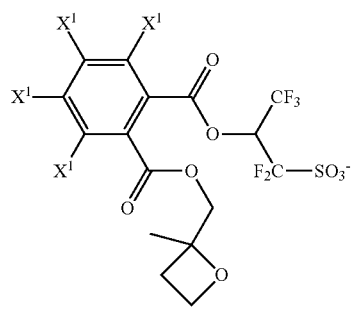
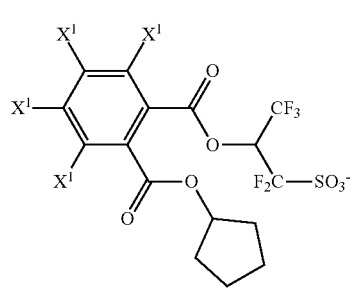
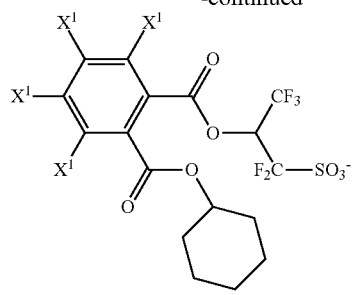
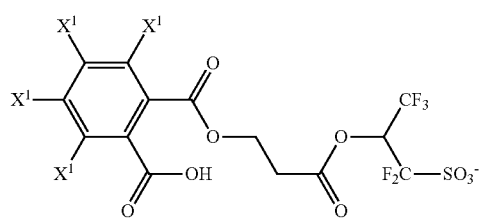
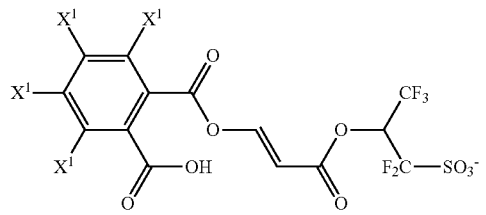
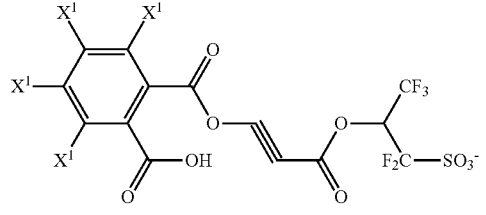
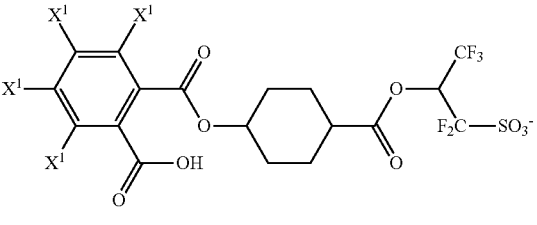
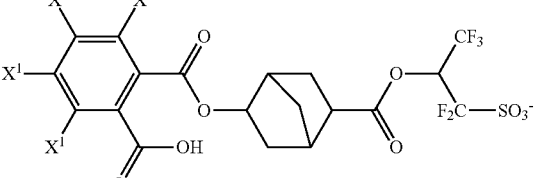
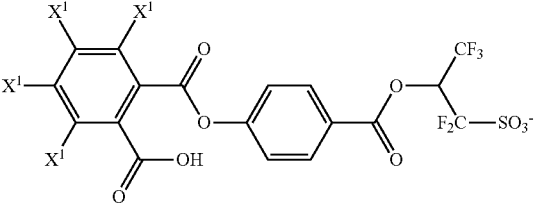

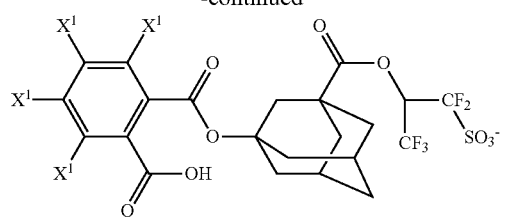
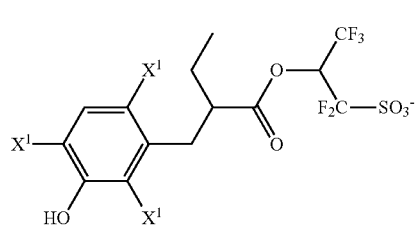
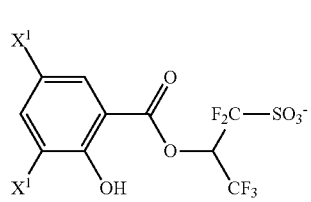
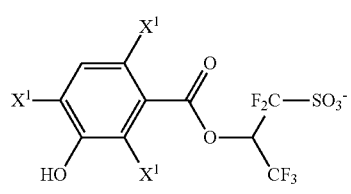
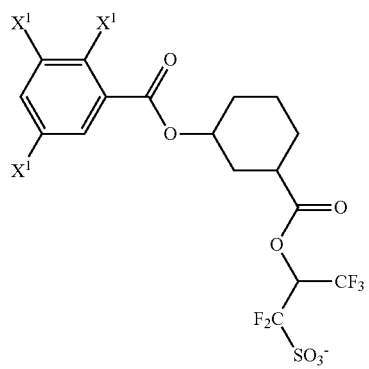
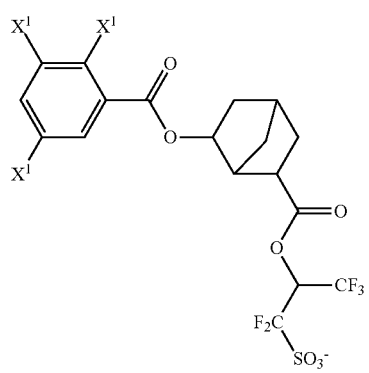
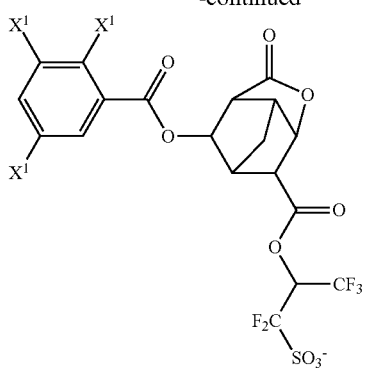
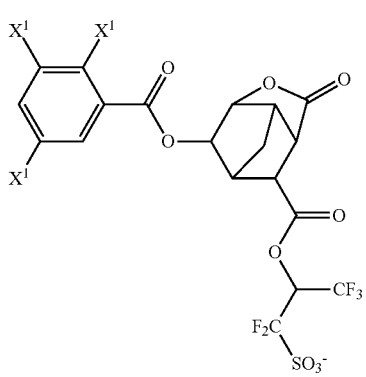
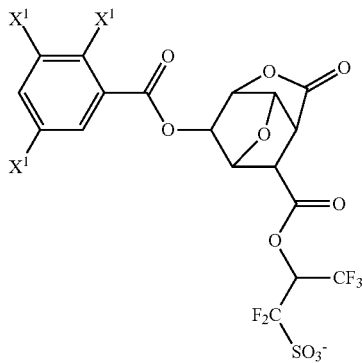
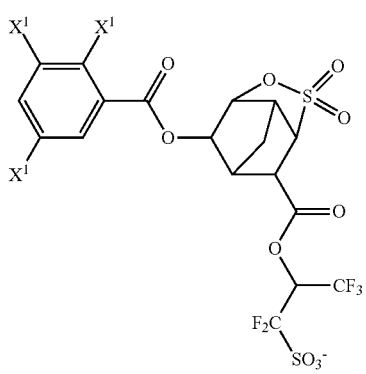

141
-continued
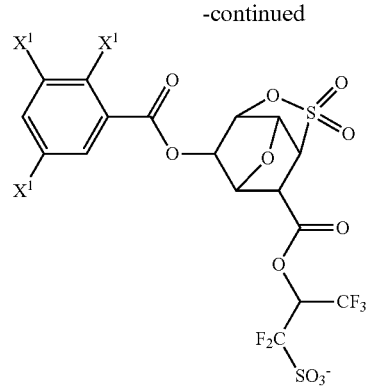
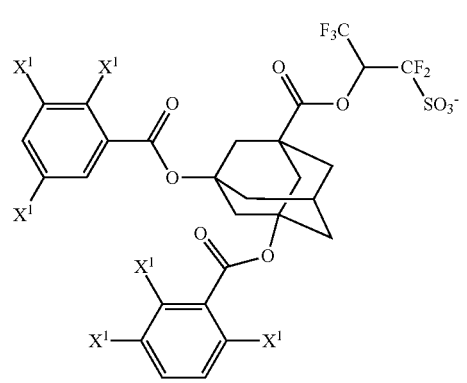
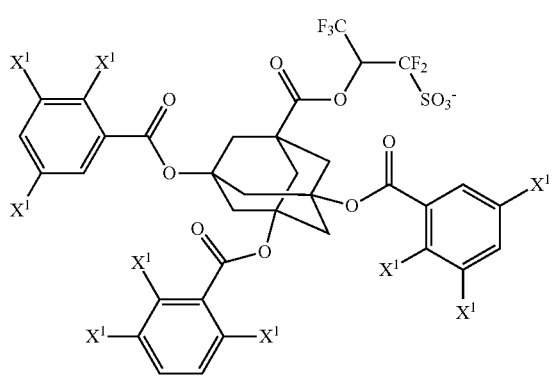
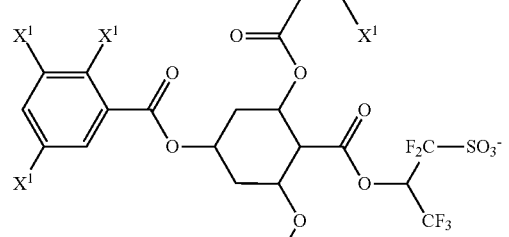
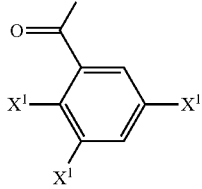
142
-continued
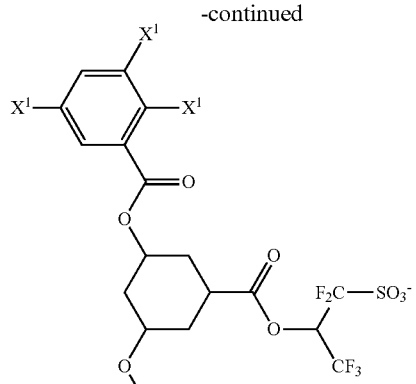
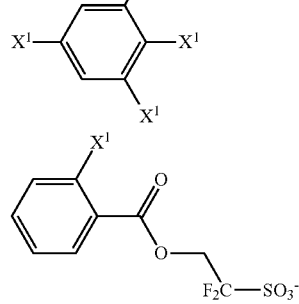
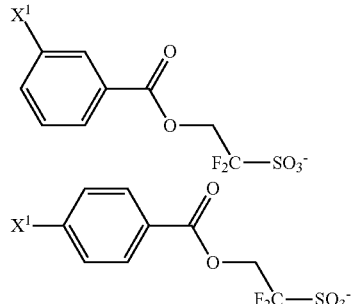
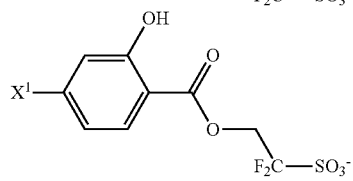
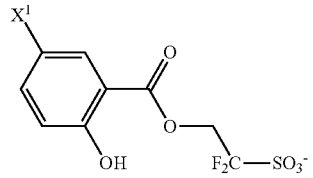
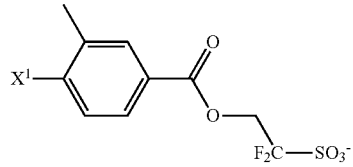
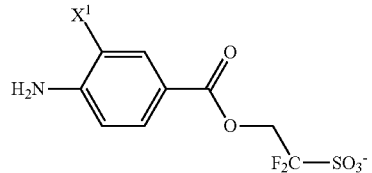

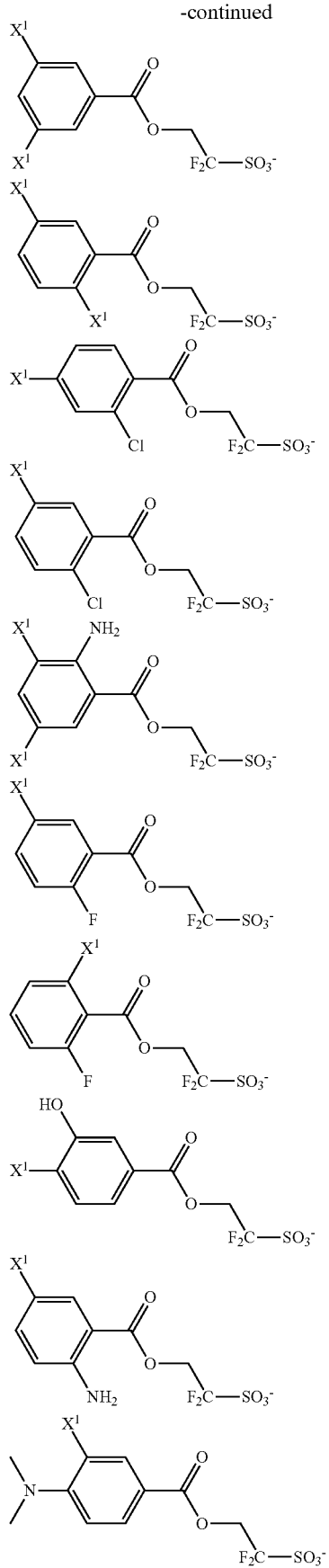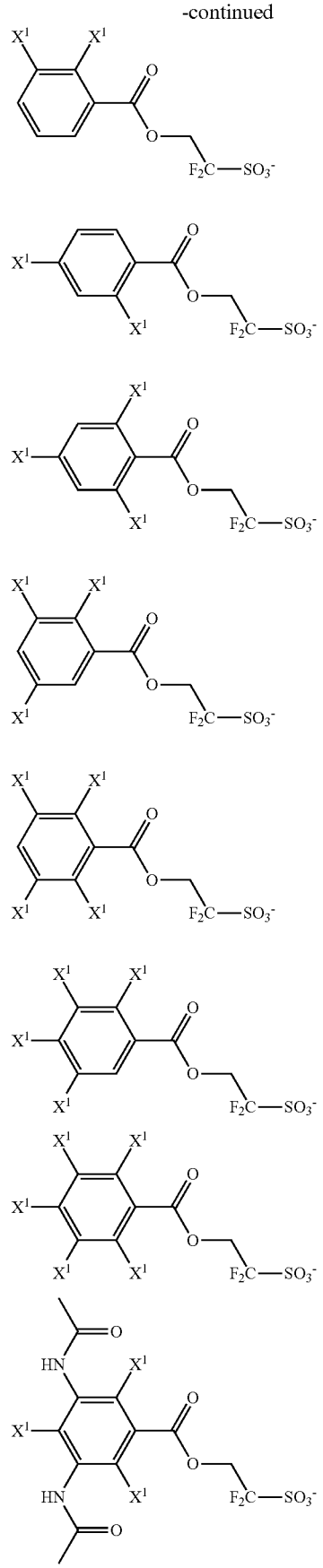

145
-continued
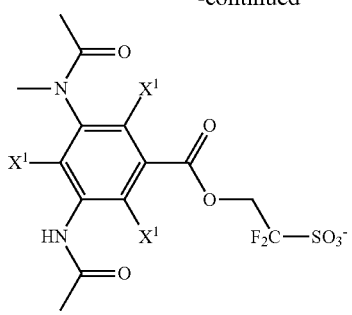
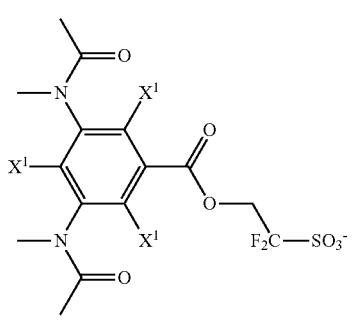
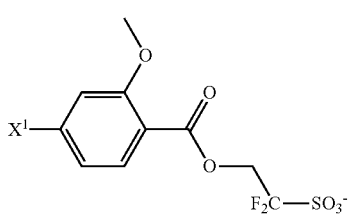
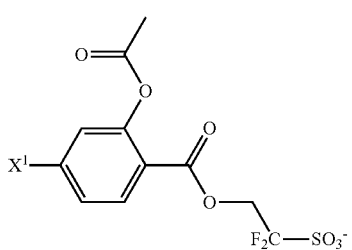
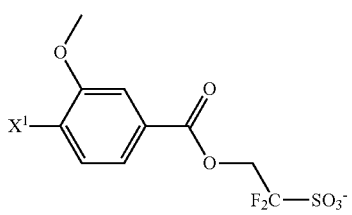
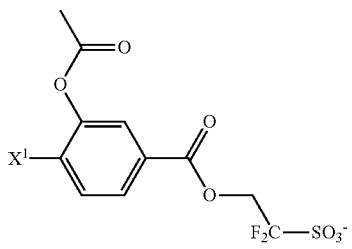
146
-continued
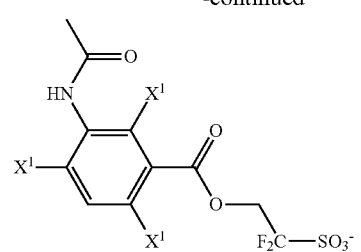
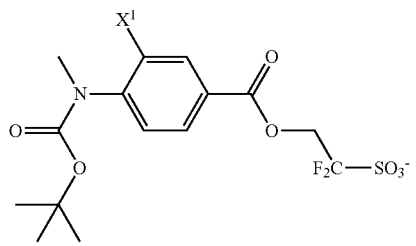
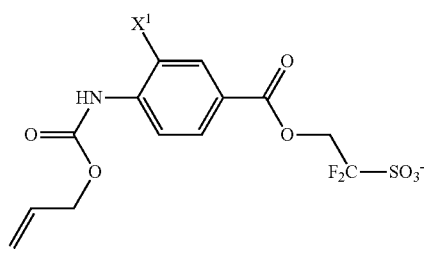
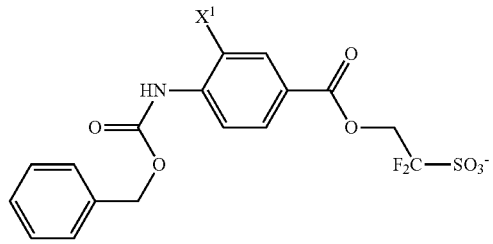
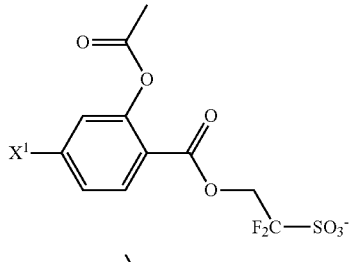
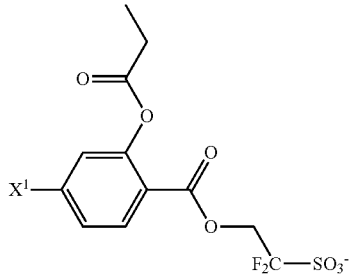

147
-continued
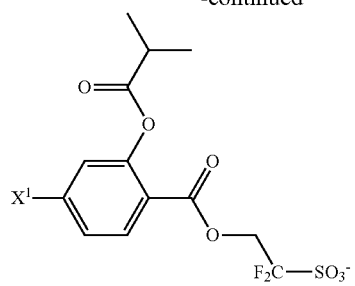
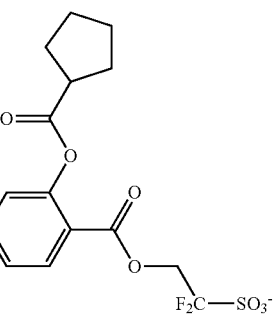
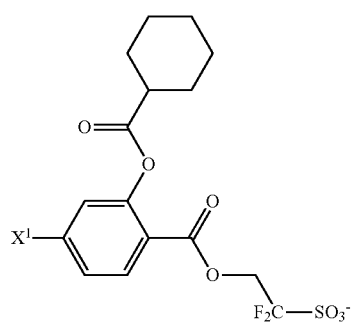
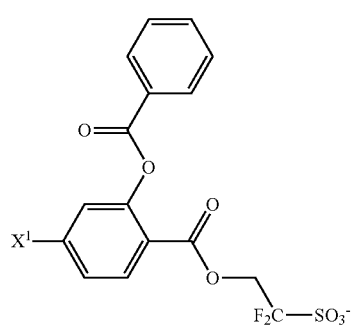
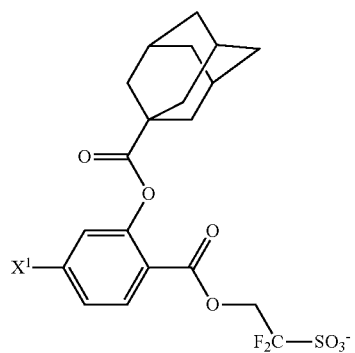
148
-continued
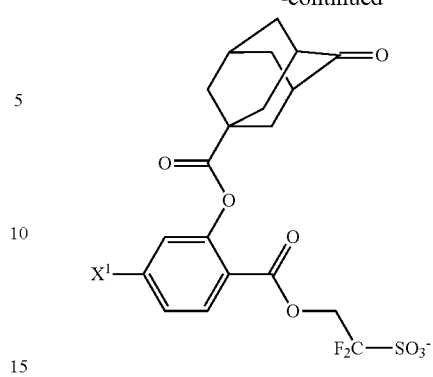
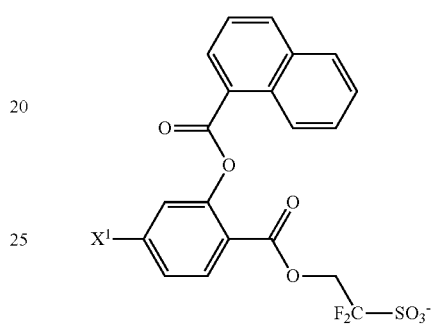
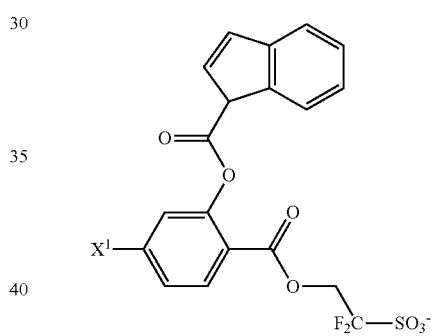
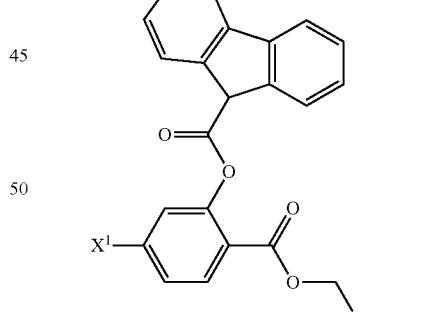
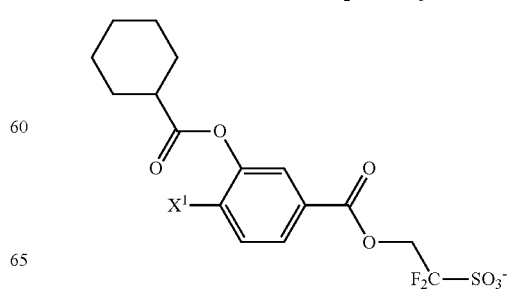

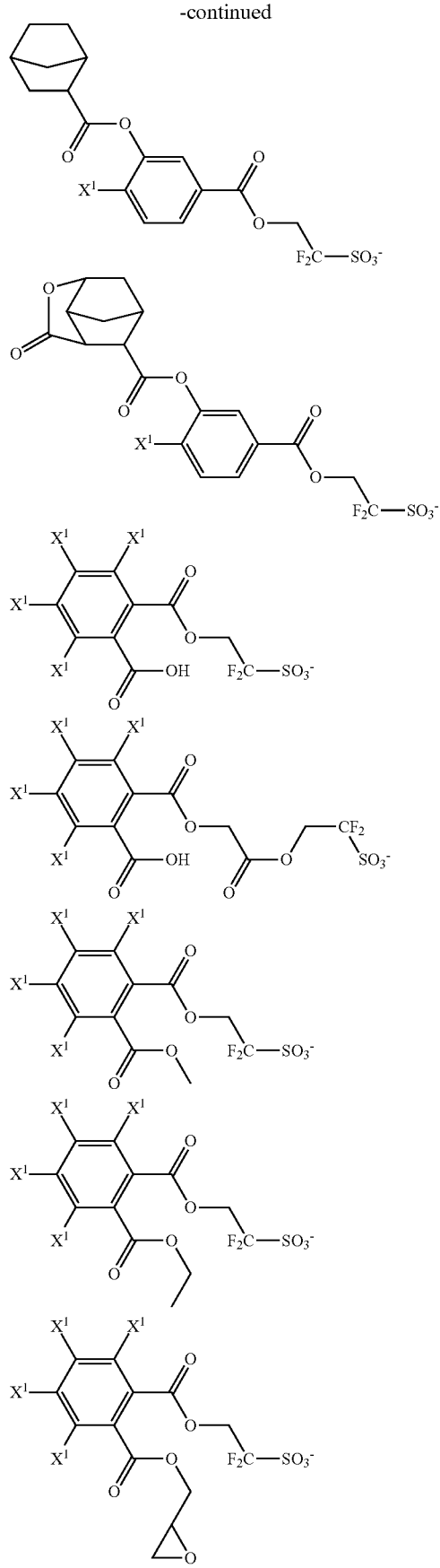
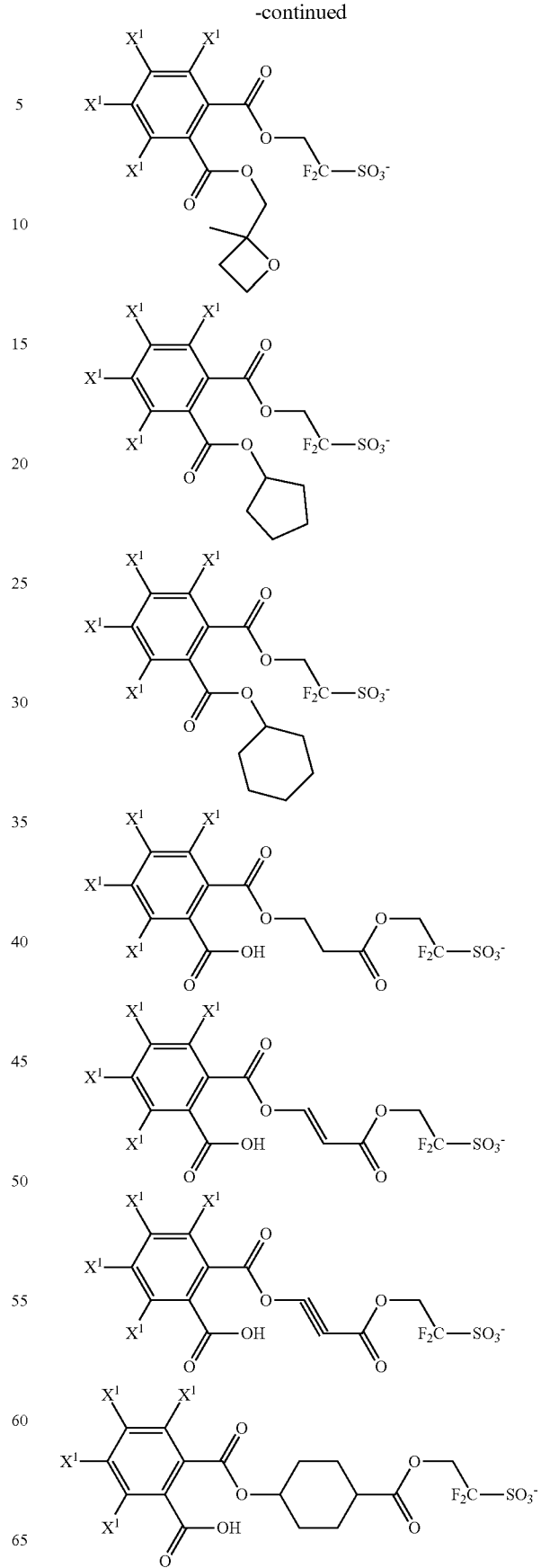

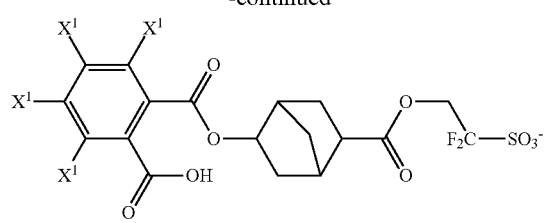
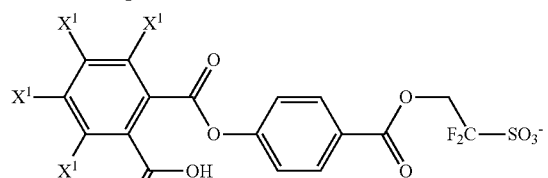
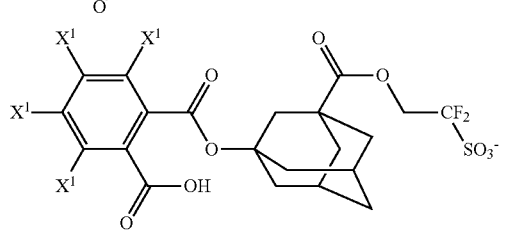
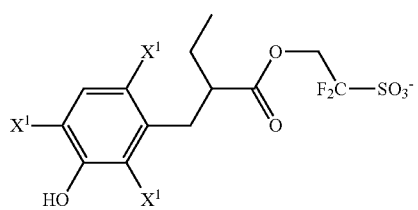
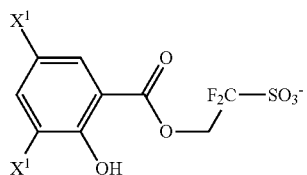
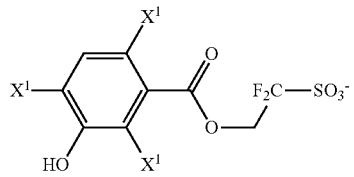
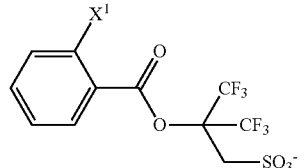
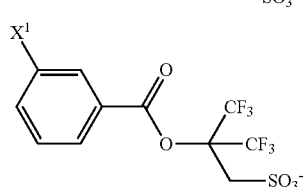
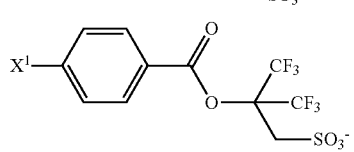
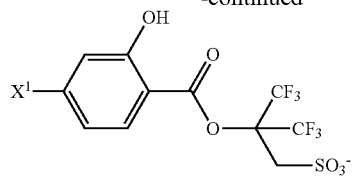
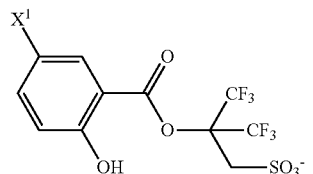
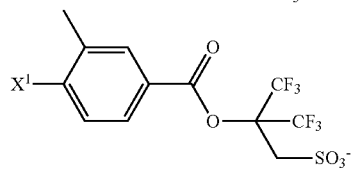
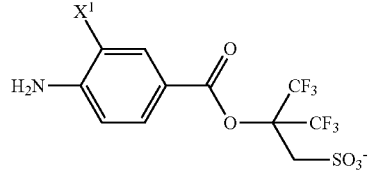
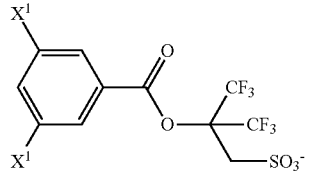
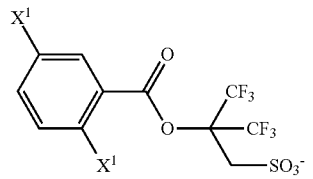
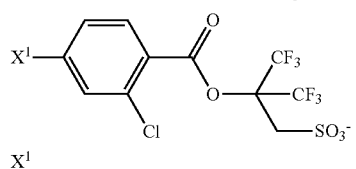
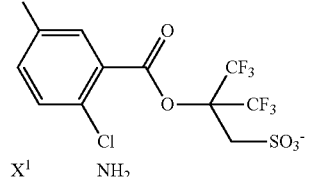
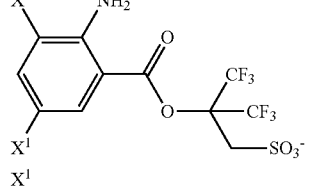
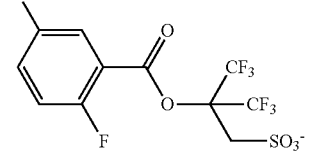

153
-continued
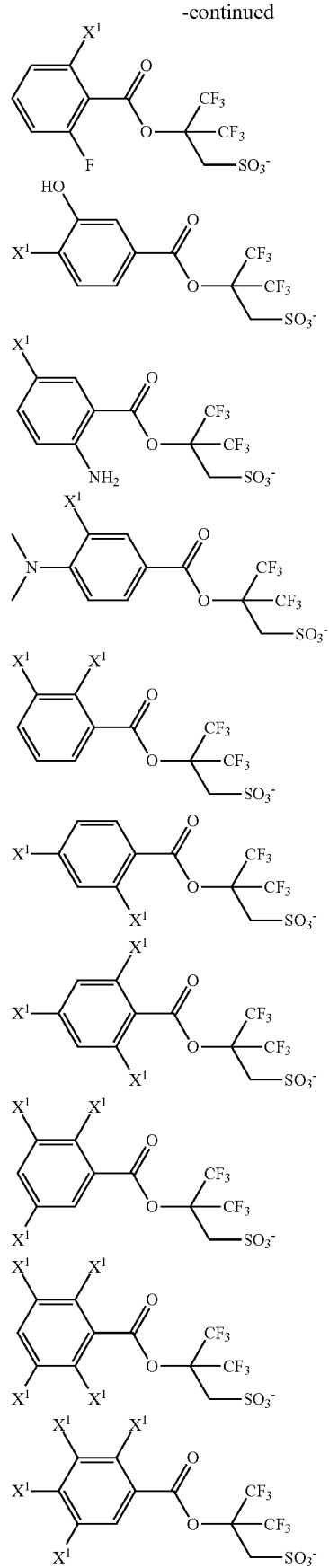
154
-continued
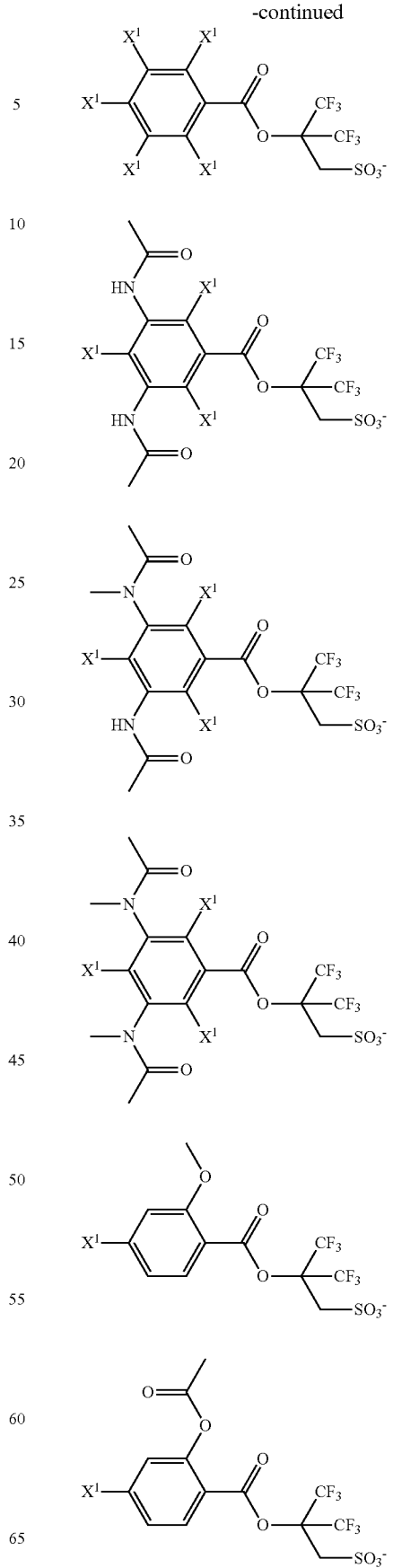

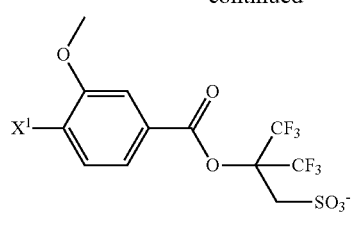
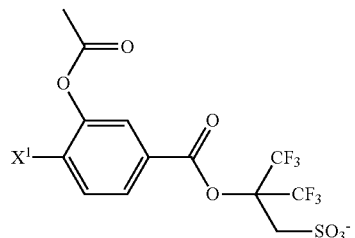
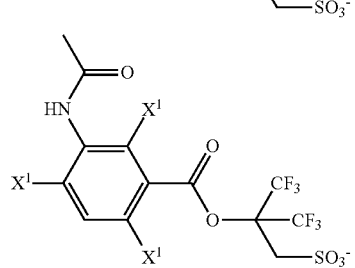
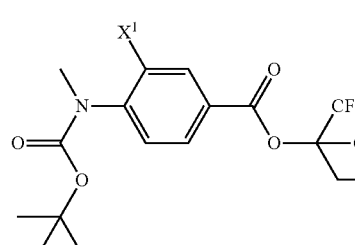
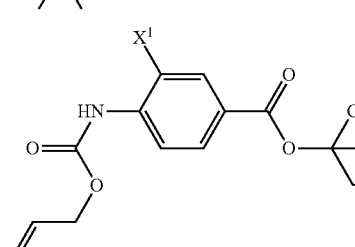
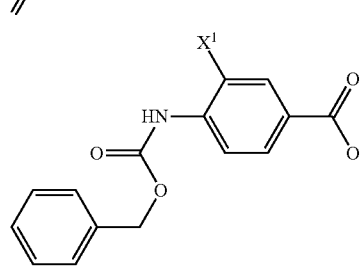
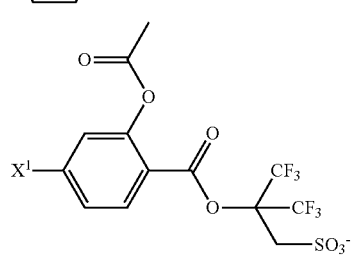
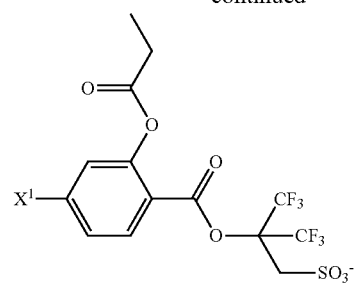
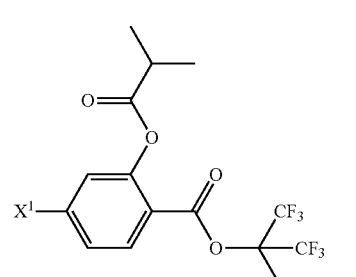
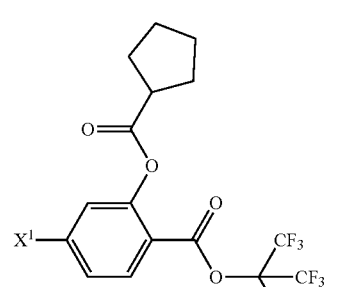
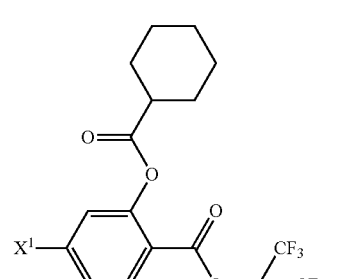
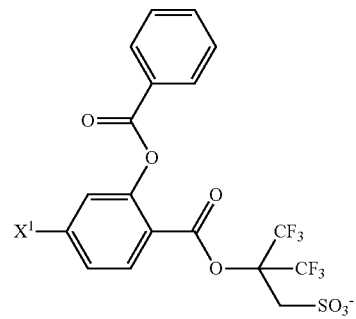

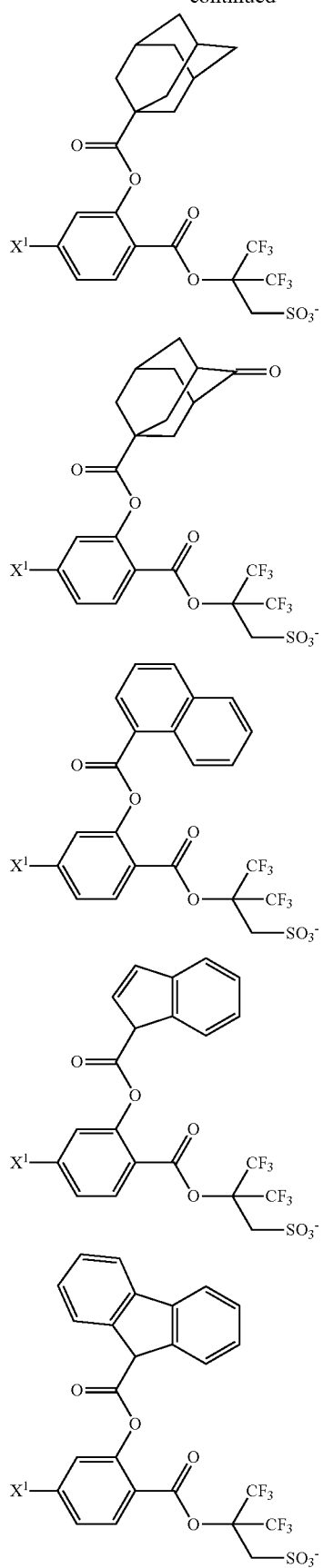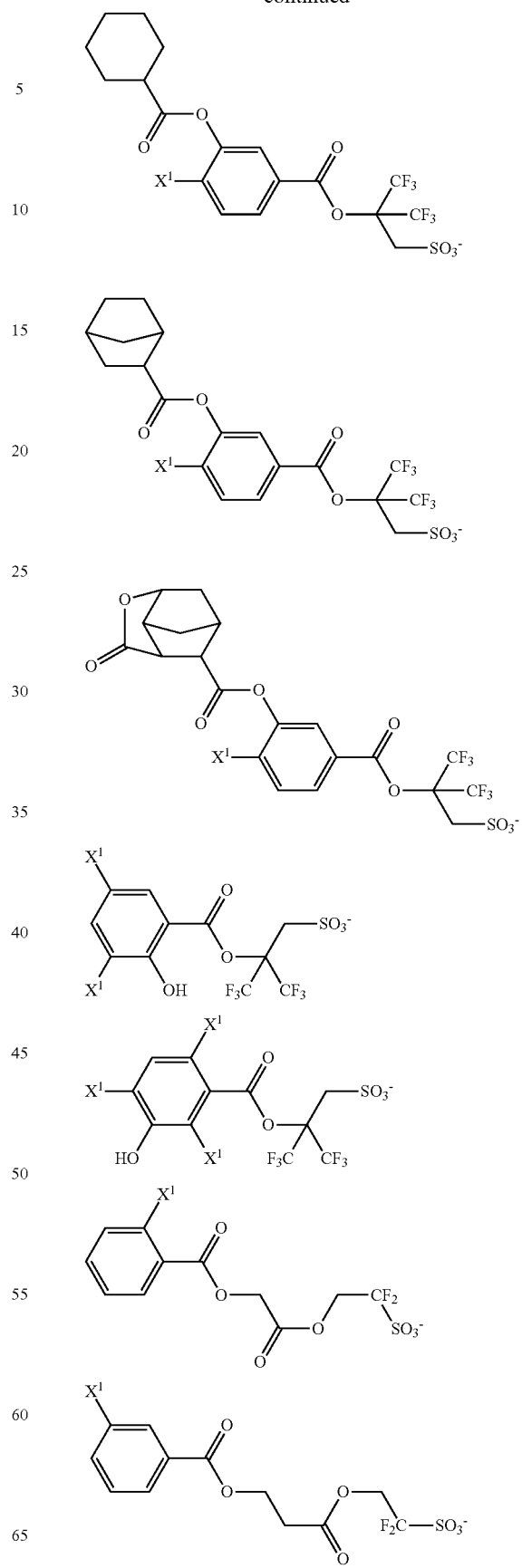

159
-continued
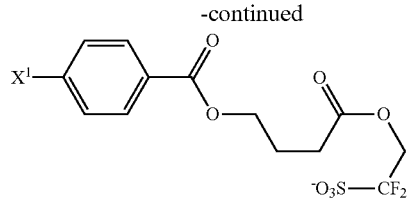
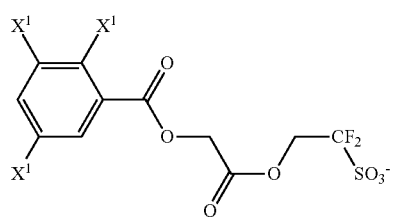
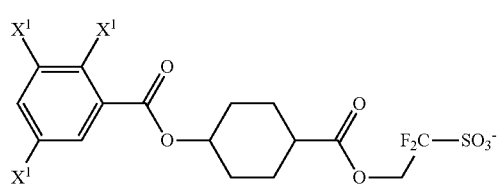
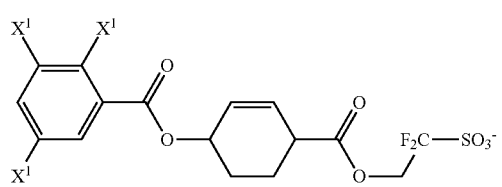
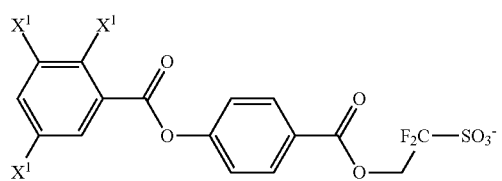
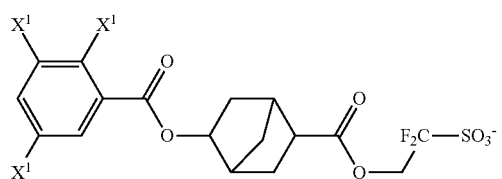
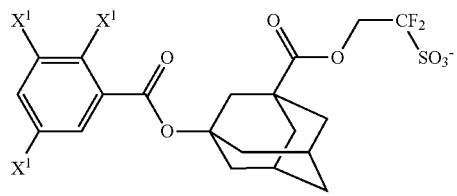
160
-continued
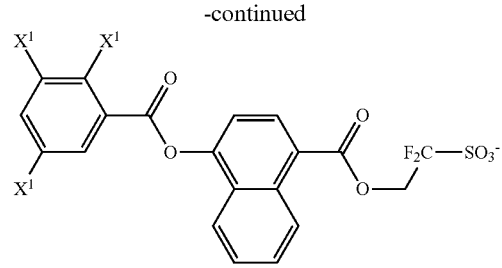
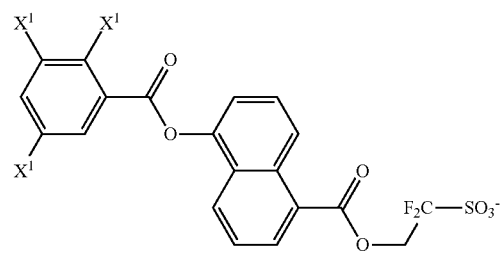
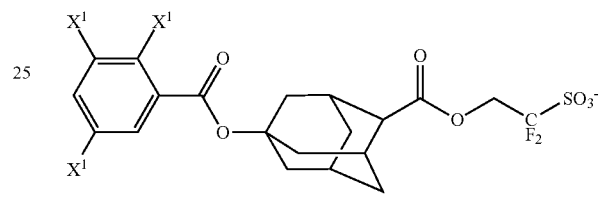
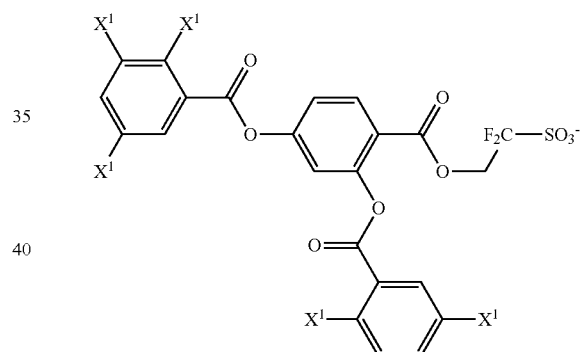
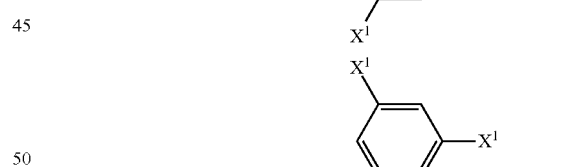
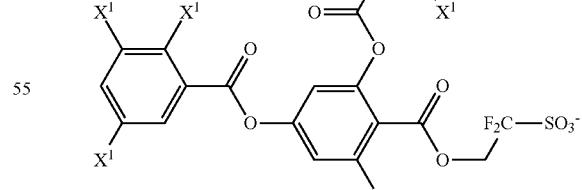
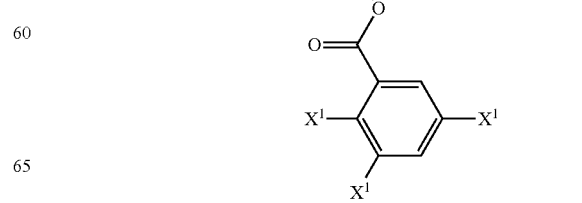

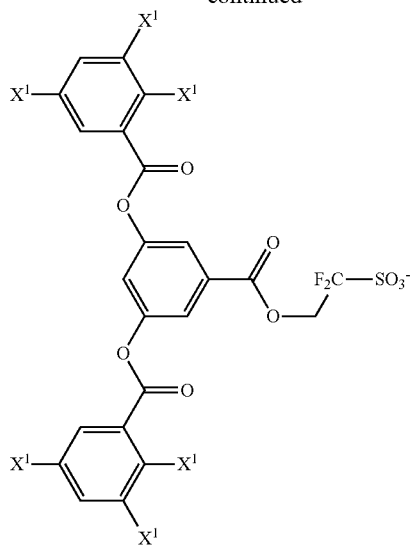
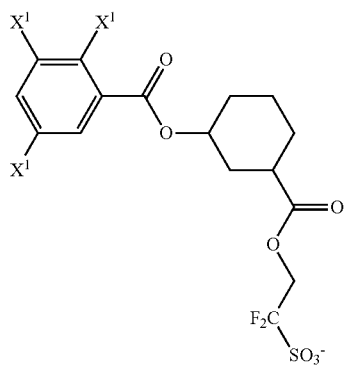
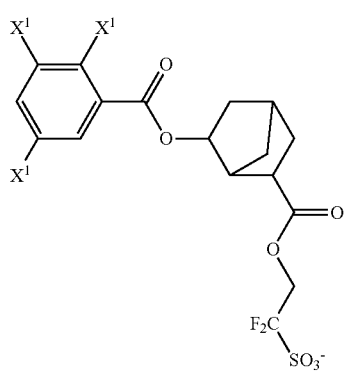
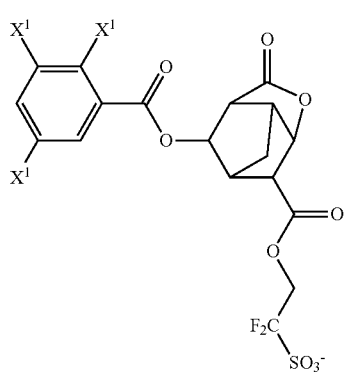
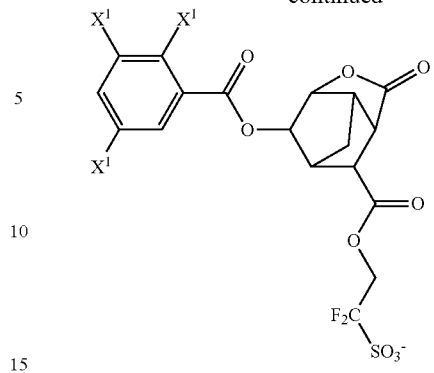
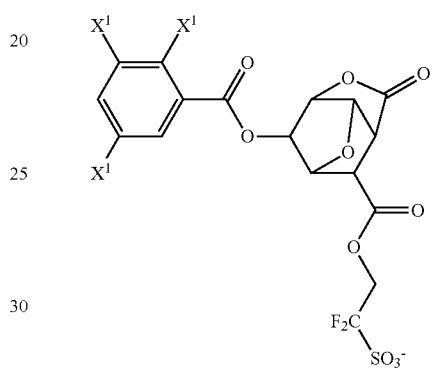
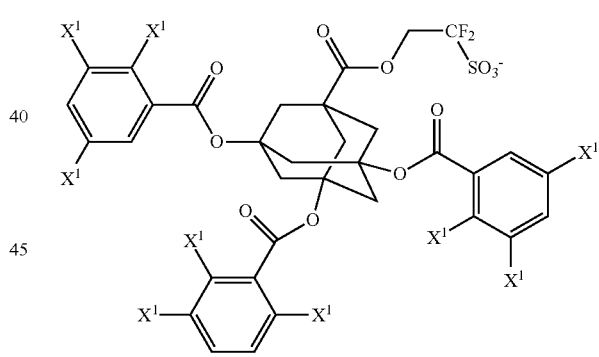
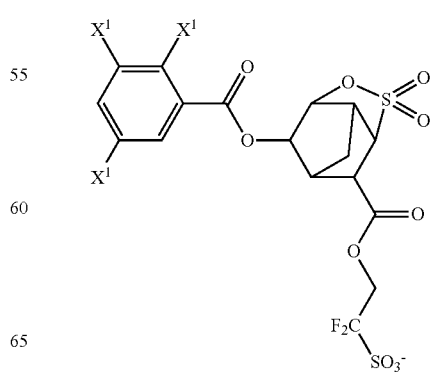

163
-continued
164
-continued
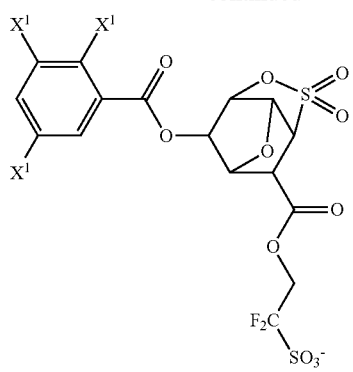
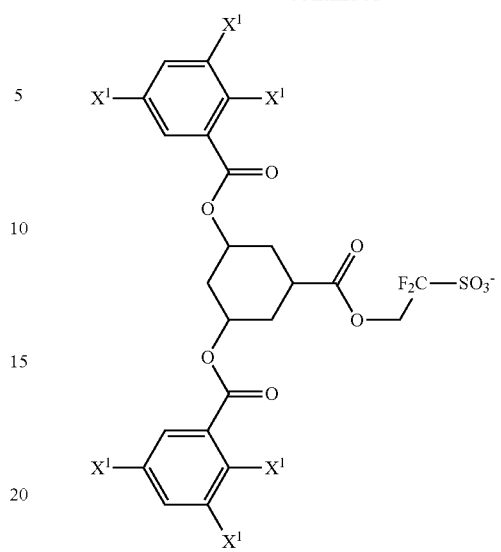
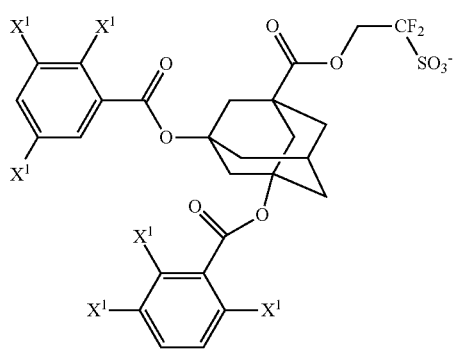
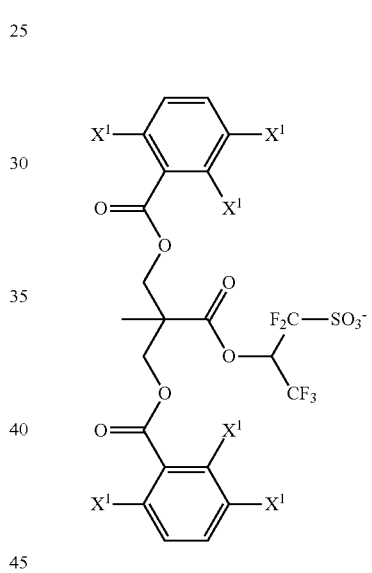
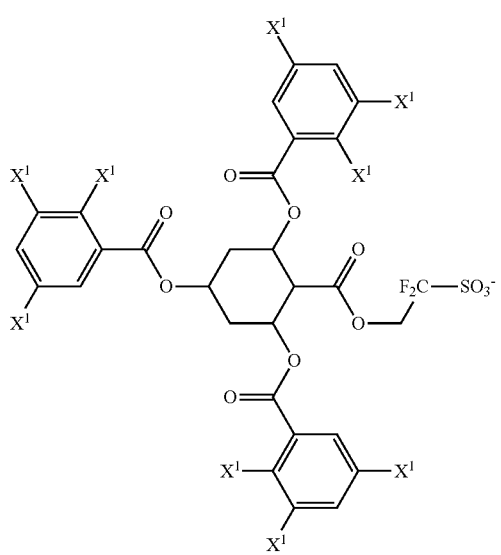
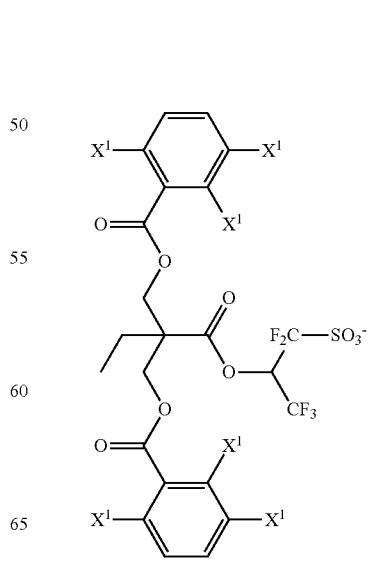

165
-continued
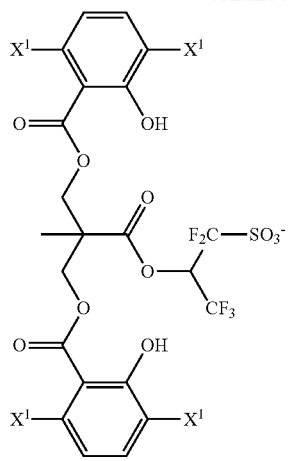
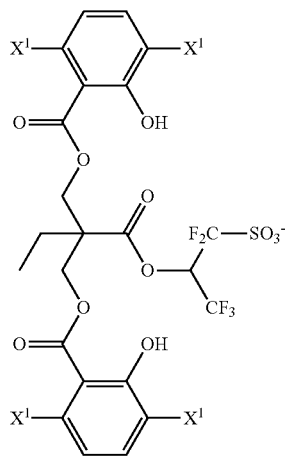
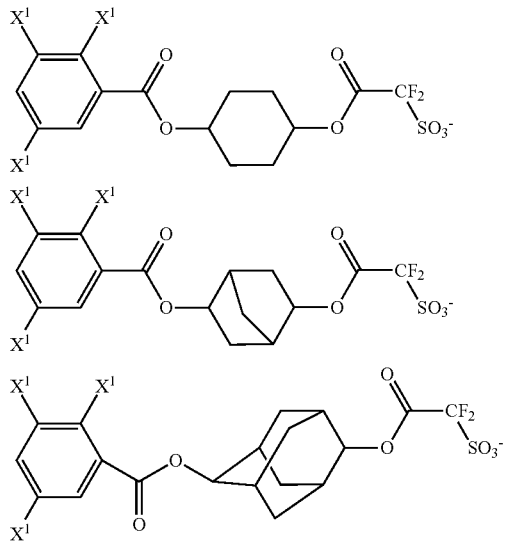
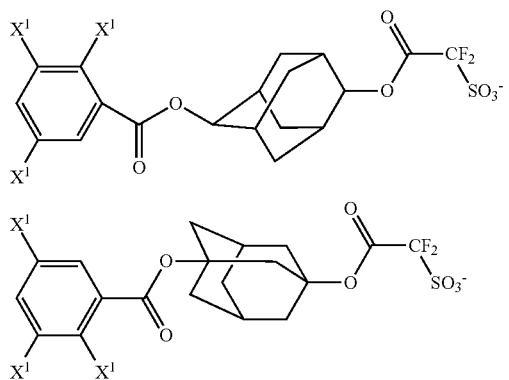
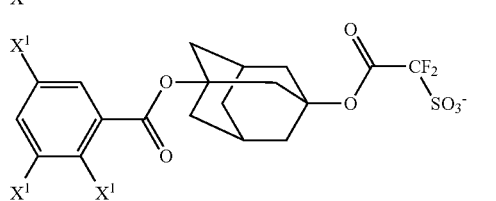
166
-continued
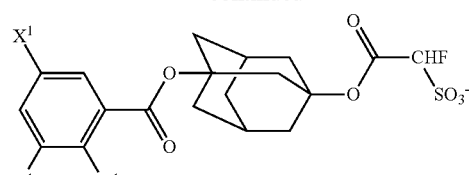
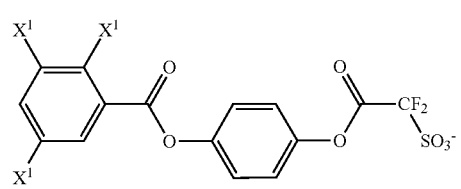
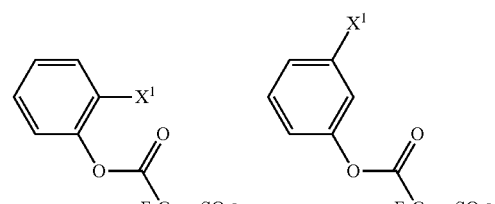
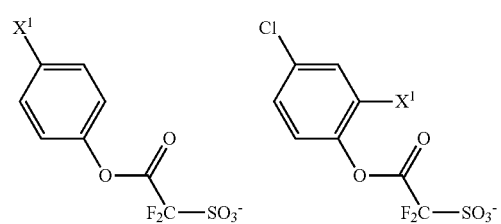
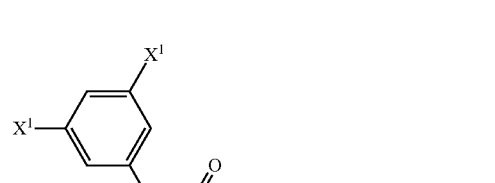
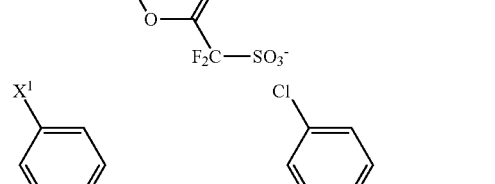
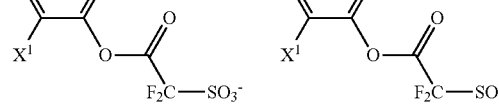
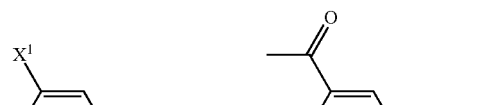
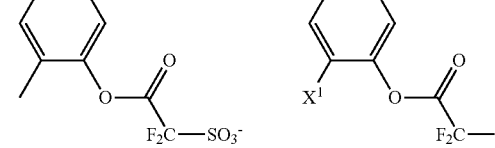

167
-continued
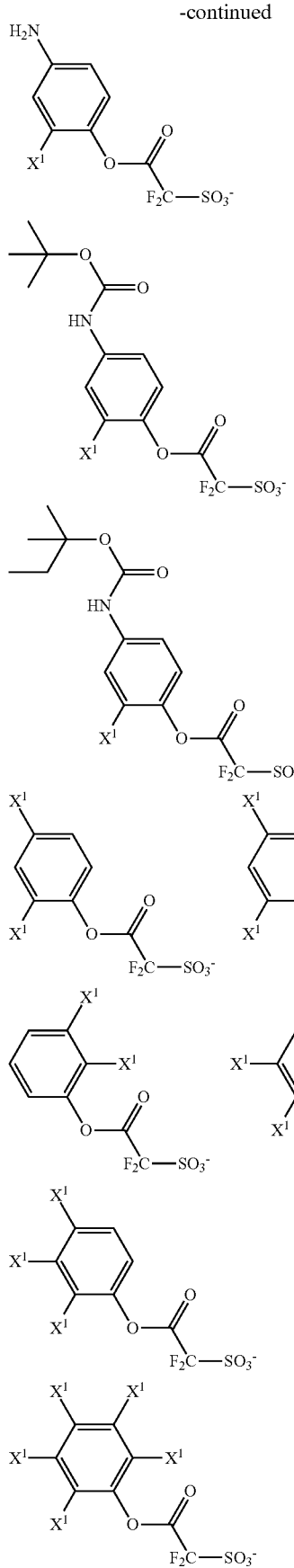
168
-continued
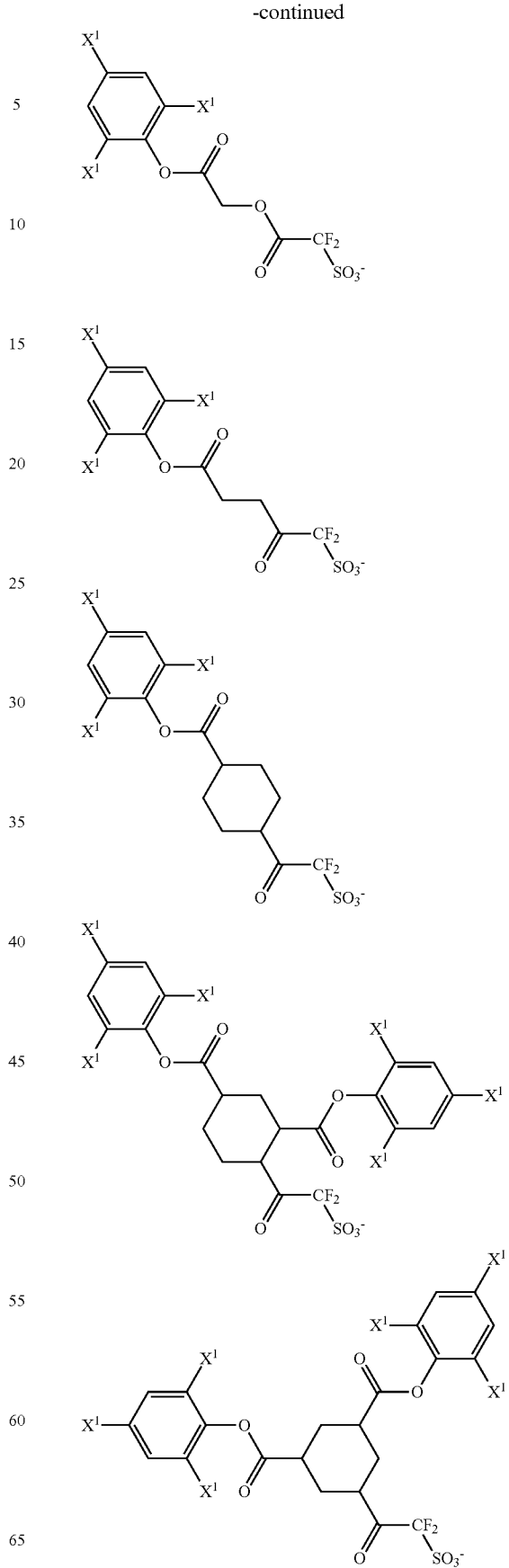

169
-continued
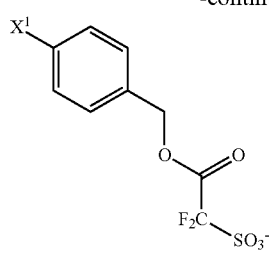
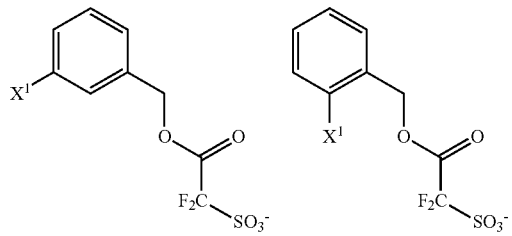
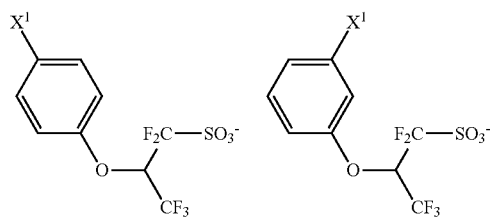
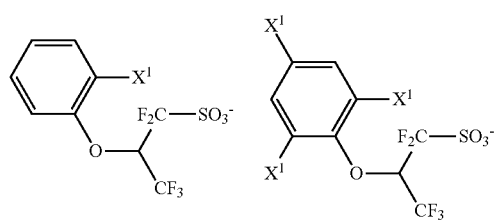
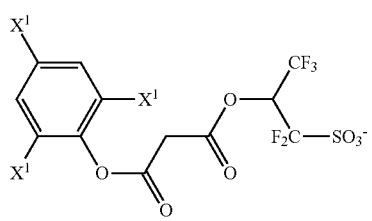
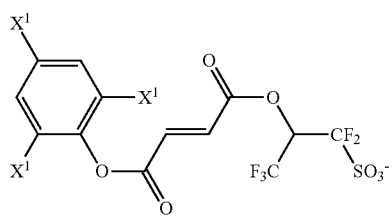
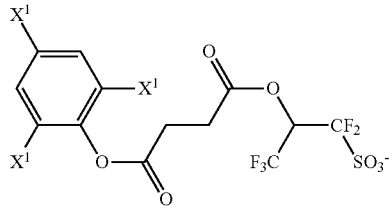
170
-continued
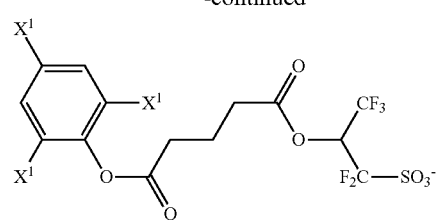
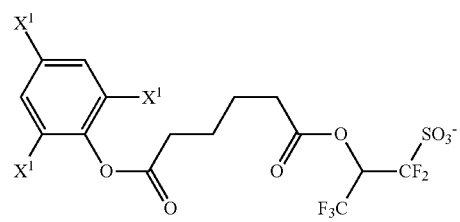
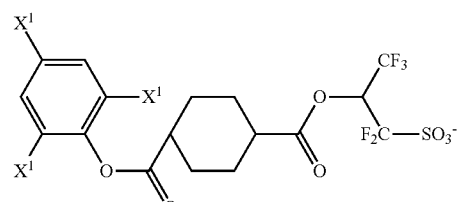
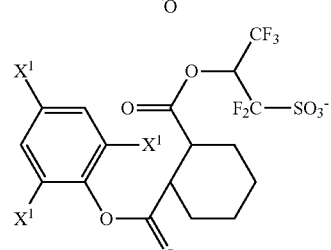
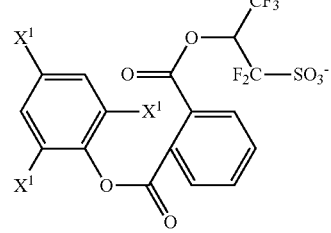
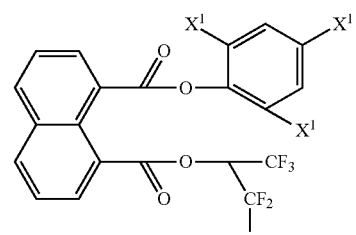
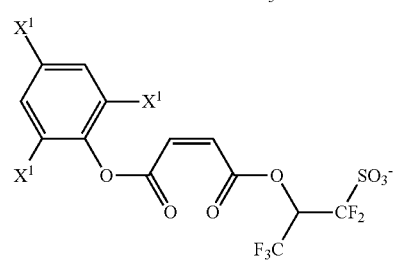

171
-continued
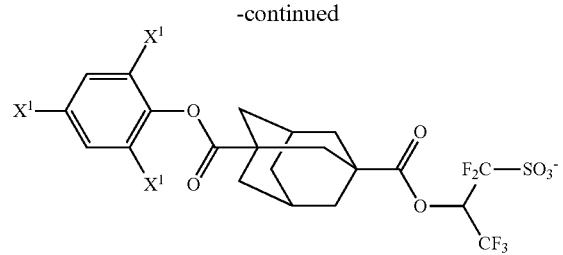
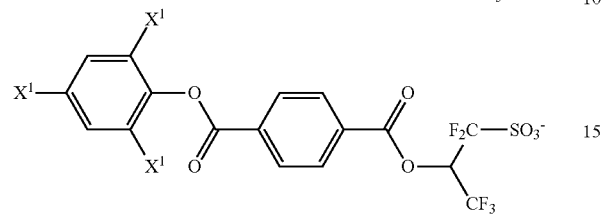
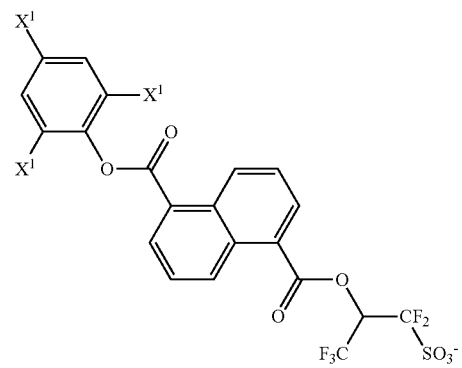
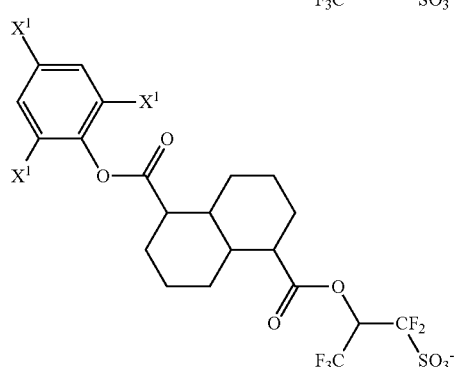
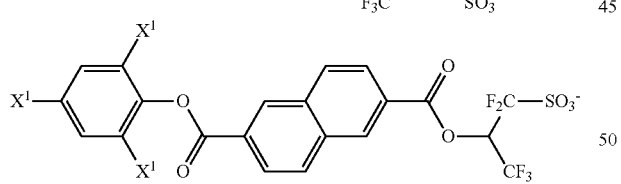
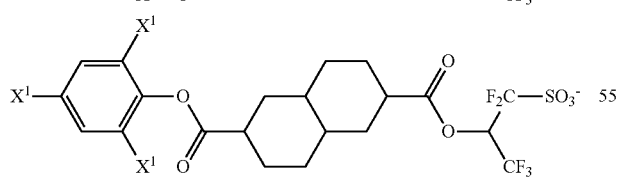
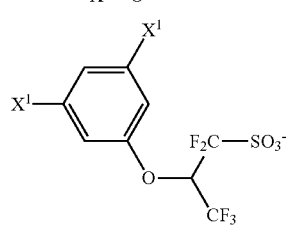
172
-continued
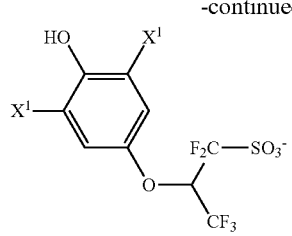
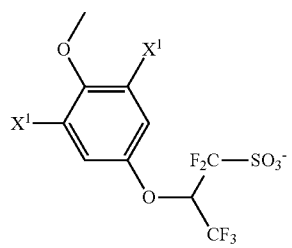
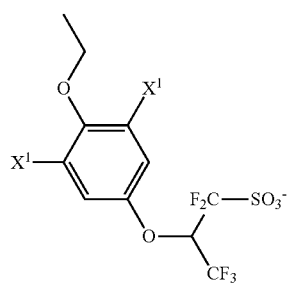
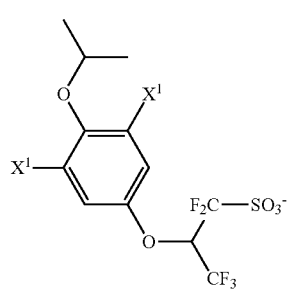
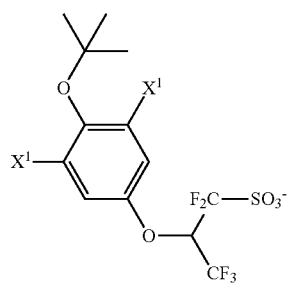
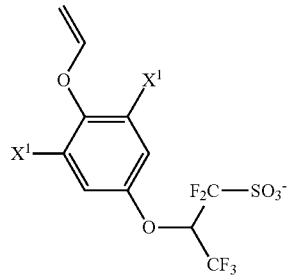

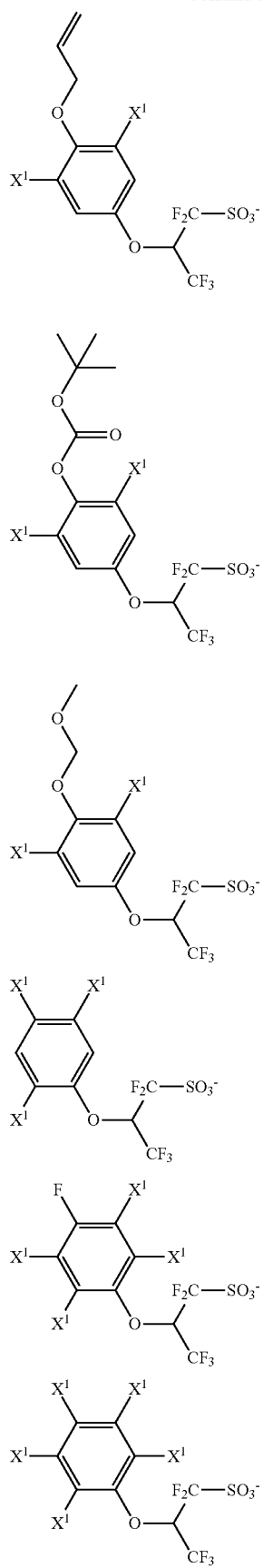
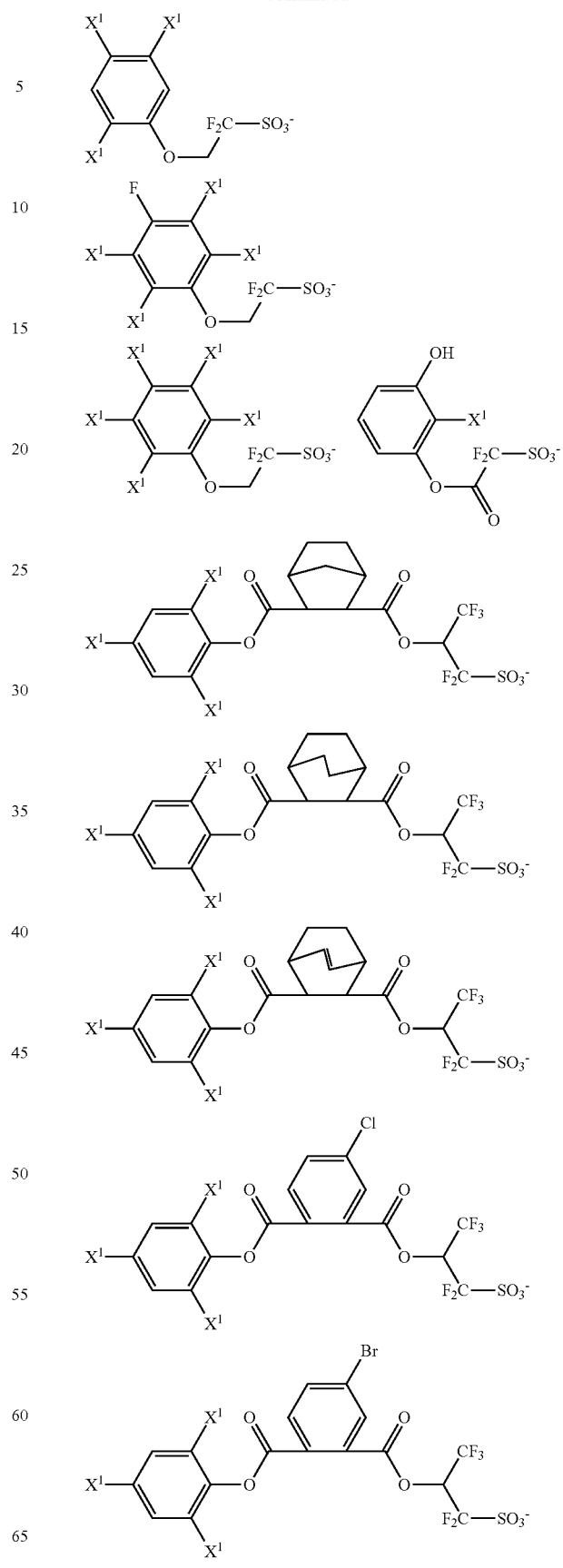

175
-continued
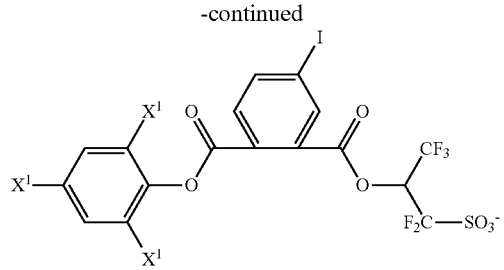
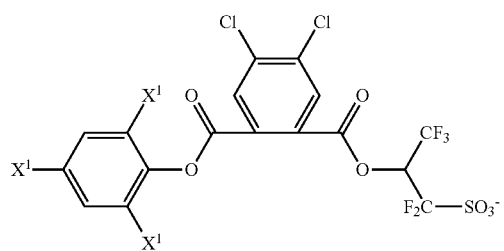
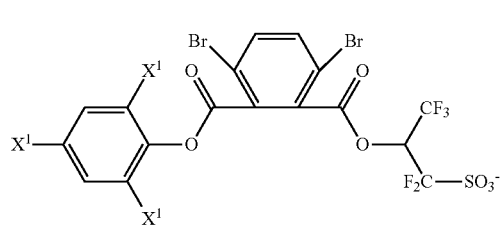
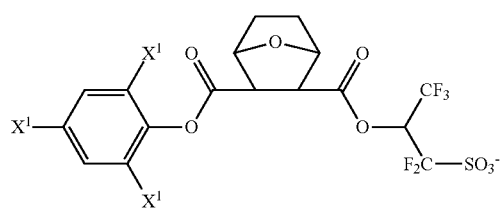
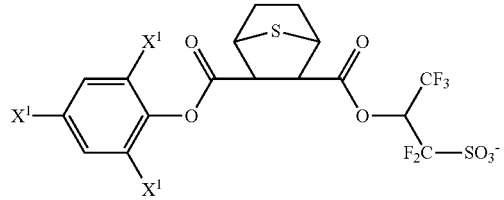
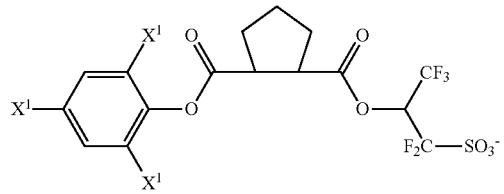
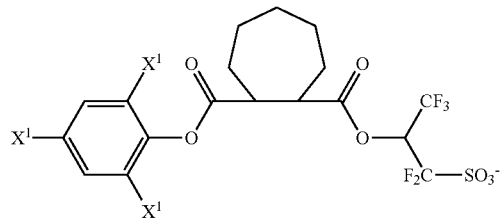
176
-continued
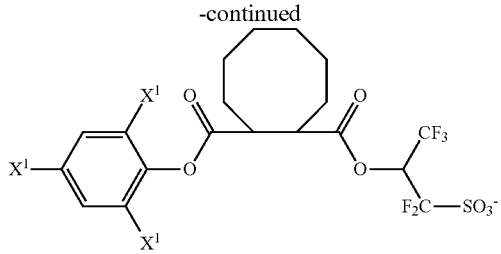
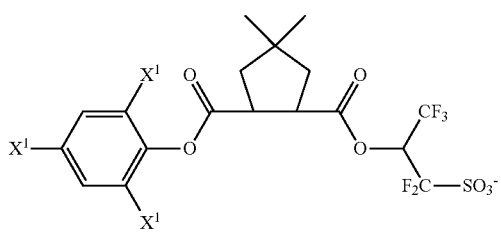
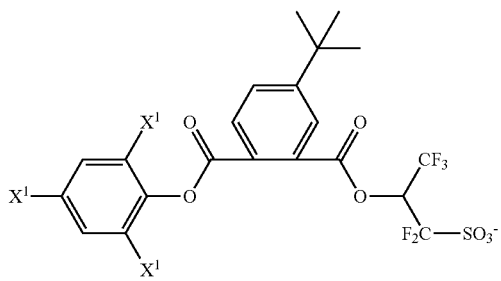
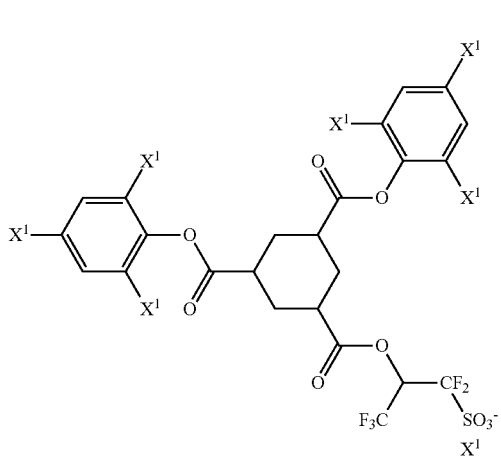
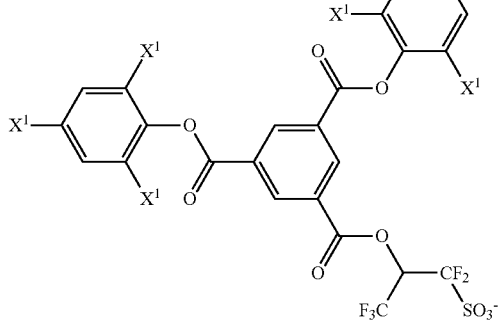

177
-continued
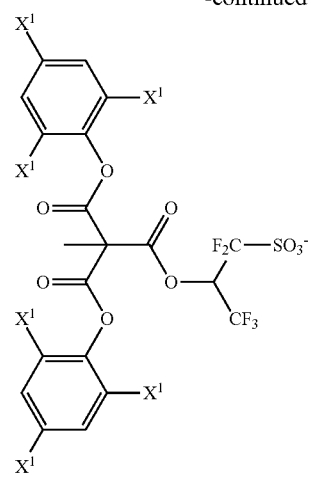
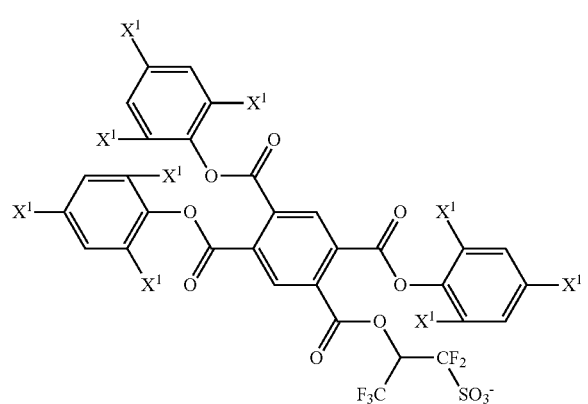
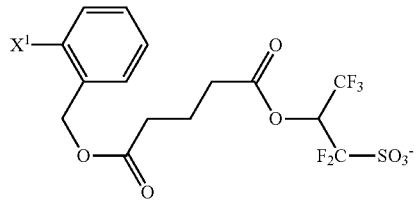
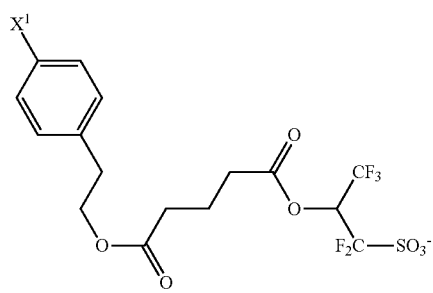
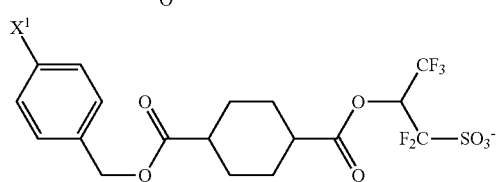
178
-continued
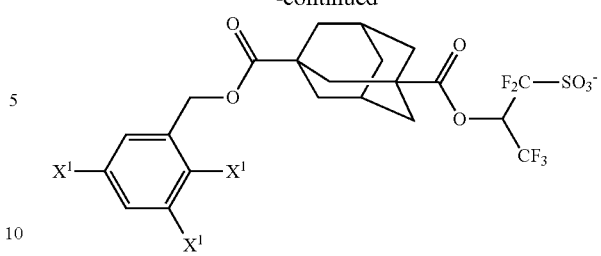
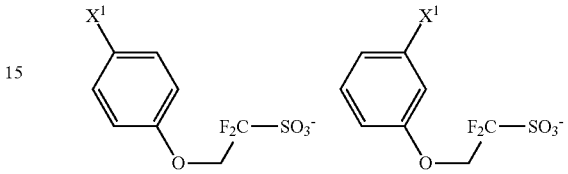
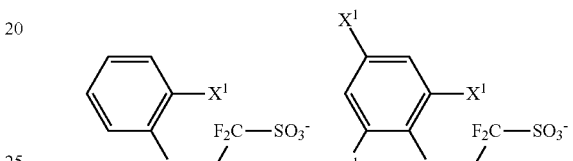
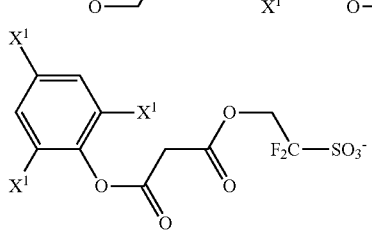
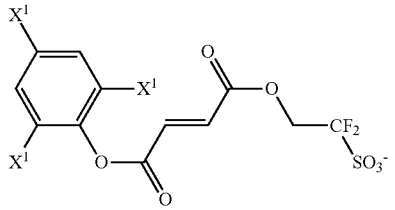
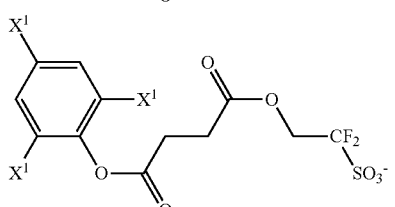
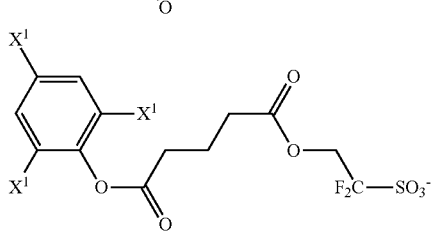
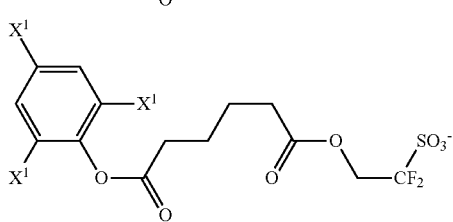

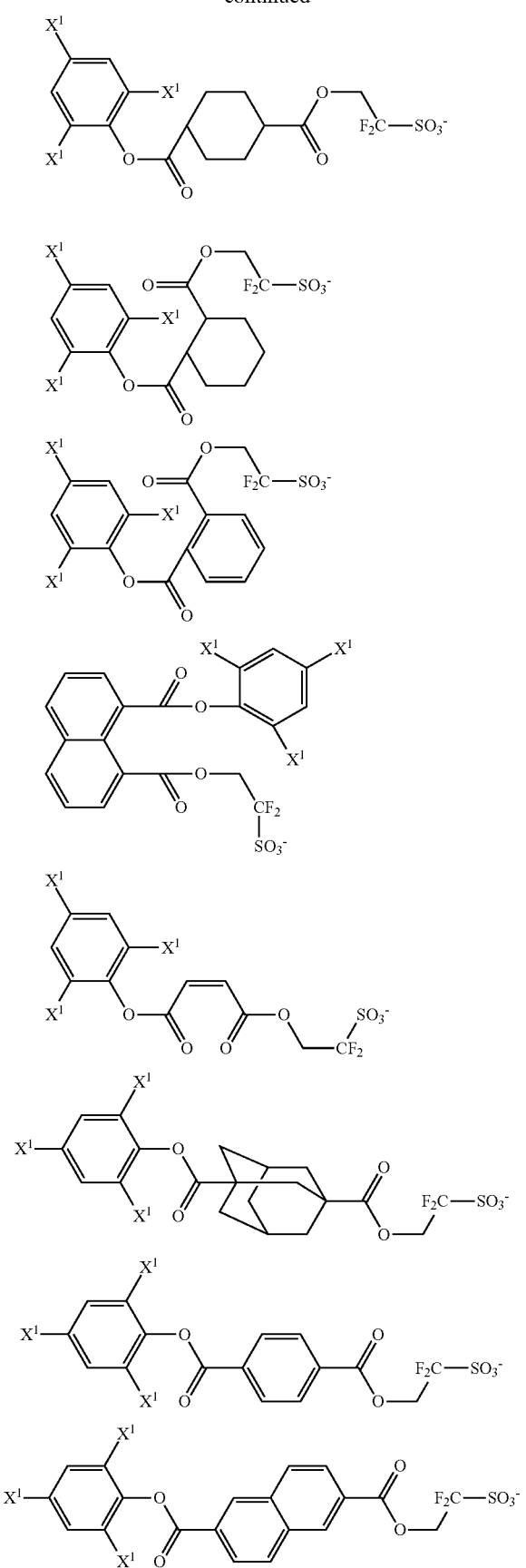
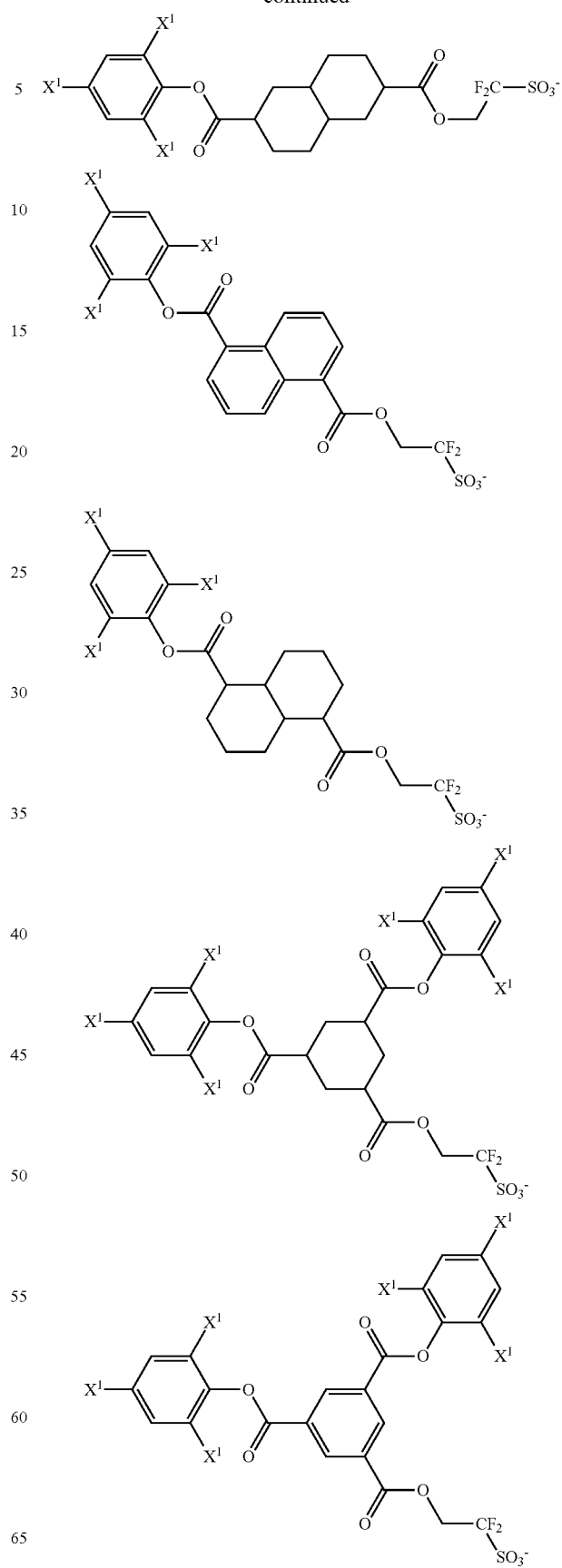

-continued
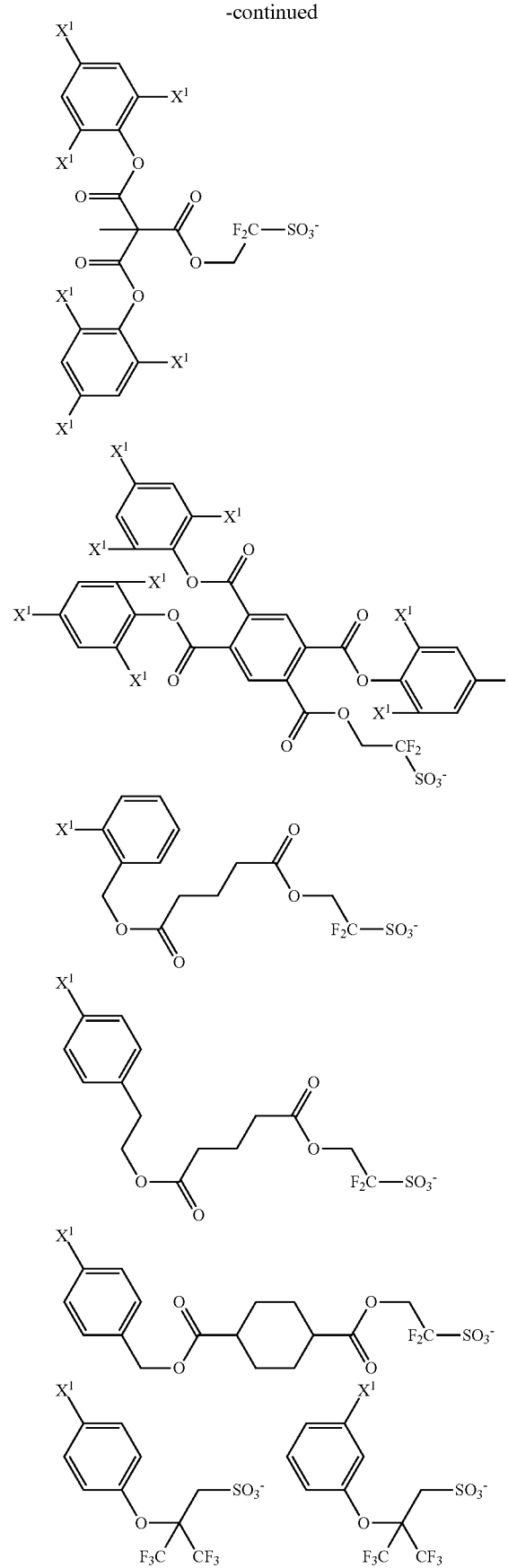
-continued
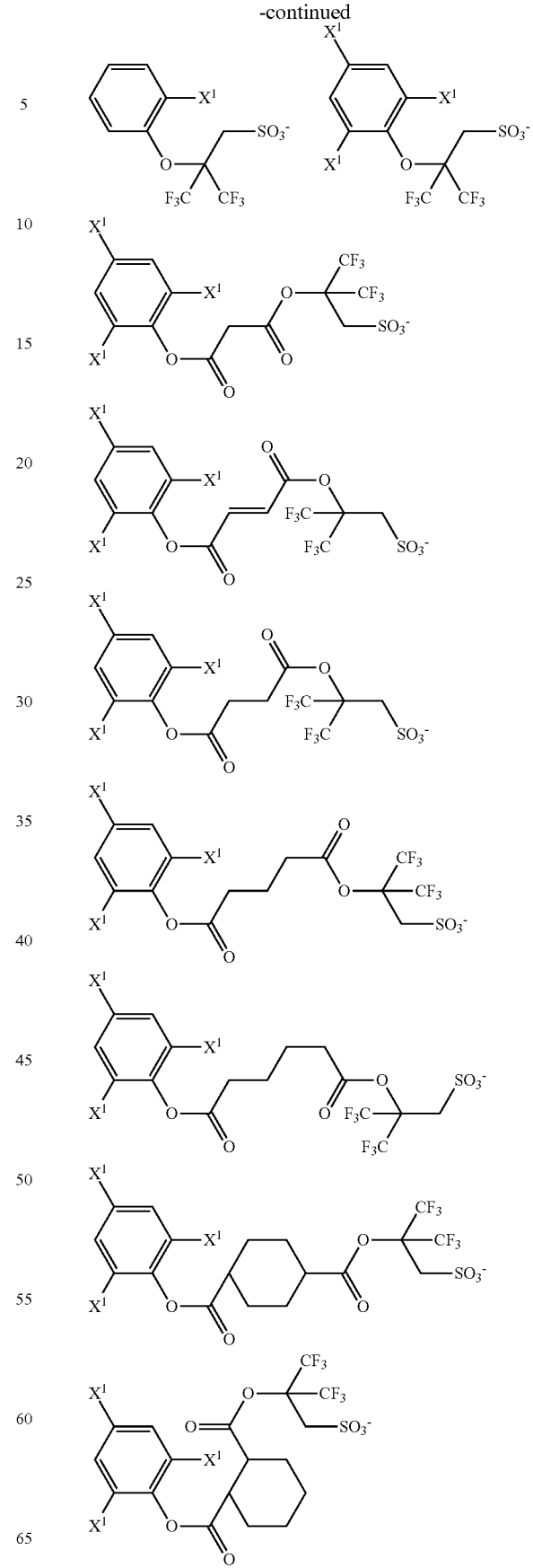

-continued
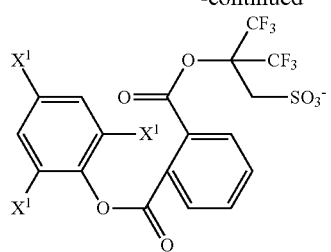
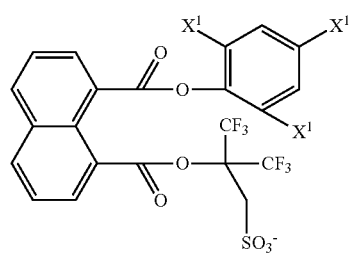
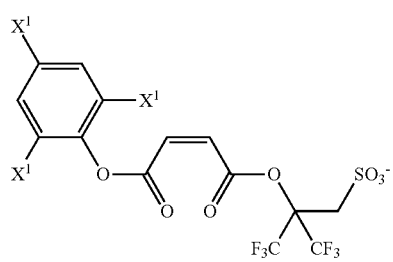
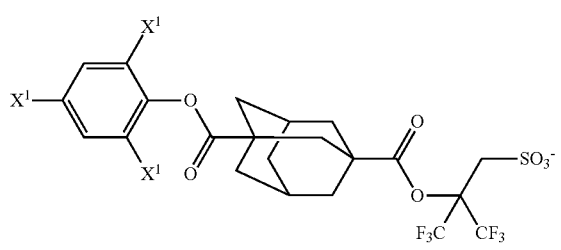
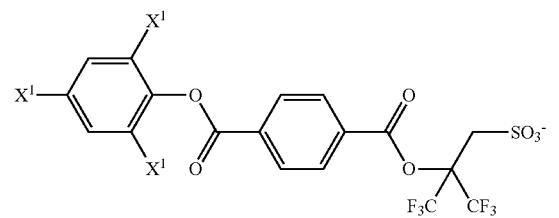
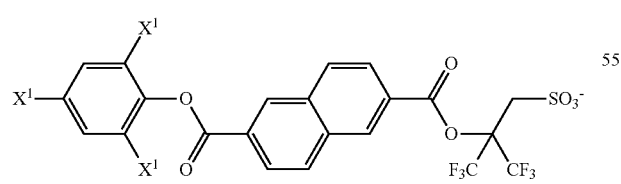
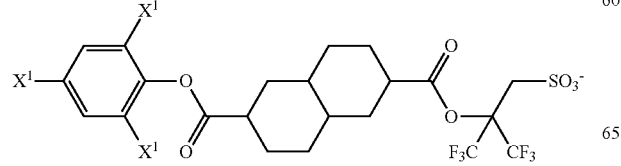
-continued
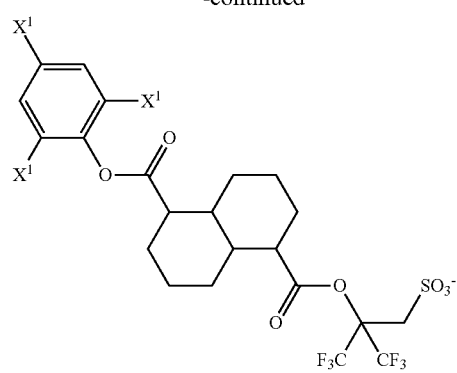
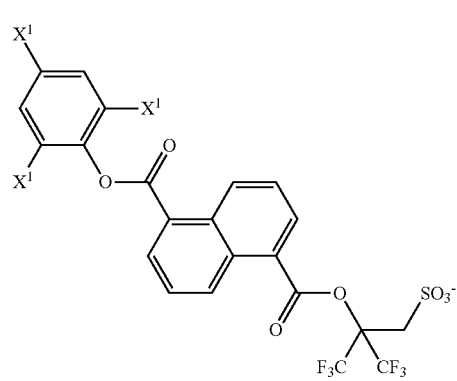
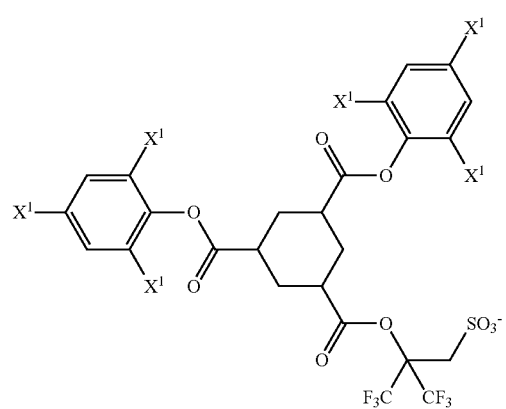
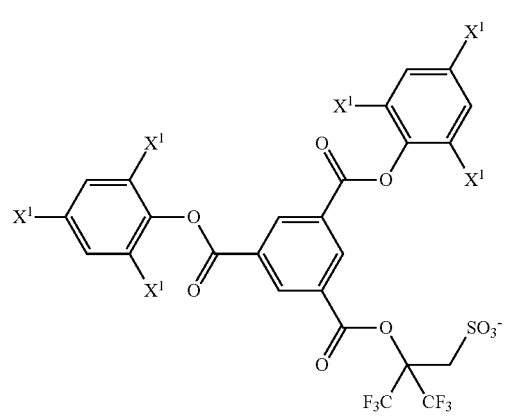

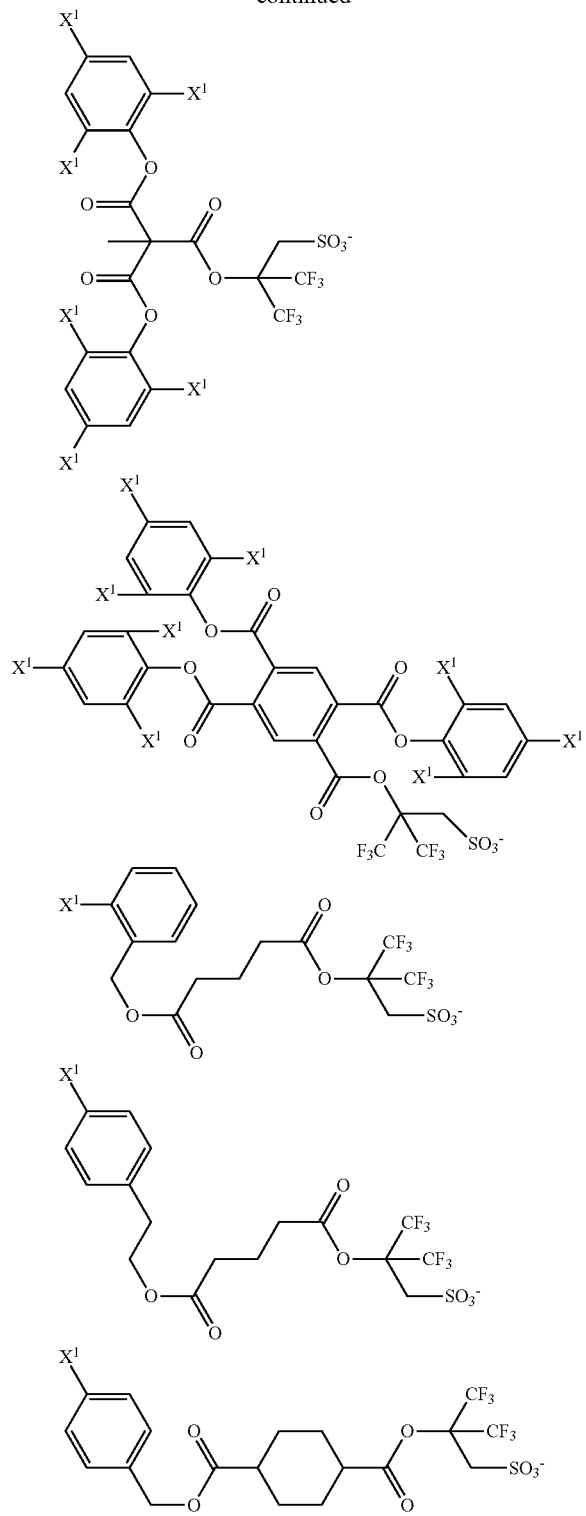

When used, the acid generator of addition type is preferably added in an amount of 0.1 to 50 parts, and more preferably 1 to 40 parts by weight per 100 parts by weight of the base polymer. The acid generator of addition type is optional when the base polymer has recurring units (f) incorporated therein, that is, an acid generator is bound in the base polymer.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of a resist film in exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. The crosslinker may be used alone or in admixture.

Of the foregoing crosslinkers, examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

In the resist composition of the invention, a quencher other than the iodized aromatic ring-containing amine compound may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Since the quencher in the form of a sulfonium salt or iodonium salt is photo-decomposable, the quencher function is reduced in the exposed region whereas acid activity is improved. This results in an improved contrast. The iodized aromatic ring-containing amine compound has a very high acid diffusion suppressing effect in the exposed region as well as in the unexposed region, but a low contrast-improving effect. Using the iodized aromatic ring-containing amine compound in combination with the quencher in the form of a sulfonium salt or iodonium salt, the desired properties including low acid diffusion and high contrast are achievable in a good balance.

Examples of the quencher in the form of an onium salt include compounds having the formula (4-1) and compounds having the formula (4-2).

In formula (4-1), $R^{q1}$ is hydrogen or a $C_1$-$C_{40}$ monovalent hydrocarbon group which may contain a heteroatom, exclusive of the hydrocarbon group in which the hydrogen bonded to the carbon atom at α-position of the sulfone group is substituted by fluorine or fluoroalkyl group. Examples of the monovalent hydrocarbon group $R^{q1}$ include alkyl, alkenyl, aryl, aralkyl and aryloxoalkyl groups. Suitable alkyl groups include methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl. Suitable alkenyl groups include vinyl, allyl, propenyl, butenyl, hexenyl, and cyclohexenyl. Suitable aryl groups include phenyl, naphthyl, thienyl, 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl, and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

In formula (4-2), $R^{q2}$ is a $C_1$-$C_{40}$ monovalent hydrocarbon group which may contain a heteroatom. Examples of the monovalent hydrocarbon group $R^{q2}$ are as exemplified above for the monovalent hydrocarbon group $R^{q1}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, aryl groups such as phenyl, tolyl, xylyl, 4-tert-butylphenyl, and naphthyl, and fluorinated aryl groups such as pentafluorophenyl, 4-trifluoromethylphenyl, and 4-amino-2,3,5,6-tetrafluorophenyl.

In formulae (4-1) and (4-2), $Mq^+$ is an onium cation. Suitable onium cations include sulfonium, iodonium and ammonium cations, with the sulfonium or iodonium cations being preferred.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

To the resist composition, a polymeric additive or water repellency improver may also be added for improving the water repellency on surface of a resist film as spin coated.

The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. The water repellency improver may be used alone or in admixture. An appropriate amount of the water repellency improver is 0 to 20 parts, more preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Pattern Forming Process

The resist composition is used in the fabrication of various integrated circuits. Pattern formation using the resist composition may be performed by well-known lithography processes. The process generally involves coating, prebaking, exposure, and development. If necessary, any additional steps may be added.

For example, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto through a mask having a desired pattern in a dose of preferably about 1 to 200 mJ/cm$^2$, more preferably about 10 to 100 mJ/cm$^2$. When EB is used as the high-energy radiation, the resist film is exposed thereto through a mask having a desired pattern or directly in a dose of preferably about 0.1 to 100 μC/cm$^2$, more preferably about 0.5 to 50 μC/cm$^2$. It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hot plate at 60 to 150° C. for 10 seconds to 30 minutes, preferably at 80 to 120° C. for 30 seconds to 20 minutes.

After the exposure or PEB, in the case of positive resist, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents.

Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-l-pentanol, 2-methyl-2-pentanol, 2-methyl-3-pentanol, 3-methyl-l-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight. Analytic instruments are as shown below.
IR: NICOLET 6700 by Thermo Fisher Scientific Inc.
$^1$H-NMR: ECA-500 by JEOL Ltd.

Synthesis Example 1

Synthesis of quenchers
(1) Synthesis of 2,3,5-triiodobenzoyl chloride

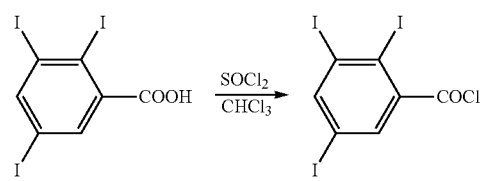

A mixture of 50.0 g of 2,3,5-triiodobenzoic acid, 0.4 g of dimethylformamide, and 350 g of chloroform was heated at 60° C., after which 23.8 g of thionyl chloride was added dropwise. Stirring was continued at 60° C. for 23 hours, after which with heating stopped, the reaction solution was allowed to resume room temperature. The reaction solution was concentrated under reduced pressure, during which a solid matter precipitated out. To the solid precipitate, 500 g of hexane was added and stirred. The solid matter was filtered and washed with hexane, obtaining 51.6 g of the desired compound, 2,3,5-triiodobenzoyl chloride. The solid was ready for use in the subsequent step as a purity 100% product without vacuum drying.
(2) Synthesis of Quencher 1

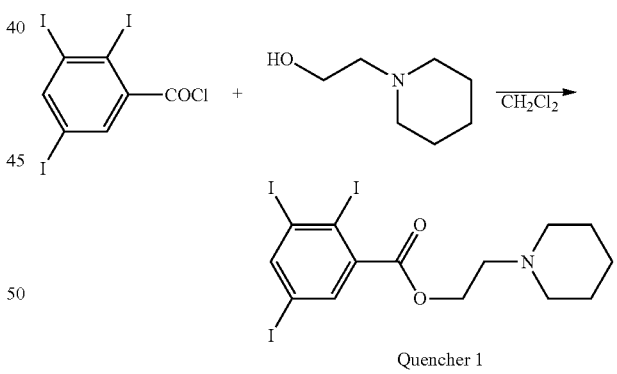

Quencher 1

In 20 g of methylene chloride, 4.4 g of 2,3,5-triiodobenzoyl chloride synthesized in (1) was dissolved. To this solution, 2.4 g of N-(2-hydroxyethyl)piperidine was added dropwise. After the solution was stirred at room temperature overnight, 20 g of deionized water was added to quench the reaction. The organic layer was taken out and washed 6 times with 20 g of deionized water, once with 20 g of 1 wt % hydrochloric acid solution, 3 times with 20 g of deionized water, once with 20 g of 1 wt % ammonia water, and 5 times with 20 g of deionized water. The organic layer was concentrated under reduced pressure. Hexane, 30 g, was added to the concentrate and stirred, during which a solid matter precipitated out. The solid precipitate was collected by filtration, washed twice with hexane, and dried in vacuum at 50° C., obtaining the target compound, Quencher 1, as solids. Amount 3.6 g, two-step yield 69%. Quencher 1 was analyzed by IR and $^1$H-NMR spectroscopy, with the data shown below.

IR (D-ATR):
ν=3107, 3053, 2936, 2848, 2778, 2754, 2700, 1716, 1521, 1465, 1452, 1439, 1398, 1387, 1357, 1303, 1285, 1275, 1235, 1191, 1131, 1105, 1051, 1026, 1005, 939, 869, 778, 760, 730, 708, 518 cm$^{-1}$ $^1$H-NMR (500 MHz, DMSO-d$_6$):
δ=1.35 (2H, m), 1.47 (4H, m), 2.38 (4H, m), 2.59 (2H, t), 4.33 (2H, t), 7.79 (1H, d), 8.36 (1H, d) ppm (3) Synthesis of Quencher 2

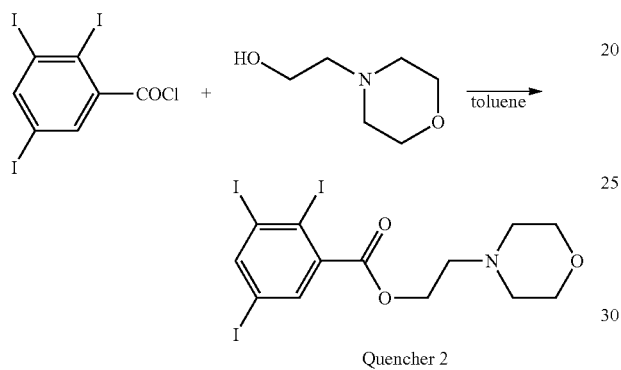

Quencher 2

In a mixture of 20 g of methylene chloride and 35 g of toluene, 11.3 g of 2,3,5-triiodobenzoyl chloride synthesized in (1) was dissolved. To this solution, 5.7 g of N-(2-hydroxyethyl)morpholine was added dropwise. After the solution was stirred at room temperature overnight, 40 g of deionized water was added to quench the reaction. 100 g of methylene chloride was added and stirred, after which the organic layer was taken out. The organic layer was washed twice with 30 g of deionized water. Thereafter, 0.5 g of active carbon was added to the organic layer, which was stirred for 2 hours and filtered. The filtrate was washed once with 30 g (0.1 molar equivalent relative to Quencher 2) of hydrochloric acid, twice with 30 g of deionized water, twice with 30 g of dilute ammonia water, and 5 times with 30 g of deionized water. The organic layer was concentrated under reduced pressure during which a solid matter precipitated out. The solid precipitate was dispersed in 100 g of hexane. After stirring for 10 minutes, the solid precipitate was collected by filtration, washed twice with hexane, and dried in vacuum at 50° C., obtaining the target compound, Quencher 2, as solids. Amount 7.3 g, two-step yield 55%. Quencher 2 was analyzed by IR and $^1$H-NMR spectroscopy, with the data shown below.

IR (D-ATR):
ν=3103, 3066, 3025, 2962, 2931, 2855, 2826, 2782, 2687, 1714, 1546, 1521, 1451, 1411, 1395, 1380, 1358, 1305, 1286, 1234, 1203, 1193, 1145, 1132, 1116, 1069, 1025, 1004, 949, 911, 898, 860, 780, 768, 729, 708, 611 cm$^{-1}$ $^1$H-NMR (500 MHz, DMSO-d$_6$):
δ=2.42 (4H, m), 2.64 (2H, t), 3.56 (4H, t), 4.36 (2H, t), 7.79 (1H, d), 8.36 (1H, d) ppm (4) Synthesis of Quenchers 3 to 28

Quenchers 3 to 28 were synthesized by the same procedure as (2) or (3) aside from using a corresponding compound instead of N-(2-hydroxyethyl)piperidine or N-(2-hydroxyethyl)morpholine.

Quenchers 1 to 28 have the structure shown below.

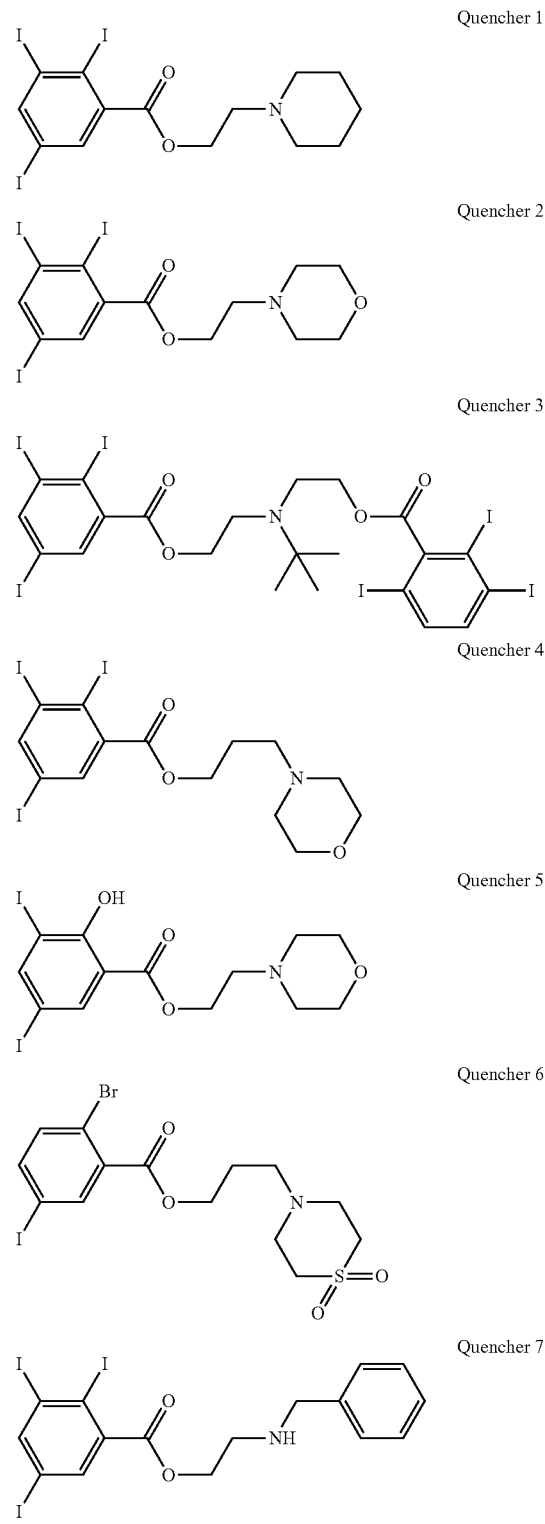

Quencher 8
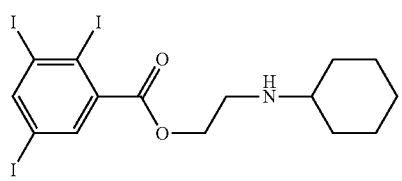
Quencher 9
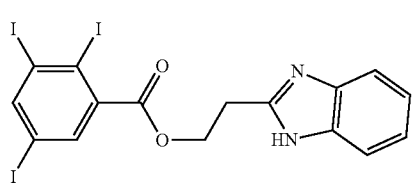
Quencher 10
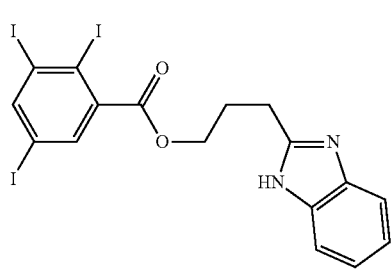
Quencher 11
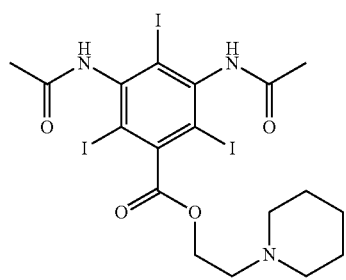
Quencher 12
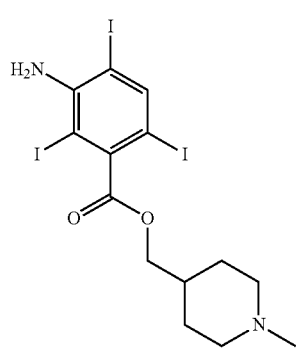
Quencher 13
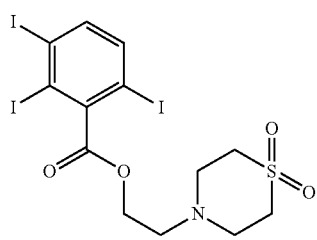
Quencher 14
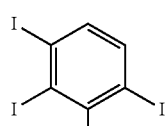
Quencher 15
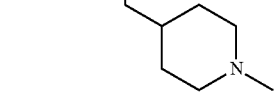
Quencher 16
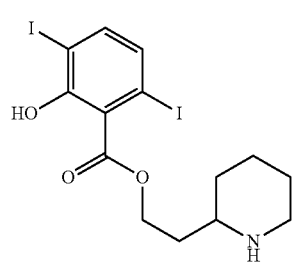
Quencher 17
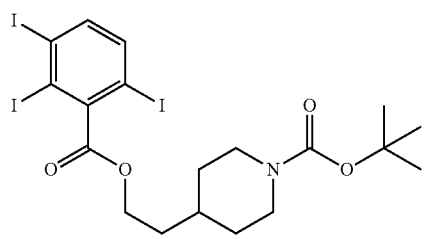
Quencher 18
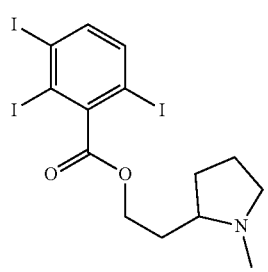
Quencher 19
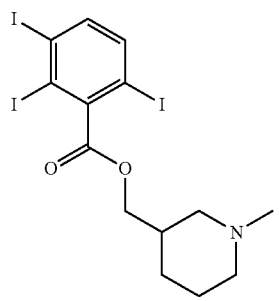
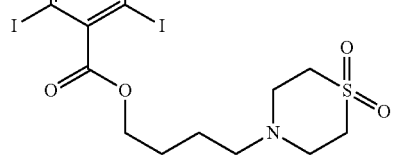

Quencher 20

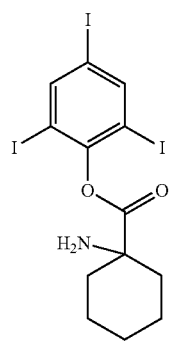

Quencher 21

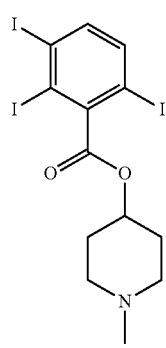

Quencher 22

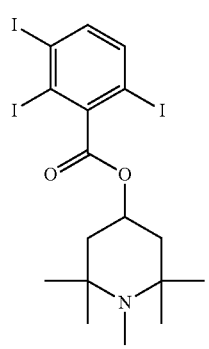

Quencher 23

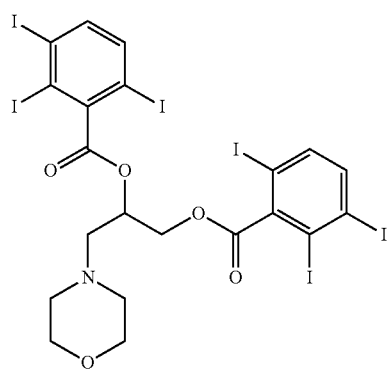

Quencher 24

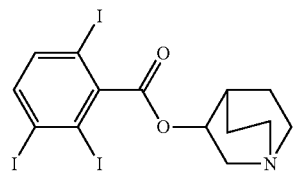

Quencher 25

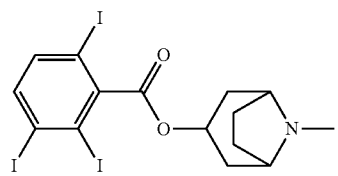

Quencher 26

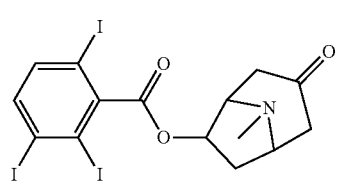

Quencher 27

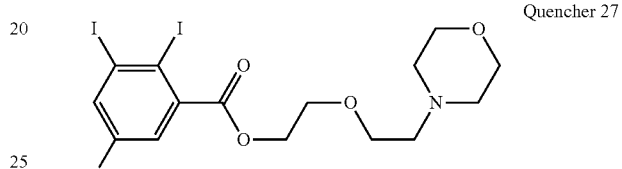

Quencher 28

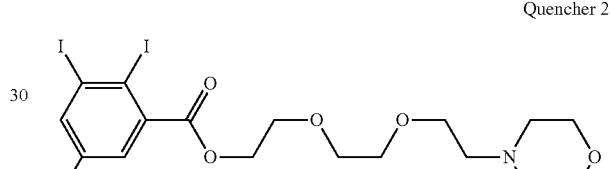

Synthesis Example 2

Synthesis of base polymers (Polymers 1 to 4)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 4, were analyzed for composition by $^1$H-NMR spectroscopy, and for Mw and Mw/Mn by GPC versus polystyrene standards using THF solvent.

Polymer 1

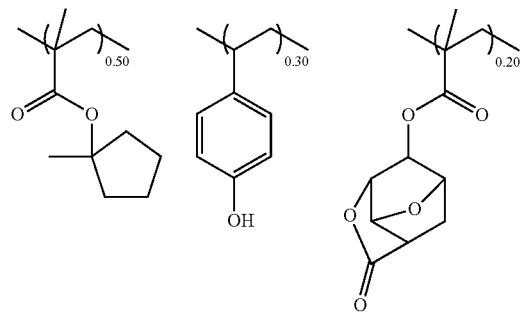

Mw = 8,600
Mw/Mn = 1.73

-continued

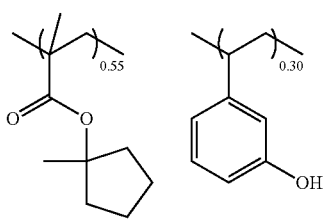

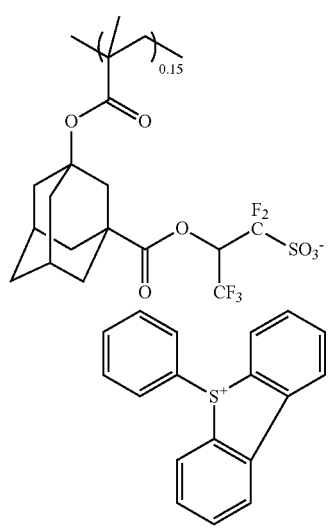

Mw = 8,900
Mw/Mn = 1.89

Polymer 2

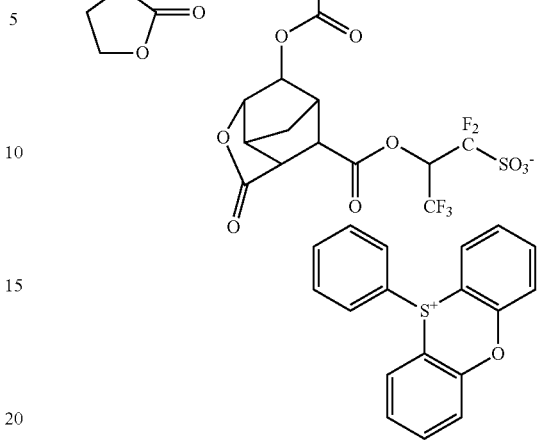

Mw = 7,600
Mw/Mn = 1.73

Polymer 4

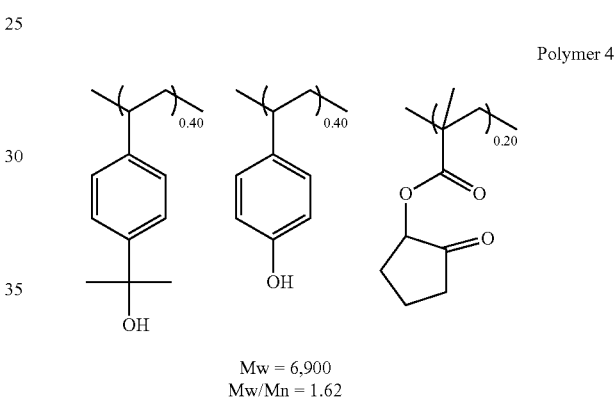

Mw = 6,900
Mw/Mn = 1.62

Examples 1 to 33 and Comparative Examples 1 to 8

Preparation and Evaluation of Resist Compositions (1) Preparation of Resist Compositions Resist compositions were prepared, under LED illumination with UV of wavelength 400 nm and shorter cut off, by dissolving the polymer and selected components in a solvent in accordance with the recipe shown in Tables 1 to 3, and filtering through a filter having a pore size of 0.2 μm. The solvent contained 100 ppm of surfactant Polyfox PF-636 (Omnova Solutions). The resist compositions of Examples 1 to 21, Examples 23 to 33, and Comparative Examples 1 to 6 and 8 were of positive tone, while the resist compositions of to Example 22 and Comparative Example 7 were of negative tone.

The components in Tables 1 to 3 are as identified below.

Organic Solvents:
  PGMEA (propylene glycol monomethyl ether acetate)
  CyH (cyclohexanone)

Polymer 3

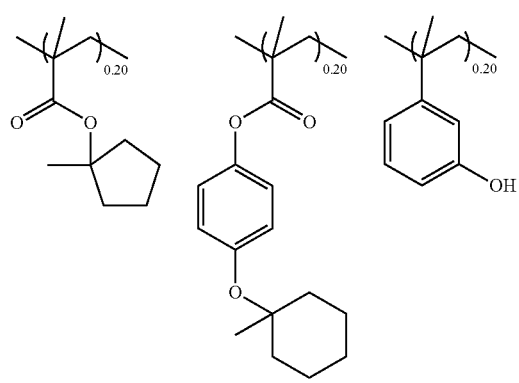

PGME (propylene glycol monomethyl ether)
DAA (diacetone alcohol)
Acid generators: PAG 1 to PAG 6 of the following structural formulae
PAG 1
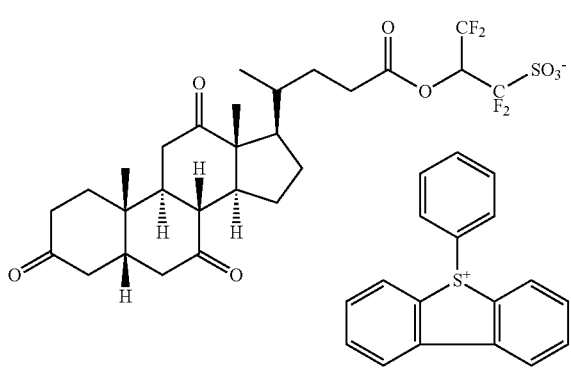
PAG 2
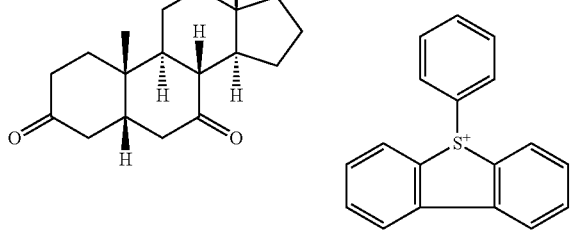
PAG 3
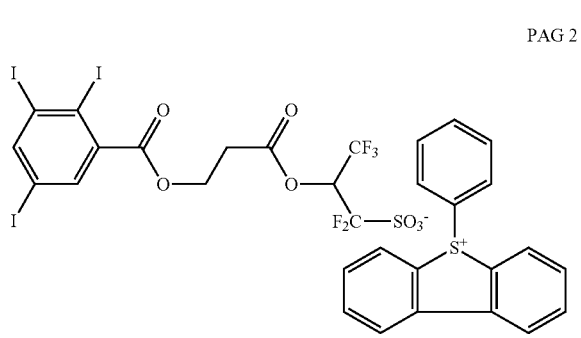
PAG 4
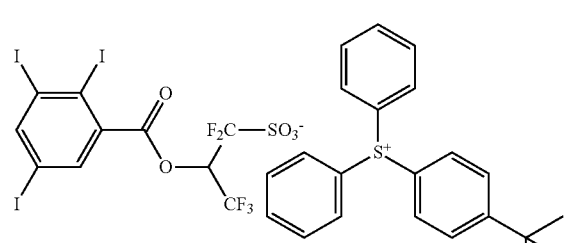
PAG 5
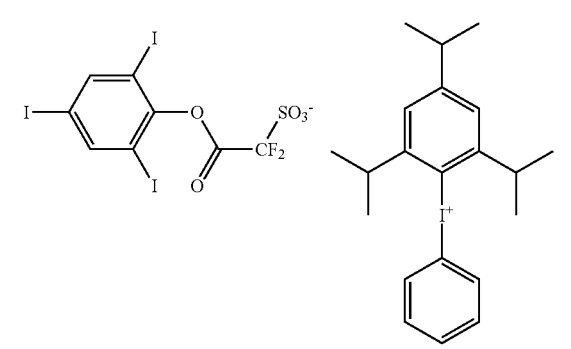
PAG 6
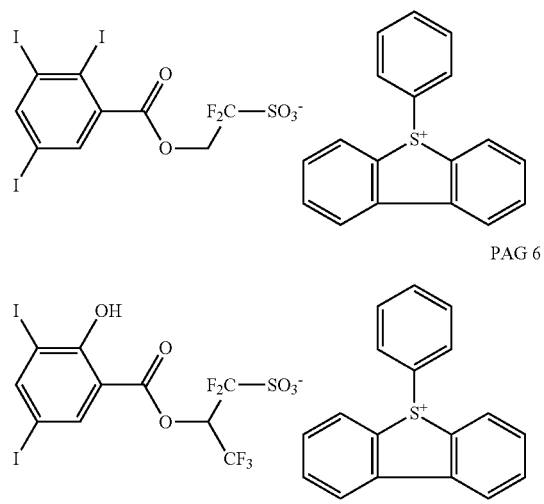
Comparative Quenchers 1 to 8 and Blend Quenchers 1 and 2 of the following structural formulae
Comparative Quencher 1
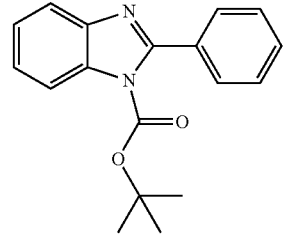
Comparative Quencher 2
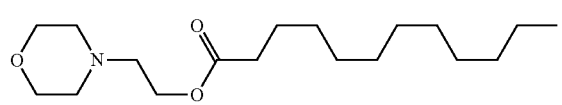
Comparative Quencher 3
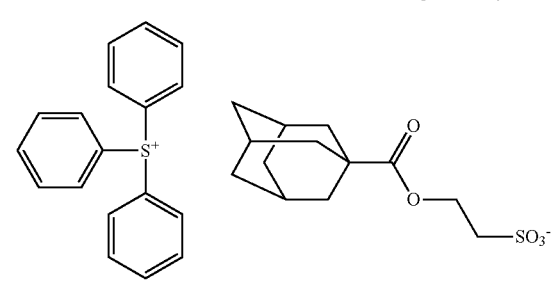
Comparative Quencher 4
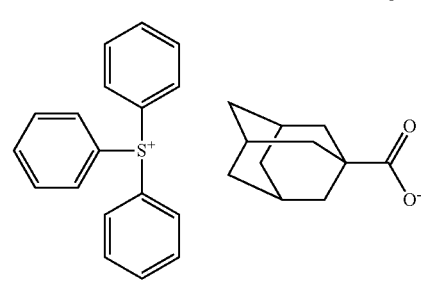

-continued

Comparative Quencher 5

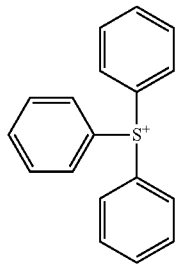
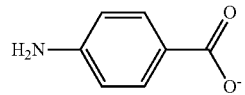

Comparative Quencher 6

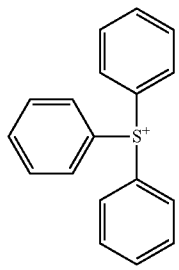
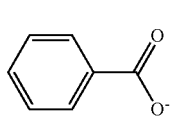

Comparative Quencher 7

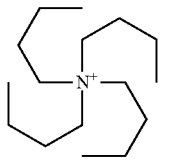
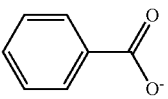

Comparative Quencher 9

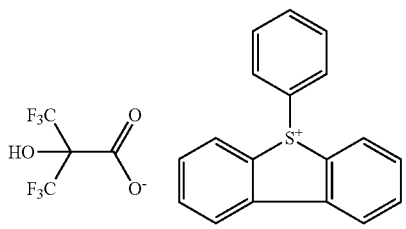

Blend Quencher 1

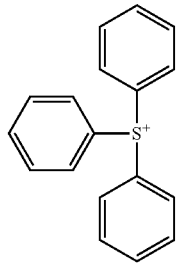
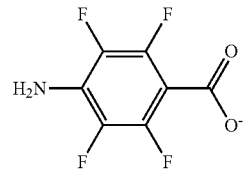

Blend Quencher 2

(2) EUV Lithography test

Each of the resist compositions in Tables 1 to 3 was spin coated on a silicon substrate having a 20-nm coating of silicon-containing spin-on hard mask SHB-A940 (Shin-Etsu Chemical Co., Ltd., silicon content 43 wt %) and prebaked on a hotplate at 105° C. for 60 seconds to form a resist film of 60 nm thick. Using an EUV scanner NXE3300 (ASML, NA 0.33, σ0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 to 3 for 60 seconds and developed in a 2.38 wt % TMAH aqueous solution for 30 seconds to form a hole pattern having a size of 23 nm in Examples 1 to 21, Examples 23 to 33, and Comparative Examples 1 to 6 and 8 or a dot pattern having a size of 23 nm in Example 22 and Comparative Example 7.

The resist pattern was evaluated using CD-SEM (CG-5000, Hitachi High-Technologies Corp.). The exposure dose that provides a hole or dot pattern having a size of 23 nm is reported as sensitivity. The size of 50 holes in that dose was measured, from which a size variation (3σ) was computed and reported as CDU.

The resist composition is shown in Tables 1 to 3 together with the sensitivity and CDU of EUV lithography.

TABLE 1

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | Polymer 1 (100) | PAG 1 (30) | Quencher 1 (6.61) | PGMEA (400) CyH (2,000) PGME (100) | 100 | 26 | 2.6 |
| | 2 | Polymer 1 (100) | PAG 2 (30) | Quencher 2 (6.12) | PGMEA (400) CyH (2,000) PGME (100) | 100 | 26 | 2.5 |
| | 3 | Polymer 1 (100) | PAG 2 (30) | Quencher 3 (11.27) | PGMEA (400) CyH (2,000) PGME (100) | 100 | 21 | 2.6 |
| | 4 | Polymer 1 (100) | PAG 2 (30) | Quencher 4 (6.27) | PGMEA (400) CyH (2,000) PGME (100) | 100 | 23 | 2.7 |

TABLE 1-continued

|   | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 5 | Polymer 1 (100) | PAG 2 (30) | Quencher 5 (5.03) | PGMEA (400) CyH (2,000) PGME (100) | 100 | 23 | 2.7 |
| 6 | Polymer 1 (100) | PAG 2 (30) | Quencher 6 (5.00) | PGMEA (400) CyH (2,000) PGME (100) | 100 | 25 | 2.5 |
| 7 | Polymer 1 (100) | PAG 2 (30) | Quencher 7 (6.33) | PGMEA (400) CyH (2,000) PGME (100) | 100 | 24 | 2.5 |
| 8 | Polymer 1 (100) | PAG 2 (30) | Quencher 8 (6.25) | PGMEA (400) CyH (2,000) PGME (100) | 100 | 24 | 2.6 |
| 9 | Polymer 1 (100) | PAG 2 (30) | Quencher 9 (6.43) | PGMEA (400) CyH (2,000) PGME (100) | 100 | 24 | 2.7 |
| 10 | Polymer 1 (100) | PAG 2 (30) | Quencher 10 (6.57) | PGMEA (400) CyH (2,000) PGME (100) | 100 | 23 | 2.4 |
| 11 | Polymer 1 (100) | PAG 2 (30) | Quencher 11 (7.25) | PGMEA (400) CyH (2,000) PGME (100) | 100 | 23 | 2.7 |
| 12 | Polymer 1 (100) | PAG 2 (30) | Quencher 12 (4.26) | PGMEA (400) CyH (2,000) PGME (100) | 100 | 25 | 2.3 |
| 13 | Polymer 1 (100) | PAG 2 (30) | Quencher 13 (6.11) | PGMEA (400) CyH (2,000) PGME (100) | 100 | 25 | 2.4 |
| 14 | Polymer 1 (100) | PAG 2 (30) | Quencher 14 (6.11) | PGMEA (400) CyH (2,000) PGME (100) | 100 | 24 | 2.3 |
| 15 | Polymer 1 (100) | PAG 2 (30) | Quencher 15 (5.01) | PGMEA (400) CyH (2,000) PGME (100) | 100 | 25 | 2.3 |
| 16 | Polymer 1 (100) | PAG 2 (30) | Quencher 16 (6.11) | PGMEA (400) CyH (2,000) PGME (100) | 100 | 24 | 2.2 |
| 17 | Polymer 1 (100) | PAG 2 (30) | Quencher 17 (6.11) | PGMEA (400) CyH (2,000) PGME (100) | 100 | 24 | 2.2 |
| 18 | Polymer 2 (100) | — | Quencher 7 (6.33) | PGMEA (400) CyH (2,000) PGME (100) | 100 | 25 | 2.1 |

TABLE 2

|   |   | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 19 | Polymer 3 (100) | — | Quencher 7 (6.33) | PGMEA (400) CyH (2,000) PGME (100) | 100 | 22 | 1.8 |
|  | 20 | Polymer 3 (100) | PAG 3 (15) | Quencher 7 (6.33) | PGMEA (400) CyH (2,000) PGME (100) | 100 | 21 | 2.4 |
|  | 21 | Polymer 3 (100) | PAG 4 (15) | Quencher 16 (6.11) | PGMEA (400) CyH (2,000) PGME (100) | 100 | 23 | 2.3 |
|  | 22 | Polymer 4 (100) | PAG 1 (20) | Quencher 7 (6.33) | PGMEA (400) CyH (2,000) PGME (100) | 120 | 29 | 3.4 |
|  | 23 | Polymer 2 (100) | PAG 5 (5.0) | Quencher 18 (6.11) | PGMEA (400) CyH (2,000) PGME (100) | 100 | 24 | 2.1 |
|  | 24 | Polymer 2 (100) | PAG 6 (5.0) | Quencher 19 (6.89) | PGMEA (400) CyH (2,000) PGME (100) | 100 | 23 | 2.3 |
|  | 25 | Polymer 2 (100) | — | Quencher 20 (5.96) Blend Quencher 1 (3.00) | PGMEA (400) CyH (2,000) PGME (100) | 100 | 29 | 1.8 |

TABLE 2-continued

| | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 26 | Polymer 2 (100) | — | Quencher 21 (4.33) Blend Quencher 2 (3.00) | PGMEA (400) CyH (2,000) PGME (100) | 100 | 28 | 1.9 |
| 27 | Polymer 2 (100) | PAG 5 (5.0) | Quencher 22 (6.53) | PGMEA (400) CyH (2,000) PGME (100) | 100 | 24 | 2.2 |
| 28 | Polymer 2 (100) | PAG 6 (5.0) | Quencher 23 (10.00) | PGMEA (2000) DAA (500) | 100 | 23 | 2.3 |
| 29 | Polymer 2 (100) | PAG 6 (5.0) | Quencher 24 (6.08) | PGMEA (2000) DAA (500) | 100 | 27 | 2.3 |
| 30 | Polymer 2 (100) | PAG 6 (5.0) | Quencher 25 (6.23) | PGMEA (2000) DAA (500) | 100 | 28 | 2.2 |
| 31 | Polymer 2 (100) | PAG 6 (5.0) | Quencher 26 (6.36) | PGMEA (2000) DAA (500) | 100 | 28 | 2.3 |
| 32 | Polymer 2 (100) | PAG 6 (5.0) | Quencher 27 (6.57) | PGMEA (2000) DAA (500) | 100 | 26 | 2.2 |
| 33 | Polymer 2 (100) | PAG 6 (5.0) | Quencher 28 (7.01) | PGMEA (2000) DAA (500) | 100 | 26 | 2.3 |

TABLE 3

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Comparative Example | 1 | Polymer 1 (100) | PAG 2 (30) | Comparative Quencher 1 (1.20) | PGMEA (400) CyH (2,000) PGME (100) | 100 | 28 | 3.5 |
| | 2 | Polymer 1 (100) | PAG 2 (30) | Comparative Quencher 2 (1.20) | PGMEA (400) CyH (2,000) PGME (100) | 100 | 28 | 3.2 |
| | 3 | Polymer 1 (100) | PAG 2 (30) | Comparative Quencher 3 (3.20) | PGMEA (400) CyH (2,000) PGME (100) | 100 | 30 | 2.9 |
| | 4 | Polymer 1 (100) | PAG 2 (30) | Comparative Quencher 4 (3.20) | PGMEA (400) CyH (2,000) PGME (100) | 100 | 28 | 2.8 |
| | 5 | Polymer 1 (100) | PAG 2 (30) | Comparative Quencher 5 (3.20) | PGMEA (400) CyH (2,000) PGME (100) | 100 | 38 | 3.0 |
| | 6 | Polymer 1 (100) | PAG 2 (30) | Comparative Quencher 6 (3.20) | PGMEA (400) CyH (2,000) PGME (100) | 100 | 30 | 3.0 |
| | 7 | Polymer 4 (100) | PAG 2 (30) | Comparative Quencher 7 (3.65) | PGMEA (400) CyH (2,000) PGME (100) | 120 | 30 | 4.9 |
| | 8 | Polymer 1 (100) | PAG 2 (30) | Comparative Quencher 8 (2.60) | PGMEA (400) CyH (2,000) PGME (100) | 100 | 26 | 3.2 |

It is demonstrated in Tables 1 to 3 that resist compositions comprising an iodized aromatic ring-containing amine compound form patterns having a high sensitivity and a reduced value of CDU.

Japanese Patent Application No. 2018-150050 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a quencher, the quencher being an amine compound, wherein the amine compound has the formula (A):

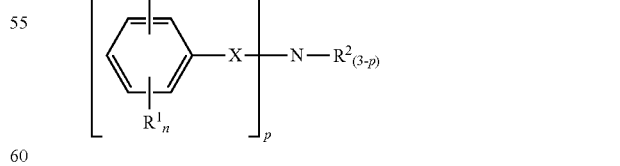

(A)

wherein $R^1$ is hydroxyl, $C_1$-$C_6$ alkyl group, $C_1$-$C_6$ alkoxy group, $C_2$-$C_6$ acyloxy group, fluorine, chlorine, bromine, amino group, —NR$^{1A}$—C(=O)—R$^{1B}$, or —NR$^{1A}$—C(=O)—O—R$^{1B}$, $R^{1A}$ is hydrogen or a $C_1$-$C_6$ alkyl group, $R^{1B}$ is a $C_1$-$C_6$ alkyl, $C_2$-$C_8$ alkenyl, $C_6$-$C_{12}$ aryl or $C_7$-$C_{13}$ aralkyl group, R² is hydrogen, nitro, or a C₁-C₂₀ monovalent hydrocarbon group which may contain at least one moiety selected from hydroxyl, carboxyl, thiol, ether bond, ester bond, nitro, cyano, halogen and amino moiety, in case of p=1, R² may bond together to form a ring with the nitrogen atom to which they are attached, the ring optionally containing a double bond, oxygen, sulfur or nitrogen, or R² and X may bond together to form a ring with the nitrogen atom to which they are attached, the ring optionally containing a double bond, oxygen, sulfur or nitrogen, X is a $C_1$-$C_{20}$ divalent hydrocarbon group which contains at least one moiety selected from ester bond and ether bond, m and n are independently an integer meeting 1≤m≤5, 0≤n≤4 and 1≤m+n≤5, and p is 1, 2 or 3.

2. The resist composition of claim 1, further comprising an acid generator capable of generating a sulfonic acid, imide acid or methide acid.

3. The resist composition of claim 1, further comprising an organic solvent.

4. The resist composition of claim 1 wherein the base polymer comprises recurring units having the formula (a1) or recurring units having the formula (a2):

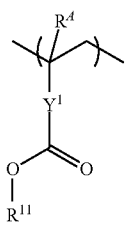
(a1)

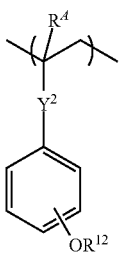
(a2)

wherein $R^A$ is each independently hydrogen or methyl, $R^{11}$ and $R^{12}$ each are an acid labile group, $Y^1$ is a single bond, phenylene group, naphthylene group, or $C_1$-$C_{12}$ linking group containing at least one moiety selected from ester bond and lactone ring, and $Y^2$ is a single bond or ester bond.

5. The resist composition of claim 4 which is a chemically amplified positive resist composition.

6. The resist composition of claim 1 wherein the base polymer is free of an acid labile group.

7. The resist composition of claim 6 which is a chemically amplified negative resist composition.

8. The resist composition of claim 1 wherein the base polymer further comprises recurring units of at least one type selected from recurring units having the formulae (f1) to (f3):

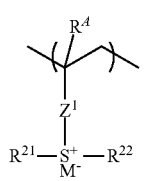
(f1)

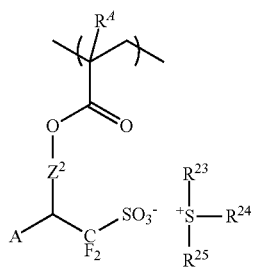
(f2)

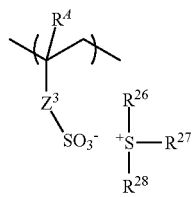
(f3)

wherein $R^A$ is each independently hydrogen or methyl, $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain a carbonyl, ester bond, ether bond or hydroxyl moiety, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain a carbonyl moiety, ester bond or ether bond, $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain a carbonyl moiety, ester bond, ether bond or hydroxy moiety, $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl, and M⁻ is a non-nucleophilic counter ion.

9. The resist composition of claim 1, further comprising a surfactant.

10. The resist composition of claim 1, further comprising a quencher other than the amine compound.

11. A process for forming a pattern comprising the steps of applying the resist composition of claim 1 onto a substrate, baking to form a resist film, exposing the resist film to high-energy radiation, and developing the exposed resist film in a developer.

12. The process of claim 11 wherein the high-energy radiation is ArF excimer laser radiation of wavelength 193 nm or KrF excimer laser radiation of wavelength 248 nm.

13. The process of claim 11 wherein the high-energy radiation is EB or EUV of wavelength 3 to 15 nm.

14. An amine compound having the formula (A'):

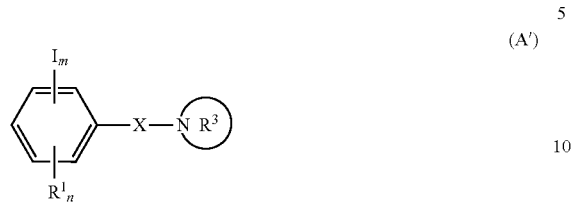

wherein $R^1$ is hydroxyl, $C_1$-$C_6$ alkyl, $C_1$-$C_6$ alkoxy group, $C_2$-$C_6$ acyloxy group, fluorine, chlorine, bromine, amino, —$NR^{1A}$—C(=O)—$R^{1B}$, or —$NR^{1A}$—C(=O)—O—$R^{1B}$, $R^{1A}$ is hydrogen or a $C_1$-$C_6$ alkyl group, $R^{1B}$ is a $C_1$-$C_6$ alkyl, $C_2$-$C_8$ alkenyl, $C_6$-$C_{12}$ aryl or $C_7$-$C_{13}$ aralkyl group, X is a $C_1$-$C_{20}$ divalent hydrocarbon group which may contain at least one moiety selected from ester bond and ether bond, the ring $R^3$ is a $C_4$-$C_6$ heterocycle formed with the nitrogen atom, which may contain an ether bond, thioether bond, —N($R^4$)—, carbonyl group or sulfonyl group, $R^4$ is hydrogen, $C_1$-$C_6$ alkyl, $C_2$-$C_6$ alkenyl, $C_2$-$C_8$ acyl, $C_7$-$C_{20}$ aralkyl or $C_1$-$C_{16}$ alkoxycarbonyl group, m and n are independently an integer meeting $1 \leq m \leq 5$, $0 \leq n \leq 4$ and $1 \leq m+n \leq 5$.

* * * * *